(12) United States Patent
Yang et al.

(10) Patent No.: US 6,545,023 B2
(45) Date of Patent: Apr. 8, 2003

(54) CYCLOPENTYL MODULATORS OF CHEMOKINE RECEPTOR ACTIVITY

(75) Inventors: Lihu Yang, Edison, NJ (US); Gabor Butora, Martinsville, NJ (US); William H. Parsons, Belle Mead, NJ (US); Alexander Pasternak, Princeton, NJ (US)

(73) Assignee: Merck & Co., Inc.

( * ) Notice: Subject to any disclaimer, the term of this patent is extended or adjusted under 35 U.S.C. 154(b) by 13 days.

(21) Appl. No.: 09/931,454

(22) Filed: Aug. 16, 2001

(65) Prior Publication Data

US 2002/0049222 A1 Apr. 25, 2002

Related U.S. Application Data

(60) Provisional application No. 60/225,923, filed on Aug. 17, 2000.

(51) Int. Cl.$^7$ .................. A61K 31/445; C07D 211/22
(52) U.S. Cl. .................. 514/331; 514/317; 546/192; 546/229; 546/233
(58) Field of Search .................. 514/317, 331; 546/192, 229, 233

(56) References Cited

U.S. PATENT DOCUMENTS 3,647,804 A * 3/1972 Rynbrandt et al. .......... 546/189
3,772,308 A * 11/1973 Pioch et al. .................. 546/304

FOREIGN PATENT DOCUMENTS

EP 962457 * 12/1999

OTHER PUBLICATIONS

R. Horuk, Trends in Pharm. Sci., 15:159–165(1994).
O. Mitsunobu, Synthesis, 1:1–28(1981).
H.K. Deng et al., Nature, 381: 661–666(1996).
A.J. Mancuso et al., J. Org. Chem., 43:2480–2482(1978).
J.P. Depres et al., J. Org. Chem., 49:928–931(1984).
K. Neote et al., Cell, 72:415–425(1993).
J.J. Gomez–Reino et al., Arthritis & Rheumatism, 42:989–992(1999).
S.Y. Sung et al., Arch. Pharm. Pharm. Med. Chem., 329–:291–300(1996).
K.S. Warmington et al., Am. J. Path., 154:1407–1416(1999).
T. Kurihara et al., J. Exp. Med., 186:1757–1762(1997).
B. Lu et al., J. Exp. Med., 187:601–608(1998).
L. Boring et al., J. Clin. Inves., 100:2552–2561(1997).
B. J. Rollins, Blood, 90:909–928(1997).
M. Samson et al., Biochemistry, 35:3362–3367(1996).
A.D. Luster, New Eng. J. Med., 338:436–445(1998).
R. M. Burk et al., Tetrahedron Lett., 34:975–978(1993).
S.W. Wright et al., Tetrahedron Lett., 38:7345–7348(1997).
W.A. Kuziel et al., Proc. Natl. Acad. Sci. USA, 94:12053–12058(1997).
H. Kita et al., J. Exp. Med., 183:2421–2426(1996).
B.M. Trost et al., J. Am. Chem. Soc., 105:2315–2325(1983).
A. Chaudhuri et al., J. Bio. Chem., 269:7835–7838(1994).
P.M. Murphy, Annu. Rev. Immunol., 12:593–633(1994).
T.J. Schall, Cytokine, 3:165–183(1991).
H. Stetter et al., Liebigs Ann. Chem., 944–949(1979).

* cited by examiner

*Primary Examiner*—Ceila Chang
(74) *Attorney, Agent, or Firm*—David L. Rose; Shu Muk Lee

(57) ABSTRACT

The present invention is directed to compounds of the formula I:

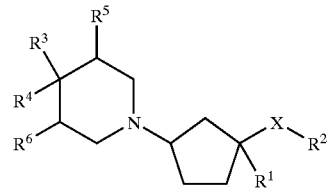

(wherein $R^1$, $R^2$, $R^3$, $R^4$, $R^5$, $R^6$ and X are defined herein) which are useful as modulators of chemokine receptor activity. In particular, these compounds are useful as modulators of the chemokine receptor CCR-2.

25 Claims, No Drawings

CYCLOPENTYL MODULATORS OF CHEMOKINE RECEPTOR ACTIVITY

This application claims the benefit of application Ser. No. 60/225,923, filed Aug. 17, 2000.

BACKGROUND OF THE INVENTION

The chemokines are a family of small (70–120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661–666 (1996)).

The chemokines are secreted by a wide variety of cell types and bind to specific G-protein coupled receptors (GPCRs) (reviewed in Horuk, *Trends Pharm. Sci.*, 15, 159–165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/ "CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood*, 90, 908–928 (1997)); CCR-4 (or "CKR-4" or "CC-CKR-4") [MIP-1α, RANTES, MCP-1] (Rollins, et al., *Blood*, 90, 908–928 (1997)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989–992 (1999)). A review of the role of eosinophils in allergic inflammation is provided by Kita, H., et al., *J. Exp. Med.* 183, 2421–2426 (1996). A general review of the role of chemokines in allergic inflammation is provided by Lustger, A. D., *New England J. Med.*, 338(7), 426–445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in nice results in marked attenuation of monocyte recruitment in response to thioglycollate injection and *Listeria monocytogenes* infection (Lu et al., J. Exp. Med 187:601–608 (1998); Kurihara et al. J. Exp. Med. 186: 1757–1762 (1997); Boring et al. J. Clin. Invest. 100:2552–2561 (1997); Kuziel et al. Proc. Natl. Acad. Sci. 94:12053–12058 (1997)). Furthermore, these animals show reduced monocyte infiltration into granulomatous lesions induced by the injection of schistosomal or mycobacterial antigens (Boring et al. J. Clin. Invest. 100:2552–2561 (1997); Warmington et al. Am J. Path. 154:1407–1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 -/- or CCR2 -/-mice backcrossed to APO-E -/-, LDL-R -/- or Apo B transgenic mice maintained on high fat diets (Boring et al. Nature 394:894–897 (1998); Gosling et al. J. Clin. Invest. 103:773–778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

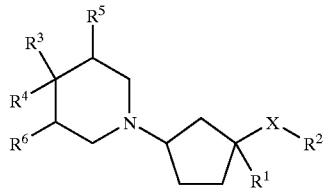

I wherein:
X is selected from:
—$NR^{10}$—, —O—, —$CH_2O$—, —$CONR^{10}$—, —$NR^{10}CO$—, —$CO_2$—, —OCO—, —$CH_2(NR^{10})CO$—, —$N(COR^{10})$—, and —$CH_2N(COR^{10})$—,
and where $R^{10}$ is independently selected from: hydrogen, $C_{1-6}$ alkyl, benzyl, phenyl, and $C_{1-6}$ alkyl-$C_{3-6}$ cycloalkyl,
which is unsubstituted or substituted with 1–3 substituents where the substituents are independently selected from: halo, $C_{1-3}$alkyl, $C_{1-3}$alkoxy and trifluoromethyl;

$R^1$ is selected from:
hydrogen,
—$C_{0-6}$alkyl-Y—($C_{1-6}$alkyl)—, and
—($C_{0-6}$alkyl)—Y—($C_{0-6}$alkyl)—($C_{3-7}$cycloalkyl)—($C_{0-6}$alkyl),
where Y is selected from:
a single bond, —O—, —S—, —SO—, —$SO_2$—, and —$NR^{10}$—,
and where the alkyl and the cycloalkyl are unsubstituted or substituted with 1–7 substituents where the substituents are independently selected from:
(a) halo,
(b) hydroxy,
(c) —O—$C_{1-3}$alkyl, and
(d) trifluoromethyl,
(e) $C_{1-3}$alkyl,
(f) —O—$C_{1-3}$alkyl,
(g) —$CO_2R^9$, wherein $R^9$ is independently selected from:
hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$alkyl, $C_{1-3}$alkoxy and trifluoromethyl,
(h) —CN,
(i) heterocycle,
(j) —$NR^9R^{10}$,
(k) —$NR^9COR^{10}$,
(l) —$NR^9SO_2R^{10}$, and
(m) —$CONR^9R^{10}$;

$R^2$ is selected from:
($C_{0-6}$alkyl)-phenyl and ($C_{0-6}$alkyl)-heterocycle,
where the alkyl is unsubstituted or substituted with 1–7 substituents where the substituents are independently selected from:
(a) halo,
(b) hydroxy,
(c) —O—$C_{1-3}$alkyl,
(d) trifluoromethyl, and
(e) —$C_{1-3}$alkyl,
and where the phenyl and the heterocycle is unsubstituted or substituted with 1–5 substituents where the substituents are independently selected from:
(a) halo,
(b) trifluoromethyl,
(c) trifluoromethoxy,
(d) hydroxy,
(e) $C_{1-6}$alkyl,
(f) $C_{3-7}$cycloalkyl,
(g) —O—$C_{1-6}$alkyl,
(h) —O—$C_{3-7}$cycloalkyl,
(i) —$SCF_3$,
(j) —S—$C_{1-6}$alkyl,
(k) —$SO_2$—$C_{1-6}$alkyl,
(l) phenyl,
(m) heterocycle,
(n) —$CO_2R^9$,
(o) —CN,
(p) —$NR^9R^{10}$,
(q) —$NR^9$—$SO_2$—$R^{10}$,
(r) —$SO_2$—$NR^9R^{10}$, and
(s) —$CONR^9R^{10}$;

$R^3$ is selected from:
($C_{0-6}$alkyl)-phenyl,
where the alkyl is unsubstituted or substituted with 1–5 substituents where the substituents are independently selected from:
(a) halo,
(b) hydroxy,
(c) —O—$C_{1-3}$alkyl, and
(d) trifluoromethyl,
and where the phenyl is unsubstituted or substituted with 1–5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$;

$R^4$ is selected from:
(a) hydrogen,
(b) hydroxy,
(c) $C_{1-6}$alkyl,
(d) $C_{1-6}$alkyl-hydroxy,
(e) —O—$C_{1-3}$alkyl,
(f) —$CO_2R^9$,
(g) —$CONR^9R^{10}$, and
(h) —CN;
or where $R^3$ and $R^4$ may be joined together to form a ring which is selected from:
(a) 1H-indene,
(b) 2,3-dihydro-1H-indene, (c) 2,3-dihydro-benzofuran,
(d) 1,3-dihydro-isobenzofuran,
(e) 2,3-dihydro-benzothiofuran, and
(f) 1,3-dihydro-isobenzothiofuran, or where $R^3$ and $R^5$ or $R^4$ and $R^6$ may be joined together to form a ring which is phenyl,
wherein the ring is unsubstituted or substituted with 1–7 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$;

$R^5$ and $R^6$ are independently selected from:
(a) hydrogen,
(b) hydroxy,
(c) $C_{1-6}$alkyl,
(d) $C_{1-6}$alkyl-hydroxy,
(e) —O—$C_{1-3}$alkyl,
(f) oxo, and
(g) halo;

and pharmaceutically acceptable salts thereof and individual diastereomers thereof.

Preferred compounds of the present invention include those of formula Ia:

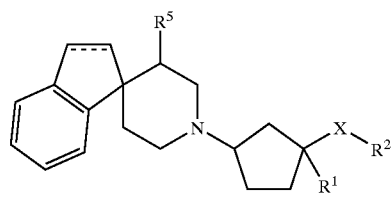

Ia wherein the dashed line represents a single or a double bond and $R^1$, $R^2$, $R^5$ and X are defined herein;
and pharmaceutically acceptable salts and individual diastereomers thereof.

Preferred compounds of the present invention also include those of formula Ib:

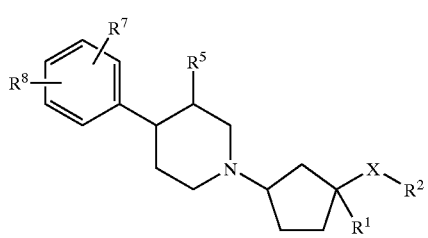

Ib wherein $R^1$, $R^2$, $R^5$ and X are defined herein,
and wherein $R^7$ and $R^8$ are independently selected from:
(a) hydrogen,
(b) halo,
(c) trifluoromethyl,
(d) hydroxy,
(e) $C_{1-3}$alkyl,
(f) —O—$C_{1-3}$alkyl,
(g) —$CO_2H$,
(h) —$CO_2C_{1-3}$alkyl, and
(i) —CN;

and pharmaceutically acceptable salts and individual diastereomers thereof.

More preferred compounds of the present invention include those of formula Ic:

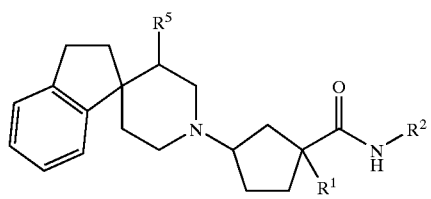

Ic wherein $R^1$, $R^2$ and $R^5$ are defined herein;
and pharmaceutically acceptable salts and individual diastereomers thereof.

More preferred compounds of the present invention also include those of formula Id:

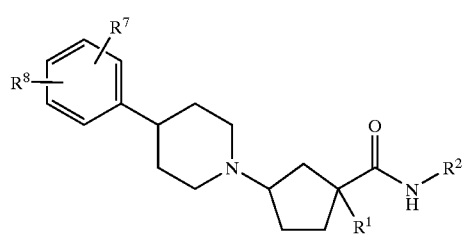

Id wherein $R^1$, $R^2$ and X are defined herein,
and wherein $R^7$ and $R^8$ are independently selected from:
(a) hydrogen,
(b) halo,
(c) trifluoromethyl,
(d) hydroxy,
(e) $C_{1-3}$alkyl,
(f) —O—$C_{1-3}$alkyl,
(g) —$CO_2H$,
(h) —$CO_2C_{1-3}$alkyl, and
(i) —CN;

and pharmaceutically acceptable salts and individual diastereomers thereof.

Still more preferred compounds of the present invention also include those of formula Ie:

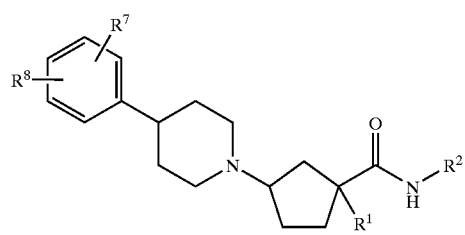

Ie wherein $R^1$, $R^2$ and X are defined herein,
and wherein $R^7$ and $R^8$ are independently selected from:
(a) hydrogen,
(b) fluoro, and
(c) trifluoromethyl;

and pharmaceutically acceptable salts and individual diastereomers thereof.

In the present invention it is most preferred that X is —CONH—.

In the present invention it is preferred that $R^1$ is selected from:
—$C_{1-6}$alkyl, —$C_{0-6}$alkyl—O—$C_{1-6}$alkyl-, —$C_{0-6}$alkyl—S—$C_{1-6}$alkyl-, and
—($C_{0-6}$alkyl)—($C_{3-7}$cycloalkyl)—($C_{0-6}$alkyl),
- where the alkyl and the cycloalkyl are unsubstituted or substituted with 1–7 substituents where the substituents are independently selected from:
  - (a) halo,
  - (b) hydroxy,
  - (c) —O—$C_{1-3}$alkyl,
  - (d) trifluoromethyl,
  - (f) $C_{1-3}$alkyl,
  - (g) —O—$C_{1-3}$alkyl,
  - (h) —$CO_2R^9$, wherein $R^9$ is independently selected from:
    - hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$alkyl, $C_{1-3}$alkoxy and trifluoromethyl,
  - (i) —CN,
  - (j) —$NR^9R^{10}$, and
  - (k) —$CONR^9R^{10}$.

In the present invention it is more preferred that $R^1$ is selected from:
(1) —$C_{1-6}$alkyl, which is unsubstituted or substituted with 1–6 substituents where the substituents are independently selected from:
  - (a) halo,
  - (b) hydroxy,
  - (c) —O—$C_{1-3}$alkyl, and
  - (d) trifluoromethyl,
(2) —$C_{0-6}$alkyl-O—$C_{1-6}$alkyl-, which is unsubstituted or substituted with 1–6 substituents where the substituents are independently selected from:
  - (a) halo, and
  - (b) trifluoromethyl,
(3) —$C_{0-6}$alkyl-S—$C_{1-6}$alkyl-, which is unsubstituted or substituted with 1–6 substituents where the substituents are independently selected from:
  - (a) halo, and
  - (b) trifluoromethyl,
(4) —($C_{3-5}$cycloalkyl)—($C_{0-6}$alkyl), which is unsubstituted or substituted with 1–7 substituents where the substituents are independently selected from:
  - (a) halo,
  - (b) hydroxy,
  - (c) —O—$C_{1-3}$alkyl, and
  - (d) trifluoromethyl.

In the present invention it is even more preferred that $R^1$ is selected from:
(1) —$CH_3$,
(2) —$CH_2CH_3$,
(3) —$CH(CH_3)_2$,
(4) —$CH_2CH_2CH_3$,
(5) —$CH_2CH(CH_3)_2$,
(6) -cyclopropyl,
(7) -cyclobutyl,
(8) -cyclopentyl,
(9) —$CH_2$-cyclopropyl,
(10) —$CH_2$-cyclobutyl,
(11) —$CH_2$-cyclopentyl,
(12) —$CH_2OH$,
(13) —$C(CH_3)_2(OH)$,
(14) —$C(CH_2OH)(CH_3)_2$,
(15) —(OH)cyclobutyl,
(16) —(OH)cyclopentyl,
(17) —$C(CH_3)_2(NHCOCH_3)$,
(18) —$C(CO_2H)(CH_3)_2$,
(19) —O—$CH_3$,
(20) —O-cyclopentyl,
(21) —O—$CH(CH_3)_2$,
(22) —S—$CH_3$,
(23) —S—$CF_3$,
(24) —$SO_2$—$CH_3$,
(25) —S—$CH(CH_3)_2$,
(26) —$SO_2$—$CH(CH_3)_2$, and
(27) —NH—$SO_2$—$CH_3$.

In the present invention it is preferred that $R^2$ is selected from:
—($C_{0-4}$alkyl)-phenyl and —($C_{0-4}$alkyl)-heterocycle,
  where heterocycle is selected from:
    furanyl, imidazolyl, oxadiazolyl, oxazolyl, pyrazolyl, pyrazinyl, pyridyl, pyridazinyl, pyrimidyl, pyrrolyl, thiadiazolyl, thiazolyl, thienyl, and triazolyl, and N-oxides thereof,
  where the alkyl is unsubstituted or substituted with 1–7 substituents where the substituents are independently selected from:
    (a) halo,
    (b) hydroxy,
    (c) —O—$C_{1-3}$alkyl, and
    (d) trifluoromethyl,
  and where the phenyl or heterocycle is unsubstituted or substituted with 1–5 substituents where the substituents are independently selected from:
    (a) halo,
    (b) trifluoromethyl,
    (c) trifluoromethoxy,
    (d) hydroxy,
    (e) $C_{1-3}$alkyl,
    (f) —O—$C_{1-3}$alkyl,
    (g) —$CO_2R^9$,
    (h) —S—$C_{1-3}$alkyl,
    (i) —$SO_2$—$C_{1-3}$alkyl,
    (j) —$SCF_3$,
    (k) —$CO_2R^9$,
    (l) —$NR^9R^{10}$,
    (m) —$NR^9$—$SO_2$—$R^{10}$,
    (n) —$SO_2$—$NR^9R^{10}$, and
    (o) —$CONR^9R^{10}$.

In the present invention it is more preferred that $R^2$ is selected from:
—($C_{0-4}$alkyl)-phenyl and —($C_{0-4}$alkyl)-heterocycle,
  where heterocycle is selected from: pyridyl, pyridazinyl, and N-oxides thereof,
  where the alkyl is unsubstituted or substituted with 1–7 substituents where the substituents are independently selected from:
    (a) halo,
    (b) hydroxy,
    (c) —O—$C_{1-3}$alkyl, and
    (d) trifluoromethyl,
  and where the phenyl or heterocycle is unsubstituted or substituted with 1–3 substituents where the substituents are independently selected from:

(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_{1-3}$alkyl,
(h) —$CO_2$H,
(i) —S—$C_{1-3}$alkyl,
(j) —$SO_2$—$C_{1-3}$alkyl,
(k) —$SCF_3$,
(l) —$NH_2$,
(m) —NH—$SO_2$—$C_{1-3}$alkyl, and
(n) —$SO_2$—$NH_2$.

In the present invention it is even more preferred that $R^2$ is selected from:

—$CH_2$-phenyl and —$CH_2$-heterocycle, where heterocycle is selected from: pyridyl, pyridazinyl, and N-oxides thereof, and where the phenyl or heterocycle is unsubstituted or substituted with 1–3 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_{1-3}$alkyl,
(h) —$CO_2$H,
(i) —S—$C_{1-3}$alkyl,
(j) —$SO_2$—$C_{1-3}$alkyl,
(k) —$SCF_3$,
(l) —$NH_2$,
(m) —NH—$SO_2$—$C_{1-3}$alkyl, and
(n) —$SO_2$—$NH_2$.

In the present invention it is still more preferred that $R^2$ is selected from:

(1) —$CH_2$—(phenyl),
(2) —$CH_2$—(4-bromophenyl),
(3) —$CH_2$—(3-chlorophenyl),
(4) —$CH_2$—(3,5-difluorophenyl),
(5) —$CH_2$—((2-trifluoromethyl)phenyl),
(6) —$CH_2$—((3-trifluoromethyl)phenyl),
(7) —$CH_2$—((4-trifluoromethyl)phenyl),
(8) —$CH_2$—((3-trifluoromethoxy)phenyl),
(9) —$CH_2$—((3-trifluoromethylthio)phenyl),
(10) —$CH_2$—((3-trifluoromethoxy-5-thiomethyl)phenyl),
(11) —$CH_2$—((3-trifluoromethoxy-5-methoxy)phenyl),
(12) —$CH_2$—((3-trifluoromethoxy-5-methanesulfonyl)phenyl),
(13) —$CH_2$—((3-trifluoromethoxy-5-amino)phenyl),
(14) —$CH_2$—((3-trifluoromethoxy-5-aminomethanesulfonyl)phenyl),
(15) —$CH_2$—((3-trifluoromethoxy-5-sulfonylamino)phenyl),
(16) —$CH_2$—((3,5-bis-trifluoromethyl)phenyl),
(17) —$CH_2$—((3-fluoro-5-trifluoromethyl)phenyl),
(18) —$CH(CH_3)$—((3,5-bis-trifluoromethyl)phenyl),
(19) —$C(CH_3)_2$—((3,5-bis-trifluoromethyl)phenyl),
(20) —$CH_2$—(4-(2-trifluoromethyl)pyridyl),
(21) —$CH_2$—(5-(3-trifluoromethyl)pyridyl),
(22) —$CH_2$—(5-(3-trifluoromethyl)pyridazinyl),
(23) —$CH_2$—(4-(2-trifluoromethyl)pyridyl-N-oxide), and
(24) —$CH_2$—(5-(3-trifluoromethyl)pyridyl-N-oxide).

In the present invention it is preferred that $R^3$ is phenyl, where the phenyl is unsubstituted or substituted with 1–5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$.

In the present invention it is more preferred that $R^3$ is phenyl, where the phenyl is unsubstituted or substituted with 1–3 substituents where the substituents are independently selected from:
(a) halo,
(c) hydroxy,
(d) $C_{1-3}$alkyl,
(e) —O—$C_{1-3}$alkyl, and
(f) —$CO_2R^9$.

In the present invention it is still more preferred that $R^3$ is phenyl, or para-fluorophenyl.

In the present invention it is more preferred that $R^4$ is selected from:
(a) hydrogen,
(b) hydroxy,
(c) —$CO_2$H,
(d) —$CO_2C_{1-6}$alkyl,
(e) —CN.

In the present invention it is more preferred that $R^5$ and $R^6$ are independently selected from:
(a) hydrogen,
(b) hydroxy,
(c) —$CH_3$,
(d) —O—$CH_3$, and
(e) oxo.

Especially preferred compounds of the present invention include those of the formula:

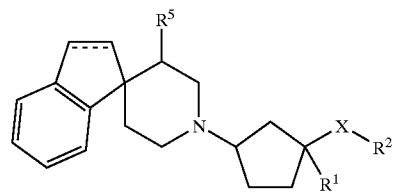

wherein the dashed line represents a single or a double bond, $R^5$ is hydrogen or methyl, and $R^1$, $R^2$, and X are defined herein;

and pharmaceutically acceptable salts and individual diastereomers thereof.

Especially preferred compounds of the present invention include those of the formula:

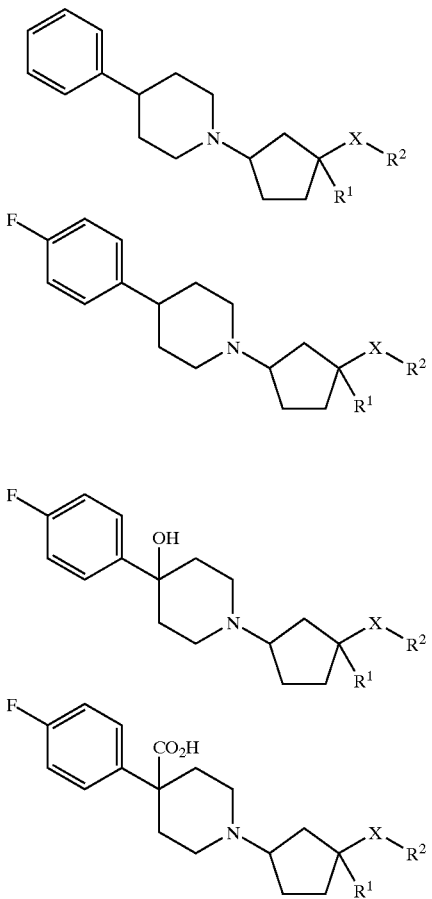

wherein $R^1$, $R^2$ and X are defined herein; and pharmaceutically acceptable salts and individual diastereomers thereof.

The compounds of the instant invention have at least two asymmetric centers at the 1- and 3-positions of the cyclopentyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of the more preferred compounds of this invention are of the orientation where the piperidinyl substituent and the X substituent are cis, i.e. as depicted:

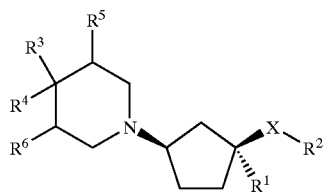

The absolute configurations of the most preferred compounds of this invention are those of the orientation as depicted:

wherein the piperidinyl substituent is designated as being of the "R" absolute configuration and the X substituent is designated as being of the "S" absolute configuration (although the designation for the X substituent may be specified as "R" if the priority for assignment of the groups at that position differs).

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-2 binding.

Receptor affinity in a CCR-2 binding assay was determined by measuring inhibition of 125I-MCP-1 to the endogenous CCR-2 receptor on various cell types including monocytes, THP-1 cells, or after heterologous expression of the cloned receptor in eukaryotic cells. The cells were suspended in binding buffer (50 mM Hepes, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM Hepes buffer containing 500 mM NaCl and cell bound $^{125}$1-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 $\mu$M Calcien-AM (Molecular Probes), for 30 min at 37° C. Labeled cells were washed twice and suspended at $5\times10^6$cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 $\mu$l). Monocytes (150,000 cells) were added to the topside of the filter (30 $\mu$l) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant.

In particular, the compounds of the following examples had activity in binding to the CCR-2 receptor in the aforementioned assays, generally with an $IC_{50}$ of less than about 1 $\mu$M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid-arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (Trichuriasis, Enterobiasis, Ascariasis, Hookworm, Strongyloidiasis, Trichinosis, filariasis), trematodes (flukes) (Schistosomiasis, Clonorchiasis), cestodes (tape worms) (Echinococcosis, Taeniasis saginata, Cysticercosis), visceral worms, visceral larva migraines (e.g., Toxocara), eosinophilic gastroenteritis (e.g., Anisaki sp., Phocanema sp.), and cutaneous larva migraines (Ancylostona braziliense, Ancylostoma caninum). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in the prevention and treatment of a wide variety of inflammatory and immunoregulatory disorders and diseases, allergic conditions, atopic conditions, as well as autoimmune pathologies. In a specific embodiment, the present invention is directed to the use of the subject compounds for the prevention or treatment of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in the prevention or treatment of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510, 332, WO95/15973, WO96/01644, WO96/06108, WO96/20216, WO96/22966, WO96/31206, WO96/40781, WO97/03094, WO97/02289, WO98/42656, WO98/53814, W98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106, 203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumnic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) anti-diabetic agents such as insulin, sulfonylureas, biguanides (metforrmin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

SCHEME 1

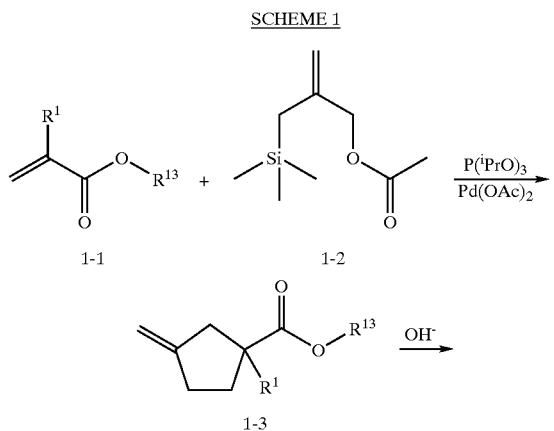
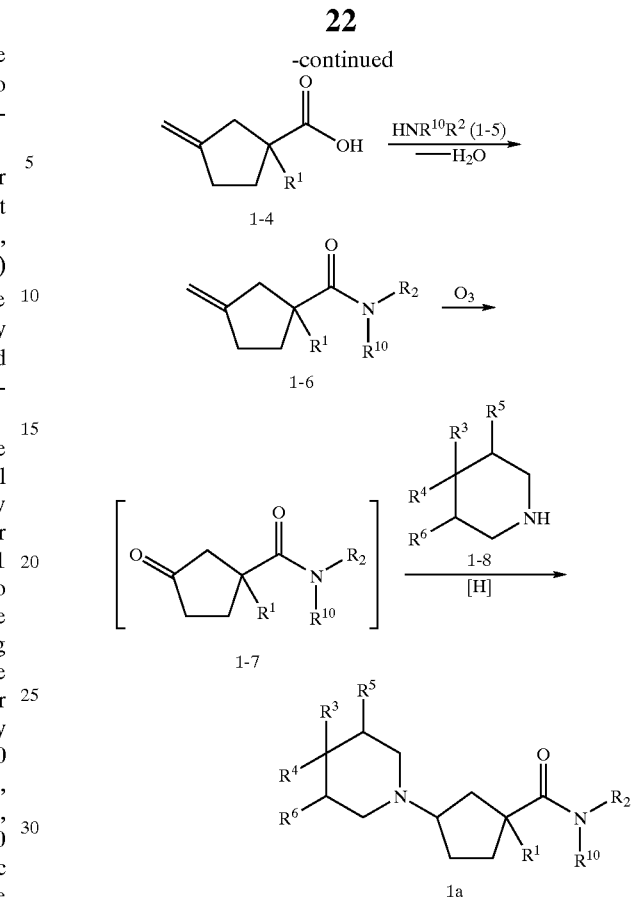

The preparation of compounds within the scope of the instant invention which bear a 1,1,3-trisubstituted cyclopentane framework is detailed in Scheme 1. Treatment of an acrylate such as 1-1 with commercially available 2-[(trimethylsilyl)-methyl]-2-propen-1-yl acetate (1-2) in the presence of a substoichiometric amount of palladium acetate and triisopropylphosphite (or other Pd⁰ equivalent) in THF, according to a known procedure (Trost, B. M., Chan, D. M. T. *J. Am. Chem. Soc.* 1983, 105, 2315) affords the 1-substituted-2-methylene carboxylate 1-3. $R^{13}$ represents an alkyl such as methyl, ethyl, tert-butyl or benzyl which serves as a protecting group (Greene, T; Wuts, P. G. M. *Protective Groups in Organic Synthesis*, John Wiley & Sons, Inc., New York, N.Y. 1991). Conversion of ester 1-3 to the carboxylic acid 1-4 can be achieved by a number of conditions depending on the nature of the ester. For example, methyl or ethyl esters can be readily saponified with sodium hydroxide, or lithium hydroxide; tert-butyl ester can be removed by treatment with TFA. Coupling of the acid 1-4 with amine 1-5 to give amide 1-6 can be accomplished by the standard amide bond formation conditions using a coupling reagent such as DCC, EDC and a catalyst such as DMAP, HOBT or HOAT. Oxidation of the olefin 1-6 to the ketone 1-7 can be carried out under numerous conditions, such as with ozone followed by treatment with methyl sulfide or triphenylphosphine, with osmium tetroxide and sodium periodate (see March J. "Advanced Organic Chemistry", 4th ed., John Wiley & Sons, New York, pp. 1167–1171 (1992)). Reductive amination with cyclic amine 1-8 in the presence of a borohydride such as sodium triacetoxyborohydride or sodium cyanoborohydride then provides the compound of formula Ia.

Alternatively, compounds of formula Ia may be prepared in one pot by reductive amination of the ozonide without converting it to the ketone. Substitutions at position 1 and 3 on the cyclopentane ring created four isomers. These isomers can be separated by chromatography using normal phase, reverse phase, or chiral columns depending on the nature of the separations.

SCHEME 1A

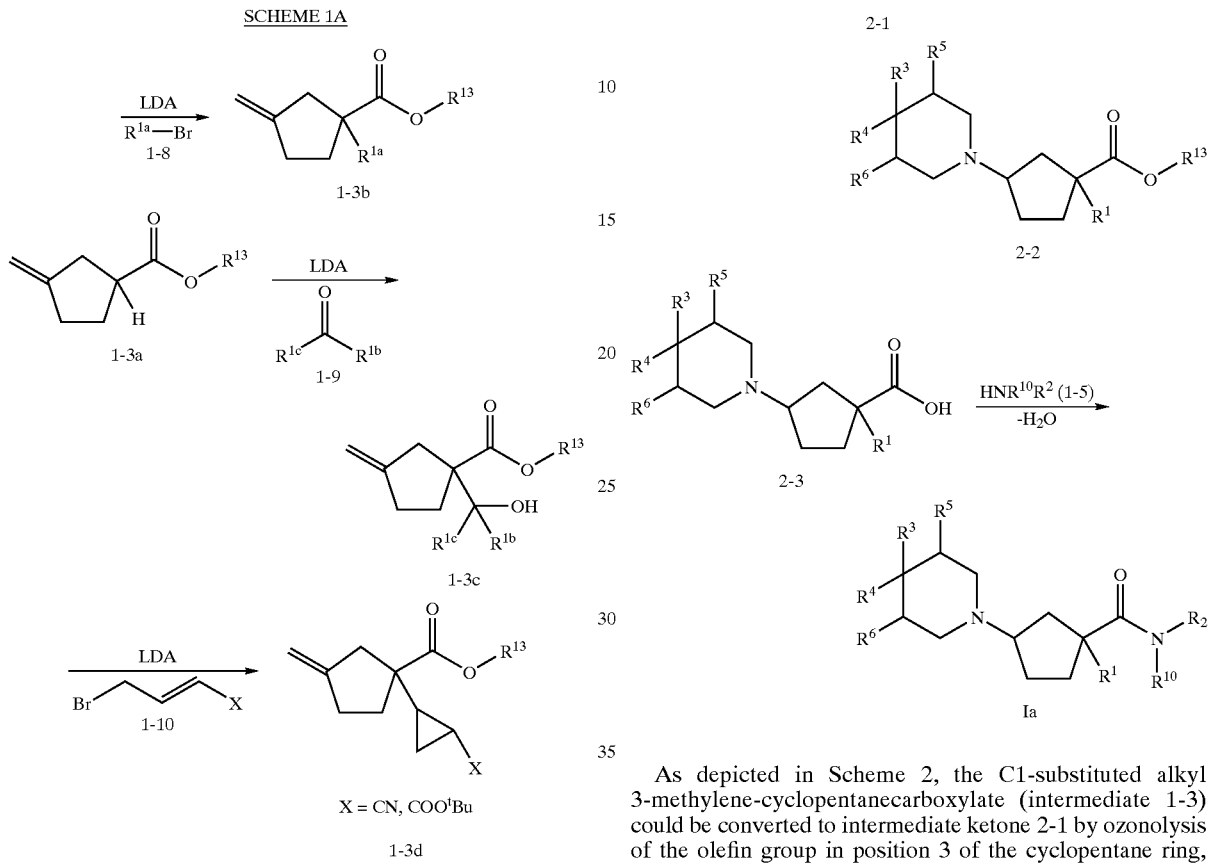

The preparation of olefin-esters 1-3 as intermediates can also be achieved through the commercially available methyl 3-methylene-1-methyl-cyclopentane carboxylate, as depicted in Scheme 1A. The methyl ester can be converted to other esters depending on need. Direct alkylation of 1-3a to give 1-3b can be achieved by an alkyl halide such as a bromide 1-8 and a strong base such as sodium, lithium or potassium hexamethyldisilazide, lithium diisopropylamide, and the like. Aldol reduction of an enolate of 1-3a with a ketone or aldehyde 1-9, as well as Michael additions with bromocrotonates 1-10 followed by ring closure yield the aldol 1-3c and cyclopropylsubstituted intermediates 1-3d, respectively. These compounds can be then converted to the compound of formula Ia according to Scheme 1.

SCHEME 2

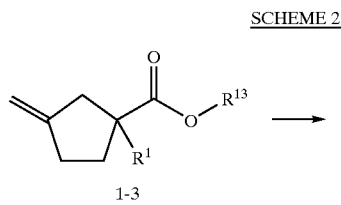

As depicted in Scheme 2, the C1-substituted alkyl 3-methylene-cyclopentanecarboxylate (intermediate 1-3) could be converted to intermediate ketone 2-1 by ozonolysis of the olefin group in position 3 of the cyclopentane ring, followed by reduction of the formed ozonide, as described for intermediate 1-7. The ketone 2-1 could be in turn reductively aminated with amine 1-5 to form the amino ester 2-2 under a variety of conditions, including sodium triacetoxyborohydride or sodium cyanoborohydride. The intermediate ozonide could be also successfully subjected to above mentioned conditions of reductive amination with amines 1-5 to form the esters 2-2 directly in a one pot operation, similarly to that described above.

The intermediate esters 2-2, formed in the above mentioned transformations represent in general a mixture of 1,3-cis- and 1,3-trans-diastereoisomers, which could be separated into respective diastereoisomeric pairs using column chromatography. A similar diastereoisomeric separation could be also accomplished later, after the esters 2-2 were hydrolytically cleaved to yield the respective acids 2-3. This hydrolysis was readily accomplished under usual conditions, including lithium, sodium or potassium hydroxide, at ambient to elevated temperatures, depending on the nature of the ester group and substituent $R^1$. These diastereoisomers could be separated by crystallization from a variety of solvents, taking advantage of the finding, that the cis-diastereoisomeric acids are less soluble, when compared to their trans- epimers.

The compounds of formula Ia are then formed from the acids 2-3 and amines 1-5 under standard amide-bond forming reaction conditions, including carbodiimide reagents, such as DCC, EDC and catalysts such as DMAP, HOAT or HOBT.

SCHEME 3

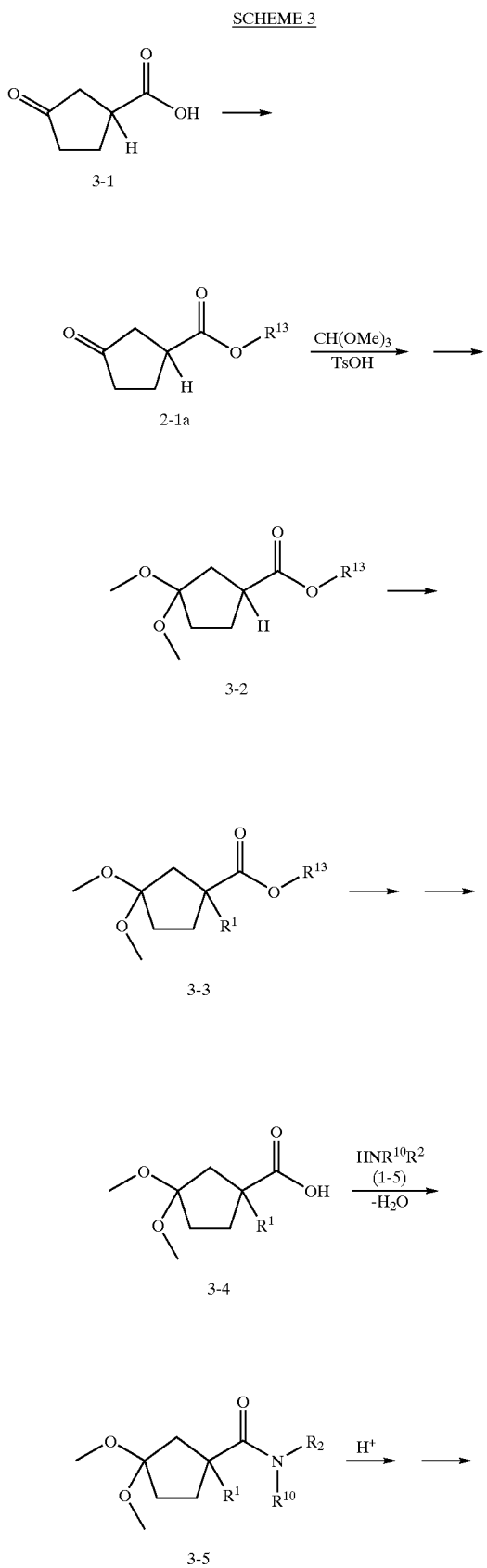

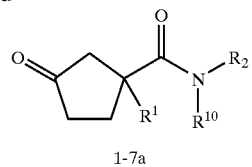

1-7a

Preparation of the ketone 1-7 for use as an intermediate in the synthesis of compounds in the instant invention can be alternatively achieved as shown in Scheme 3. The known 3-oxocyclopentane carboxylic acid 3-1 (Stetter & Kuhlmann, *Liebigs Ann. Chem.* 1979, 944–949) is converted to ester 2-1a through conventional esterification conditions. The tert-Butyl ester was conveniently prepared by reaction of isobutylene, generated from tert-butyl alcohol with an appropriate acid in situ (Wright, S. W., Hageman, D. L., Wright, A. S., McClure, L. D. *Tetrahedron Lett.*, 1997, 38, 7345) or using N,N'-diisopropyl-O-tert-Butyl-iso-urea (Burk, R. M., Berger, G. D., Bugianesi, R. L., Girotra, N. N., Parsons, W. H., Ponpipom, M. M. *Tetrahedron Lett.*, 1993, 34, 975) as a convenient reagent. Treatment of 2-1a with trimethyl orthoformate in the presence of a catalytic acid such as p-toluenesulfonic acid, gives the dimethyl acetal 3-2. Conversion of 3-2 to 3-3 can be achieved through alkylation or aldol condensation as shown in Scheme 1A. Conversion of esters 3-3 to the carboxylic acids 3-4 can be achieved by a number of conditions depending on the nature of the ester. For example, methyl or ethyl esters can be readily saponified with sodium hydroxide, or lithium hydroxide; benzyl ester can be cleaved through palladium catalyzed hydrogenolysis. These conditions of ester removal are especially advantageous when Intermediates 3-3 were synthesized from Intermediate 3-2 by an alkylation reaction. Coupling of the acid 3-4 with amine 1-5 gives amide 3-5 can be accomplished by the standard amide bond formation conditions, as discussed above. Removal of the dimethyl acetal protecting group from 3-5 can be accomplished by treatment of the acetal 3-5 with an acid such as TFA or hydrogen chloride. Intermediate 1-7a can be then easily converted to the compound of formula Ia in a reductive amination step as described in Scheme 1.

SCHEME 3A

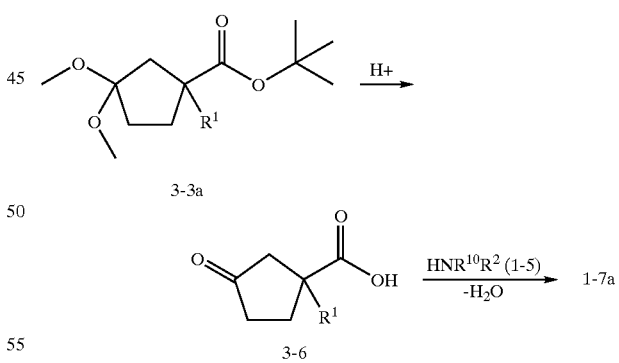

In the case where $R^{13}$ in 3-3 is tert-butyl (3-3a in Scheme 3A), the removal of the ester and the acetal groups can conveniently accomplished in an one-pot operation using acids, such as TFA or hydrogen chloride as reagent, applied neat or in an appropriate solvent, as depicted in Scheme 3A. Conversion of the intermediate keto-acids 3-6 to the respective keto-amids 1-7a could be accomplished under standard amide-bond forming conditions, as described above. The synthesis of the present compounds follows the above described conditions.

SCHEME 4

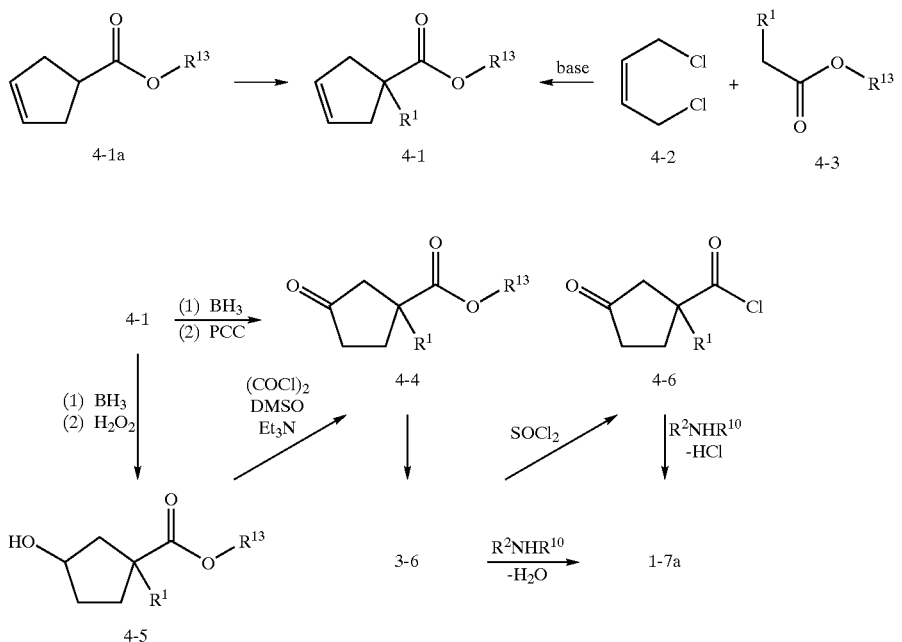

Scheme 4 shows an alternative method in the preparation of the intermediate keto acid 3-6. The readily available 3-cyclopentene-1-carboxylate 4-1a (Depres, J.-P.; Greene, A. E. J. Org. Chem. 1984, 49, 928–931) can be alkylated according to the procedures from Scheme 1A to give compound 4-1. The same intermediate 4-1 can be synthesized by a ring-forming reaction, in which the substituted acetic ester 4-3 is dialkylated with cis-1,4-dichloro-2-butene 4-2 using a strong base such as sodium hydride, sodium, lithium or potassium hexamethyl-disilazide, lithium diisopropylamide, and the like in an appropriate solvent such as DMF, DMPU, DME or a mixture of them (Depres, J.-P.; Greene, A. E. J. Org. Chem. 1984, 49, 928–931).

Hydroboration of olefin 4-1, followed by oxidation with PCC affords the ketone 4-4. Replacing the PCC in the previous sequence by milder hydrogen peroxide, the Intermediate alcohols 4-5 could be obtained. Their oxidation, e.g. by DMSO and oxalyl chloride/triethylamine (Mancuso, A. J., Huang, S-L., Swemn, D. J. Org. Chem., 43, 2480 (1978)) afforded the above mentioned keto-esters 4-4 which could be transformed into the carboxylic acids 3-6 by a number of conditions depending on the nature of the ester. For example, methyl or ethyl esters can be readily saponified with sodium hydroxide, or lithium hydroxide; benzyl ester can be cleaved through palladium catalyzed hydrogenolysis; tert-butyl ester can be removed by treatment with TFA. The acids 3-6 were coupled with amines 1-5 as described above to form Intermediates 1-7a.

Alternatively, under standard acid-chloride forming reaction conditions (e.g. thionyl chloride, oxalyl chloride and such), intermediates 3-6 could be converted into the respective acyl chlorides 4-6, and reacted with amines 1-5 to form the keto amids 1-7a. The last reaction required a presence of an appropriate base in order to neutralize the forming hydrogen chloride.

SCHEME 5

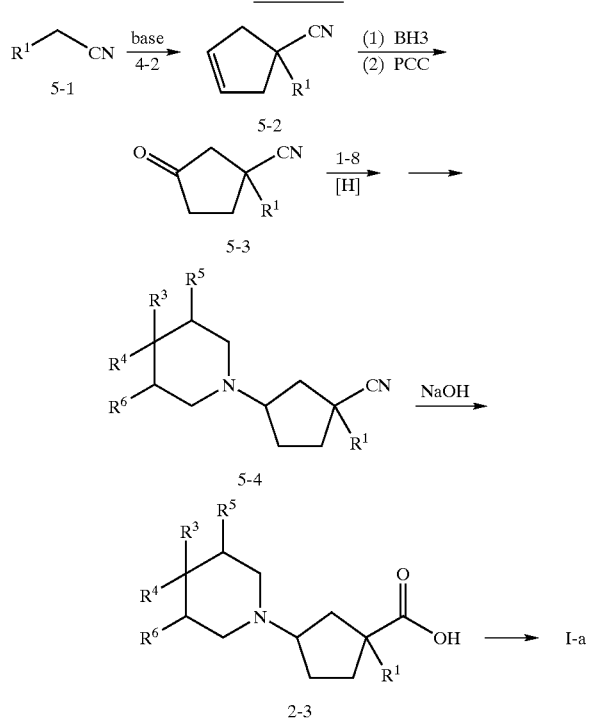

As depicted in Scheme 5, the intermediate amino acids 2-3 could be prepared starting from nitrites 5-1 (similarly to the synthetic sequence described in Scheme 2). Alkylation of the nitrile 5-1 with cis-1,4-dichloro-2-butene (4-2) as described in Scheme 4, affords the cyclic nitrile 5-3. Hydroboration, followed by oxidation affords the ketone 5-3. Reductive amination with amine 1-8 under the aforementioned conditions yields the amino nitrites 5-4, conversion of which to the corresponding carboxylic acid 2-3 can be achieved by stirring at reflux with a base such as sodium hydroxide in a protic solvent such as ethanol and water. Once again, the respective cis- and trans diastereoisomeric acids formed in the hydrolysis step can be conveniently separated by crystallization (or trituration) of the crude acid mixtures with appropriate protic or aprotic solvents, such as water, alcohols, ketones, various chlorinated solvents, DMF, DMSO or mixtures thereof. Transformation of 2-3 to the compound of formula Ia can then achieved by amide formation reactions with 1-5 as described in Scheme 1.

-continued

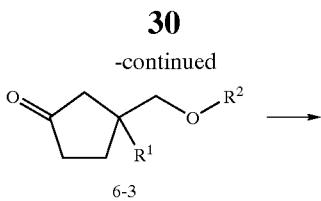

6-3

SCHEME 5A

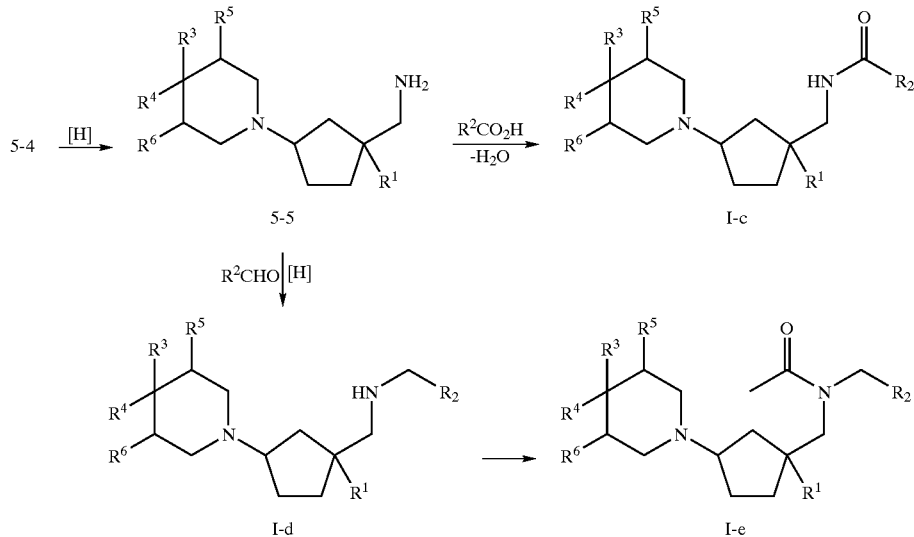

As depicted in Scheme 5A, reduction of the nitrite in 5-4 using a metal hydride such as lithium aluminum hydride or hydrogenation with a catalyst such as Raney nickel gives amine 5-5. The resulting amine can be further capped with an acylating or sulfonylating agent to give the present compounds. Shown in Scheme 5A is an example of acylating the amine 5-5 with a carboxylic acid under amide bond formation reaction conditions to give the amide 1-c. Alternatively, reductive amination with an aldehyde gives a secondary amine 1-d. Capping the secondary amine formed in the latter transformation with an acylating or sulfonylating reagent yields additional compounds, compound I-e being an example with an acetyl group.

SCHEME 6

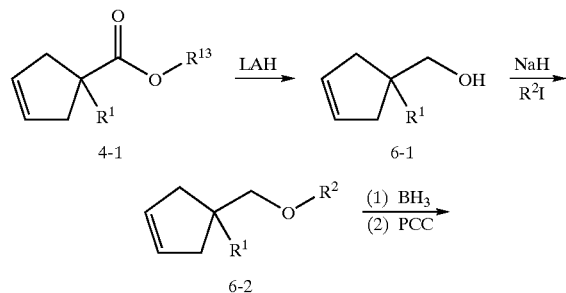

-continued

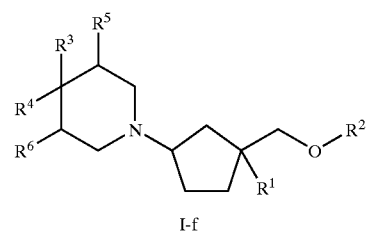

I-f

As depicted in Scheme 6, reduction of the ester 4-1 with lithium aluminum hydride gives alcohol 6-1 (similarly to the synthetic sequence described in Scheme 5A). Ether formation can be accomplished in many ways, shown in the Scheme is the direct alkylation of the alcohol with an alkylation agent such as alkyl iodide. When $R^2$ is aryl, the ether formation reaction can be accomplished by reacting with a phenol under the Mitsunobu reaction conditions (Mitsunobu, O. *Synthesis* 1981, 1). Conversion of the olefin 6-2 to ketone 6–3 is done similarly to the description in Schemes 4 and 5. Transformation of 6-3 to the compound of the formula 1-f can be achieved by reductive amination reaction conditions as described in Scheme 1. It should be noted that the intermediate 6-3 can also be prepared from intermediates 1-3 and 3-3 under similar conditions as described in the previous Schemes and known to those skilled in the art.

SCHEME 6A

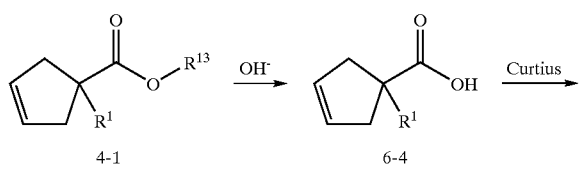

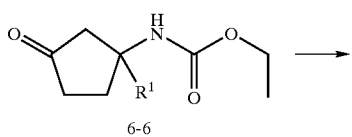

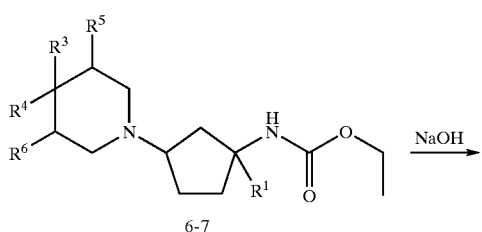

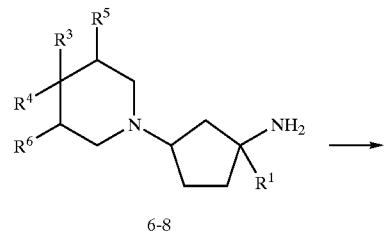

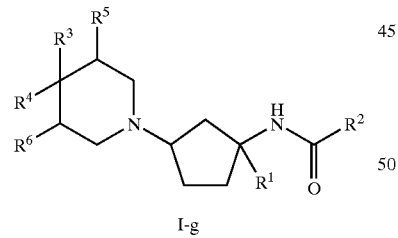

SCHEME 7

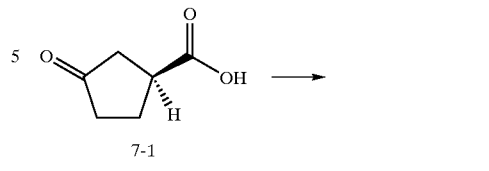

As depicted in Scheme 6A, saponification of ester 4-1 using a base such as sodium hydroxide or lithium hydroxide gives acid 6-4. Curtius rearrangement gives a carbamate 6-5. Oxidation of the olefin 6-5 to the respective ketone 6-6 can be accomplished as described in Schemes 4 and 5. Reductive amination according to procedures described in Scheme 1 gives intermediate 6-7. Removal of the ethoxycarbonyl protecting group with sodium hydroxide in refluxing aqueous ethanol gives the amine 6-8. The resulting amine can be further capped with an acylating or sulfonylating agent to give the present compounds. Shown in Scheme 6A is an example of acylating the amine to give the amide I-g.

Scheme 7 shows the preparation of optically pure compounds from optical pure (S)-3-oxocyclopentane carboxylic acid 3-1a (Sung, S-Y., Frahm, A. W.; Arch. Pharm. Med. Chem., 1996, 329, 291–300). Acid 7-1 is protected as its ester 7-2 under conditions described in Scheme 3 for the racemic material. Reductive amination with amine 1–8 gives a mixture of cis and trans diastereoisomers, which are homochiral at carbon C1 of the cyclopentane ring. These can be readily separated by column chromatography into the homochiral cis- and homochiral trans-enantiomer. This separation can be performed in the later stage of the synthesis: after the reductive amination step the ester protecting group can be removed and the resulting amino acid can be separated by crystallization, where the desired cis isomer preferably crystallizes over its trans epimer in a variety of solvents. The acid can then be converted back to the ester 7-3 under above mentioned esterification conditions. Alkylation of the ester 7-3 under conditions described in Scheme 1A affords homochiral material 7-4 after chromatographic separation from the trans isomer. Once again, the separation of the cis- and trans isomers could be achieved after the ester protecting group was removed by simple crystallization under conditions similar to those mentioned above.

Converting the ester 7-4 to acid 7-5 is accomplished by appropriate conditions depending on the nature of the ester. Transformation of the chiral acid 7-5 the compound I-g is accomplished according to the aforementioned conditions.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230–400 mesh). NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

INTERMEDIATE 1

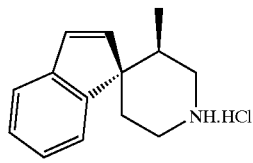

Step A

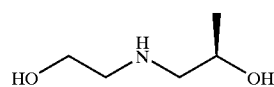

To a cooled (0° C.) solution of ethanolamine (41.8 g, 0.685 mol) in water (90 mL) was added neat (R)-propylene oxide (4.97 g, 85.6 mmol), dropwise. After 1 h at 0° C. the reaction was allowed to rise to rt and stirred overnight. The reaction mixture was concentrated at ~80° C. in vacuo to remove the water and most of the ethanolamine, to give 11.79 g of crude product, containing some residual ethanolamine. This material was used without further purification in Step B.

Step B

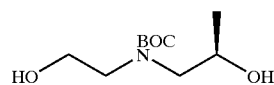

The diol prepared in Step A (11.8 g crude [~86% pure], ca. 83 mmol) was dissolved in DCM (150 mL) and treated with Boc$_2$O (23.4 g, 107 mmol) in DCM (75 mL) over 15 min. The reaction mixture was stirred over the weekend, concentrated, and purified by MPLC, eluting with 5% MeOH/EtOAc to provide 14.8 g (81%) of product.

Step C

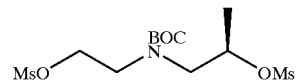

To a solution of the Boc-protected diol prepared in Step B (13.2 g, 60.3 mmol) and triethylamine (21.0 mL, 15.3 g, 151 mmol) in DCM (150 mL) at 0° C. was added dropwise methanesulfonyl chloride (9.56 mL, 14.1 g, 125 mmol). The reaction mixture was then stirred for 1.5 h, diluted with more DCM (100 mL) and washed with 3N HCl (250 mL). The aqueous layer was extracted again with DCM (200 mL), and the organic layers were combined and washed with 1N HCl (250 mL), saturated NaHCO$_3$ solution (250 mL), and brine (250 mL). The organic layer was dried over MgSO$_4$, filtered, and concentrated to give 22.8 g of crude bis-mesylate, which was used immediately. If not used immediately the bis-mesylate underwent decomposition.

Step D

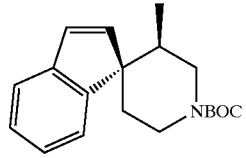

Indene (7.03 mL, 7.00 g, 60.3 mmol) was added dropwise over 4 min to a 1.0 M THF solution of LHMDS (127 mL, 127 mmol) at 0° C. After stirring for an additional 30 min., this solution was transferred via cannula to a solution of bis-mesylate (22.6 g, 60.3 mmol), prepared as described in Step C above, in THF (75 mL) at 0° C. The mixture was stirred for 2 h, warmed to rt and stirred overnight. The reaction mixture was partially concentrated and then partitioned between ethyl acetate and water. The aqueous layer was extracted again with ethyl acetate and the organic layers were combined. The organic phase was then washed with brine, dried over MgSO$_4$, filtered and concentrated to give 17.3 g of crude product. Purification by MPLC, eluting with 15% ethyl acetate/hexane, afforded 9.51 g (53%) of piperidine as a ~3:1 mixture of trans to cis (determined by H NMR). The mixture was crystallized from hot hexane to give 6 g (33%) of pure trans isomer (>20:1 by H NMR). H NMR (CDCl$_3$, 400 MHz): δ 7.29 (dt, J=6.4, 1.6 Hz, 1H), 7.20 (m, 3H), 6.83 (d, J=6.0 Hz, 1H), 6.67 (d, J=5.6 Hz, 1H), 4.20 (br s, 2H), 2.97 (br t, J=3.2 Hz, 1H), 2.69 (br t, J=2.4 Hz, 1H), 2.16 (m, 1H), 2.07 (dt, J=4.4, 13.2 Hz, 1H), 1.49 (s, 9H), 1.25 (m, 1H), 0.31 (d, J=6.8 Hz, 3H).

Step E

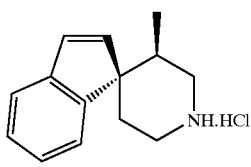

The Boc-piperidine prepared in Step D (4.35 g, 14.5 mmol) was dissolved in an anhydrous 4 N HCl solution in dioxane and stirred at rt for 1 h. The reaction mixture was then concentrated to afford 3.81 g of product. El-MS calc. for C14H17N: 199; Found: 200 $(M)^+$.

INTERMEDIATE 2

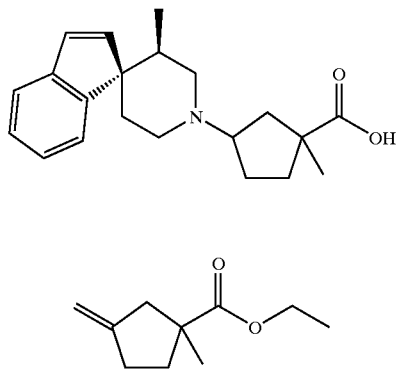

A solution of 2-[(trimethylsilyl)methyl]-2-propen-1-yl acetate (9.64 mL, 45.36 mmol), ethyl acrylate (5.18 g 45.36 mmol), palladium acetate (510 mg, 2.268 mmol) in 50 mL of tetrahydrofuran was thoroughly degassed (vacuum/nitrogen cycle) and triisopropyl phosphite (2.80 mL, 11.34 mmol) was added via syringe. The pale yellow solution was stirred under reflux overnight. The solvent was concentrated in vacuo (80 torr), the residue diluted with water (50 mL) and extracted with diethyl ether (3×50 mL). The combined organic extracts were washed with water (2×30 mL), brine (1×30 mL), dried (anh. sodium sulfate) and the solvent was removed on rotavap (80 torr). The crude product was distilled under reduced pressure to yield 3.96 g (52%) of pure product. B.P.: 90–96° C. (20 torr). $^1$H NMR (500 MHz, CDCl$_3$): 4.89 (m, 2H), 4.16 (q, 7.0 Hz, 2H), 2.82 (bd, 15.8 Hz, 1H), 2.41 (m, 2H), 2.20 (m, 3H), 1.25 (s, 3H), 1.26 (q, 7 Hz, 3H).

Step B

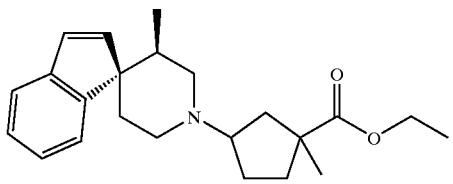

A solution of ethyl 3-methylenecyclopentane carboxylate (647 mg, 3.85 mmol) in dichloromethane (30 mL) was cooled to −78° C. and a stream of ozone was passed through the well stirred solution until the persistant blue color indicated complete consumption of the olefin. The excess ozone was purged with a stream of nitrogen and the reaction mixture was allowed to warm up to ambient temperature. The solution was treated with anhydrous magnesium sulfate and the drying agent was filtered off. 3-Methyl-4-(1,1-spiroindenyl)piperidine hydrochloride (Intermediate 1, 801 mg, 3.40 mmol) was then added to the filtrate, followed by diisopropylethylamine (592 μL, 3.40 mmol), crushed 4 A molecular sieves (1.3 g) and sodium triacetoxyborohydride (2.161 g, 10.20 mmol). The reaction mixture was stirred at ambient temperature for 72 hrs and the molecular sieves were removed by filtration through a Celite plug which was thoroughly washed with dichloromethane. The filtrate was washed with a saturated solution of sodium bicarbonate (1×50 mL), water (1×50 mL) and brine (1×50 mL). After drying with anhydrous sodium sulfate the solvent was concentrated in vacuo and further purified on preparative TLC (100% ethyl acetate) to yield 534 mg (45%) of the pure product in the form of a viscous oil. $^1$H NMR (500 MHz, CDCl$_3$) confirmed that the product consists of a mixture of cis-and trans- isomers in a ratio of approximately 4 to 1. LC-MS: for $(M+H)^+$ calculated 354.24, found 354.10.

Step C

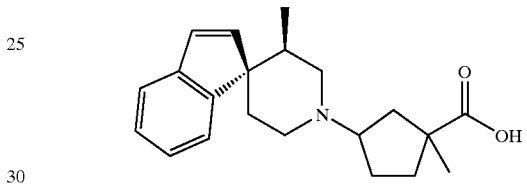

A solution of the ester prepared in step B (534 mg, 1.51 mmol) in a mixture of dioxane (5 mL) and methanol (5 mL) was treated with lithium hydroxide (254 mg, 6.05 mmol) in water (5 mL) and stirred at ambient temperature overnight. The solution was concentrated in vacuo, the remaining solid was dissolved in water (5 mL) and the pH was adjusted to neutral with 2N HCl. The crude acid was extracted with chloroform (5×30 mL), the combined extracts were dried (anhydrous sodium sulfate) and the solvent was removed in vacuo to leave 410 mg of the desired acid as a mixture of cis- and trans-isomers. LC-MS: for $C_{21}H_{28}NO_2$ $(M+H)^+$ calculated 326.20, found 236.30.

EXAMPLE 1

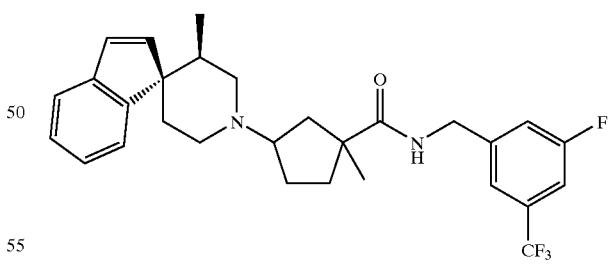

A mixture of the acid (Intermediate 2, 10.0 mg, 0.031 mmol), 3-trifluoromethyl-5-fluorobenzylamine (6.0 mg, 0.031 mmol), 1-hydroxy-7-azabenzotriazole (4.22 mg, 0.031 mmol) in dichloromethane (4 mL) was treated with 1-[3-(dimethylamino)propyl]-3-ethylcarbodiimide hydrochloride (EDC, 8.9 mg, 0.065 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 16 mg of crude product, which was purified by preparative TLC (eluent: 4% of methanol:ammonium hydroxide/9:1 in dichloromethane) to yield 11.5 mg (64%) of pure product. Single enantiomers were obtained via chiral HPLC, using Diacel's Chiralcel OD semipreparative column, eluent hexane/ethanol (99:1). The retention times of the isolated cis-enantiomers were found on an identical analytical column (250×4.6 mm, 1 mL/min) to be 17.7 and 22.3 minutes, respectively. LC-MS for $C_{32}H_{35}F_6N_2O$ $[M+H]^+$ calculated 577.26, found 577.30.

EXAMPLE 2

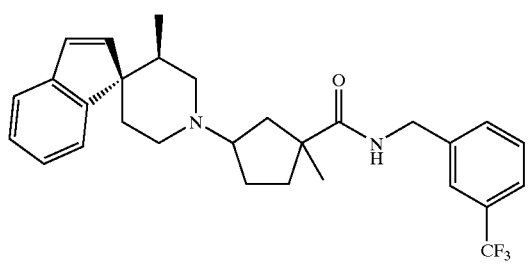

The title compound was synthesized as described in Example 1 using Intermediate 2 and 3-trifluoromethylbenzylamine. Single enantiomers were obtained via chiral HPLC, using Diacel's Chiralcel OD semipreparative column, eluent hexane/ethanol (97:3). The respective retention times under analytical conditions (250× 4.6 mm, 1.0 mL/min) were 9.47 and 10.94 minutes. LC-MS for $C_{29}H_{34}F_3N_2O$ $[M+H]^+$ calculated 483.22, found 483.23.

EXAMPLE 3

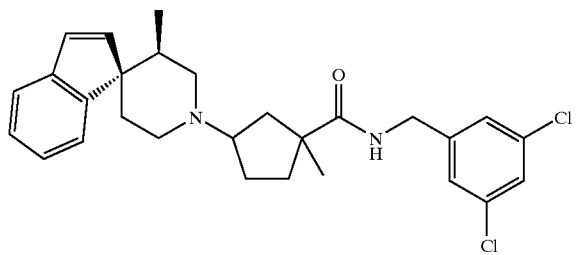

The title compound was synthesized as described in Example 1 using Intermediate 2 and 3,5-dichlorobenzylamine in Step D. Single enantiomers were obtained via chiral HPLC, using Diacel's Chiralcel OD semipreparative column, eluent hexane/ethanol (97:3). The respective retention times under analytical conditions (250× 4.6 mm, 1.0 mL/min) were 11.20 and 14.20 minutes. LC-MS for $C_{28}H_{33}Cl_2N_2O$ $[M+H]^+$ calculated 483.19, found 483.20.

EXAMPLE 4

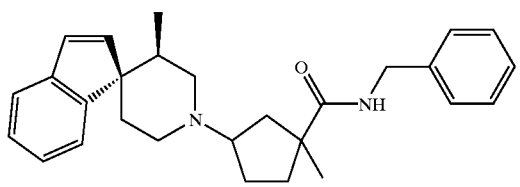

The title compound was synthesized as described in Example 1 using Intermediate 2 and benzylamine. The respective 1,3-czs- and 1,3-trans-diastereoisomers could be separated using preparative TLC, eluent: 4% of methanol:ammonium hydroxide/9:1 in dichloromethane. LC-MS for $C_{28}H_{35}N_2O$ $[M+H]^+$ calculated 415.23, found 415.30.

EXAMPLE 5

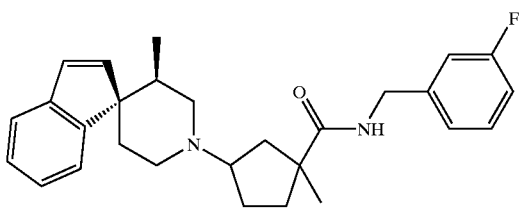

The title compound was synthesized as described in Example 1 using Intermediate 2 and 3-fluorobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{34}N_2OF$ $[M+H]^+$ calculated 433.27, found 433.30.

EXAMPLE 6

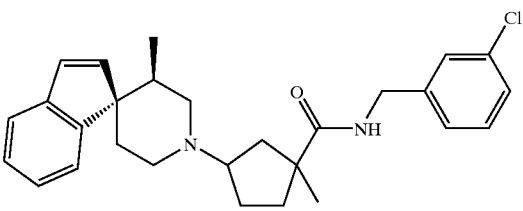

The title compound was synthesized as described in Example 1 using Intermediate 2 and 3-chlorobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{34}N_2OCl$ $[M+H]^+$ calculated 449.24, found 449.20.

EXAMPLE 7

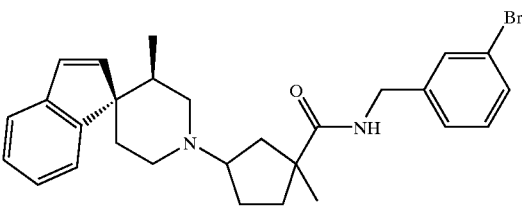

The title compound was synthesized as described in Example 1 using Intermediate 2 and 3-bromobenzylamine.

EXAMPLE 8

The respective 1,3-cis- and 1,3-trans-diastereoisomers could be separated using preparative TLC, eluent: 4% of methanol:ammonium hydroxide/9:1 in dichloromethane. LC-MS for $C_{28}H_{34}N_2OBr$ [M+H]$^+$ calculated 493.19, found 495.25.

EXAMPLE 8

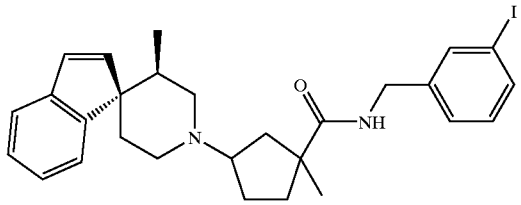

The title compound was synthesized as described in Example 1 using Intermediate 2 and 3-iodobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{34}N_2O$ [M+H]$^+$ calculated 541.17, found 541.15.

EXAMPLE 9

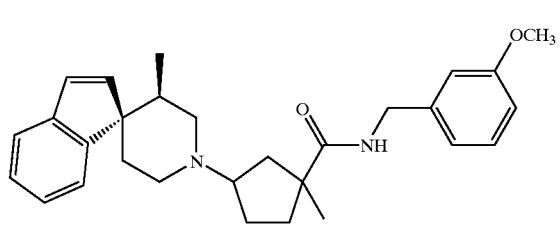

The title compound was synthesized as described in Example 1 using Intermediate 2 and 3-methoxybenzylamine. The respective 1,3-cis- and 1,3-trans-diastereoisomers could be separated using preparative TLC, eluent: 4% of methanol:ammonium hydroxide9:1 in dichloromethane. LC-MS for $C_{29}H_{37}N_2O_2$[M+H]$^+$ calculated 445.29, found 445.30.

EXAMPLE 10

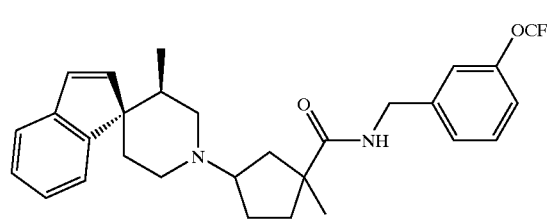

The title compound was synthesized as described in Example 1 using Intermediate 2 and 3-trifluoromethoxybenzylamine. The respective 1,3-cis- and 1,3-trans-diastereoisomers could be separated using preparative TLC, eluent: 4% of methanol:ammonium hydroxide9:1 in dichloromethane. LC-MS for $C_{29}H_{34}N_2O_2F_3F_3$ [M+H]$^+$ calculated 499.26, found 499.15.

EXAMPLE 11

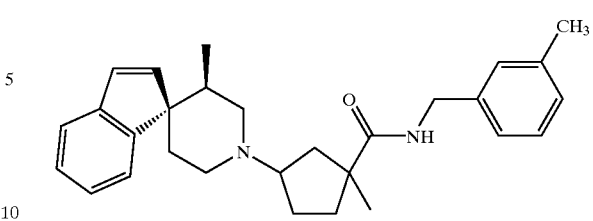

The title compound was synthesized as described in Example 1 using Intermediate 2 and 3-methylbenzylamine. The respective 1,3-cis- and 1,3-trans-diastereoisomers could be separated using preparative TLC, eluent: 4% of methanol:ammonium hydroxide/9:1 in dichloromethane. LC-MS for $C_{29}H_{34}N_2O_2F_3$ [M+H]$^+$ calculated 499.26, found 499.15.

EXAMPLE 12

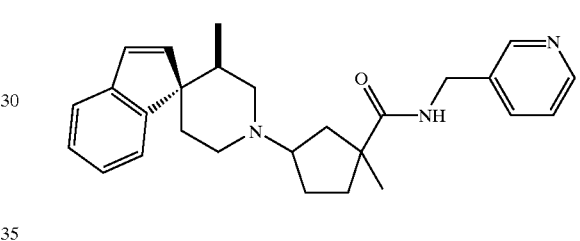

The title compound was synthesized as described in Example 1 using Intermediate 2 and 3-aminomethylpyridine. The respective 1,3-cis- and 1,3-trans-diastereoisomers could be separated using preparative TLC, eluent: 4% of methanol:ammonium hydroxide/9:1 in dichloromethane. LC-MS for $C_{27}H_{34}N_3O_3O_2$ [M+H]$^+$ calculated 416.27, found 416.30.

EXAMPLE 13

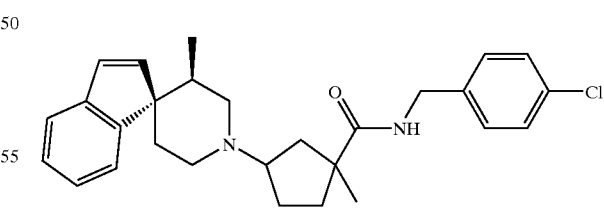

The title compound was synthesized as described in Example 1 using Intermediate 2 and 4-chlorobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{34}N_2OCl$ [M+H]$^+$ calculated 449.24, found 449.20.

EXAMPLE 14

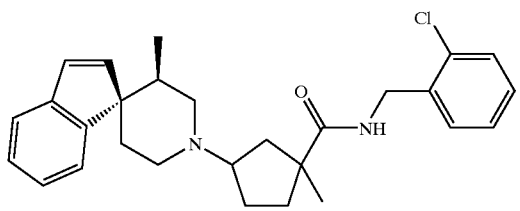

The title compound was synthesized as described in Example 1 using Intermediate 2 and 2-chlorobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{34}N_2OCl$ $[M+H]^+$ calculated 449.24, found 449.20.

EXAMPLE 15

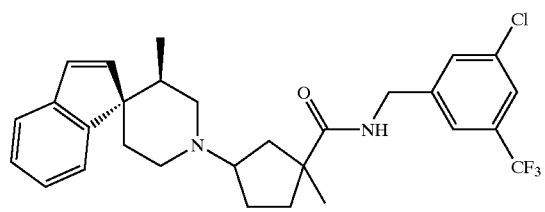

The title compound was synthesized as described in Example 1 using Intermediate 2 and 3-chloro-5-trifluoromethylbenzylamine. The respective 1,3-cis- and 1,3-trans-diastereoisomers could be separated using preparative TLC, eluent: 4% of methanol:ammonium hydroxide/9:1 in dichloromethane. LC-MS for $C_{29}H_{33}N_2OClF_3$ $[M+H]^+$ calculated 517.22, found 517.30.

EXAMPLE 16

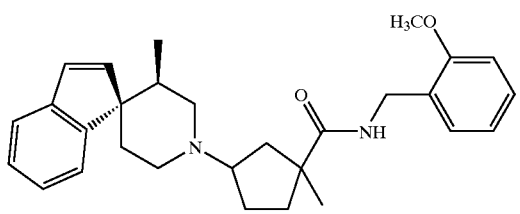

The title compound was synthesized as described in Example 1 using Intermediate 2 and 2-methoxybenzylamine. The respective 1,3-cis- and 1,3-trans-diastereoisomers could be separated using preparative TLC, eluent: 4% of methanol:ammonium hydroxide/9:1 in dichloromethane. LC-MS for $C_{29}H_{37}N_2O_2$ $[M+H]^+$ calculated 445.29, found 445.30.

EXAMPLE 17

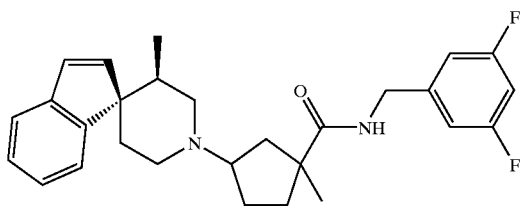

The title compound was synthesized as described in Example 1 using Intermediate 2 and 3,5-difluorobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{33}N_2OF_2$ $[M+H]^+$ calculated 451.26, found 451.30.

EXAMPLE 18

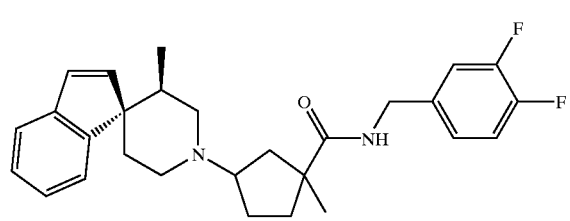

The title compound was synthesized as described in Example 1 using Intermediate 2 and 3,4-difluorobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{33}N_2OF_2$ $[M+H]^+$ calculated 451.26, found 451.30.

EXAMPLE 19

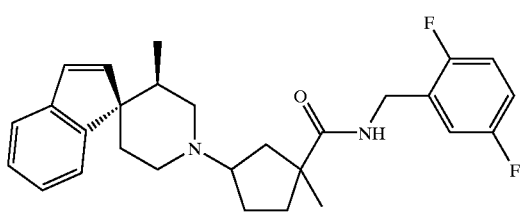

The title compound was synthesized as described in Example 1 using Intermediate 2 and 2,5-difluorobenzylamine. The respective 1,3-cis- and 1,3-trans-diastereoisomers could be separated using preparative TLC, eluent: 4% of methanol:ammonium hydroxide/9:1 in dichloromethane. LC-MS for $C_{28}H_{33}N_2OF_2$ $[M+H]^+$ calculated 451.26, found 451.30.

EXAMPLE 20

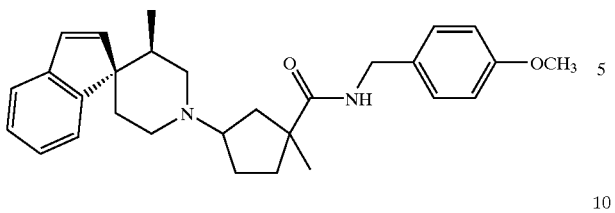

The title compound was synthesized as described in Example 1 using Intermediate 2 and 4-methoxybenzylamine. The respective 1,3-cis- and 1,3-trans-diastereoisomers could be separated using preparative TLC, eluent: 4% of methanol:ammonium hydroxide/9:1 in dichloromethane. LC-MS for $C_{29}H_{37}N_2O_2$ [M+H]$^+$ calculated 445.29, found 445.30.

EXAMPLE 21

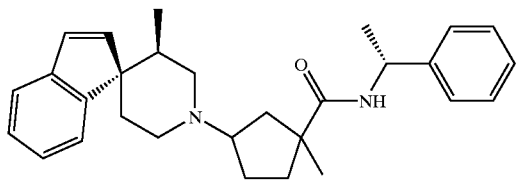

The title compound was synthesized as described in Example 1 using Intermediate 2 and α-(R)-Methylbenzylamine. The respective 1,3-cis- and 1,3-trans-diastereoisomers could be separated using preparative TLC, eluent: 4% of methanol:ammonium hydroxide/9:1 in dichloromethane. LC-MS for $C_{29}H_{37}N_2O$ [M+H]$^+$ calculated 429.29, found 429.20.

EXAMPLE 22

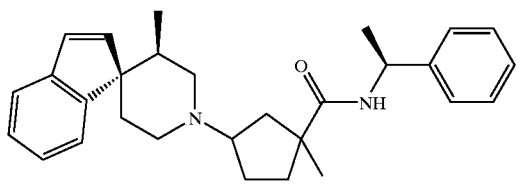

The title compound was synthesized as described in Example 1 using Intermediate 2 and α-(S)-Methylbenzylamine. The respective 1,3-cis- and 1,3-trans-diastereoisomers could be separated using preparative TLC, eluent: 4% of methanol:ammonium hydroxide/9:1 in dichloromethane. LC-MS for $C_{29}H_{37}N_2O$ [M+H]$^+$ calculated 429.29, found 429.25.

EXAMPLE 23

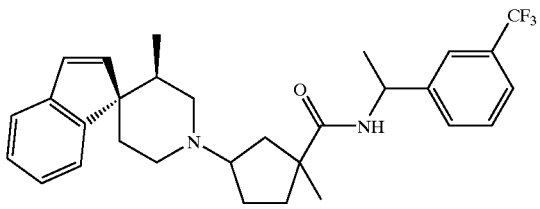

The title compound was synthesized as described in Example 1 using Intermediate 2 and α-Methyl-3-trifluoromethylbenzylamine. The respective 1,3-cis- and 1,3-trans-diastereoisomers could be separated using preparative TLC, eluent: 4% of methanol:ammonium hydroxide/9:1 in dichloromethane. LC-MS for $C_{30}H_{36}N_2OF_3$ [M+H]$^+$ calculated 497.28, found 497.30.

INTERMEDIATE 3

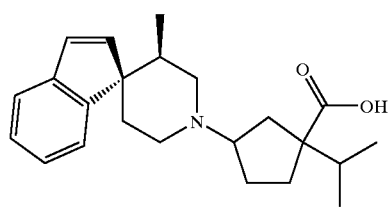

Step A
Methyl 3-Methylene-1-isopropylcyclopentane carboxylate

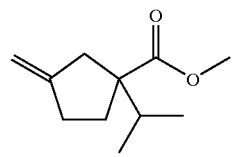

A solution of diisopropylamine (530 μL, 3.76 mmol) in tetrahydrofuran (15 mL) was cooled to −78° C. and nBuLi (1.50 mL, 3.76 mmol, 2.5 M sol. in hexanes) was added via syringe. The neat methyl 3-methylenecyclopentane carboxylate was added via syringe 15 minutes later, and the stirring at −78° C. was continued for another 30 minutes. Isopropyl bromide (921 μL, 9.81 mmol) was injected, and the resulting solution was allowed to warm up to +5° C. overnight and stirred at room temperature for additional 8 hrs. The reaction was quenched with a sat. solution of ammonium chloride (50 mL) and extracted with diethyl ether (2×50 mL). The combined organic extracts were washed with water (2×40 mL), brine (1×40 mL), dried (anh. magnesium sulfate) and the solvent was evaporated under reduced pressure (80 torr) to yield 340 mg (57%) of product with satisfactory purity. $^1$H NMR (500 MHz, CDCl$_3$) 4.86 (bs, 1H), 4.81 (bs, 1H), 3.67 (s, 3H), 2.87 (bd, 16.7 Hz, 1H), 2.29 (m, 3H), 1.90 (m, 1H), 1.60 (m, 1H), 1.34 (d, 6.2 Hz, 1H), 0.93 (d, 3.7 Hz, 3H), 0.91 (d, 3.7 Hz, 3H).

Step B

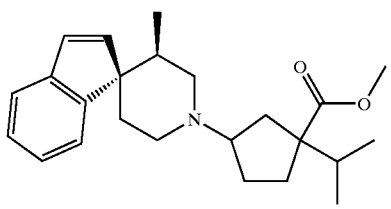

The title compound was prepared starting from the above described methyl 3-methylene-1-isopropylcyclopentane carboxylate and 3-methyl-4-spiroindenyl piperidine (Intermediate 1), as described in Intermediate 2, Step B. LC-MS for $C_{24}H_{34}NO_2$ [M+H]$^+$ calculated 368.25, found 368.30.

Step C

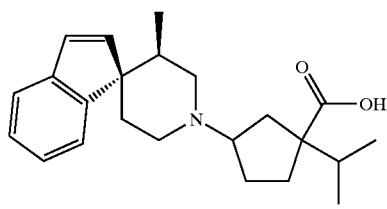

To a solution of the ester (222 mg, 0.604 mmol) in dioxane (4 mL) and water (4 mL) containing lithium hydroxide (101 mg, 2.41 mmol) was added methanol to homogenize and the reaction mixture was heated to 80° C., 48 hrs. The solvent was removed in vacuo, the residual solid was dissolved in water (10 mL) and the pH was adjusted to neutral. The product was extracted with chloroform, the combined organic extracts were dried with sodium sulfate, and the solvent was removed in vacuo to yield the desired acid as a mixture of cis- and trans-diastereoisomers. LC-MC: for $C_{23}H_{32}NO_2$ calculated 354.24, found 354.25.

EXAMPLE 24

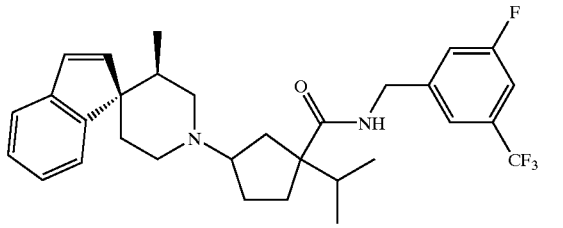

A mixture of the acid (Intermediate 3, 70.0 mg, 0.2 mmol), 3-fluoro-5-trifluoromethylbenzylamine (39 mg, 0.2 mmol), 1-hydroxy-7-azabenzotriazole (27 mg, 0.2 mmol) in dichloromethane (4 mL) was treated with 1-[3-(dimethylamino)propyl]-3-ethylcarbodiimide hydrochloride (EDC, 58 mg, 0.3 mmol) and stirred at r.t. for 2 hours. The reaction mixture was diluted with dichloromethane (4 mL), washed with water (3×3 mL), brine (1×3 mL), dried over anhydrous sodium sulfate and the solvent was evaporated under reduced pressure to yield 114.7 mg of crude product, which was purified by preparative TLC (100% ethyl acetate) to yield 45 mg (42%) of pure product. The respective enantiomers were obtained via chiral HPLC, using Diacel's Chiralcel OD semipreparative column, eluent hexane/ethanol (98:2). The observed retention times of the respective diastereoisomers on an identical analytical (250×4.6 mm, 1.0 mL/min) column were 8.50, 9.30, 14.80 and 17.50 minutes, respectively. LC-MS for $C_{31}H_{37}F_4N_2O$ [M+H]$^+$ calculated 529.28, found 529.30.

EXAMPLE 25

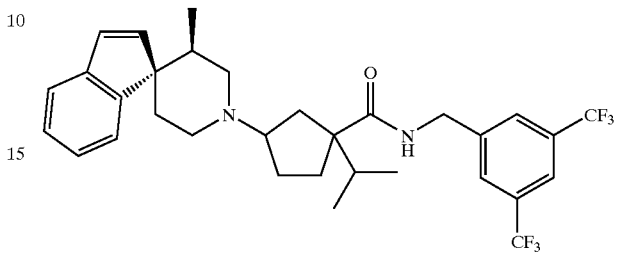

The title compound was prepared using a synthetic sequence analogous to that described in Example 24 except that 3,5-bistrifluoromethylbenzylamine was used instead of 3-fluoro-5-trifluoromethylbenzylamine. The cis- and trans-diastereoisomeric pairs were obtained via chiral HPLC, using Diacel's Chiralcel OD semipreparative column, eluent hexane/ethanol (98:2). The observed retention times of the respective diastereoisomers on an identical analytical (250× 4.6 mm, 1.0 mL/min) column were 6.90 and 12.0 minutes, respectively. LC-MS for $C_{32}H_{37}F_6N_2O$ [M+H]$^+$ calculated 579.27, found 579.25.

INTERMEDIATE 4

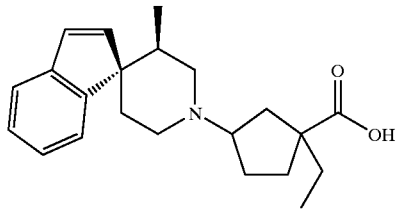

Step A: Methyl 3-methylene-1-ethylcyclopentane carboxylate

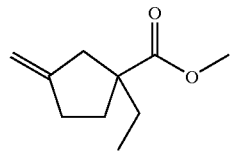

A solution of diisopropylamine (530 µL, 3.76 mmol) in THF (15 mL) was cooled to −78° C. and treated with butyl lithium (1.50 mL of 2.5M solution in hexanes, 3.76 mmol). After stirring at −78° C. for 15 minutes, the neat methyl 3-methylene-cyclopentane carboxylate (Trost, B. M., Chan, M. T., *J.Am.Chem.Soc.*, 1983, 105, 2315) (400 µL, 3.27 mmol) was added via syringe, and the reaction mixture was stirred at −78° C. for 2 hrs. Neat ethyl iodide (675 µL, 6.54 mmol) was added via syringe, the reaction mixture was stirred at −78° C. for 1 hour, and allowed to stand at +5° C. overnight. The reaction was quenched by pouring onto aqueous solution of citric acid (10%, 50 mL), and the product was extracted into diethyl ether (6×30 mL). The combined organic extracts were dried with magnesium sulfate, and the solvent was evaporated in vacuo (150 torr). The volatile crude product (545 mg, 100%) was used in the subsequent reaction step as obtained.

Step B

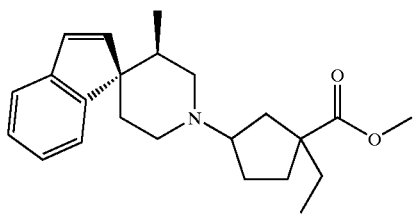

A solution of methyl 3-methylene-1-ethylcyclopentane carboxylate (462 mg, 2.13 mmol) in dichloromethane (60 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added of 3-methyl-4-spiroindenylpiperidine hydrochloride (Intermediate 1,500 mg, 2.13 mmol), diisopropylethylamine (371 µL, 2.13 mmol), crushed 4 A molecular sieves (1.2 g) and the resulting mixture was treated with sodium triacetoxyborohydride (1.355 g, 6.39 mmol). After stirring at ambient temperature for 24 hours, the sieves were filtered off, the filtrate was washed with saturated solution of sodium bicarbonate (1×50 mL), water (3×50 mL) and brine (1×50 mL). After drying (anhydrous sodium sulfate) the solvent was evaporated to dryness under reduced pressure to leave 650 mg of crude product, which was further purified by preparative TLC (100% ethyl acetate) to yield 346 mg (46%) of the pure product in a form of a cis-/trans-diastereoisomeric mixture. The approximate ratio of the respective diastereoisomers was 1:1. LC-MS for $C_{23}H_{32}NO_2$ [M+H]$^+$ calculated 354.22, found 354.10.

Step C

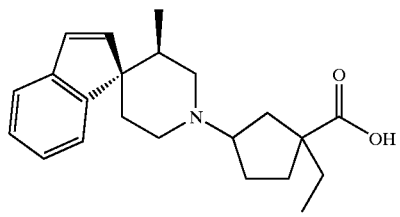

A solution of the ester from the previous step (346 mg, 0.979 mmol) in dioxane (4 mL) and water (4 mL) mixture containing lithium hydroxide monohydrate (165 mg, 3.915 mmol) was homogenized with methanol and stirred at 80° C. for 4 hours. The solvents were evaporated under reduced pressure, the residue was dissolved in water (10 mL). The pH was set with 2N HCl to neutral, and the amino acid was extracted with chloroform (6×50 mL). The combined aqueous phases were dried with anhydrous sodium sulfate, and the solvent was evaporated in vacuo. The remaining mixture of the cis- and trans-diastereoisomeric acids was further purified by preparative TLC (dichloromethane:methanol/ 95:5) to yield 179.5 mg (54%) of the pure cis-diastereoisomer. LC-MS for $C_{22}H_{30}NO_2$ [M+H]$^+$ calculated 340.22, found 340.30.

EXAMPLE 26

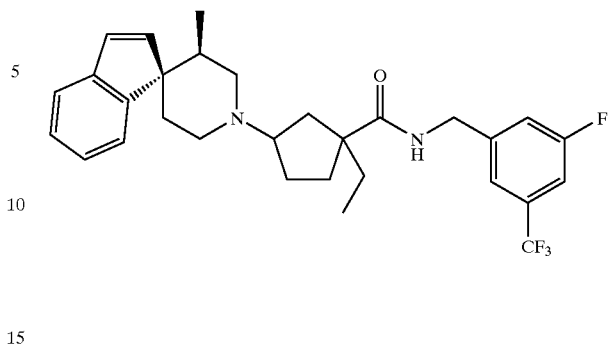

A mixture of the acid (Intermediate 4, 35.0 mg, 0.1 mmol), 3-trifluoromethyl-5-fluorobenzylamine (15 µL, 0.1 mmol), 1-hydroxy-7-azabenzotriazole (13.6 mg, 0.1 mmol) in dichloromethane (4 mL) was treated with 1-[3-(dimethylamino)propyl]-3-ethylcarbodiimide hydrochloride (EDC, 26 mg, 0.15 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 16 mg of crude product, which was purified by preparative TLC (eluent: 4% of methanol:ammonium hydroxide9:1 in dichloromethane) to yield 11.5 mg (64%) of pure product. Single enantiomers were obtained via chiral HPLC, using Diacel's Chiralcel OD semipreparative column, eluent hexane/ethanol (98:2). The observed retention times of the respective diastereoisomers on an identical analytical (250×4.6 mm, 1.0 mL/min) column were 9.25 and 15.7 minutes, respectively. LC-MS for $C_{30}H_{35}F_4N_2O$ [M+H]$^+$ calculated 515.26, found 515.35.

EXAMPLE 27

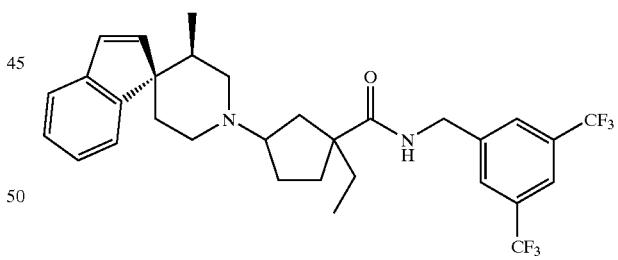

The title compound was prepared using a synthetic sequence analogous to that described in Example 26 except that 3,5-bistrifluoromethylbenzylamine was used instead of 3-fluoro-5-trifluoromethylbenzylamine. Single enantiomers were obtained via chiral HPLC, using Diacel's Chiralcel OD semipreparative column, eluent hexane/ethanol (97:3). The observed retention times of the respective diastereoisomers on an identical analytical (250×4.6 mm, 1.0 mL/min) column were 8.12 and 15.3 minutes, respectively. LC-MS for $C_{31}H_{35}F_6N_2O$ [M+H]$^+$ calculated 564.26, found 565.30.

EXAMPLE 28

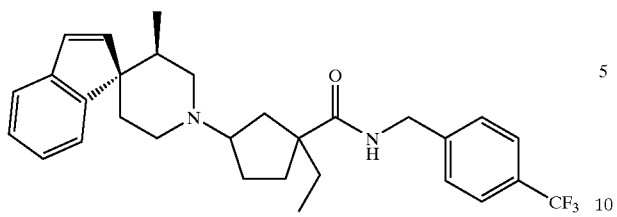

The title compound was prepared in a form of a pure cis-diastereoisomer using a synthetic sequence analogous to that described in Example 26 except that 4-trifluoromethylbenzylamine was used instead of 3-fluoro-5-trifluoromethylbenzylamine. LC-MS for $C_{30}H_{36}F_3N_2O$ $[M+H]^+$ calculated 497.77, found 497.30.

EXAMPLE 29

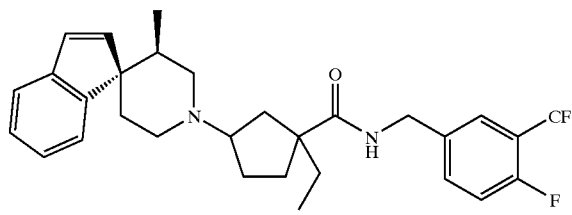

The title compound was prepared in a form of a pure cis-diastereoisomer using a synthetic sequence analogous to that described in Example 26 except that 4-fluoro-3-(trifluoromethyl)benzylamine was used instead of 3-fluoro-5-trifluoromethylbenzylamine. LC-MS for $C_{30}H_{35}F_4N_2O$ $[M+H]^+$ calculated 515.26, found 515.20.

EXAMPLE 30

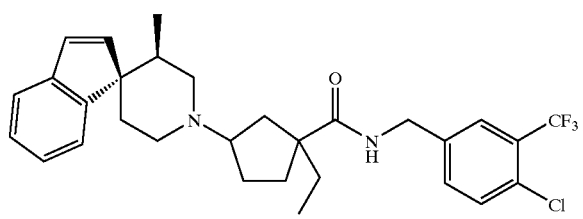

The title compound was prepared in a form of a pure cis-diastereoisomer using a synthetic sequence analogous to that described in Example 26 except that 4-chloro-3-(trifluoromethyl)benzylamine was used instead of 3-fluoro-5-trifluoromethylbenzylamine. LC-MS for $C_{30}H_{35}ClF_3N_2O$ $[M+H]^+$ calculated 531.23, found 531.25.

INTERMEDIATE 5

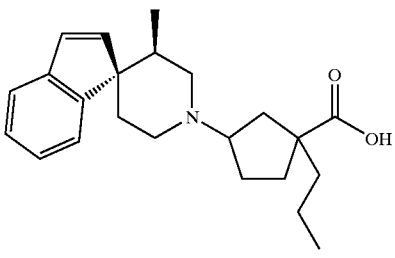

Step A

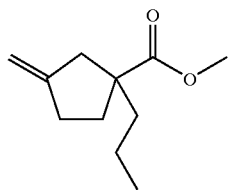

A solution of diisopropylamine (650 μL, 4.64 mmol) in THF (15 mL) was cooled to −78° C. and treated with butyl lithium (1.86 mL of 2.5M solution in hexanes, 4.64 mmol). After stirring at −78° C. for 15 minutes, the neat methyl 3-methylenecyclopentane carboxylate (Trost, B. M., Chan, M. T., *J.Am.Chem.Soc.*, 1983, 105, 2315) (500 μL, (=575 mg) 4.104 mmol) was added via syringe, and the reaction mixture was stirred at −78° C. for 2 hrs. Neat 1-bromopropane (972 μL, 10.70 mmol) was added via syringe, the reaction mixture was stirred at −78° C. for 1 hour, and allowed to stand at +5° C. overnight. The reaction was quenched by pouring onto an aqueous solution of citric acid (10%, 50 mL), and the product was extracted into diethyl ether (6×30 mL). The combined organic extracts were dried with magnesium sulfate, and the solvent was evaporated in vacuo (150 torr). The volatile crude product (773 mg, 100%) was used in the subsequent reaction step as obtained.

Step B

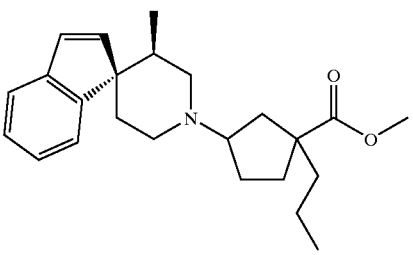

A solution of methyl 3-methylene-1-propylcyclopentane carboxylate (712 mg, 3.906 mmol) in dichloromethane (60 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added 3-methyl-4-spiroindenylpiperidine hydrochloride (Intermediate 1, 828 mg, 3.51 mmol), diisopropylethylamine (611 μL, 3.51 mmol), crushed 4 Å molecular sieves (1.0 g) and the resulting mixture was treated with sodium triacetoxyborohydride (2.48 g, 11.72 mmol). After stirring at ambient temperature for 24 hours, the sieves were filtered off, the filtrate was washed with a saturated solution of sodium bicarbonate (1×50 mL), water (3×50 mL) and brine (1×50 mL). After drying (anhydrous sodium sulfate) the solvent was evaporated to dryness under reduced pressure to leave 1.3081 g (91%) of crude product, in a form of a cis-/trans- diastereoisomeric mixture. The approximate ratio of the respective diastereoisomers was 1:1. It was used in the subsequent reaction step without any further purification. LC-MS for $C_{24}H_{34}NO_2$ $[M+H]^+$ calculated 367.25, found 367.30.

Step C

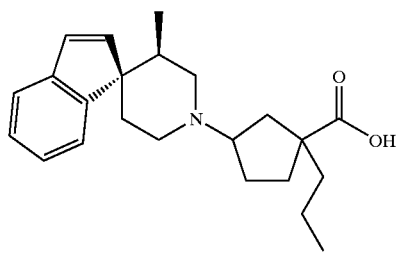

A mixture of the ester from the previous step (1.3081 g, 3.559 mmol) and 50% aqueous sodium hydroxide (20 mL) was homogenized with ethanol and stirred at 60° C. for 0.5 hours. The solvents were evaporated under reduced pressure, the residue was dissolved in water (50 mL). The pH was set with 2N HCl to neutral, and the amino acid was extracted with chloroform (6×100 mL). The combined organic phases were dried with anhydrous sodium sulfate, and the solvent was evaporated in vacuo. The remaining mixture of the cis- and trans-diastereoisomeric acids (738 mg) was further purified by preparative TLC (dichloromethane:methanol/90:10) to yield 254.4 mg (20%) of the pure cis-diastereoisomer. LC-MS for $C_{23}H_{32}NO_2$ $[M+H]^+$ calculated 354.24, found 354.25.

EXAMPLE 31

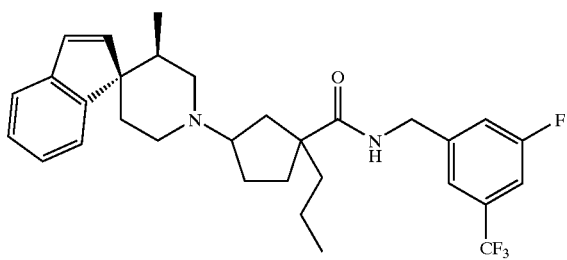

A mixture of the acid (Intermediate 5, 35.4 mg, 0.1 mmol), 5-fluoro-3-trifluoromethylbenzylamine (15 µL, 0.1 mmol), 1-hydroxy-7-azabenzotriazole (13.6 mg, 0.1 mmol) in dichloromethane (4 mL) was treated with 1-[3-(dimethylamino)-propyl]-3-ethylcarbodiimide hydrochloride (EDC, 29 mg, 0.15 mmol) and stirred at r.t. overnight. The reaction mixture was diluted with dichioromethane (4 mL), washed with water (3×3 mL), brine (1×3 mL), dried over anhydrous sodium sulfate and the solvent was evaporated under reduced pressure to yield 67.1 mg of crude product, which was purified by preparative TLC (eluent: 100% ethyl acetate) to yield 27.8 mg (52%) of pure product as the cis-diastereoisomeric pair. LC-MS for $C_{31}H_{37}F_4N_2$ $[M+H]^+$ calculated 529.28, found 529.30.

INTEMEDIATE 6

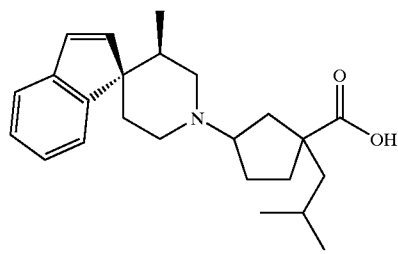

Step A
Methyl 3-methylene-1-isobutyl-cyclopentanecarboxylate

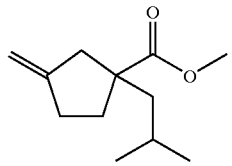

A solution of diisopropylamine (5.30 mL, 37.6 mmol) in THF (15 mL) was cooled to −78° C. and n-butyl lithium (15 mL of 2.5 M solution in hexanes, 37.6 mmol) was added via syringe. After stirring at −78° C. for 15 minutes, methyl 3-methylene cyclopentane carboxylate (4.00 mL, 32.7 mmol) was added, dropwise. The solution was stirred at −78° C. for an additional hour, and 2-methyl-1-bromopropane (7.12 mL, 75.2 mmol) was added, via syringe. The resulting reaction mixture was stirred at −78° C. for an additional hour, and than it was kept at +5° C. for 24 hours. The reaction was quenched by pouring it onto 10% solution of citric acid and extracted with hexane (3×50 mL). The combined organic extracts were washed with water and brine, dried (anhydrous magnesium sulfate) and the solvent was evaporated to dryness. The remaining oil (6.71 g) was further purified by distillation (B.P.: 105–108 at 15 torr) to yield 3.9211 g (61%) of the pure product. $^1$H NMR (CDCl$_3$, 500 MHz): 4.88 (bs, 1H), 4.81 (bs, 1H), 3.67 (s, 3H), 2.85 (bd, J=16.25 Hz, 1H), 2.34 (m, 2H), 2.22 (m, 2H), 1.50 (m, 4H), 0.86 (bd, J=6.0 Hz, 6H). $^{13}$C NMR (CDCl$_3$, 500 MHz): 177.73, 150.24, 106.12, 53.48, 51.61, 46.79, 43.41, 35.96, 30.62, 25.90, 23.52, 23.42.

Step B

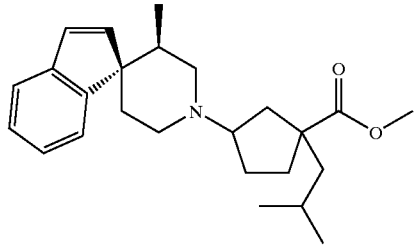

A solution of methyl 3-methylene-1-isobutylcyclopentane carboxylate (400 µL, 2.12 mmol) in dichloromethane (60 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added 3-methyl-4-spiroindenylpiperidine hydrochloride (Intermediate 1, 500 mg, 2.12 mmol), diisopropylethylamine (314 µL, 2.12 mmol), crushed 4 A molecular sieves (1.4 g) and the resulting mixture was treated with sodium triacetoxyborohydride (1.36 g, 6.39 mmol). After stirring at ambient temperature for 24 hours, the sieves were filtered off, the filtrate was washed with a saturated solution of sodium bicarbonate (1×50 mL), water (3×50 mL) and brine (1×50 mL). After drying (anhydrous sodium sulfate) the solvent was evaporated to dryness under reduced pressure to leave 800 mg of crude product, which was further purified by preparative TLC (eluent 100% ethyl acetate) to yield 360 mg (44%) of pure product in a form of a cis-/trans-diastereoisomeric mixture in an approximate ratio of 1:1. It was used in the subsequent reaction step without any further purification. LC-MS for $C_{25}H_{36}NO_2$ $[M+H]^+$ calculated 382.27, found 382.05.

Step C

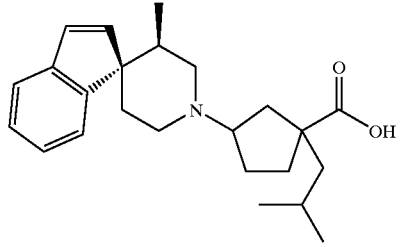

A solution of the ester from the previous step (360 mg, 0.944 mmol) in dioxane (4 mL) and water (4 mL) mixture containing lithium hydroxide monohydrate (165 mg, 3.915 mmol) was homogenized with methanol and stirred at 80° C. for 8 hours. The solvents were evaporated under reduced pressure, the residue was dissolved in water (10 mL). The pH was set with 2N HCl to neutral, and the amino acid was extracted with chloroform (6×50 mL). The combined organic phases were dried with anhydrous sodium sulfate, and the solvent was evaporated in vacuo to yield 342.4 mg of the desired product as a mixture of the cis- and trans-diastereoisomeric acids in a approximate ratio of 4:1. LC-MS for $C_{24}H_{34}NO_2$ $[M+H]^+$ calculated 368.25, found 368.20.

EXAMPLE 32

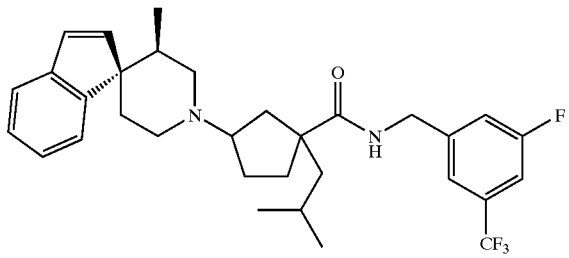

A mixture of the acid (Intermediate 6, 37.0 mg, 0.1 mmol), 3-fluoro-5-trifluoromethylbenzylamine (15 µL, 0.1 mmol), 1-hydroxy-7-azabenzotriazole (13.6 mg, 0.1 mmol) in dichloromethane (4 mL) was treated with 1-[3-(dimethylamino)-propyl]-3-ethylcarbodiimide hydrochloride (EDC, 26 mg, 0.15 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 52.7 mg of crude product, which was purified by preparative TLC (eluent: 100% ethyl acetate) to yield 28.3 mg (52%) of pure product. The single enantiomers were obtained via chiral HPLC, using Diacel's Chiralcel OD semipreparative column, eluent hexane/ethanol (98:2). The observed retention times (area %) of the respective diastereoisomers on an identical analytical (250×4.6 mm, 1.0 mL/min) column were 6.9 (40%), 7.5 (40 %), 12.4 (9%) and 16.9 minutes (7%), respectively. LC-MS for $C_{32}H_{39}F_4N_2O$ $[M+H]^+$ calculated 543.29, found 543.30.

EXAMPLE 33

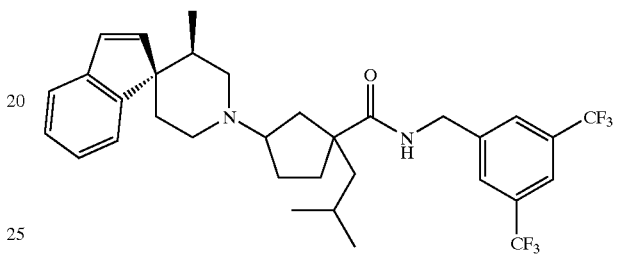

The title compound was prepared using a synthetic sequence analogous to that described in Example 32 except that 3,5-bis-trifluoromethylbenzylamine was used instead of 3-fluoro-5-trifluoromethylbenzylamine. The single enantiomers were obtained via chiral HPLC, using Diacel's Chiralcel OD semipreparative column, eluent hexane/ethanol (98:2). The observed retention times of the respective diastereoisomers on an identical analytical (250×4.6 mm, 1.0 mL/min) column were 6.4 (42%), 7.3 (42%), 9.7 (7%) and 12.2 minutes (8%), respectively. LC-MS for $C_{33}H_{38}F_6N_2O$ $[M+H]^+$ calculated 593.29, found 593.30.

INTERMEDIATE 7

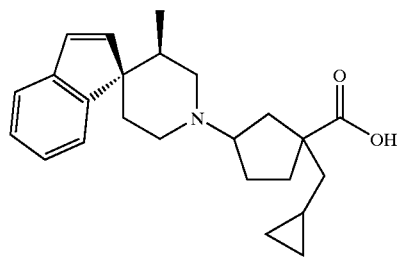

Step A

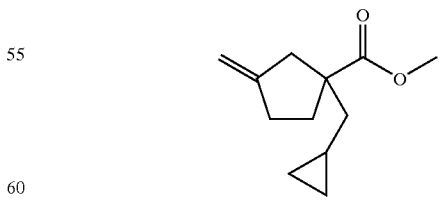

A solution of diisopropylamine (662 µL, 4.72 mmol) in THF (10 mL) was cooled to −78° C. and treated with butyl lithium (1.89 mL of 2.5M solution in hexanes, 4.72 mmol). After stirring at −78° C. for 15 minutes, the neat methyl 3-methylenecyclopentane carboxylate (Trost, B. M., Chan, M. T., *J.Am.Chem.Soc.*, 1983, 105, 2315) (500 μL, 4.104 mmol) was added via syringe, and the reaction mixture was stirred at −78° C. for 2 hrs. Neat cyclopropylmethyl bromide (1.20 mL, 12.312 mmol) was added via syringe, the reaction mixture was stirred at −78° C. for 1 hour, and allowed to stand at +5° C. overnight. The reaction was quenched by pouring onto an aqueous solution of citric acid (10%, 50 mL), and the product was extracted into diethyl ether (6×30 mL). The combined organic extracts were dried with magnesium sulfate, and the solvent was evaporated in vacuo (150 torr). The volatile crude product (771 mg, 97%) was used in the subsequent reaction step as obtained.

Step B

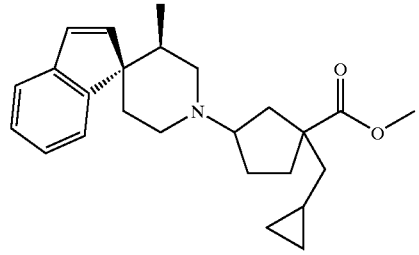

A solution of methyl 3-methylene-1-cyclopropylcyclopentane carboxylate (771 μL, 3.96 mmol) in dichloromethane (60 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added 3-methyl-4-spiroindenylpiperidine hydrochloride (Intermediate 1, 840 mg, 3.56 mmol), diisopropylethylamine (620 μL, 3.56 mmol), crushed 4 A molecular sieves (1.4 g) and the resulting mixture was treated with sodium triacetoxyborohydride (2.52 g, 10.68 mmol). After stirring at ambient temperature for 24 hours, the sieves were filtered off, the filtrate was washed with saturated solution of sodium bicarbonate (1×50 mL), water (3×50 mL) and brine (1×50 mL). After drying (anhydrous sodium sulfate) the solvent was evaporated to dryness under reduced pressure to leave 1.27 g of crude cis-/trans-diastereoisomeric mixture in an approximate ratio of 2:1. It was used in the subsequent reaction step without any further purification. LC-MS for $C_{25}H_{34}NO_2$ [M+H]$^+$ calculated 380.25, found 380.20.

Step C

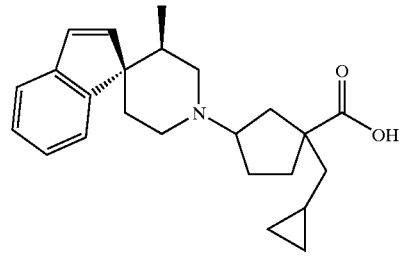

A mixture of the ester from the previous step (1.27 g, 3.3462 mmol) and 50% aqueous sodium hydroxide (20 mL) was homogenized with ethanol and stirred at 60° C. for 0.5 hours. The solvents were evaporated under reduced pressure, the residue was dissolved in water (50 mL). The pH was set with 2N HCl to neutral, and the amino acid was extracted with chloroform (6×100 mL). The combined organic phases were dried with anhydrous sodium sulfate, and the solvent was evaporated in vacuo. The remaining mixture of the cis- and trans-diastereoisomeric acids (653 mg) was further purified by preparative TLC (dichloromethane:methanol/90:10) to yield 256.1 mg (21%) of the pure cis-diastereoisomer. LC-MS for $C_{24}H_{32}NO_2$ [M+H]$^+$ calculated 366.24, found 366.25.

EXAMPLE 34

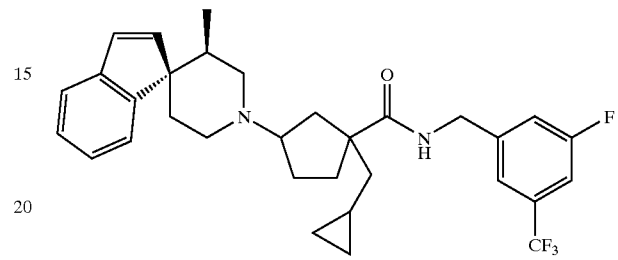

A mixture of the acid (Intermediate 7, 37.0 mg, 0.1 mmol), 3-fluoro-5-trifluoromethylbenzylamine (15 μL, 0.1 mmol), 1-hydroxy-7-azabenzotriazole (13.6 mg, 0.1 mmol) in dichloromethane (4 mL) was treated with 1-[3-(dimethylamino)-propyl]-3-ethylcarbodiimide hydrochloride (EDC, 26 mg, 0.15 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 55.7 mg of crude product, which was purified by preparative TLC (eluent: 100% ethyl acetate) to yield 28.3 mg (52%) of pure cis-diastereoisomer pair. LC-MS for $C_{32}H_{36}F_4N_2$ [M+H]$^+$ calculated 541.28, found 541.30.

INTERMEDIATE 8

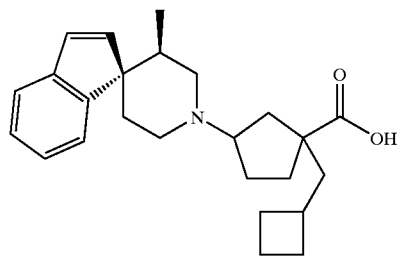

Step A

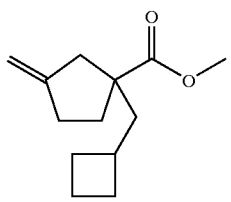

A solution of diisopropylamine (530 μL, 3.76 mmol) in THF (15 mL) was cooled to −78° C. and treated with butyl lithium (1.50 mL of 2.5M solution in hexanes, 3.76 mmol). After stirring at −78° C. for 15 minutes, the neat methyl 3-methylenecyclopentane carboxylate (Trost, B. M., Chan, M. T., *J.Am.Chem.Soc.*, 1983, 105, 2315) (400 μL, 3.27 mmol) was added via syringe, and the reaction mixture was stirred at −78° C. for 2 hrs. Neat cyclobutylmethyl bromide (1.10 mL, 9.81 mmol) was added via syringe, the reaction mixture was stirred at −78° C. for 1 hour, and allowed to stand at +5° C. overnight. The reaction was quenched by pouring onto an aqueous solution of citric acid (10%, 50 mL), and the product was extracted into diethyl ether (6×30 mL). The combined organic extracts were dried with magnesium sulfate, and the solvent was evaporated in vacuo (150 torr). The volatile crude product (477 mg, 70%) was used in the subsequent reaction step as obtained.

Step B

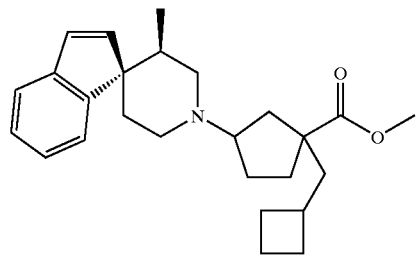

A solution of methyl 3-methylene-1-cyclobutylmethylcyclopentane carboxylate (434 mg, 2.085 mmol) in dichloromethane (60 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added 3-methyl-4-spiroindenylpiperidine hydrochloride (Intermediate 1, 492 mg, 2.085 mmol), diisopropylethylamine (363 µL, 2.085 mmol), crushed 4 A molecular sieves (1.76 g) and the resulting mixture was treated with sodium triacetoxyborohydride (1.33 g, 6.255 mmol). After stirring at ambient temperature for 24 hours, the sieves were filtered off, the filtrate was washed with a saturated solution of sodium bicarbonate (1×50 mL), water (3×50 mL) and brine (1×50 mL). After drying (anhydrous sodium sulfate) the solvent was evaporated to dryness under reduced pressure to leave 727 mg of crude product. It was further purified by preparative TLC (eluent: 100% ethyl acetate) to yield 469 mg (57%) of cis-/trans-diastereoisomeric mixture. LC-MS for $C_{26}H_{36}NO_2$ [M+H]$^+$ calculated 394.27, found 394.20.

Step C

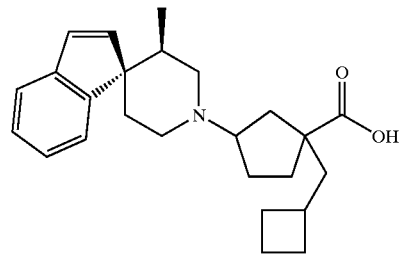

A mixture of the ester from the previous step (469 mg, 31.19 mmol) and lithium hydroxide monohydrate (200 mg, 4.765 mmol) in dioxane (4 mL) and water (4 mL) was homogenized with methanol and heated to 80° C. for 4 hours. The solvents were evaporated under reduced pressure, the residue was dissolved in water (50 mL). The pH was set with 2N HCl to neutral, and the amino acid was extracted with chloroform (6×100 mL). The combined organic phases were dried with anhydrous sodium sulfate, and the solvent was evaporated in vacuo. The remaining mixture of the cis- and trans-diastereoisomeric acids (374 mg, 83%) was used in the subsequent step without any further purification. LC-MS for $C_{25}H_{34}NO_2$ [M+H]$^+$ calculated 380.25, found 380.20.

EXAMPLE 35

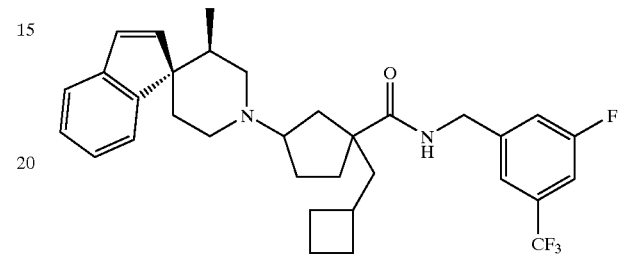

A mixture of the acid (Intermediate 8, 38.0 mg, 0.1 mmol), 3-fluoro-5-trifluoromethylbenzylamine (15 µL, 0.1 mmol), 1-hydroxy-7-azabenzotriazole (13.6 mg, 0.1 mmol) in dichloromethane (8 mL) was treated with 1-[3-(dimethylamino)propyl]-3-ethylcarbodiimide hydrochloride (EDC, 26 mg, 0.15 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 55.7 mg of crude product, which was purified by preparative TLC (eluent: 100% ethyl acetate) to yield 30.3 mg (55%) as a mixture of isomers. The single enantiomers were obtained via chiral HPLC, using Diacel's Chiralcel OD semipreparative column, eluent hexane/ethanol (98:2). The observed retention times of the respective pure enantiomers on an identical analytical (250× 4.6 mm, 1.0 mL/min) column and the obtained amounts were 8.34 minutes (6.8 mg), 9.6 minutes (4.8 mg), 15.7 minutes (5.8 mg) and 22.5 minutes (2.4 mg), respectively. LC-MS for $C_{33}H_{38}F_6N_2O$ [M+H]$^+$ calculated 593.29, found 593.30. LC-MS for $C_{33}H_{39}F4N_2O$ [M+H]$^+$ calculated 555.29, found 555.25.

EXAMPLE 36

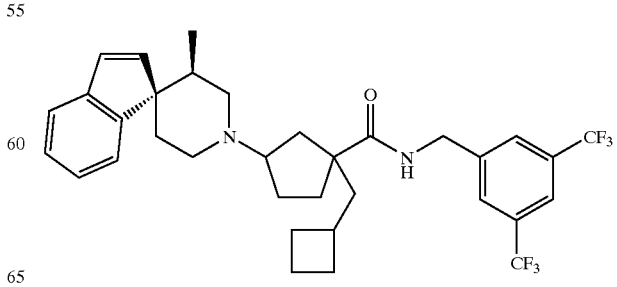

The title compound was prepared using a synthetic sequence analogous to that described in Example 35 except that 3,5-bis-trifluoromethylbenzylamine was used instead of 3-fluoro-5-trifluoromethylbenzylamine. Single enantiomers were obtained via chiral HPLC, using Diacel's Chiralcel OD semipreparative column, eluent hexane/ethanol (98:2). The observed retention times of the respective pure enantiomers on an identical analytical (250×4.6 mm, 1.0 mL/min) column and the obtained amounts were 6.26 minutes (6.2 mg), 8.30 minutes (6.8 mg), 9.95 minutes (6.8 mg) and 13.2 minutes (8.0 mg), respectively. LC-MS for $C_{34}H_{39}F_6N_2O$ $[M+H]^+$ calculated 605.29, found 605.35.

INTERMEDIATE 9

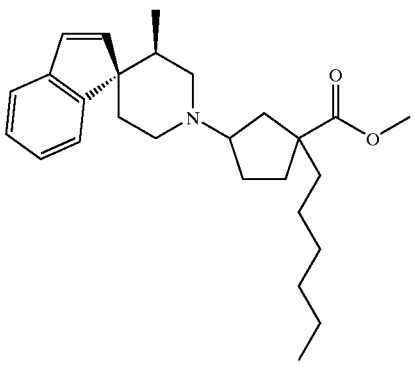

Step A

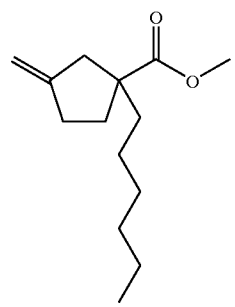

A solution of diisopropylamine (530 μL, 3.76 mmol) in THF (15 mL) was cooled to −78° C. and treated with butyl lithium (1.50 mL of 2.5M solution in hexanes, 3.76 mmol). After stirring at −78° C. for 15 minutes, the neat methyl 3-methylenecyclopentane carboxylate (Trost, B. M., Chan, M. T., *J.Am. Chem. Soc.*, 1983, 105, 2315) (400 μL, 3.27 mmol) was added via syringe, and the reaction mixture was stirred at −78° C. for 2 hrs. Neat 1-iodohexane (1.45 mL, 9.81 mmol) was added via syringe, the reaction mixture was stirred at −78° C. for 1 hour, and allowed to stand at +5° C. overnight. The reaction was quenched by pouring onto an aqueous solution of citric acid (10%, 50 mL), and the product was extracted into diethyl ether (6×30 mL). The combined organic extracts were dried with magnesium sulfate, and the solvent was evaporated in vacuo (150 torr). The volatile crude product (600.5 mg, 82%) was used in the subsequent reaction step as obtained.

Step B

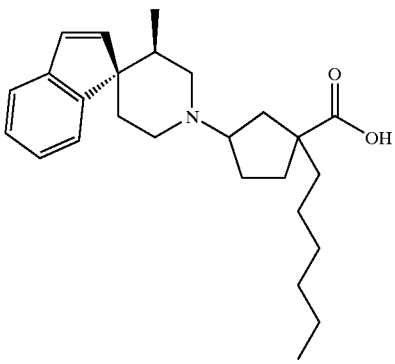

A solution of methyl 3-methylene-1-hexylcyclopentane carboxylate (600 mg, 2.674 mmol) in dichloromethane (60 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added 3-methyl-4-spiroindenylpiperidine hydrochloride (Intermediate 1, 630 mg, 2.674 mmol), diisopropylethylamine (466 μL, 2.674 mmol), crushed 4 Å molecular sieves (1.51 g) and the resulting mixture was treated with sodium triacetoxyborohydride (1.33 g, 6.255 mmol). After stirring at ambient temperature for 24 hours, the sieves were filtered off, the filtrate was washed with a saturated solution of sodium bicarbonate (1×50 mL), water (3×50 mL) and brine (1×50 mL). After drying (anhydrous sodium sulfate) the solvent was evaporated to dryness under reduced pressure to leave 872 g of crude product. It was further purified by preparative TLC (eluent: 100% ethyl acetate) to yield 493 mg (45%) of product as a cis-/trans-diastereoisomeric mixture. LC-MS for $C_{27}H_{40}NO_2$ $[M+H]^+$ calculated 410.60, found 410.40.

Step C

A mixture of the ester from the previous step (478 g, 1.16 mmol) and lithium hydroxide monohydrate (196 mg, 4.66 mmol) in dioxane (4 mL) and water (4 mL) was homogenized with methanol and heated to 80° C. for 4 hours. The solvents were evaporated under reduced pressure, the residue was dissolved in water (50 mL). The pH was set with 2N HCl to neutral, and the amino acid was extracted with chloroform (6×100 mL). The combined organic phases were dried with anhydrous sodium sulfate, and the solvent was evaporated in vacuo. The remaining mixture of the cis- and trans-diastereoisomeric acids (367 mg, 80%) was used in the subsequent step without any further purification. LC-MS for $C_{26}H_{38}NO_2$ [M+H]$^+$ calculated 396.28, found 396.25.

EXAMPLE 37

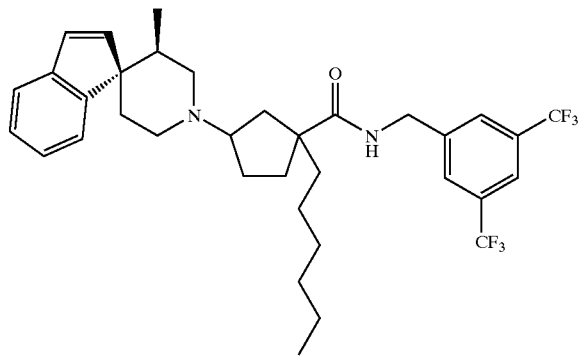

A mixture of the acid (Intermediate 9, 38.0 mg, 0.1 mmol), 3,5-bis(trifluoromethyl)benzylamine (24 mg, 0.1 mmol), 1-hydroxy-7-azabenzotriazole (13.6 mg, 0.1 mmol) in dichloromethane (8 mL) was treated with 1-[3-(dimethylamino)propyl]-3-ethylcarbodiimide hydrochloride (EDC, 26 mg, 0.15 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 55.7 mg of crude product, which was purified by preparative TLC (eluent: 100% ethyl acetate) to yield 52.7 mg (85%) of a mixture of isomers. The respective cis- and trans-diastereoisomeric pairs were obtained via chiral HPLC, using Diacel's Chiralcel OD semipreparative column, eluent hexane/ethanol (98:2). The observed retention times of the respective diastereoisomeric pairs on an identical analytical (250×4.6 mm, 1.0 mL/min) column and the obtained amounts were 6.20 minutes (14.6 mg), 11.5 minutes (16.5 mg), respectively. LC-MS for $C_{35}H_{43}F_6N_2O$ [M+H]$^+$ calculated 621.32, found 621.40.

EXAMPLE 38

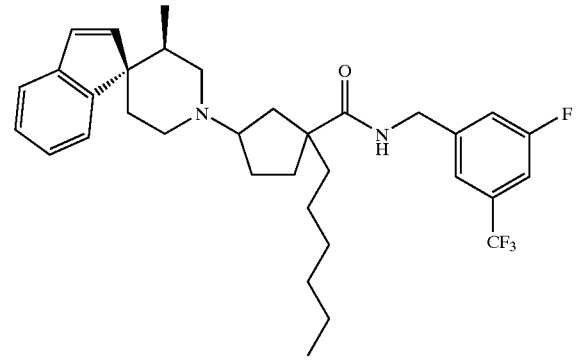

The title compound was prepared using a synthetic sequence analogous to that described in Example 37 except that 3-fluoro-5-trifluoromethylbenzylamine was used instead of 3,5-bis-trifluoromethylbenzylamine. The respective cis- and trans-diastereoisomeric pairs were obtained via chiral HPLC, using Diacel's Chiralcel OD semipreparative column, eluent hexane/ethanol (98:2). The observed retention times of the respective diastereoisomeric pairs on an identical analytical (250×4.6 mm, 1.0 mL/min) column were 8.50 and 11.5 minutes, respectively. LC-MS for $C_{34}H_{43}F_4N_2O$ [M+H]$^+$ calculated 571.32, found 571.30.

INTERMEDIATE 10

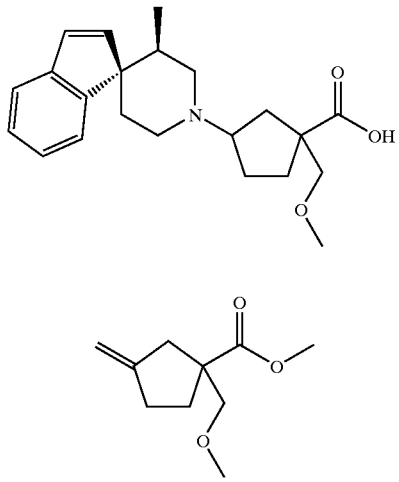

Step A

A solution of diisopropylamine (530 µL, 3.76 mmol) in THF (15 mL) was cooled to −78° C. and treated with butyl lithium (1.50 mL of 2.5M solution in hexanes, 3.76 mmol). After stirring at −78° C. for 15 minutes, the neat methyl 3-methylenecyclopentane carboxylate (Trost, B. M., Chan, M. T., *J.Am.Chem.Soc.*, 1983, 105, 2315) (400 µL, 3.27 mmol) was added via syringe, and the reaction mixture was stirred at −78° C. for 2 hrs. Neat methoxymethyl chloride (467 µL, 9.81 mmol) was added via syringe, the reaction mixture was stirred at −78° C. for 1 hour, and allowed to stand at +5° C. overnight. The reaction was quenched by pouring onto an aqueous solution of citric acid (10%, 50 mL), and the product was extracted into diethyl ether (6×30 mL). The combined organic extracts were dried with magnesium sulfate, and the solvent was evaporated in vacuo (150 torr). The volatile crude product (426 mg, 70%) was used in the subsequent reaction step as obtained.

Step B

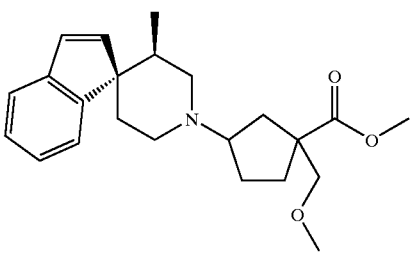

A solution of methyl 3-methylene-1-methoxymethylcyclopentane carboxylate (426 mg, 2.312 mmol) in dichloromethane (60 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added 3-methyl-4-spiroindenylpiperidine hydrochloride (Intermediate 1, 545 mg, 2.312 mmol), diisopropylethylamine (402 μL, 2.312 mmol), crushed 4 Å molecular sieves (1.76 g) and the resulting mixture was treated with sodium triacetoxyborohydride (1.47 g, 6.936 mmol). After stirring at ambient temperature for 24 hours, the sieves were filtered off, the filtrate was washed with a saturated solution of sodium bicarbonate (1×50 mL), water (3×50 mL) and brine (1×50 mL). After drying (anhydrous sodium sulfate) the solvent was evaporated to dryness under reduced pressure to leave 783 mg of crude product. It was further purified by preparative TLC (eluent: 100% ethyl acetate) to yield 315.8 mg (37%) of product as a cis-/trans-diastereoisomeric mixture. LC-MS for $C_{23}H_{32}NO_3$ [M+H]$^+$ calculated 370.23, found 370.15.

Step C

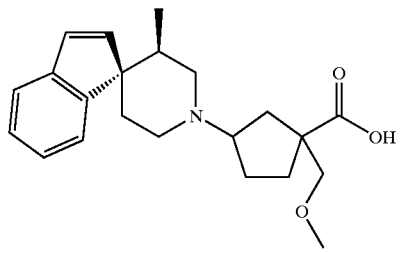

A mixture of the ester from the previous step (466 g, 1.2611 mmol) and lithium hydroxide monohydrate (511.7 mg, 5.044 mmol) in dioxane (4 mL) and water (4 mL) was homogenized with methanol and stirred at ambient temperature overnight. The solvents were evaporated under reduced pressure, the residue was dissolved in water (50 mL). The pH was set with 2N HCl to neutral, and the amino acid was extracted with chloroform (6×100 mL). The combined organic phases were dried with anhydrous sodium sulfate, and the solvent was evaporated in vacuo. The remaining mixture of the cis- and trans-diastereoisomeric acids (276 mg, 62%) was used in the subsequent step without any further purification. LC-MS for $C_{22}H_{30}NO_3$ [M+H]$^+$ calculated 356.21, found 356.05.

EXAMPLE 39

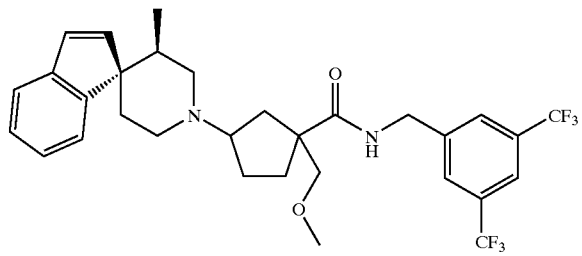

A mixture of the acid (Intermediate 10, 32.0 mg, 0.0903 mmol), 3,5-bistrifluoromethylbenzylamine (25 mg, 0.0903 mmol), 1-hydroxy-7-azabenzotriazole (13.6 mg, 0.1 mmol) in dichloromethane (8 mL) was treated with 1-[3-(dimethylamino)propyl]-3-ethylcarbodiimide hydrochloride (EDC, 24 mg, 0.135 mmol) and stirred at r.t. for 2 hours. The reaction mixture was diluted with dichloromethane (4 mL), washed with water (3×3 mL), brine (1×3 mL), dried over anhydrous sodium sulfate and the solvent was evaporated under reduced pressure to yield 42.7 mg of the desired product as a mixture of isomers. The respective cis- diastereoisomeric pair and the enantiomers of the trans- diastereoisomeric pair were obtained via chiral HPLC, using Diacel's Chiralcel OD semipreparative column, eluent hexane/ethanol (98:2). The observed retention times of the respective diastereoisomeric pairs on an identical analytical (250×4.6 mm, 1.0 mL/min) column and the obtained amounts were 11.9 minutes (14.4 mg, the cis-diastereoisomeric pair), 13.8 minutes (9.2 mg, single enantiomer, trans diastereoisomeric pair) and 23.2 minutes (3.4 mg, single enantiomer, trans diastereoisomeric pair) respectively. LC-MS for $C_{31}H_{35}F_6N_2O_2$ [M+H]$^+$ calculated 581.25, found 581.35.

EXAMPLE 40

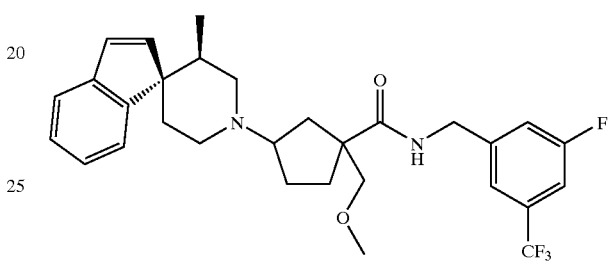

The title compound was prepared using a synthetic sequence analogous to that described in Example 39 except that 3-fluoro-5-trifluoromethylbenzylamine was used instead of 3,5-bistrifluoromethylbenzylamine. The respective cis- and trans-diastereoisomeric pairs were obtained via chiral HPLC, using Diacel's Chiralcel OD semipreparative column, eluent hexane/ethanol (98:2). The observed retention times of the respective diastereoisomeric pairs on an identical analytical (250×4.6 mm, 1.0 mL/min) column were 19.0 and 29.5 minutes, respectively. LC-MS for $C_{30}H_{35}F_4N_2O_2$ [M+H]$^+$ calculated 531.26, found 531.25.

EXAMPLE 41

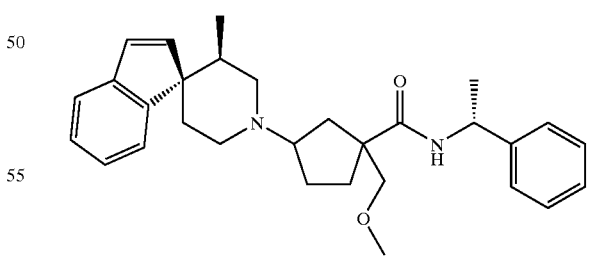

The title compound was prepared using a synthetic sequence analogous to that described in Example 39 except that α-(R)-methylbenzylamine was used instead of 3,5-bistrifluoromethylbenzylamine. LC-MS for $C_{30}H_{39}N_2O_2$ [M+H]$^+$ calculated 459.29, found 459.25.

INTERMEDIATE 11

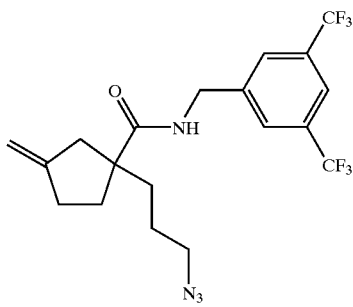

Step A
Methyl 3-methylene-1-(3-bromopropan-1-yl)cyclopentane carboxylate

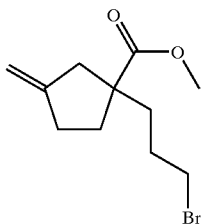

A solution of diisopropylamine (662 μL, 4.72 mmol) in THF (10 mL) was cooled to −78° C. and treated with butyl lithium (1.88 mL of 2.5M solution in hexanes, 4.72mmol). After stirring at −78° C. for 15 minutes, the neat methyl 3-methylenecyclopentane carboxylate (Trost, B. M., Chan, M. T., J.Am.Chem.Soc., 1983, 105, 2315) (500 μL, 4.102 mmol) was added via syringe, and the reaction mixture was stirred at −78° C. for 2 hrs. Neat 1,3-dibromopropane (1.25 mL, 12.31 mmol) was added via syringe, the reaction mixture was stirred at −78° C. for 1 hour, and allowed to stand at +5° C. overnight. The reaction was quenched by pouring onto an aqueous solution of citric acid (10%, 50 mL), and the product was extracted into diethyl ether (6×30 mL). The combined organic extracts were dried with magnesium sulfate, and the solvent was evaporated in vacuo (150 torr). The volatile crude product (1.96 g) was used in the subsequent reaction step as obtained.

Step B
Methyl 3-methylene-1-(3-azidopropan-1-yl)cyclopentane carboxylate

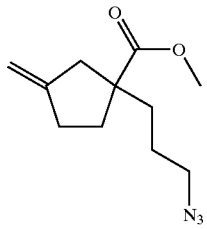

A solution of methyl 3-methylene-1-(3-bromopropan-1-yl)cyclo-pentane carboxylate (1.8 g, from the previous step, max. 4.102 mmol) and sodium azide (2.66 g, 41.02 mmol) in dimethylformamide (10 mL) was heated with stirring to 60° C. for 30 minutes. The reaction mixture was allowed to cool to ambient temperature and diluted with diethyl ether (100 mL). The DMF was washed out with water (5×100 mL), the organic phase was dried with magnesium sulfate and the solvent was removed in vacuo to yield 1.04 g of a mobile oil. It was used in the subsequent step without any further purification.

Step C

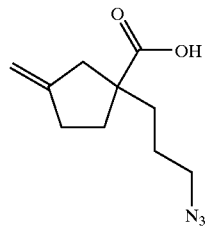

A solution of methyl 3-methylene-1-(3-azidopropan-1-yl) cyclopentane carboxylate (1.04 g, max 4.102 mmol) in dioxane (4 mL) and water (4 mL) containing lithium hydroxide monohydrate (688 mg, 16.41 mmol) was heated to 85° C. for 75 minutes. The solvents were evaporated in vacuo and the residue was dissolved in water (10 mL). The pH was adjusted with 2N HCl to acidic and the product was extracted with diethyl ether (6×50 mL). The combined organic extracts were dried (anhydrous magnesium sulfate) and evaporation of the solvent in vacuo gave 546 mg of the crude acid. This was used in the subsequent step without further purification.

Step D

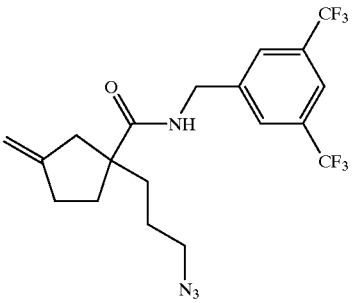

A mixture of the crude acid (546 mg, 2.61 mmol), 3,5-bistrifluoro-methyl-benzylamine hydrochloride (720 mg, 2.61 mmol), diisopropylethylamine (455 μL, 2.61 mmol), 1-hydroxy-7-azabenzotriazole (355 mg, 2.61 mmol) in dichloromethane (20 mL) was treated with 1-[3-(dimethylamino)propyl]-3-ethylcarbodiimide hydrochloride (EDC, 750 g, 3.92 mmol) and stirred at r.t. overnight. The reaction mixture was diluted with dichloromethane (20 mL), washed with water (3×30 mL), brine (1×30 mL), dried over anhydrous sodium sulfate and the solvent was evaporated under reduced pressure to yield 887 mg of the desired product which was further purified by column chromatography (silica gel, ethyl acetate:hexanes (1:3) to 479 mg (42%) of the pure desired product. $^1$H NMR (500 MHz, CDCl$_3$): 7.79 (s, 1H), 7.71 (s, 2H), 6.25 (bt, J=5.49 Hz, 1H), 5.0 (bs, 1H), 4.93 (bs, 1H), 4.62 (dd, J=15.56, 6.18 Hz, 1H), 4.54 (dd, 15.56, 5.95 Hz, 1H), 3.27 (m, 2H), 2.75 (bd, J=16.24 Hz, 1H), 2.50–2.33 (bm, 3H), 2.16 (m, 1H), 1.84 (m, 1H), 1.72 (m, 1H), 1.65–1.50 (bm, 3H). LC-MS for $C_{19}H_{21}F_6N_4O$ [M+H]$^+$ calculated 435.15, found 435.10.

EXAMPLE 42

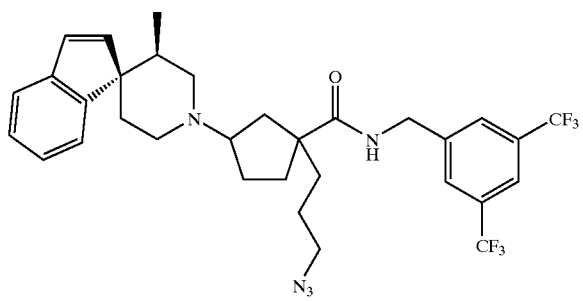

A solution of the olefin 3,5-bis(trifluoromethyl)benzyl 3-methylene-1-(3-azidopropan-1-yl)cyclopentane-carboxamide (Intermediate 11, 470 mg, 1.082 mmol) in dichloromethane (20 mL) was ozonized at −78° C. The excess ozone was removed with a stream of nitrogen. Intermediate 1 (255 mg, 1.082 mmol), diisopropylethylamine (190 μL, 1.082 mmol) and 1.0 g of molecular sieves (4A, crushed) were added, followed by sodium triacetoxyborohydride (690 mg, 3.25 mmol). The reaction mixture was stirred at room temperature for 48 hrs after which it was diluted with dichloromethane (50 mL). The sieves were filtered off (Celite), the filtrate was washed with a saturated solution of sodium bicarbonate (1×50 mL), water (2×50 mL) and brine (1×50 mL). After drying (anh. sodium sulfate), the solvent was evaporatd under reduced pressure, and the residue (587.7 mg) was further purified by preparative thin layer chromatography (Analtech, Silica Gel GF, 1000μ, 100% ethyl acetate) to yield 313 mg (47%) of the desired product as a mixture of cis- and trans diastereoisomeric pairs. This mixture was separated into the respective cis-enantiomers and the trans diastereoisomeric pair using Diacel's Chiralcel OD chiral preparative HPLC column, eluent hexane:ethanol (97:3) at flowrate of 9 mL/min. The retention times of the individual isomers (analytical 250×4.6 mm column, 1.0 mL/min) were 8.06 min (54%, cis-pair), 11.30 (23%, trans-enantiomer), 18.03 (23%, trans-enantiomer). LC-MS for $C_{32}H_{36}F_6N_5O$ [M+H]$^+$ calculated 620.27, found 620.30.

EXAMPLE 43

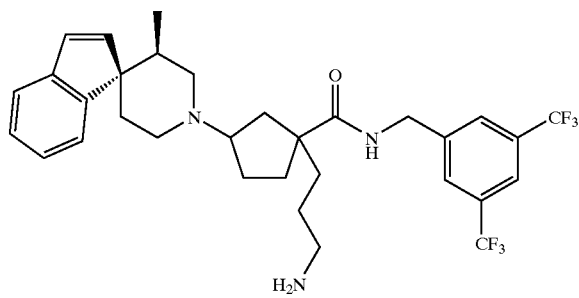

A solution of the fastest eluting diastereoisomeric pair of the azide from Example 42 (133 mg, 0.2146 mmol) in THF (4 ml) containing 40 μL of water was treated with triphenylphosphine (85 mg, 0.322 mmol) and stirred at ambient temperature for 5 days. The solvent was removed under reduced pressure and the residue was diluted with water (10 mL). The pH was set acidic with 2N HCl, and the non-basic compounds were extracted into hexane:ether (4:1). The aqueous phase was basified (5N NaOH) and the amine was extracted into dichloromethane (5×50 mL). The combined organic extracts were dried with anhydrous sodium sulfate and the solvent was evaporated in vacuo to yield 95.3 mg (75%) of the pure cis-diastereoisomeric product. LC-MS for $C_{32}H_{38}F_6N_3O$ [M+H]$^+$ calculated 594.28, found 594.25.

EXAMPLE 44

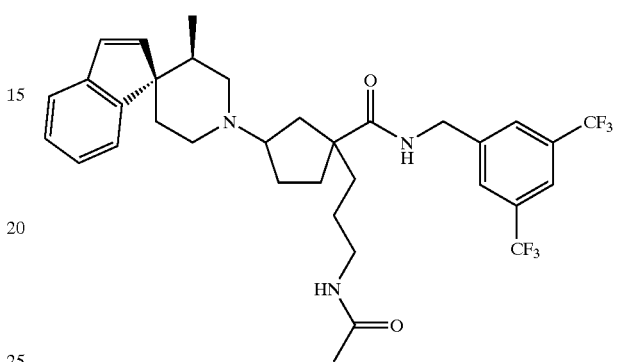

A solution of the amine hydrochoride from Example 43 (14.0 mg, 0.0237 mmol) and diisopropylethylamine (12.3 μL, 0.071 mmol) in dichioromethane (2 mL) was treated with acetic anhydride (4.7 μL, 0.05 mmol) and stirred at ambient temperature for 10 minutes. The reaction mixture was diluted with dichloromethane (8 mL), washed with water (2×4 mL), dried with anhydrous sodium sulfate and concentrated in vacuo. The pure cis-diastereoisomeric product (14.2 mg, 94%) was obtained in a form of a viscous oil. LC-MS for $C_{34}H_{40}F_6N_3O_2$ [M+H]$^+$ calculated 636.29, found 636.40.

EXAMPLE 45

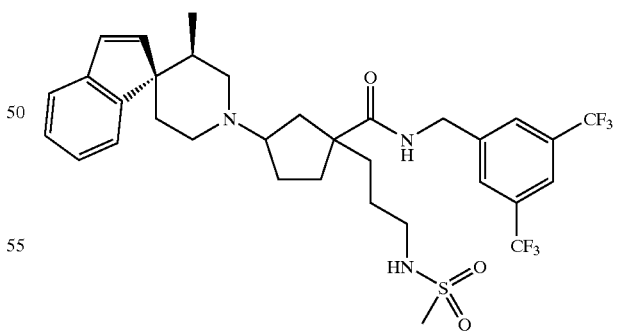

The title compound was synthesized in the form of the cis-diastereoisomeric product following the procedure described in Example 44, except that methanesulfonyl chloride was used instead of acetic anhydride. LC-MS for $C_{33}H_{40}F_6N_3O_3S$ [M+H]$^+$ calculated 672.26, found 672.25.

INTERMEDIATE 12

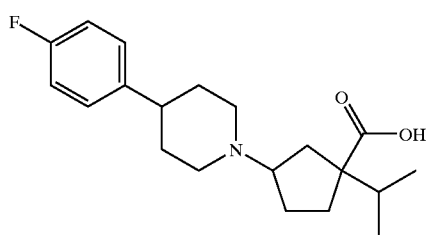

Step A

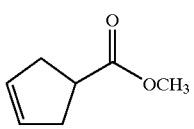

To a solution of 3-cyclopentene-1-carboxylic acid (Org. Synth. 75, p195–200, 1998) (31.5 g, 281 mmol) in anhydrous N,N-dimethylformamide (300 mL), under an atmosphere of nitrogen, was added potassium carbonate (97 g, 703 mmol), and iodomethane (35 mL, 563 mmol). The resulting mixture was stirred at room temperature for 16 hours, then poured into water (1 litre), and extracted with diethyl ether (3×400 mL). The combined diethyl ether layers were washed with water (3×500 mL), saturated NaCl (200 mL), dried over MgSO$_4$, filtered and concentrated in vacuo, to give 34 g (96%) of crude product. H NMR (CDCl$_3$, 500 MHz): δ 5.64 (s, 2H), 3.68 (s, 3H), 3.11 (quintet, J=8.5 Hz, 1H), 2.63 (d, J=8.3 Hz, 4 H).

Step B

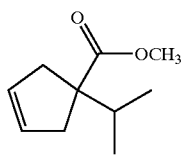

To a cooled (−78° C.) solution of diisopropylamine (34.4 mL, 0.25 Mol) in anhydrous tetrahydrofuran (250 mL) under an atmosphere of nitrogen was slowly added butyl lithium (100 mL of a 2.5M solution in hexanes, 0.25 Mol), and the resulting mixture stirred at −78° C. for 10 min. To this mixture was added methyl-3-cyclopentenecarboxylate (25.75 g, 0.2 Mol), after stirring for a further 15 min 2-iodopropane (41 mL, 0.409 Mol) was added, and the mixture continued stirring at −78° C. for 30 min then allowed to rise to +4° C. and left standing at this temperaturefor 72 hours. The reaction mixture was poured into 5% citric acid (700 mL) solution and extracted with diethyl ether (3×300 mL). The combined diethyl ether layers were washed with water (2×500 mL), saturated NaCl (1×100ml), dried over MgSO$_4$, filtered and concentrated in vacuo. The residue was purified by vacuum distillation 50° C. @ 5 mm Hg to provide 28.9 g (86%) of product. H NMR (CDCl$_3$, 500 MHz): δ 5.54 (s, 2H), 3.67 (s, 3H), 2.85 (d, J=15.1 Hz, 2H), 2.30 (dd, J=14.9Hz 2H), 2.07 (quintet, J=6.6 Hz, 1H), 0.82 (d, J=6.6 Hz, 6H).

Step C

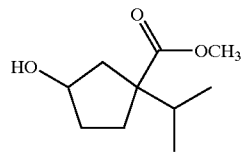

To a cooled (0° C.) solution of borane-methyl sulfide (20 mL, 200 mmol) in anhydrous tetrahydrofuran (100 mL), under an atmosphere of nitrogen, was added using a canula, a solution of cyclopentene ester prepared in step B (28.9 g, 172 mmol). After complete addition the reaction mixture was stirred at room temperature for 20 hours. The mixture was cooled in an ice bath and sodium hydroxide (60 mL of a 3N solution, 181 mmol) added dropwise, followed by 30% hydrogen peroxide (65 mL) and the resulting mixture stirred at 40° C. for 1 hour. The mixture was poured into water (600ml) and extracted with diethyl ether (3×200 mL), the combined diethyl ether layers were washed with water (3×500 mL), saturated NaCl (100 mL), dried over MgSO$_4$, filtered and concentrated in vacuo. The residue was purified by column chromatography on silica elution with 20% EtOAc/hexanes to give 18.5 g (58%) of product.

Step D

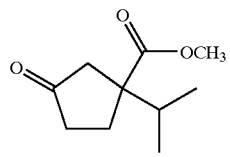

To a (−78° C.) solution of oxalyl chloride (55 mL of a 2M solution in dichloromethane, 109 mmol) in anhydrous dichloromethane (300 mL) under an atmosphere of nitrogen was added in a dropwise manner dimethyl sulfoxide (15.5 mL, 219 mmol), and the resulting mixture stirred at −78° C. for 10 mins. To this mixture was added, using a canula, a solution of the product from step C (18.5 g, 99 mmol) in anhydrous dichloromethane (100 mL). The reaction mixture was stirred at −78° C. for a further 15 mins, then triethylamine (69 mL, 497 mmol) was added and the resulting mixture was allowed to rise to room temperature over 2 hours. The reaction mixture was washed with water (500 mL), saturated NaCl (150 mL), dried over MgSO$_4$, filtered and concentrated in vacuo, to give 18 g, which was used in the next step without further purification.

Step E

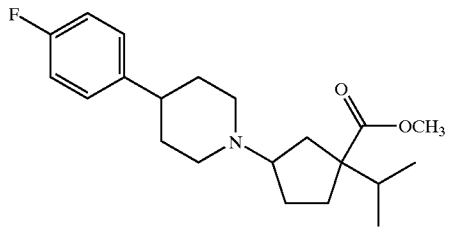

To a solution of the cyclopentanone prepared in step D (18 g, 98 mmol) in anhydrous 1,2-dichloroethane (500 mL), under an atmosphere of nitrogen, was added 4-(4-fluorophenyl)piperidine hydrochloride (25 g, 116 mmol), diisopropylethylamine (20.4 mL, 116 mmol), sodium triacetoxyborohydride (112 g, 531 mmol), and 4A° molecular sieves (powder, 10 g). The mixture was stirred at room temperature for 48hours, and then diluted with dichloromethane (500 mL), and filtered through celite. The filtrate was washed with saturated NaHCO₃ solution (500 mL), water (500 mL), saturated NaCl (200 mL), dried over Na₂SO₄, filtered and concentrated in vacuo to give 28 g (82%). This material was used in the next step without further purification.

Step F
I-Isopropyl-3-(4-(4-fluorophenyl)piperidin-1-yl)cyclopentanecarboxylic acid

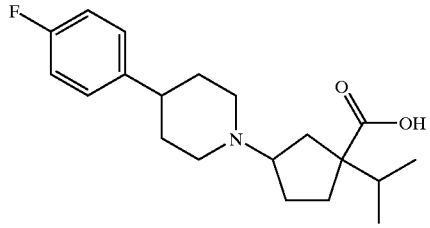

To a solution of the cyclopentane methyl ester prepared in step E (28 g, 81 mmol) in ethanol (500 mL), was added a solution of potassium hydroxide (30 g, 535 mmol) in water (100 mL), and the resulting mixture heated at reflux for 18hours. The cooled mixture was concentrated in vacuo to remove the ethanol, and water (200 mL) added to the residue. The mixture was extracted with diethyl ether (3×200 mL), and the aqueous layer brought to pH=7 by the addition of concentrated hydrochloric acid. The mixture was extracted with a mixture of 9/1 chloroform/2-propanol (3×150 mL), and the combined organic extracts were dried over Na₂SO₄, filtered and concentrated in vacuo. To the residue was added acetone (70 mL) and the mixture heated to boiling then left standing at +5° C. for 16 hours. The acetone was decanted away from the white solid, and the remaining solid dried to give 11.5 g (43%) of product which was a 9:1 mixture of cis and trans isomers. ESI-MS calc. for C20H28FNO2: 333; Found: 334 (M+H).

INTERMEDIATE 13

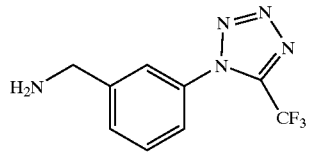

Step A

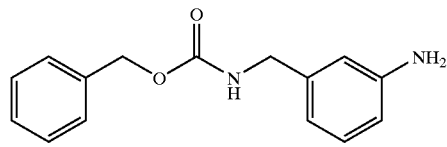

To a suspension of 3-nitrobenzylamine hydrochloride (5 g, 26.5 mmol), and benzyl chloroformate (3.8mL, 26.5 mmol) in dichloromethane (150 mL) was added a solution of potassium carbonate (8 g, 58.3 mmol) in water (100 mL), and the resulting mixture stirred rapidly for 18hours. The organic layer was separated, washed with 5% citric acid solution (200 mL), saturated NaHCO₃ (150 mL), saturated NaCl (100 mL) and concentrated in vacuo. The residue was dissolved in acetic acid (50 mL) and water (200 mL) and activated iron powder (12 g, 215 mmol) was added, and the resulting mixture heated at 90° C. with overhead stirring for 2 hours. The cooled reaction mixture was filtered through celite and the filter cake was washed with EtOAc (200 mL). The filtrate was separated and the aqueous layer extracted with further portions of EtOAc (2×200 mL), the EtOAc layers were combined and washed with water (3×300 mL), saturated NaHCO₃ (300 mL), saturated NaCl (150 mL), dried over MgSO₄, filtered and concentrated in vacuo. The residue was purified by MPLC (silica, elution 20% EtOAc/hexanes) to give 4.8 g (71%) of product. H NMR (CDCl₃, 400 MHz): δ 7.38(m, 5H), 7.12 (t, J=8.6 Hz, 1H), 6.67 (d, J=7.8Hz, 1H), 6.60 (m, 2H), 5.15 (s, 2H), 5.05 (br s, 1H), 4.31 (d, J=5.7 Hz, 2H).

Step B

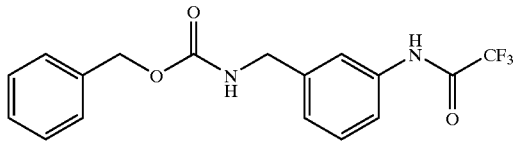

To an cooled (0° C.) solution of the aniline prepared in Step A (4.8 g, 18.8 mmol), and pyridine (3.8 mL, 46.9 mmol) in anhydrous dichloromethane (100 mL) under an atmosphere of nitrogen was added trifluoroacetic anhydride (4.0 mL, 28.1 mmol), and the resulting mixture stirred at room temperature for 16 hours. The reaction mixture was poured into a mixture of ice/water (500 mL), the organic layer separated and the aqueous layer extracted with further portions of dichloromethane (3×100 mL). The combined organics were washed with 1N HCl (4×100 mL), saturated NaCl (100 mL), dried over MgSO₄, filtered and concentrated in vacuo. The residue was purified by MPLC (silica, elution with a gradient rising from 10% EtOAC/hexanes to 30% EtOAc/hexanes) to give 2.52 g (38%) of product. H NMR (CDCl₃, 400 MHz): δ 8.18(br s, 1H), 7.52 (d, J=7.6 Hz, 1H), 7.44 (s, 1H), 7.35 (m, 6H), 7.14 (d, J=7.4 Hz, 1H), 5.22 (br s, 1H), 5.14 (s, 2H), 4.36 (d, J=6.1 Hz, 2H).

Step C

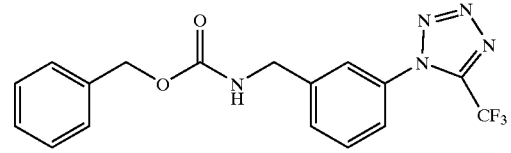

A suspension of the trifluoroacetamide prepared in step B (2.52 g, 7.2 mmol) and triphenyl phosphine (2.81 g, 10.7 mmol) in anhydrous carbon tetrachloride (100 mL) was heated to reflux under an atmosphere of nitrogen for 16 hours. The cooled reaction mixture was concentrated in vacuo, and the resulting residue dissolved in anhydrous N,N-dimethylformamide (100 mL). This solution was added using a canula to a solution of sodium azide (465 mg, 7.2 mmol) in anhydrous N,N-dimethylformamide (75 mL), and the resulting mixture stirred at room temperature for 5 hours. The mixture was poured into water (600 mL) and extracted with EtOAc (3×100 mL), the combined EtOAc layers were washed with water (2×100 mL), saturated NaCl (100 mL), dried over MgSO₄, filtered and concentrated in vacuo. The residue was purified by MPLC (silica, elution with 25%

EtOAc/hexanes to give 1.6 g (59%) of product. H NMR (CDCl₃, 400 MHz): δ 7.62–7.43 (m, 3H), 7.43–7.26 (m, 6H), 5.43 (br s, 1H), 5.15 (s, 2H), 4.50 (d, J=6.1 Hz, 2H).

Step D

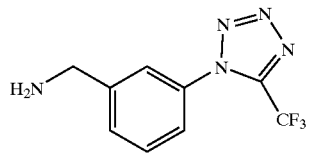

To a nitrogen flushed solution of the benzyl carbamate prepared in step C (1.6 g, 4.2 mmol) in methanol (75 mL), was added 10% palladium on carbon (200 mg), and the resulting mixture stirred under a balloon of hydrogen for 7 hours. The mixture was filtered through celite and the filtrate concentrated in vacuo. The residue was purified by MPLC (silica, elution 0.5/2.5/97 concentrated ammonium hydroxide/methanol/dichloromethne) to give 850 mg (81%) of product. H NMR (CDCl₃, 500 MHz): δ 7.62 (d, J=7.8Hz, 1H), 7.56 (t, J=7.8Hz, 1H), 7.52 (s, 1H), 7.35 (d, J=7.6 Hz, 1H), 4.01 (s, 2H), 1.53 (s, 2H). ESI-MS calc. for C9H8F₃N5:243; Found:244 (M+H).

EXAMPLE 46

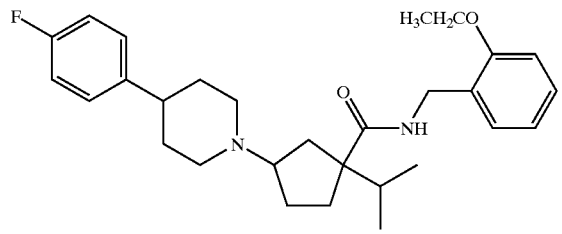

A mixture of the acid (Intermediate 12, 50.0 mg, 0.15 mmol), 2-ethoxybenzylamine (25 μL, 0.15 mmol), 1-hydroxy-7-azabenzotriazole (21.0 mg, 0.15 mmol) in dichloromethane (4 mL) was treated with 1-[3-(dimethylamino)propyl]-3-ethylcarbodiimide hydrochloride (EDC, 45.0 mg, 0.23 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 39 mg of the desired product of sufficient purity (>97%, HPLC, >90% cis-diastereoisomer). LC-MS for C₃₂H₃₅F₆N₂O [M+H]⁺ calculated 467.30, found 467.35.

EXAMPLE 47

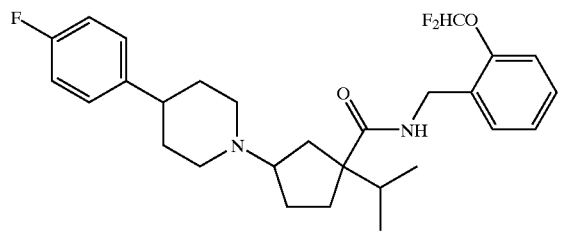

The title compound was prepared as described in Example 46, except that 2-difluoromethoxybenzylamine was used instead of 2-ethoxybenzylamine. The product contained more than 90% of the respective cis-diastereoisomer. LC-MS for C₂₈H₃₆N₂O₂F₃ [M+H]⁺ calculated 489.27, found 489.25.

EXAMPLE 48

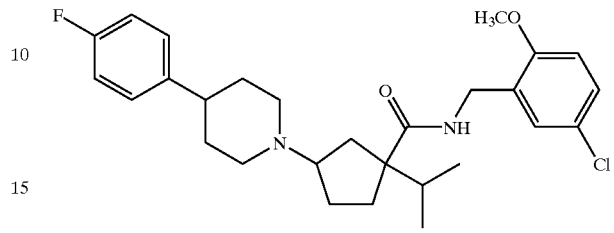

The title compound was prepared as described in Example 46, except that 5-chloro-2-methoxybenzylamine was used instead of 2-ethoxybenzylamine. The product contained more than 90% of the respective cis-diastereoisomer. LC-MS for C₂₈H₃₇N₂O₂ClF [M+H]⁺ calculated 487.24, found 487.30.

EXAMPLE 49

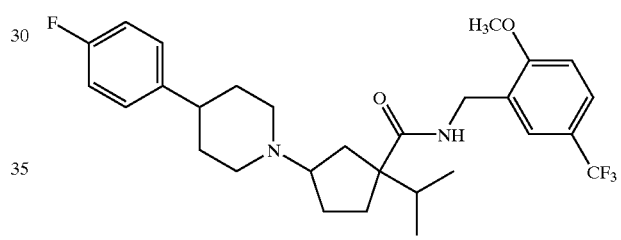

The title compound was prepared as described in Example 46, except that 2-methoxy-5-trifluoromethylbenzylamine was used instead of 2-ethoxybenzylamine. The product contained more than 90% of the respective cis-diastereoisomer. LC-MS for C₂₉H₃₇N₂O₂F₄ [M+H]⁺ calculated 521.27, found 521.35.

EXAMPLE 50

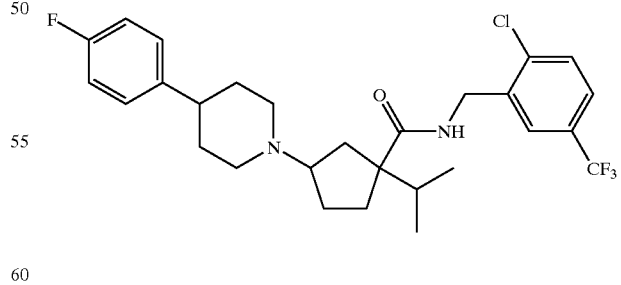

The title compound was prepared as described in Example 46, except that 2-chloro-5-trifluoromethylbenzylamine was used instead of 2-ethoxybenzylamine. The product contained more than 90% of the respective cis-diastereoisomer. LC-MS for C₂₈H₃₄N₂OClF₄ [M+H]⁺ calculated 525.22, found 525.25.

EXAMPLE 51

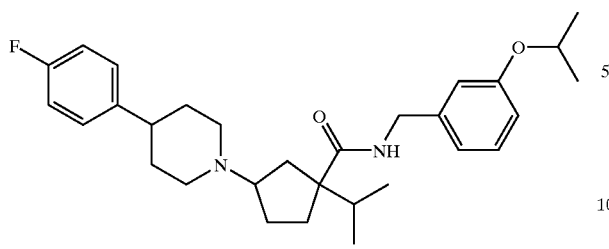

The title compound was prepared as described in Example 46, except that 3-isopropoxybenzylamine was used instead of 2-ethoxybenzylamine. LC-MS for $C_{30}H_{42}N_2O_2F$ [M+H]$^+$ calculated 481.32, found 481.30.

EXAMPLE 52

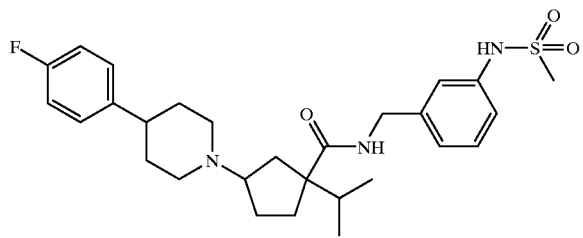

The title compound was prepared as described in Example 46, except that 3-methanesulfonylaminobenzylamine was used instead of 2-ethoxybenzylamine. The product contained more than 90% of the respective cis-diastereoisomer. LC-MS for $C_{28}H_{39}N_3O_3FS$ [M+H]$^+$ calculated 515.26, found 516.25.

EXAMPLE 53

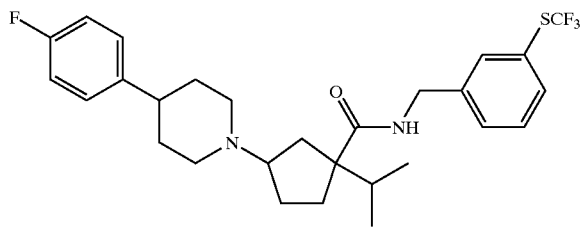

The title compound was prepared as described in Example 46, except that 3-trifluoromethylthiobenzylamine was used instead of 2-ethoxybenzylamine. The product contained more than 90% of the respective cis-diastereoisomer. LC-MS for $C_{28}H_{35}N_2OF_4S$ [M+H]$^+$ calculated 523.23, found 523.30.

EXAMPLE 54

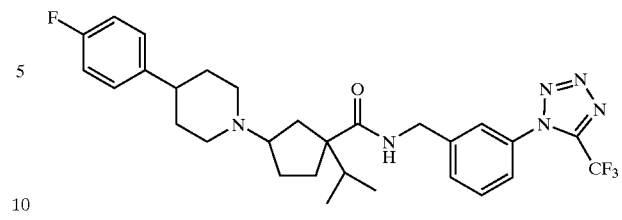

Intermediate 13 (104 mg, 0.43 mmol) was combined with Intermediate 12 (150 mg, 0.43 mmol), EDC (166 mg, 0.86 mmol), and HOAt (59 mg, 0.43 mmol) in dichloromethane (10 mL), and the resulting mixture stirred at room temperature for 1 hour. Diluted with more dichloromethane (15 mL) and washed with water (2×25 mL), saturated NaCl (15 mL), dried over $Na_2SO_4$, filtered and concentrated in vacuo. The residue was applied to 2 preparative TLC plates (silica, 1.0 mm) and eluted with 0.5/5/94.5 concentrated ammonium hydroxide/methanol/dichloromethane. The purified product (cis racemate) was converted to its hydrochloride salt by dissolving in methanol (2 mL) and adding 4 N HCl in dioxane (1 mL) and concentrating. The residue was suspended in 1:2 $CH_2Cl_2$:hexanes (5 mL) and evaporated to give a white powder 155 mg (61%). ESI-MS calc. for C29H34F4N6O: 558; Found: 559 (M+H).

EXAMPLE 55

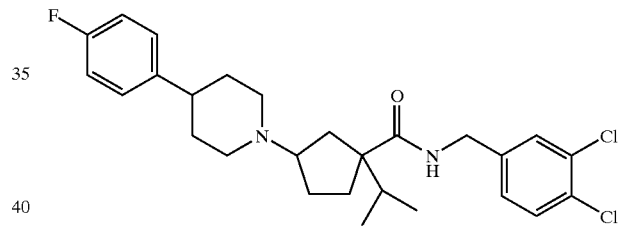

Example 55 was prepared in a similar manner to Example 54 substituting 3,4-dichlorobenzylamine for Intermediate 13. The product contained more than 90% of the respective cis-diastereoisomer. ESI-MS calc. for C27H33Cl2FN2O: 490; Found: 491 (M+H).

EXAMPLE 56

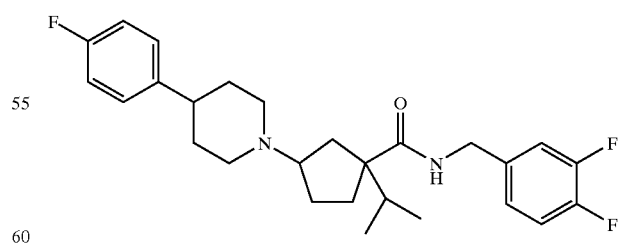

Example 56 was prepared in a similar manner to Example 54 substituting 3,4-difluorobenzylamine for Intermediate 13. The product contained more than 90% of the respective cis-diastereoisomer. ESI-MS calc. for C27H33F3N2O: 458; Found: 459 (M+H).

EXAMPLE 57

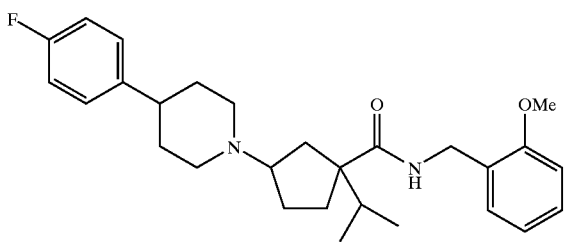

Example 57 was prepared in a similar manner to Example 54 substituting 2-methoxybenzylamine for Intermediate 13. The product contained more than 90% of the respective cis-diastereoisomer. ESI-MS calc. for C28H37FN2O2: 452; Found: 453 (M+H).

EXAMPLE 58

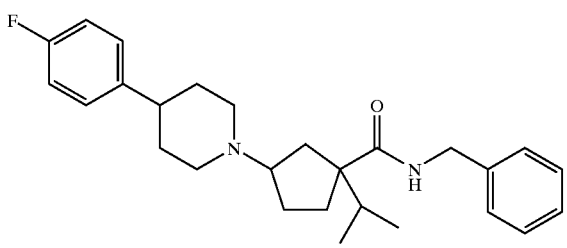

Example 58 was prepared in a similar manner to Example 54 substituting benzylamine for intermediate 13. The product contained more than 90% of the respective cis-diastereoisomer. ESI-MS calc. for C27H35FN2O: 422; Found: 423 (M+H).

EXAMPLE 59

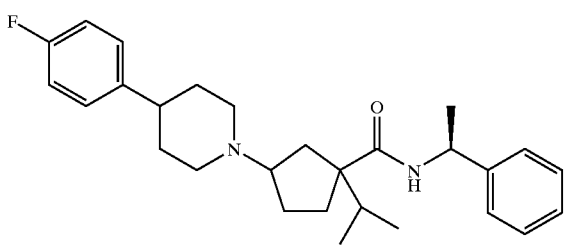

Example 59 was prepared in a similar manner to Example 54 substituting (S)-(−)-α-methylbenzylamine for Intermediate 13. The product contained more than 90% of the respective cis-diastereoisomer. ESI-MS calc. for C28H37FN2O: 436; Found: 437 (M+H).

EXAMPLE 60

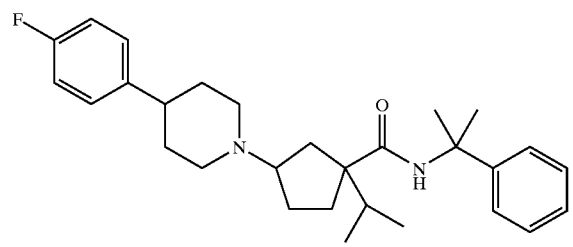

Example 60 was prepared in a similar manner to Example 54 substituting 2-amino-2-phenylpropane for intermediate 13. The product contained more than 90% of the respective cis-diastereoisomer. ESI-MS calc. for C29H39FN2O: 450; Found: 451 (M+H).

EXAMPLE 61

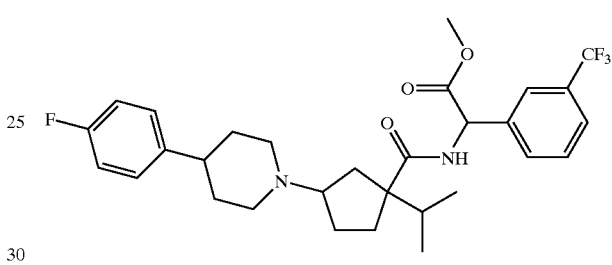

The title compound was prepared as described in Example 46, except that α-methyloxycarbonyl-3-trifluoromethylbenzylamine was used instead of 2-ethoxybenzylamine. The product contained more than 90% of the respective cis-diastereoisomer. LC-MS for C30H37N2O3F4 [M+H]+ calculated 549.27, found 549.25.

INTERMEDIATE 14

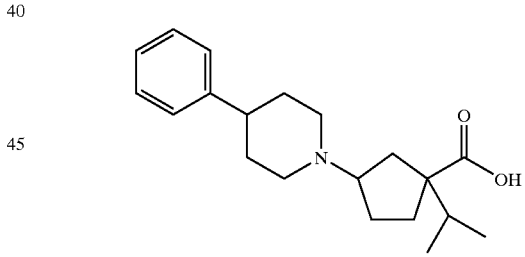

Step A

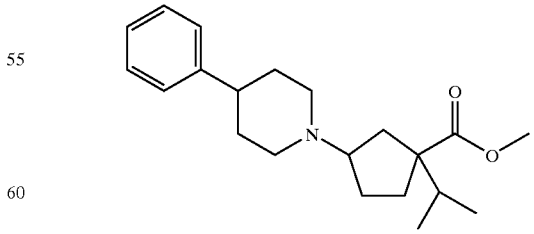

Methyl 3-(4-phenyl)piperidin-1-yl)-1-isopropylcyclopentane carboxylate

To a solution of the methyl 3-oxo-1-isopropylcyclopentane carboxylate (see Intermediate 12, Step D, 1.0 g, 5.43 mmol), 4-phenylpiperidine hydrochloride (1.074, 5.43 mmol), crushed 4 A molecular sieves (3.84 g) in anhydrous 1,2-dichloroethane (50 mL) and diisopropylethylamine (946 μL, 5.43 mmol), was added sodium triacetoxyborohydride (3.45 g, 16.3 mmol). The mixture was stirred at room temperature for 48 hours, diluted with dichloromethane (50 mL), and filtered through celite. The filtrate was washed with saturated NaHCO$_3$ solution (50 mL), water (50 mL), saturated NaCl (20 mL), dried over anhydrous Na$_2$SO$_4$, filtered and concentrated in vacuo to give 1.83 g (100%) of the desired product as a approximately 1:1 mixture of the respective cis- and trans-diastereoisomeric esters. This material was used in the next step without further purification. LC-MS for C$_{21}$H$_{32}$NO$_2$ [M+H]$^+$ calculated 330.24, found 330.35.

Step B

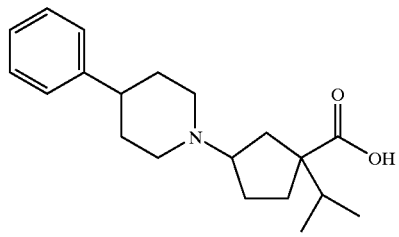

A solution of methyl 3-((4-phenyl)piperidin-1-yl)-1-isopropylcyclopentane carboxylate (1.831 g, 5.56 mmol) in a mixture of dioxane (6.0 mL) and water (6.0 mL) containing lithium hydroxide monohydrate (933 mg, 22.3 mmol) was homogenized with methanol and heated to 80° C. for 48 hours. The solvents were evaporated in vacuo and the residue was picked up into water (10 mL). It was extracted with diethyl ether (3×20 mL) after which the pH of the aqueous phase was set to neutral with 2N HCl. The amino acid was extracted with chloroform (6×50 mL), the combined organic extracts were dried with anhydrous magnesium sulfate and the solvent was evaporated in vacuo. The remaining solid was triturated with hot acetone to give 840 mg (48%) of the pure acid in a form of white solid, which contained only traces (<5%) of the respective trans-diastereoisomer. LC-MS for C$_{20}$H$_{30}$NO$_2$ [M+H]$^+$ calculated 316.22, found 316.30.

EXAMPLE 62

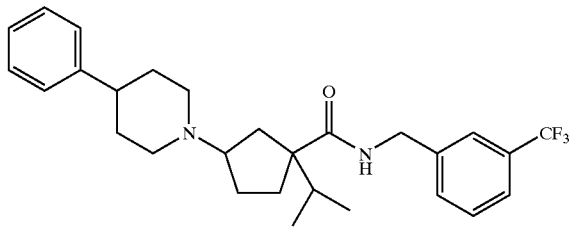

A mixture of the acid (Intermediate 14, 63.0 mg, 0.20 mmol), 3-trifluoromethylbenzylamine (29 μL, 0.20 mmol), dimethylaminopyridine (3.0 mg, 0.03 mmol) in dichloromethane (6 mL) was treated with 1-[3-(dimethylamino)propyl]-3-ethylcarbodiimide hydrochloride (EDC, 58.0 mg, 0.30 mmol) and stirred at r.t. overnight. The reaction mixture was diluted with dichloromethane (4 mL), washed with water (3×3 mL), brine (1×3 mL), dried over anhydrous sodium sulfate and the solvent was evaporated under reduced pressure to yield 87 mg of the crude product, which was further purified by preparative TLC (100% ethyl acetate) to obtain 84 mg (89%) of the pure compound. Single enantiomers were obtained via chiral HPLC, using Diacel's Chiralcel OD semipreparative column, eluent hexane/isopropyl alcohol (93:7). The retention times of the respective cis-enantiomers, observed on an analogous analytical column (4.6×250 mm, 1.0 mL/min flow) were 14.7, and 17.5 minutes. LC-MS for C$_{28}$H$_{36}$F$_3$N$_2$O [M+H]$^+$ calculated 473.27, found 473.35.

EXAMPLE 63

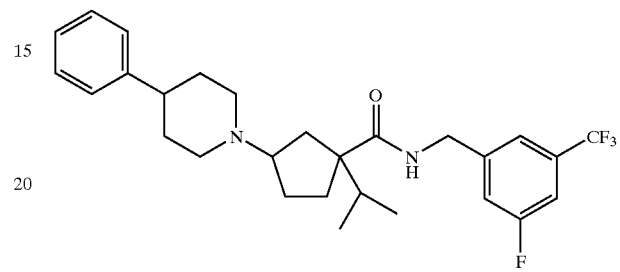

The title compound was prepared using a synthetic sequence analogous to that described in Example 62 except that 3-fluoro-5-trifluoromethylbenzylamine was used instead of 3-trifluoromethylbenzylamine. LC-MS for C$_{28}$H$_{35}$F$_4$N$_2$O [M+H]$^+$ calculated 491.26, found 491.30.

EXAMPLE 64

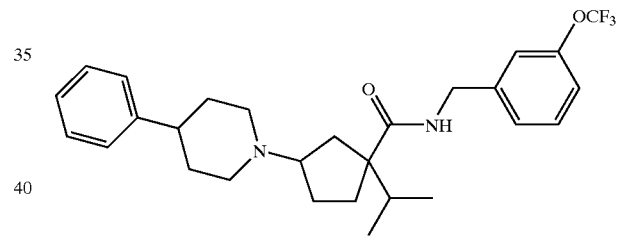

The title compound was prepared using a synthetic sequence analogous to that described in Example 62 except that 3-trifluoromethoxybenzylamine was used instead of 3-trifluoromethylbenzylamine. LC-MS for C$_{28}$H$_{36}$N$_2$O$_2$F$_3$ [M+H]$^+$ calculated 489.27, found 489.30.

EXAMPLE 65

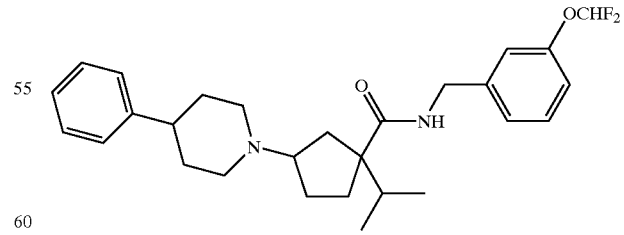

The title compound was prepared using a synthetic sequence analogous to that described in Example 62 except that 3-difluoromethoxybenzylamine was used instead of 3-trifluoromethylbenzylamine. Single enantiomers were obtained using Diacel's Chiralpak AD column, hexane:ethanol/97:3 as eluent. LC-MS for $C_{28}H_{37}N_2O_2F_2$ [M+H]$^+$ calculated 471.27, found 471.30.

EXAMPLE 66

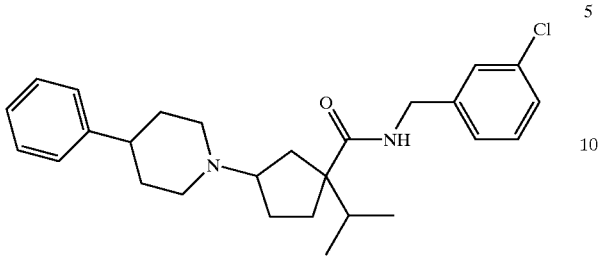

The title compound was prepared using a synthetic sequence analogous to that described in Example 62 except that 3-chlorobenzylamine was used instead of 3-trifluoromethylbenzylamine. Single enantiomers were obtained using Diacel's Chiralpak AD column, hexane:ethanol/97:3 as eluent. LC-MS for $C_{27}H_{36}N_2OCl$ [M+H]$^+$ calculated 389.24, found 389.30.

INTERMEDIATE 15

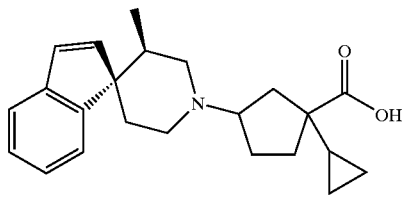

Step A

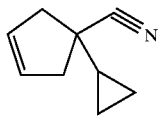

4-Cyano-4-cyclopropylcyclopentene

A neat mixture of cyclopropylacetonitrile (40 g, 0.493 mol) and 1,4-dichloro-cis-2-butene (40 mL, 0.380 mol) was placed into a 1 L three-neck reaction flask, equipped with an addition funnel, reflux condenser and mechanical stirrer and set under static nitrogen atmosphere. A solution of lithium hexamethyldisilazane (250 g, 1.49 mol) in dry dimethoxyethane (330 mL) and 1,3-dimethyl-3,4,5,6-tetrahydro-2 (1H)-pyrimidinone (30 mL) was added. The temperature of the reaction mixture spontaneously rose to app. 90° C., and the remaining base was added with a pace that maintaned this temperature. After the addition was complete the temperature was allowed to cool down to r.t. and the reaction was quenched by pouring onto 500 g of ice. The aqueous layer was extracted with hexanes (3×300 mL), the combined organic portions were back-washed with water (3×200 mL), brine (1×100 mL) and dried over magnesium sulfate. Filtration through a plug of Silica Gel and evaporation of the solvent gave 136 g of mobile oil, which was further purified by distillation to give 84.7 g of hexanethyldisilazane (40 to 50° C. at 40 mmHg) and 22.8 g (45%) of the desired product, b.p.: 98 to 103° C. at 20 mmHg. $^1$H NMR (500 MHz, CDCl$_3$) 5.69 (s, 2H), 2.92 (bd, 14.9 Hz, 2H), 2.63 (bd, 14.7 Hz, 2H), 1.12 (m, 1H), 0.55 (m, 5H).

Step B

3-Cyclopropyl-3-cyanocyclopentanone

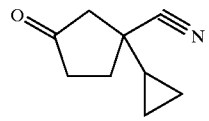

A solution of 4-cyano-4-cyclopropylcyclopentene (4.3439 g, 32.61 mmol) in tetrahydrofuran (10 mL) was cooled to −78° C. and borane (20 mL, 20 mmol, 1 M solution in THF) was added via syringe. Stirring at −78° C. was continued for 30 minutes, and the reaction mixture was allowed to warm up to r.t. The solvent was distilled off at reduced pressure (Rotavap) and the residue was dissolved in dichloromethane (150 mL). A mixture of pyridinium chlorochromate (29.0 g, 137 mmol) and magnesium sulfate (28 g) was added via spatula to the well-stirred suspension over a period of 1 hr. After 4 hrs of stirring at r.t. the reaction mixture was filtered through a Silica Gel plug, and washed with acetone, until all of the product was removed (TLC). The combined acetone filtrate was evaporated to dryness, the residue was dissolved in a mixture of ethyl acetate and hexanes (1:1, 200 mL) and passed through a fresh plug of Silica Gel and washed several times with the ethyl acetate/hexane (1:1) mixture. The combined filtrates were evaporated to dryness, and the residue (2.95 g) was further purified via mplc (ethyl acetate/hexanes, 1:1) to yield 2.1085 g (43%) of pure product. $^1$H NMR (500 MHz, CDCl$_3$) 2.72 (d, 18.3 Hz, 1H), 2.50 (m, 3H), 2.37 (d, 19 Hz, 1H), 2.20 (m, 1H), 1.05 (m, 1H), 0.69 (m, 2H), 0.59 (m, 2H).

Step C

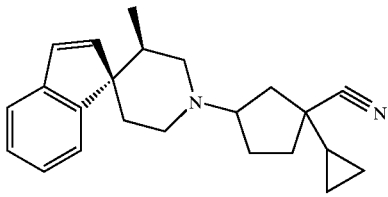

A solution of the ketone (200 mg, 1.33 mmol), Intermediate 1 (314 mg, 1.33 mmol), diisopropylethylamine (230 μL, 1.33 mmol) and crushed 4 A molecular sieves (1.0 g) in dichloroethane (10 mL) was treated with sodium triacetoxyborohydride (1.41 g, 6.65 mmol), and stirred at room temperature for 24 hrs. The molecular sieves were filtered off through Celite, and washed with dichloromethane. The filtrate was washed with a saturated solution of sodium bicarbonate (1×100 mL), water (3×50 mL) and brine (1×50 mL), dried over sodium sulfate and the solvent was evaporated to dryness. The crude product (534 mg) was further purified via preparative TLC (ethyl acetate) to yield 321 mg (73%) of product as a mixture of cis/trans isomers (5:3 by HPLC). MS (M+H$^+$) calculated 333.23, found 333.25.

Step D

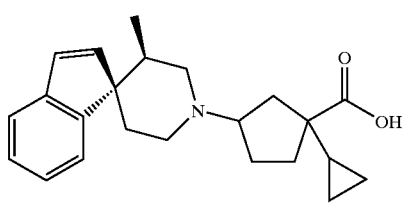

The nitrile (320 mg, 0.963 mmol) was mixed with aq. NaOH (50%, 11 mL) and ethanol was added to homogenize the mixture. The solution was heated to 100° C. overnight, and the solvent was removed on Rotavap. Water (50 mL) was added, and the non-acidic impurities were extracted with diethyl ether. (3×50 mL). The organic extracts were back washed with water (2×10 mL). The pH of the combined aqueous phases was set to neutral (2N HCl), and the acid was extracted with chloroform (8×50 mL). The combined extracts were dried (sodium sulfate) and the solvent was distilled off at reduced pressure to yield 272 mg (78%) of the product as an off-white solid. The respective cis and trans isomers (approximate ratio of 5:3) were separated on preparative TLC using a mixture of dichloromethane and methanol (4:1). MS (M+H$^+$) calculated 352.23, found 352.15.

EXAMPLE 67

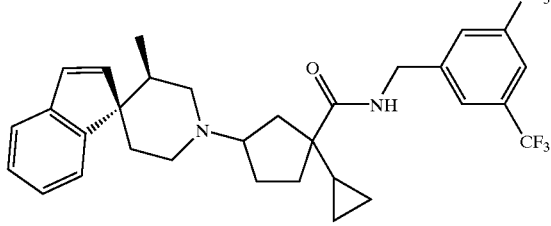

A mixture of the acid (Intermediate 15, 39.5 mg, 0.112 mmol), 3,5-bistrifluoromethylbenzylamine hydrochloride (26.5 mg, 0.112 mmol), diisopropylethylamine (20 µL, 0.112 mmol), 1-hydroxy-7-azabenzotriazole (15.2 mg, 0.112 mmol) in dichloromethane (8 mL) was treated with 1-[3-(dimethylamino)propyl]-3-ethylcarbodiimide hydrochloride (EDC, 33 mg, 0.168 mmol) and stirred at r.t. overnight. The reaction mixture was diluted with dichloromethane (20 mL), washed with water (3×30 mL), brine (1×30 mL), dried over anhydrous sodium sulfate and the solvent was evaporated under reduced pressure to yield 52.3 mg (83%) of the pure product. Single enantiomers were obtained via chiral HPLC, using Diacel's Chiralcel OD semipreparative column, eluent hexane/ethanol (98:2). The respective retention times observed on an identical analytical column (250×4.6 mm, 1.0 mL/min) were 10.78 and 11.19 minutes, respectively. LC-MS for $C_{32}H_{35}F_6N_2O$ [M+H]$^+$ calculated 577.26, found 577.30.

EXAMPLE 68

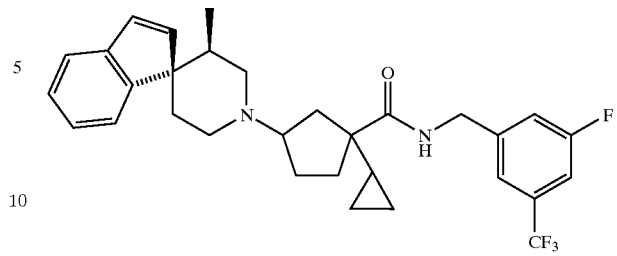

The title compound was prepared using a synthetic sequence analogous to that described in Example 67 except that 3-fluoro-5-trifluoromethylbenzylamine was used instead of 3,5-bistrifluoromethylbenzylamine. Single enantiomers were obtained via chiral HPLC, using Diacel's Chiralcel OD semipreparative column, eluent hexane/ethanol (98:2). The respective retention times observed on an identical analytical column (250×4.6 mm, 1.0 mL/min) were 14.17 and 15.60 minutes, respectively. LC-MS for $C_{31}H_{35}F_4N_2O$ [M+H]$^+$ calculated 527.61, found 527.30.

EXAMPLE 69

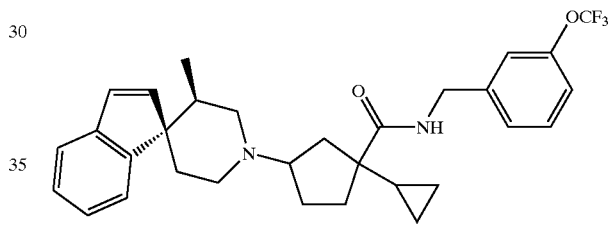

The title compound was prepared using a synthetic sequence analogous to that described in Example 67 except that 3-trifluoromethoxybenzylamine was used instead of 3,5-bistrifluoromethylbenzylamine. LC-MS for $C_{31}H_{36}F_3N_2O_2$ [M+H]$^+$ calculated 525.27, found 525.25.

EXAMPLE 70

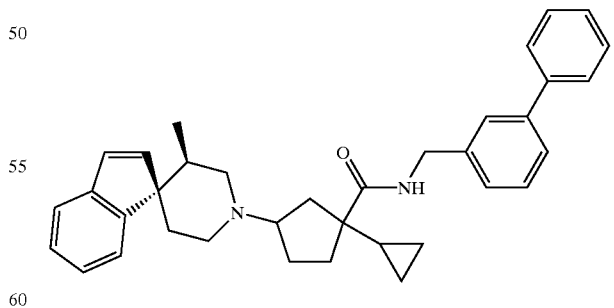

The title compound was prepared using a synthetic sequence analogous to that described in Example 67 except that 3-phenylbenzylamine was used instead of 3,5-bistrifluoromethylbenzylamine. LC-MS for $C_{36}H_{41}N_2O$ [M+H]$^+$ calculated 517.31, found 517.30.

INTERMEDIATE 16

Step A

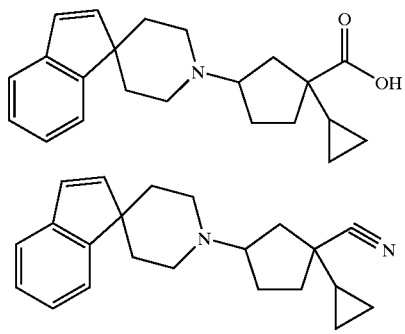

A solution containing 3-cyano-3-cyclopropylcyclopentanone (see Intermediate 15, Step B) (205 mg, 1.38 mmol), diisopropylethylamine (240 μL, 1.38 mmol), 4-spiroindenylpiperidine hydrochloride (306 mg, 1.38 mmol) and 4 A molecular sieves (crushed, 2.76 g) in dichloroethane (10 mL) was treated with sodium triacetoxyborohydride (878 mg, 4.14 mmol) and stirred at ambient temperature for 4 days. The sieves were filtered off through Celite, the filtrate was washed with a saturated solution of sodium bicarbonate (1×30 mL), water (3×30 mL) and brine (1×30 mL). The organic phase was dried with anhydrous sodium sulfate and the solvent was evaporated in vacuo to yield 410 mg (93%) of the crude product, which was used in the subsequent step without any firther purification.

Step B

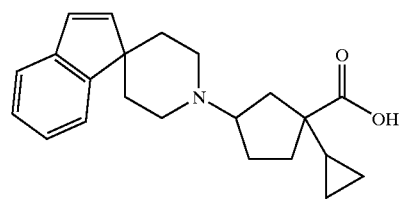

The suspension of the nitrile from the previous step (1.62 g, 5.15 mmol) in aq. sodium hydroxide (50%, 30 mL) was homogenized by addition of ethyl alcohol, and heated to 90° C. for 48 hrs. The solvents were evaporated under reduced pressure and the residue was disolved in water (50 mL). The non-acidic components were extracted with diethyl ether (3×30 mL), combined organic extracts were backwashed with water (1×30 mL). The pH of the combined aqueous phases was set to neutral with 2N HCl, and the product was extracted with chloroform (8×30 mL). The combined organic extracts were dried with anhydrous sodium sulfate, and the solvent was evaporated in vacuo to give 257 mg (59%) of the desired product as a mixture of the respective cis- and trans-diastereoisomers. The pure cis-diastereoisomeric pair (Higher Rf) was obtained by preparative TLC (methylene chloride:methanol/9:1), 122 mg. LC-MS for $C_{22}H_{28}NO_2$ [M+H]$^+$ calculated 338.20, found 338.20.

EXAMPLE 71

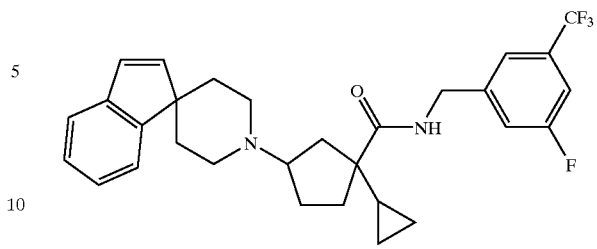

A mixture of the acid (Intermediate 16, 40.0 mg, 0.119 mmol), 3-fluoro-5-trifluoromethylbenzylamine hydrochloride (26 mg, 0.112 mmol), dimethylaminopyridine (1.7 mg, 0.014 mmol) in dichloromethane (5 mL) was treated with 1-[3-(dimethylamino)propyl]-3-ethylcarbodiimide hydrochloride (EDC, 45 mg, 0.238 mmol) and stirred at r.t. overnight. The reaction mixture was diluted with dichloromethane (20 mL), washed with water (3×30 mL), brine (1×30 mL), dried over anhydrous sodium sulfate and the solvent was evaporated under reduced pressure o yield 53.7 mg (88%) of the pure cis-diastereisomeric product. LC-MS for $C_{30}H_{33}F_4N_2O$ [M+H]$^+$ calculated 513.25, found 513.25.

EXAMPLE 72

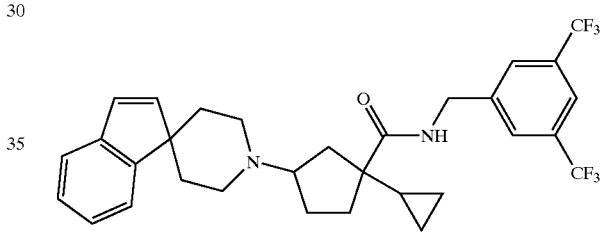

The title compound was prepared in a form of the pure cis-diastereoisomer using a synthetic sequence analogous to that described in Example 71 except that 3,5-bistrifluoromethylbenzylamine was used instead of 3-fluoro-5-trifluoromethylbenzylamine. LC-MS for $C_{31}H_{33}F_6N_2O$ [M+H]$^+$ calculated 489.25, found 489.25.

EXAMPLE 73

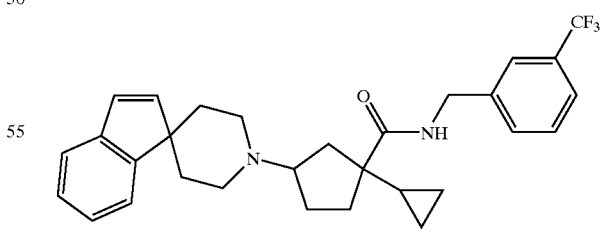

The title compound was prepared in a form of the pure cis-diastereoisomer using a synthetic sequence analogous to that described in Example 71 except that 3-trifluoromethylbenzylamine was used instead of 3-fluoro-5-trifluoromethylbenzylamine. LC-MS for $C_{30}H_{34}F_3N_2O$ [M+H]$^+$ calculated 495.25, found 495.25.

INTERMEDIATE 17

Step A

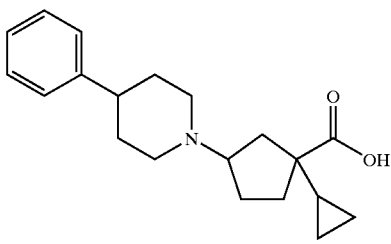

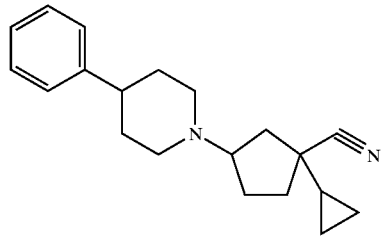

A solution containing 3-cyano-3-cyclopropylcyclopentanone (see Intermediate 15, Step B) (205 mg, 1.38 mmol) diisopropylethylamine (228 µL, 1.42 mmol), 4-phenylpiperidine hydrochloride (281 mg, 1.42 mmol) and 4 Å molecular sieves (crushed, 1.38 g) in dichloroethane (20 mL) was treated with sodium triacetoxyborohydride (1.29 mg, 6.09 mmol) and stirred at ambient temperature for 4 days. The sieves were filtered off through Celite, the filtrate was washed with a saturated solution of sodium bicarbonate (1×30 mL), water (3×30 mL) and brine (1×30 mL). The organic phase was dried with anhydrous sodium sulfate and the solvent was evaporated in vacuo to yield 498 mg of the crude product, which was used in the subsequent step without any further purification.

Step B

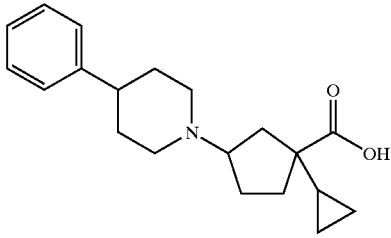

A suspension of the nitrile from the previous step (498 mg) in aqueous sodium hydroxide (50%, 10 mL) was homogenized with ethyl alcohol and heated to 90° C. for 24 hrs. The reaction mixture was concentrated in vacuo, and dissolved in water (10 mL). The non-acidic compounds were extracted with diethyl ether. The pH was set to neutral with 2N HCl, and the product was extracted with chloroform (5×30 mL). The combined organic extracts were dried with anhydrous sodium sulfate, and the solvent was evaporated in vacuo to give 276 mg (60% as an average of two steps). The crude product was triturated with hot acetone to leave the practically pure cis-diastereoisomer behind in a form of a white powder (219 mg). LC-MS for $C_{20}H_{28}NO_2$ $[M+H]^+$ calculated 314.20, found 314.20.

EXAMPLE 74

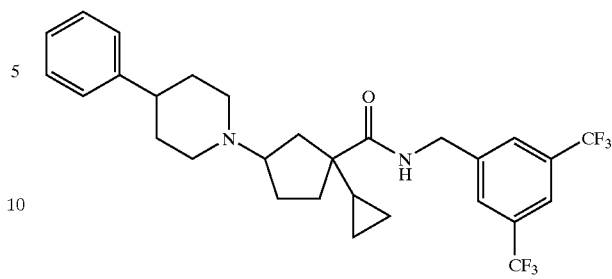

The title compound was prepared in a form of the pure cis-diastereoisomer using a synthetic sequence analogous to that described in Example 71 except that 3,5-bistrifluoromethylbenzylamine was used instead of 3-fluoro-5-trifluoromethylbenzylamine and Intermediate 17 was used instead of Intermediate 16. LC-MS for $C_{29}H_{33}F_6N_2O$ $[M+H]^+$ calculated 539.24, found 539.35.

EXAMPLE 75

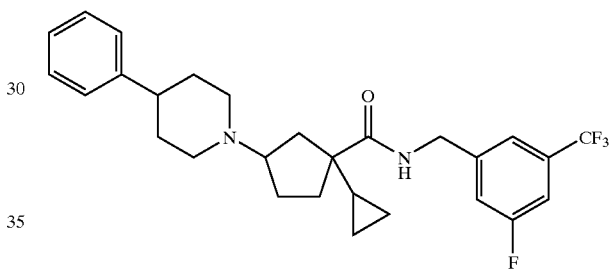

The title compound was prepared in a form of the pure cis-diastereoisomer using a synthetic sequence analogous to that described in Example 71 except that Intermediate 17 was used instead of Intermediate 16. LC-MS for $C_{28}H_{33}F_4N_2O$ $[M+H]^+$ calculated 489.25, found 489.25.

EXAMPLE 76

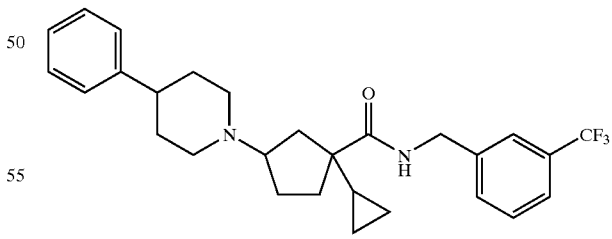

The title compound was prepared in a form of the pure cis-diastereoisomer using a synthetic sequence analogous to that described in Example 71 except that 3-trifluoromethylbenzylamine was used instead of 3-fluoro-5-trifluoro-methylbenzylamine and Intermediate 17 was used instead of Intermediate 16. LC-MS for $C_{28}H_{34}F_3N_2O$ $[M+H]^+$ calculated 471.25, found 471.25.

INTERMEDIATE 18

Step A

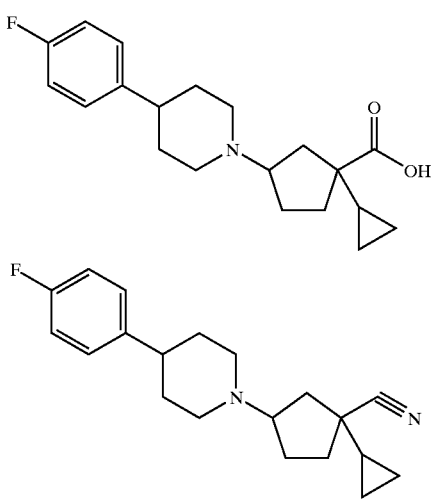

The title compound was synthesized starting from 3-cyano-3-cyclopropylcyclopentanone (see Intermediate 15, Step B) and 4-(4-fluorophenyl)-piperidine hydrochloride as described in Intermediate 17, Step A.

Step B

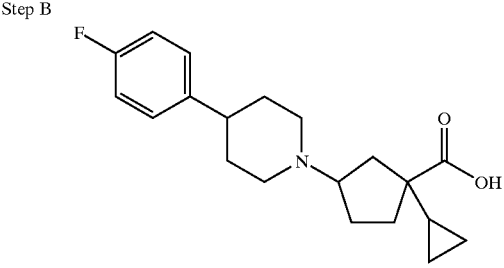

The title compound was synthesized from the corresponding nitrile (previous step) as described in Intermediate 17, Step B. The cis-diastereoisomer was obtained by trituration of the crude product with hot acetone. LC-MS for $C_{20}H_{2}NO_{2}$ [M+H]$^+$ calculated 332.19, found 332.20.

EXAMPLE 77

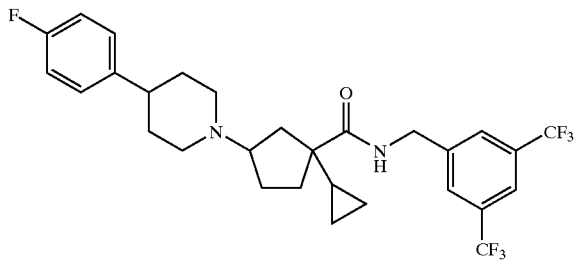

The title compound was prepared using a synthetic sequence analogous to that described in Example 71 except that 3,5-bistrifluoromethylbenzylamine was used instead of 3-fluoro-5-trifluoromethylbenzylamine and Intermediate 18 was used instead of Intermediate 16. Single enantiomers were obtained via chiral HPLC, using Diacel's Chiralcel OD semipreparative column, eluent hexane/ethanol (98:2). The observed retention times on this column (250×20 mm, 9.0 mL/min) were 12.23, and 14.63 minutes, respectively. LC-MS for $C_{29}H_{32}F_{7}N_{2}O$ [M+H]$^+$ calculated 557.23, found 557.30.

EXAMPLE 78

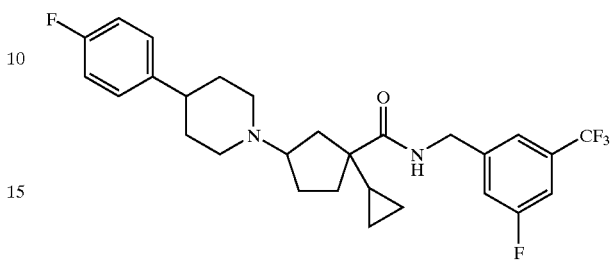

The title compound was prepared using a synthetic sequence analogous to that described in Example 71 except that Intermediate 18 was used instead of Intermediate 16. Single enantiomers were obtained via chiral HPLC, using Diacel's Chiralcel OD semipreparative column, eluent hexane/ethanol (98:2). The observed retention times on this column (250×20 mm, 9.0 mL/min) were 15.6, and 19.3 minutes, respectively. LC-MS for $C_{28}H_{32}F_{7}N_{2}O$ [M+H]$^+$ calculated 507.24, found 507.25.

EXAMPLE 79

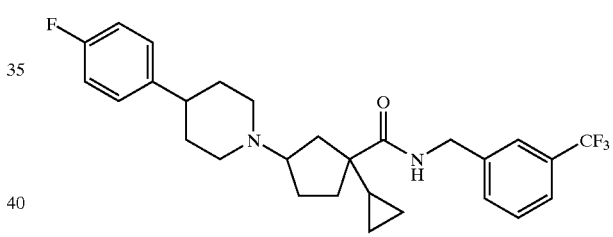

The title compound was prepared using a synthetic sequence analogous to that described in Example 71 except that 3-trifluoromethylbenzylamine was used instead of 3-fluoro-5-trifluoromethylbenzylamine and Intermediate 18 was used instead of Intermediate 16. Single enantiomers were obtained via chiral HPLC, using Diacel's Chiralcel OD semipreparative column, eluent hexane/ethanol (98:2). The observed retention times on an analytical column (250×4.6 mm, 1.0 mL/min) were 10.5, and 11.1 minutes, respectively. LC-MS for $C_{28}H_{33}F_{4}N_{2}O$ [M+H]$^+$ calculated 489.25, found 489.25.

INTERMEDIATE 19

Step A

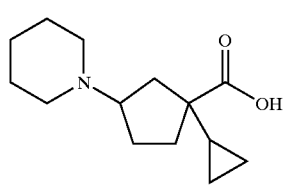

-continued

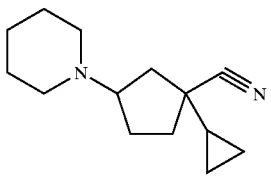

The title compound was synthesized starting from 3-cyano-3-cyclopropylcyclopentanone (see Intermediate 15, Step B) and piperidine as described in Intermediate 17, Step A, without the use of diisopropylethylamine.

Step B

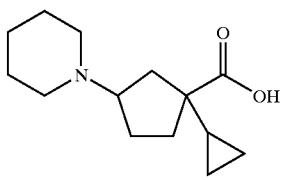

The title compound was synthesized from the corresponding nitrile (previous step) as described in Intermediate 17, Step B. The acid was used as a mixture of cis- and trans-diastereoisomeric pairs.

EXAMPLE 80

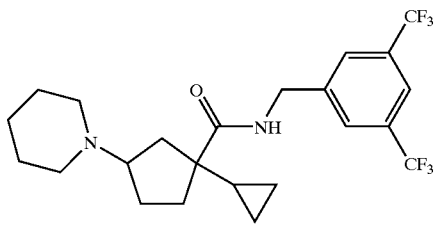

The title compound was prepared using a synthetic sequence analogous to that described in Example 71 except that 3,5-bistrifluoromethylbenzylamine was used instead of 3-fluoro-5-trifluoromethylbenzylamine and Intermediate 19 was used instead of Intermediate 16. LC-MS for $C_{23}H_{29}F_6N_2O$ [M+H]$^+$ calculated 463.21, found 463.15.

EXAMPLE 81

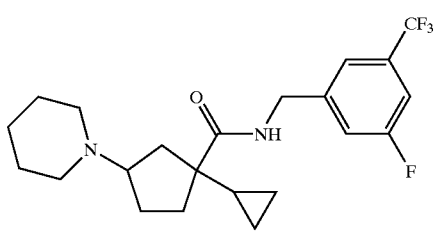

The title compound was prepared using a synthetic sequence analogous to that described in Example 71 except that Intermediate 19 was used instead of Intermediate 16. LC-MS for $C_{22}H_{29}F_4N_2O$ [M+H]$^+$ calculated 413.21, found 413.20.

EXAMPLE 82

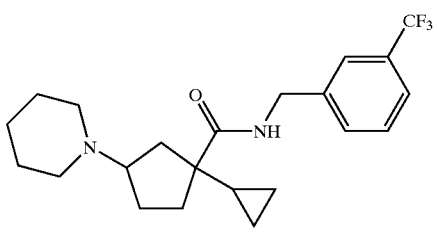

The title compound was prepared using a synthetic sequence analogous to that described in Example 71 except that 3-trifluoromethylbenzylamine was used instead of 3-fluoro-5-trifluoromethylbenzylamine and Intermediate 19 was used instead of Intermediate 16. LC-MS for $C_{22}H_{30}F_3N_2O$ [M+H]$^+$ calculated 395.22, found 395.20.

INTERMEDIATE 20

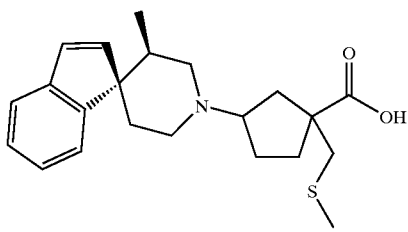

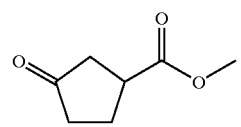

A solution of 3-oxocyclopentane carboxylic acid (Stetter, H., Kuhlman, H. *Liebeig's Ann. Chem.*, 1979, 7, 944–9, 167.5 mg, 1.30 mmol), dimethylaminopyridine (9 mg, 0.073 mmol) in methanol (2.0 mL) was treated with 1-[3-(dimethylamino)propyl]-3-ethylcarbodiimide hydrochloride (747 mg, 3.90 mmol) and the reaction mixture was stirred at r.t. for 30 minutes. The solvent was distilled off on Rotavap, water (10 mL) was added, and the the product was extracted with dichloromethane (4×30 mL). The combined organic extracts were washed with water (2×30 mL), brine (1×30 mL), dried (anhydrous magnesium sulfate) and the solvent was distilled off (Rotavap) to yield 139.2 mg (78%) of pure product as a viscous oil. $^1$H NMR (500 MHz, CDCl$_3$): 3.72 (s, 3H), 3.13 (p, 8.2, 1H), 2.10–2.55 (m, 6H).

Step A-2

Methyl 3-Oxocyclopentane Carboxylate

A solution of methyl 3-methylenecyclopentane carboxylate (Trost, B. M., Chan, M. T., *J. Am. Chem. Soc.*, 1983, 105, 2315) (2.84 g, 20.26 mmol) in dichloromethane (60 mL) was cooled to −78° C. and a slow stream of ozone was passed through until the permanent blue color indicated complete ozonide formation. The excess ozone was purged with stream of nitrogen. Triphenylphosphine (10.62 g, 40.52 mmol) was added, and stirring was continued overnight, allowing the temperature to warm up to ambient. Solvent was removed in vacuo, the residue dissolved in 10 mL of ethyl acetate/hexane (1:4) mixture. The crystalline triphenylphosphine oxide was removed by filtration, and the residue was purified by mplc (ethyl acetate/hexanes (1:4) to yield 1.5651 g (54%) of the desired product.

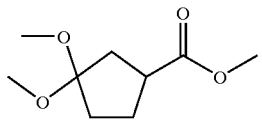

A solution of methyl 3-oxocyclopentane carboxylate, (1.5651 g, 11.00 mmol), camphorsulfonic acid (150 mg), trimethylorthoformate (2.41 mL, 22.01 mmol) in dichloromethane was stirred at ambient temperature overnight. The reaction mixture was washed with a saturated solution of sodium bicarbonate (1×20 mL), water (3×20 mL), brine (1×20 mL), dried (anhydrous magnesium sulfate) and the solvent was evaporated to dryness. Mplc purification (ethyl acetate/hexanes (1:3)) gave 1.6692 g (81%) of the desired acetal as a colorless liquid. $^1$H NM (500 MHz, CDCl$_3$): 3.68 (s, 3H), 3.21 (s, 3H), 3.19 (s, 3H), 2.88 (ddd, 16.94, 8.47 and 7.78 Hz, 1H), 2.15–1.75 (m, 5H).

Step C

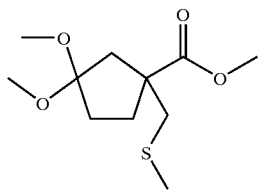

A solution of diisopropylamine (337 mg, 3.37 mmol) in tetrahydrofuran (10 mL) was cooled to −78° C. and n-butyl lithium (1.35 mL of 2.5 M solution in hexane, 3.37 mmol) was added dropwise, followed by slow addition of a solution of methyl 3,3-dimethoxycyclopentane carboxylate (551 mg, 400 mL, 2.93 mmol) in THF (5 mL). After stirring at −78° C. for 30 minutes, neat chloromethylmethylsulfide (492 µL, 5.87 mmol) was added via syringe. The reaction mixture was stirred at −78° C. for 1 hour and than placed in a −15° C. cooler overnight. The reaction was quenched by pouring onto 50 mL of a saturated solution of ammonium chloride, and the crude ester was extracted with diethyl ether. The combined organic extracts were dried with anhydrous magnesium sulfate and the solvent was evaporated in vacuo (100 torr) to leave 644 mg of crude product in the form of a mobile, volatile oil. Given its volatility, it was used in the subsequent step without any further purification.

Step D
Methyl 3-oxo-l-methylthiomethylcyclopentanecarboxylate

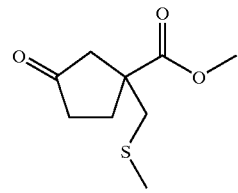

The crude methyl 3,3-dimethoxy-1-methylthiomethylcyclopentane carboxylate was briefly stirred with trifluoroacetic acid (containing 10% of water, 420 mL) and diluted with diethyl ether. The TFA was removed with a saturated solution of sodium bicarbonate, the organic phase was dried with magnesium sulfate and the solvent was evaporated under reduced pressure (100 torr) to leave 315 mg of crude keto-ester in the form of a volatile oil. Given its volatility, it was used in the subsequent step without any further purification.

Step E

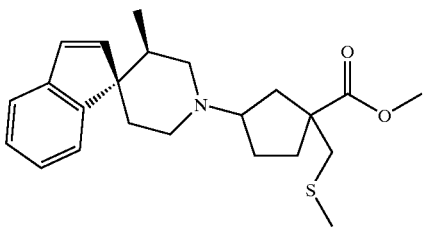

A solution of methyl 3-oxo-1-methylthiomethylcyclopentane-carboxylate (315 mg, 1.558 mmol) and Intermediate 1 (257.1 mg, 1.09 mmol), diisopropylethylamine (175 µL, 1.09 mmol) and crushed 4 A molecular sieves (920 mg) in dichloroethane (15 mL) was treated with sodium triacetoxyborohydride (990 mg, 4.674 mmol) and the resulting mixture was stirred at ambient temperature for 72 hrs. Molecular sieves were removed by filtration through a plug of Celite, and the filtrate was washed with a saturated solution of sodium bicarbonate, water and brine. It was dried with anhydrous sodium sulfate, and the solvent was evaporated in vacuo. The remaining oil (447 mg) was purified by preparative TLC to give 198.3 mg (33% as an average of previous three steps) of pure product as a mixture of cis- and trans-diastereoisomers. LC-MS for $C_{23}H_{32}N_2OS$ [M+H]$^+$ calculated 386.21, found 386.20.

Step F

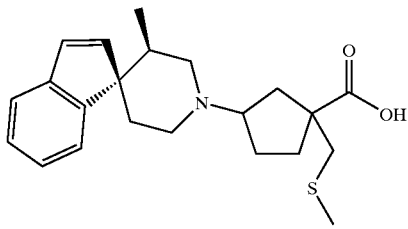

A solution of the amino-ester prepared according to Step E (198 mg, 0.514 mmol) in a mixture of dioxane (4 mL) and water (4 mL) containing 86.2 mg (2.054 mmol) of lithium hydroxide monohydrate was homogenized with methanol and heated to 80° C. for 3 hrs. The solvent was evaporated in vacuo, the residue was dissolved in water (6 mL) and the pH was adjusted with 2N HCl to neutral. The product was extracted with chloroform (6×50 mL), the combined organic phases were dried with anhydrous sodium sulfate, and the product (182 mg, 95%) was obtained by evaporation of the solvent in vacuo. The practically pure cis-diastereoisomer was obtained by trituration of the crude mixture with hot acetone. LC-MS for $C_{22}H_{30}N_2OS$ [M+H]$^+$ calculated 372.19, found 372.25.

EXAMPLE 83

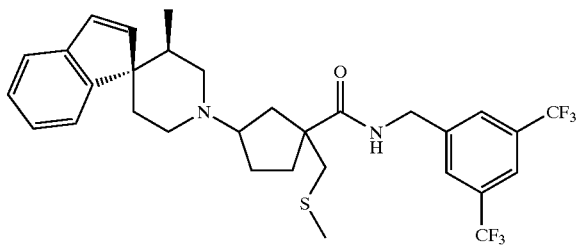

A mixture of the acid (Intermediate 20, 37 mg, 0.1 mmol), 3,5-bistrifluoromethylbenzylamine hydrochloride (24.0 mg, 0.1 mmol), diisopropylethylamine (15 mg, 0.1 mmol), 1-hydroxy-7-azabenzotriazole (14.0 mg, 0.1 mmol) in dichloromethane (8 mL) was treated with 1-[3-(dimethylamino)propyl]-3-ethylcarbodiimide hydrochloride (EDC, 29 mg, 0.15 mmol) and stirred at r.t. overnight. The reaction mixture was diluted with dichloromethane (20 mL), washed with water (3×30 mL), brine (1×30 mL), dried over anhydrous sodium sulfate and the solvent was evaporated under reduced pressure to yield 61.8 mg (100%) of the pure product as a mixture of cis- and trans-diastereoisomers. Single enantiomers were obtained via chiral HPLC, using Diacel's Chiralcel OD semipreparative column, eluent hexane/ethanol (98:2), at 9.0 mL/min flowrate. The retention times of the individual enantiomers observed (analytical conditions, 1.0 mL/min flowrate, 250×4.6 mm column) were: 9.9 mins, 10.5 mins, 19.5 mins and 33.6 minutes, respectively. LC-MS for $C_{31}H_{35}F_6N_2OS$ $[M+H]^+$ calculated 597.23, found 597.25.

EXAMPLE 84

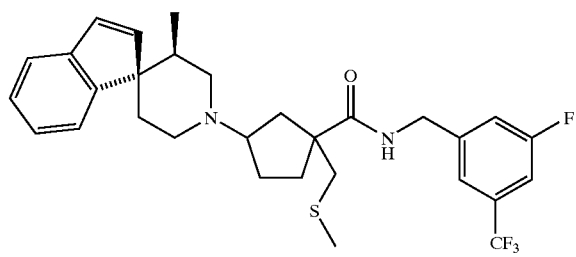

The title compound was prepared using a synthetic sequence analogous to that described in Example 83 except that 3-fluoro-5-trifluoromethylbenzylamine was used instead of 3,5-bistrifluoromethylbenzylamine. The respective enantiomers could be separated on a semipreparative Chiralcel OD (Diacel) column, eluted with 2% ethanol in hexanes at a flowrate of 9.0 mL/min. The respective retention times (area %) observed under analytical conditions were 13.48 (30%), 15.25 (33%), 32.58 (9%) and 63.80 minutes (10%), respectively. LC-MS for $C_{30}H_{35}F_6N_2OS$ $[M+H]^+$ calculated 547.23, found 547.30.

INTERMEDIATE 21

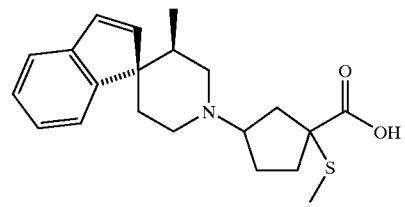

The title compound was synthesized starting from methyl 3-oxocyclopentane carboxylate according to procedures described in Intermediate 20 except that chloromethylmethylsulfide was replaced by dimethyldisulfide in Step C. The practically pure cis-diastereoisomers were obtained from the crude product by trituration with hot acetone. LC-MS for $C_{21}H_{28}F_6NO_2S$ $[M+H]^+$ calculated 358.18, found 358.15.

EXAMPLE 85

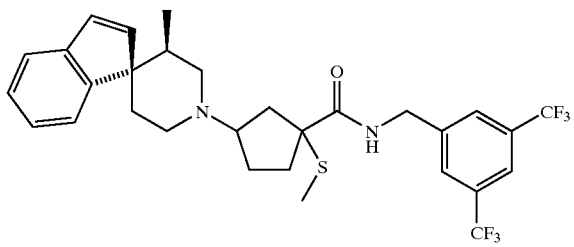

The title compound was prepared using a synthetic sequence analogous to that described in Example 83 except that Intermediate 20 was replaced by Intermediate 21. Single enantiomers were obtained using Diacel's Chiralpak AD column with Hexane:Ethanol/98:2 eluent. The observed retention times on a identical analytical column (250×4.6 mm, 1.0 mL/min) were 11.15 and 17.0 minutes, respectively. LC-MS for $C_{22}H_{30}F_3N_2O$ $[M+H]^+$ calculated 395.22, found 395.20. LC-MS for $C_{30}H_{33}F_6N_2OS$ $[M+H]^+$ calculated 583.21, found 583.30.

EXAMPLE 86

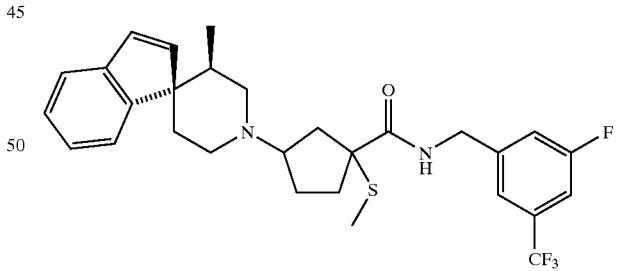

The title compound was prepared using a synthetic sequence analogous to that described in Example 83 except that 3-fluoro-5-trifluoromethylbenzylamine was used instead of 3,5-bistrifluoromethylbenzylamine and Intermediate 20 was replaced by Intermediate 21. Single enantiomers were obtained using Diacel's Chiralpak AD column with Hexane:Ethanol/98:2 eluent. The observed retention times on a identical analytical column (250×4.6 mm, 1.0 mL/min) were 15.9 and 30.8 minutes, respectively. LC-MS for $C_{29}H_{33}F_4N_2OS$ $[M+H]^+$ calculated 533.22, found 533.20.

INTERMEDIATE 22

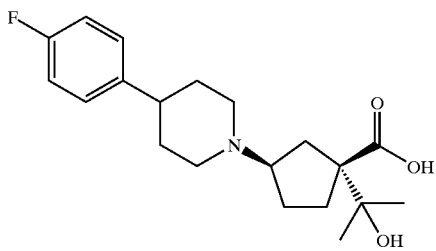

Step A
Procedure A
tert-Butyl 3-Oxocyclopentane carboxylate

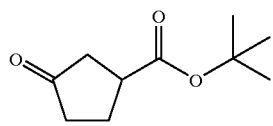

A solution of 3-oxo-cyclopentane carboxylic acid (Stetter, H., Kuhlmann, H. Liebigs Ann. Chem., 1979, 7, 944–9)(5.72 g, 44.64 mmol) in dichloromethane (30 mL) was treated with N,N'-di-iso-propyl-O-tert-Butyl-iso-urea (21.2 mL, 89.29 mmol) and the the reaction mixture was stirred at ambient temperature overnight. The precipitated N,N'-di-iso-propyl urea was filtered off, the filtrate concentrated in vacuo and the residue was purified by distillation (b.p.: 125–129° C. @ 18 mmHg) to yield 4.7446 g (58%) of the pure product. $^1$H NMR (500 MHz, CDCl$_3$): 3.02 (p, J=7.8 Hz, 1H), 2.05–2.50 (m, 6H), 1.45 (s, 9H). $^{13}$C NMR (125 MHz, CDCl$_3$): 217.00, 173.47, 80.99, 41.88, 41.14, 27.94, 26.57.

Procedure B

A 2 L round RBF was charged with anhydrous magnesium sulfate (113.2 g, 940 mmol) and dichloromethane (940 mL) was added. While stirring, the suspension was treated with concentrated sulfuric acid (12.5 mL, 235 mmol) followed in 15 minutes by 3-oxo-cyclopentane carboxylic acid (30.12 g, 235 mmol). After stirring for 15 minutes, tert-butanol (87 g, 1.175 mol) was added. The reaction vessel was closed with a stopper to aid retention of isobutylene, and stirred at ambient temperature for 72 hrs. The solid was filtered off through a plug of Celite, volume of the filtrate was reduced to appr. 500 mL, and washed with satd. solution of sodium bicarbonate (2×150 mL). The organic phase was dried with anhydrous magnesium sulfate, filtered, and the solvent was removed by distillation at reduced pressure (180 mmHg). The crude product was purified by distillation to yield 39.12 g (90%) of pure product.

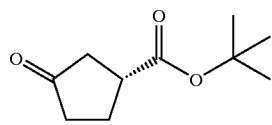

The title compound tert-Butyl (1R)-3-Oxocyclopentane carboxylate was prepared starting from (1R)-3-Oxocyclopentane carboxylic acid (Sung, S-Y., Frahm, A. W. Arch. Pharm. Pharm. Med. Chem. 1996 329, 291–300) according to Procedure A.

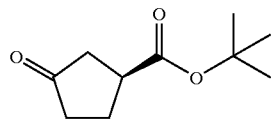

The title compound tert-Butyl (1S)-3-Oxocyclopentane carboxylate was prepared starting from (1S)-3-Oxocyclopentane carboxylic acid (Sung, S-Y., Frahm, A. W. Arch. Pharm. Pharm. Med. Chem. 1996 329, 291–300) according to Procedure A. $[\alpha]_D^{20}$=25.5° (c=7.93, chloroform).

Step B

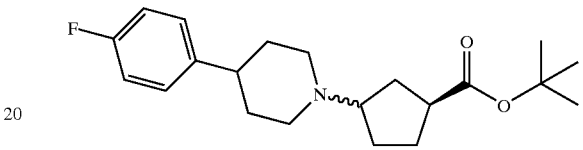

A solution of tert-Butyl (1S)-3-Oxocyclopentane carboxylate (4.70 g, 25.51 mmol), 4-(4-fluorophenyl)piperidine hydrochloride (5.50 g, 25.51 mmol) crushed molecular sieves (6.90 g) diisopropylethylamine (4.44 mL, 25.51 mmol) in dichloroethane was treated with sodium triacetoxyborohydride (27.03 g, 127.55 mmol) and the reaction mixture was stirred at ambient temperature for 72 hrs. The sieves were removed by filtration through a plug of Celite, the filtrate was washed with a saturated solution of sodium bicarbonate (1×100 mL), water (1×100 mL) and brine (1×100 mL). The organic phase was dried over anhydrous sodium sulfate, and the solvent was removed under reduced pressure to leave the crude product (8.0712 g). This was further purified by column chromatography (silica gel, biotage cartridge, 100% ethyl acetate as eluent) to yield 6.8849 g (78%) of the pure product as a mixture of cis- and trans-enantiomeres in a ratio of about 8 to 2 as established by its $^1$H NMR spectrum.

Step C
(1S,3R)-3-(4-(4-fluorophenyl)piperidin-1-yl)cyclopentane carboxyla t(

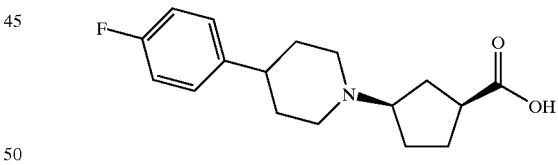

The mixture of cis- and trans enantiomers of the amino ester from previous step (6.88 g, 19.80 mmol) was stirred 6 hrs at ambient temperature in a mixture of TFA and dichloromethane (40 mL, 1:1). The solvents were removed in vacuo and the residue was diluted with water (20 mL). The pH was adjusted with 2 N HCl to neutral, and the amino acid was extracted with chloroform (10×50 mL). The organic phase was dried with anhydrous sodium sulfate, and evaporation of the solvent gave 1.737 g of crude acid, as a mixture of cis- and trans-enantiomers. The pure cis-enantiomer was obtained by trituration of the solid acid mixture with hot acetone. The remaining white solid represents the pure cis-enantiomer (860.5 mg). The acid in a pure form exhibits extremely poor solubility (estimated to be less than 10 mg/mL in dimethyl sulfoxide), and therefore it was characterized after performing Step D.

Step D

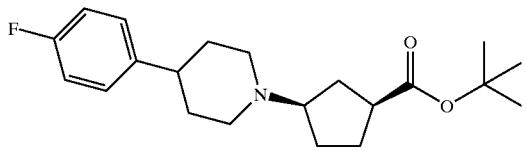

A solution of tert-Butyl (1S,3R)-3-(4-(4-fluorophenyl)piperidin-1-yl)cyclopentane carboxylate (1.73 g, 5.938 mmol) in dichloromethane (50 mL) was treated with N,N'-diisopropyl-O-tert-butyl-isourea (4.73 g, 23.75 mmol) and the resulting mixture was stirred at ambient temperature for 24 hrs. The diisopropylurea was filtered off, and the filtrate was concentrated in vacuo. The residue was purified by column chromatography (silica gel, biotage cartridge, ethyl acetate:hexane (4:1) eluent) to yield 1.4925 g (72%) of the pure product as a single enantiomer. $^1$H NMR (500 MHz, CDCl$_3$): 7.17 (m, 2H), 6.96 (m, 2H), 3.12 (bd, J=11.44 Hz, 1H), 2.70 (m, 1H), 2,60 (m, 1H), 2.43 (m, 1H) 2.18 (bp, J~6.1 Hz, 1H), 2.08 (dd, J=11.9, 2.74 Hz, 1H), 2.04 (dd, J=11.7, 2.74 Hz, 1H), 1.60–1.99 (m, 10H), 1.45 (s, 9H). $^{13}$C NMR (125 MHz, CDCl$_3$): 175.00, 161.3 (d, 244 Hz), 142 (d, 2.9 Hz), 128.2 (d, 7.7 Hz), 115.1 (d, 21.1 Hz), 115.0, 79.9, 67.1, 52.26, 52.73, 43.39, 41.98, 34.46, 33.62, 33.59, 29.29, 28.03, 26.99. These spectral characteristics were found to be identical to those, recorded for the major component of the isomeric mixture in Step B.

Step E

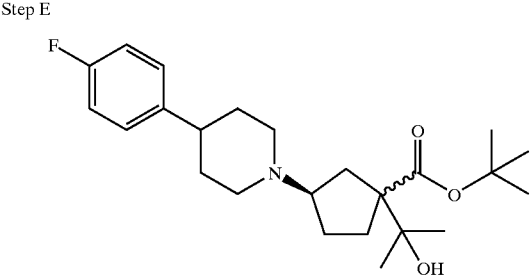

A solution of diisopropylamine (901 μL, 6.43 mmol) in tetrahydrofuran (30 mL) was cooled to −78° C. and butyl lithium (2.5 M in hexanes, 2.57 mL, 6.43 mmol) was added via syringe followed in ten minutes by the ester from Step D. The solution was stirred at −78° C. for 30 minutes, and the temperature of the cooling bath was raised to −15° C. and this temperature was maintained for another 30 minutes. The solution of the enolate was then cooled to −78° C. and neat acetone (1.75 mL, 21.44 mmol) was added via syringe. The reaction mixture was stirred at −15° C. overnight, and quenched by pouring into an aqueous saturated solution of ammonium chloride (50 mL). The crude product was extracted with dichloromethane (6×100 mL), dried with anhydrous sodium sulfate and evaporated to dryness to leave 1.70 g of the desired product (100%) as mixture of (1S, 3R) and (1R, 3R) enantiomers in a ratio of approximately 7:3 as established from the $^1$H NMR spectrum. LC MS: for C$_{24}$H$_{37}$NOF$_3$ [M+H]$^+$ calculated 406.27, found 406.26.

Step F

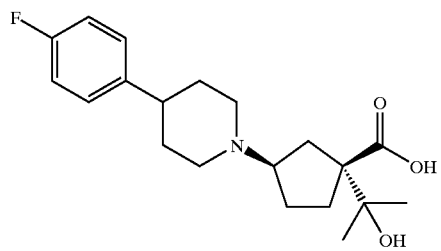

The ester hydrolysis was performed similarly to that described in Step C. Starting from 1.70 g of the ester, 1.261 g of crude acid was obtained, which was triturated with hot acetone (leaving 944 mg of solid) and recrystallized from hot dimethyl sulfoxide to yield 809 mg of a mixture of (1S, 3R) and (1R, 3R) enantiomers. LC MS: for C$_{20}$H$_{29}$NO$_3$F [M+H]$^+$ calculated 350.21, found 350.20.

EXAMPLE 87

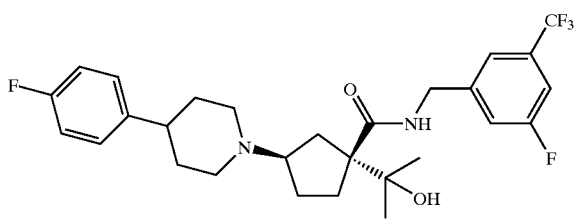

A mixture of the acid (Intermediate 22, 76 mg, 0.218 mmol), 3-fluoro-5-trifluoromethylbenzylamine (61.0 mg, 0.218 mmol), 1-hydroxy-7-azabenzotriazole (30.0 mg, 0.218 mmol) in dichloromethane (10 mL) was treated with 1-[3-(dimethylamino)propyl]-3-ethylcarbodiimide hydrochloride (EDC, 63 mg, 0.327 mmol) and stirred at r.t. for 24 hrs. The reaction mixture was diluted with dichloromethane (20 mL), washed with water (3×30 mL), brine (1×30 mL), dried over anhydrous sodium sulfate and the solvent was evaporated under reduced pressure to yield 125.8 mg (100%) of the pure product as a mixture of (1S, 3R) and (1R, 3R) enantiomers. Single enantiomers were obtained by preparative TLC (Ethyl acetate:ethanol:ammonium hydroxide/90:8:2. LC-MS for C$_{31}$H$_{35}$F$_6$N$_2$OS [M+H]$^+$ calculated 597.23, found 597.25.

$^1$H NMR (500 MHz, CDCl$_3$): Higher Eluting Enantiomer: 9.84 (bs, 1H), 7.36 (s, 1H), 7.20 (m, 3H), 6.98 (m, 4H), 5.80 (s, 1H), 4.55 (dd, J=15.56, 6.17 Hz, 1H), 4.46 (dd, J=15.33, 5.50 Hz, 1H), 3.24 (bd, J=11.7 Hz, 1H), 3.10 (m, 2H), 2.80 (bd, J=5.72 Hz, 1H), 2.47 (m, 1H), 2.20–1.70 (bm, ~10H), 1.53 (m, 2H), 1.32 (s, 3H), 1.21 (s, 3H). LC MS: for C$_{28}$H$_{34}$N$_2$O$_2$F$_5$ [M+H]$^+$ calculated 525.25, found 525.25. Lower Eluting Enantiomer: 7.76 (s, 1H), 7.74 (s, 2H), 7.63 (bt, J=5.95 Hz), 7.18 (m, 2H), 6.97 (m, 2H), 4.64 (dd, J=15.56, 6.18 Hz, 1H), 4.53 (J=15.56, 5.95 Hz, 1H), 3.14 (t, 12.35 Hz, 2H), 2.65–2.40 (m, 4H), 2.20–1.50 (bm, 12H), 1.29 (s, 6H). LC MS: for C$_{28}$H$_{34}$N$_2$O$_2$F$_5$ [M+H]$^+$ calculated 525.25, found 525.25.

EXAMPLE 88

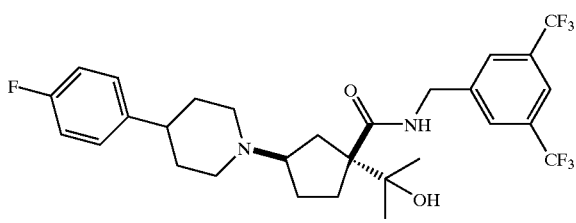

The title compound was prepared using a synthetic sequence analogous to that described in Example 87, except that 3,5-bistrifluoromethylbenzylamine was used instead of 3-fluoro-5-trifluoromethylbenzylamine.

Higher Eluting Enantiomer: $^1$H NMR (500 MHz, CDCl$_3$): 9.90 (bs, 1H), 7.78 (s, 1H), 7.77 (s, 2H), 6.96 (m, 4H), 5.67 (s, 1H), 4.59 (dd, J=15.56, 5.95 Hz, 1H), 4,53 (dd, J=10.07, 5.49 Hz, 1H), 3.23 (d, J=11.21 Hz, 1H), 3.12 (d, 11.43 Hz, 1H), 2.81 (m, 1H), 2.49 (bt (J=12.13 Hz, 1H), 1.6 to 2.3 (m, 10H), 1.50 (m, 1H), 1.31 (s, 3H), 1.25 m (1H), 1.21 (s, 3H). LC-MS for C$_{29}$H$_{34}$N$_2$O$_2$F$_7$ [M+H]$^+$ calculated 575.24, found 575.20.

INTERMEDIATE 23

Step A

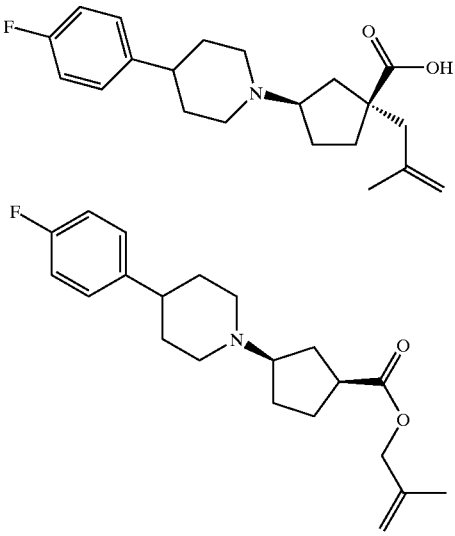

A solution of the homochiral (1S,3R)-3-(4-(4-fluorophenyl)piperidin-1-yl)cyclopentane carboxylate (Intermediate 22, Step C, 455 mg (1.5616 mmol), 2-methyl-2-propen-1-ol (145 μL, 1.7178 mmol) and dimethylaminopyridine (27 mg, 0.2186 mmol) in dichloromethane (10 mL) was treated with 1-[3-(dimethylamino)-propyl]-3-ethylcarbodiimide hydrochloride (EDC, 450 mg, 2.3424 mmol) and stirred at ambient temperature for 1 hour. More dichloromethane was added and the mixture was washed with a saturated solution of sodium bicarbonate, water and brine. After drying with sodium sulfate the solvent was removed in vacuo to yield 439.1 mg (81%) of the desired homochiral product of suficient purity. $^1$H NMR (500 MHz, CDCl$_3$): 7.18 (m, 2H), 6.98 (m, 2H), 4.98 (bs, 1H), 4.93 (bs, 1H), 4.56 (bs, 2H), 3.14 (bd, J=9.84 Hz, 2H), 2.85 (m, 1H), 2.66 (m, 1H), 2.48 (m, 1H), 2.25 (m, 1H), 2.13–1.65 (bm, 14H).

Step B

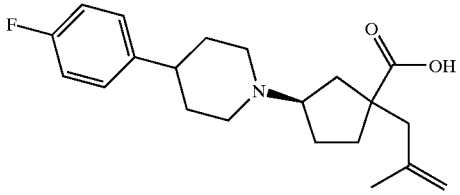

A solution of diisopropylamine (210 μL, 1.4937 mmol) in THF (30 mL) was cooled to –78° C. and nButyl lithium (600 μL of 2.5M solution in hexanes, 1.4937 mmol) was added via syringe. The solution of the ester from Step A (430 mg, 1.2447 mmol in 15 mL of THF) was added slowly via syringe, followed by trimethylsilyl chloride (316 μL, 2.4894 mmol, dried over sodium) and the resulting solution was allowed to warm up to ambient temperature overnight. After a total of 24 hrs, the reaction was quenched by adding 100 mL of water. The THF was removed in vacuo, the residual aqueous phase was extracted with diethyl ether to remove all non-acidic products. The pH of the aqueous phase was set neutral (2N HCl) and the product was extracted into chloroform (6×50 mL). The combined organic phases were dried with anhydrous sodium sulfate and the solvent was evaporated to dryness in vacuo. The crude solid was triturated with acetone to yield 204 mg (47%), containing a mixture of (1S,3R)- and (1R,3R) acids in a ratio of 3:2.

EXAMPLE 89

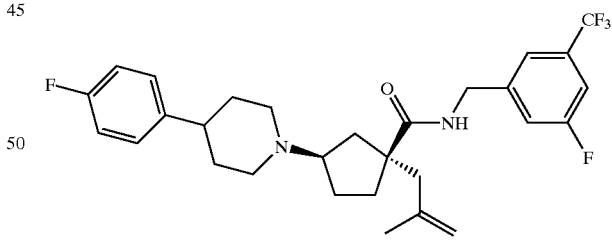

The title compound was prepared using a synthetic sequence analogous to that described in Example 87, except that Intermediate 22 was replaced by Intermediate 23. The retention times of the two respective cis- and trans-enantiomers were 8.22 and 11.40 minutes on an analytical Chiralcel OD column, flowrate 1.0 mL/minute, eluted with a mixture of hexane and ethanol 97:3. Analogous 200×20 mm column was used to separate the enantiomers on a semipreparative scale. LC-MS for C$_{29}$H$_{34}$N$_2$OF$_5$ [M+H]$^+$ calculated 521.25, found 521.30.

INTERMEDIATE 24

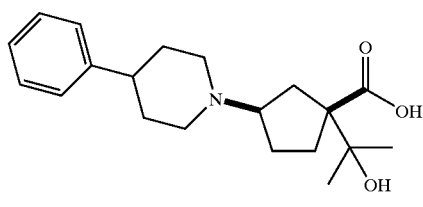

Step A: tert-Butyl 3-Methylenecyclopentane carboxylate

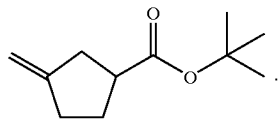

A solution of 2-[(trimethylsilyl)methyl]-2-propen-1-yl acetate (25 mL, 117.7 mmol), tert-butyl acrylate (517.24 mL, 117.7 mmol), palladium acetate (1.47 g, 6 mmol) in 50 mL of tetrahydrofuran was thoroughly degassed (vacuum/nitrogen cycle) and triisopropyl phosphite (5.81 mL, 23.5 mmol) was added via syringe. The pale yellow solution was stirred under reflux for 4 days. The solvent was removed on Rotavap (80 torr), the residue diluted with water (50 mL) and extracted with diethyl ether (3×50 mL). The combined organic extracts were washed with water (2×30 mL), brine (1×30 mL), dried (anh. sodium sulfate) and the solvent was removed on rotavap (80 torr). The crude product was distilled under reduced pressure to yield 20.80 g (97%) of pure product. B.P.: 92–97° C. (20 torr). $^1$H NMR (500 MHz, CDCl$_3$): 4.89 (m, 2H), 2.75 (m, 1H), 2.53 (m, 2H), 2.42 (m, 1H), 2.28 (m, 1H), 1.98 (m, 1H), 1.85 (m, 1H), 1.46 (bs, 9H).

Step B: tertButyl 3-methylene-1-(2-hydroxypropan-2-yl) cyclopentanecarboxylate

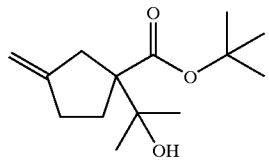

A solution of diisopropylamine (920 µL, 6.54 mmol) in tetrahydrofuran (20 mL) was cooled to −78° C. and nbutyl lithium (2.61 mL of 2.5 N hexane solution. 6.54 mmol) was added dropwise, via syringe, followed by tertButyl 3-methylenecyclopentane carboxylate (1.00 mL, 5.45 mmol). The reaction mixture was stirred at −78° C. for 3 hrs, and neat acetone (633 µL, 10 mmol) was added via syringe. The resulting solution was stirred at −78° C. for 1 hr, and allowed to stand overnight at +5° C. The reaction mixture was quenched by pouring onto a saturated solution of ammonium chloride, and the crude product was extracted with diethyl ether. After drying with anhydrous magnesium sulfate and removal of solvent in vacuo. The remaining oil (1.066 g) was further purified by column chromatography (silica gel, eluent ethyl acetate:hexane/(1:4) to yield 406 mg (31%) of pure product. $^1$H NMR (500 MHz, CDCl$_3$): 4.86 (bs, 1H), 4.82 (bs, 1H), 3.67 (s, 1H), 2.73 (bd, J=16.47 Hz, 1H), 2.56 (bd, J=16.71 Hz, 1H), 2.44–2.30 (m, 2H), 2.15 (m, 1H), 1.85 (m, 1H), 1.47 (s, 9H), 1.22 (s, 2H).

Step C: tertButyl 3-oxo-1-(2-hydroxypropan-2-yl) cyclopentanecarboxylate

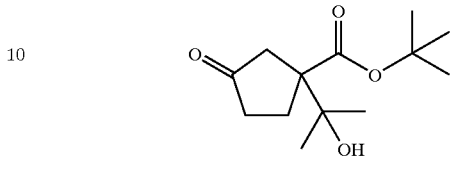

A solution of tertButyl 3-methylene-1-(2-hydroxypropan-2-yl)cyclopentanecarboxylate (400 mg, 1.664 mmol) in dichloromethane (20 mL) was cooled to −78° C. and a stream of ozone was passed through the stirred solution until a permanent blue color indicated complete ozonolysis of the olefin. The excess ozone was removed with a stream of nitrogen and triphenyl phosphine (873 mg, 3.33 mmol) was added. The cooling bath was removed and the reaction mixture was stirred at ambient temperature overnight. The solvent was evaporated under reduced pressure, the residue was picked up into a mixture of ethyl acetate and hexane (1:4) and filtered through a plug of silica gel. The filtrate was concentrated in vacuo and further purified by column chromatography (Silica gel, ethyl acetate:hexanes (1:4)) to yield 338.4 mg (84%) of pure keto ester. $^1$H NMR (500 MHz, CDCl$_3$): 3.36 (s, 1H), 2.68 (d, J=18.31 Hz, 1H), 2.45–2.18 (m, 5H), 1.48 (s, 9H), 1.30 (s, 3H), 1.26 (s, 3H).

Step D: tert-Butyl 3-(4-phenylpiperidin-1-yl)-1-(2-hydroxyproan-2-yl) cyclopentane carboxylate

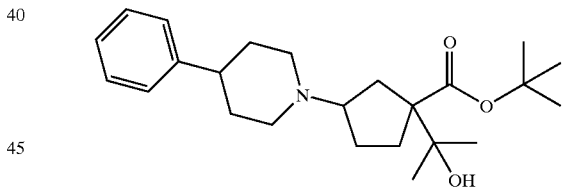

A solution of the ketone from step C (330 mg, 1.362 mmol), 4-phenylpiperidine hydrochloride (270 mg, 1.362 mmol), crushed 4 A molecular sieves (470 mg), diisopropylethylamine (275 µL, 1.362 mmol) in dichloroethane (10 mL) was treated with sodium triacetoxyborohydride (1.66 mmol, 8.16 mmol) and the resulting mixture was stirred at ambient temperature overnight. The sieves were filtered off through a plug of Celite, the filtrate was washed with a saturated solution of sodium bicarbonate, water and brine. The combined aqueous solutions were back extracted with dichloromethane, the combined organic extracts were dried with anhydrous sodium sulfate, and the solvent was evaporated in vacuo to leave 467 mg (88%) of the desired product as mixture of cis- and trans diastereoisomeric pairs ($^1$H NMR). LC MS: for C$_{24}$H$_{38}$NO$_3$ [M+H]$^+$ calculated 388.28, found 388.30.

Step E

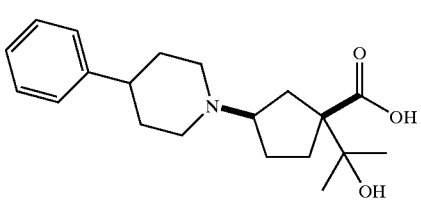

A solution of the tert-Butyl 3-(4-phenylpiperidin-1-yl)-1-(2-hydroxypropan-2-yl)cyclopentane carboxylate (447 mg, 1.15 mmol) in dichloromethane (10 mL) was treated with trifluoroacetic acid (2 mL) and stirred at ambient temperature for 3 hrs. The solvent was removed in vacuo, the residue was dissolved in water (5 mL), and the pH was adjusted to neutral with 2N HCl. The amino acid was extracted with a mixture of chloroform and isopropyl alcohol (85:15, 6×50 mL), combined extracts were dried with anhydrous sodium sulfate and the solvent was evaporated in vacuo to leave 350.4 mg of crude acids as a mixture of the respective cis- and trans diastereoisomeric pairs. The crude residue was triturated with hot acetone leaving behind the practically pure cis-diastereoisomer. Extremely low solubility of the compound made the recording of an NMR spectrum inpractical. LC MS: for $C_{20}H_{30}NO_3$ $[M+H]^+$ calculated 332.21, found 332.20.

EXAMPLE 90

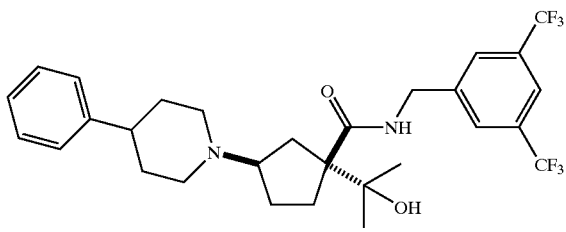

A mixture of the acid (Intermediate 24, 37 mg, 0.110 mmol), 3,5-bistrifluoromethylbenzylamine hydrochloride (31.0 mg, 0.110 mmol), diisopropylethylamine (19 μL, 0.110 mmol), 1-hydroxy-7-azabenzotriazole (15.0 mg, 0.110 mmol) in dichloromethane (6 mL) was treated with 1-[3-(dimethylamino)propyl]-3-ethylcarbodiimide hydrochloride (EDC, 42 mg, 0.221 mmol) and stirred at r.t. for 2 hrs. The reaction mixture was diluted with dichloromethane (20 mL), washed with water (3×30 mL), brine (1×30 mL), dried over anhydrous sodium sulfate and the solvent was evaporated under reduced pressure to yield 65.0 mg (100%) of the crude product, which was further purified by preparative TLC to give 30.5 mg of the desired amine in a form of a cis-diastereoisomeric mixture. -MS for $C_{39}H_{35}F_6N_2O_2$ $[M+H]^+$ calculated 557.25, found 557.30.

EXAMPLE 91

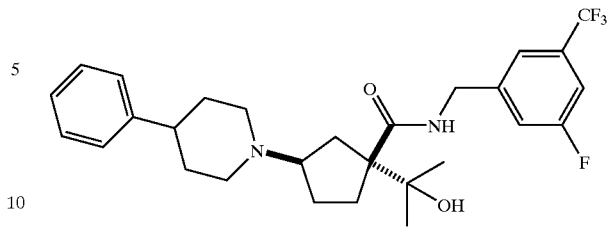

The title compound was prepared in a form of a cis-diastereoisomer using a synthetic sequence analogous to that described in Example 90, except that 3-fluoro-5-trifluoromethylbenzylamine was used instead of 3,5-bistrifluoromethylbenzylamine. LC-MS for $C_{28}H_{35}N_2O_2F_4$ $[M+H]^+$ calculated 507.26, found 507.30.

EXAMPLE 92

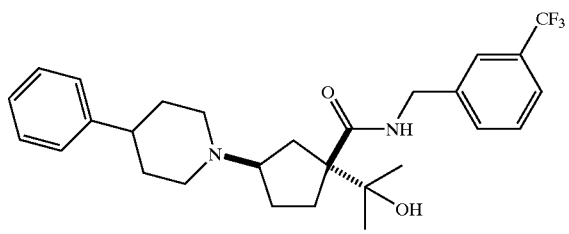

The title compound was prepared in a form of a cis-diastereoisomer using a synthetic sequence analogous to that described in Example 90, except that 3-trifluoromethylbenzylamine was used instead of 3,5-bistrifluoromethylbenzylamine. LC-MS for $C_{28}H_{36}N_2O_2F_3$ $[M+H]^+$ calculated 489.27, found 489.25.

EXAMPLE 93

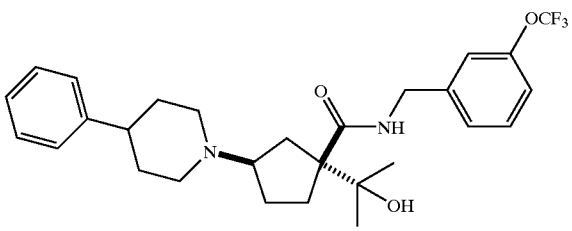

The title compound was prepared in a form of a cis-diastereoisomer using a synthetic sequence analogous to that described in Example 90, except that 3-trifluoromethoxybenzylamine was used instead of 3,5-bistrifluoromethylbenzylamine. LC-MS for $C_{28}H_{36}N_2O_3F_3$ $[M+H]^+$ calculated 505.58, found 505.25.

EXAMPLE 94

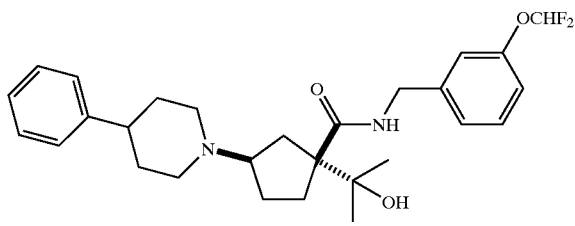

The title compound was prepared in a form of a cis-diastereoisomer using a synthetic sequence analogous to that described in Example 90, except that 3-difluoromethoxybenzylamine was used instead of 3,5-bistrifluoromethylbenzylamine. LC-MS for $C_{28}H_{37}N_2O_3F_3$ [M+H]$^+$ calculated 487.27, found 487.30.

INTERMEDIATE 25

Step A

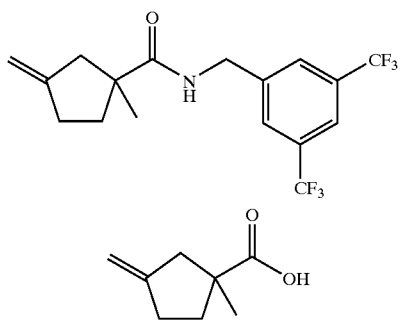

A solution of ethyl 3-methylenecyclopentane carboxylate (see Intermediate 2, Step A, 1.689 g, 10 mmol) in THF (6 mL) and water (6 mL) containing 412 mg (20 mmol) of lithium hydroxide monohydrate was homogenized with methanol and stirred at gentle reflux for 30 minutes. The solvent was evaporated to dryness, the residue was dissolved in water, extracted with diethyl ether (3×30 mL). The pH was set acidic with 2N HCl, and the desired product was extracted with diethyl ether. The combined organic phases were dried with anhydrous magnesium sulfate, and the solvent was evaporated in vacuo to leave 600 mg (43%) of the crude acid. Its relatively high volatility made further attempts at purification impractical, and the acid was used in the subsequent reaction step as obtained.

Step B: 3,5-Bis(trifluoromethyl)benzyl 3-methylene-1-methylcyclopentanecarboxamide

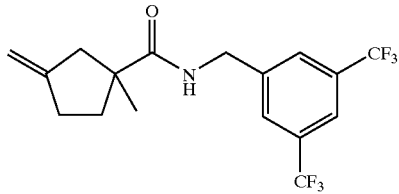

A solution of 3-methylene-1-methylcyclopentanecarboxylic acid, (600 mg, 4.28 mmol) 3,5-bis(trifluoromethyl)benzylamine hydrochloride (1.196 g, 4.28 mmol), 1-hydroxy-7-azabenzotriazole (583 mg, 4.28 mmol) and diisopropylethylamine (745 µL, 4.28 mmol) and 1-[3-(dimethylamino)propyl]-3-ethylcarbodiimide hydrochloride (EDC, 1.230 g, 0.168, 6.42 mmol) in dichloromethane (10 mL) was stirred at room temperature for 1 hr. The reaction mixture was diluted with dichloromethane (40 mL) and washed with water (3×30 mL), brine (1×30 mL), dried (anhydrous sodium sulfate) and the solvent was evaporated under reduced pressure. The crude product was purified via mplc (Lobar Fertigsaule, LiChroprep, 40–63 µm, ethyl acetate/hexanes (1:4)) yielding 777.6 mg (49%) of pure product. $^1$H NMR (500 MHz, CDCl$_3$) 7.79 (s, 1H), 7.70 (s, 2H), 6.19 (bs, 1H), 4.98 (bs, 1H), 4.92 (bs, 1H), 4.62 (dd, 15.6 Hz, 6.2 Hz, 1H), 4.54 (dd, 15.8 Hz, 6.0 Hz, 1H), 2.78 (bd, 15.8 Hz, 1H), 2.46 (m, 2H), 2.30 (bd, 15.8 Hz, 1H), 2.18 (m, 1H), 1.70 (m, 1H), 1.31 (s, 3H).

EXAMPLE 95

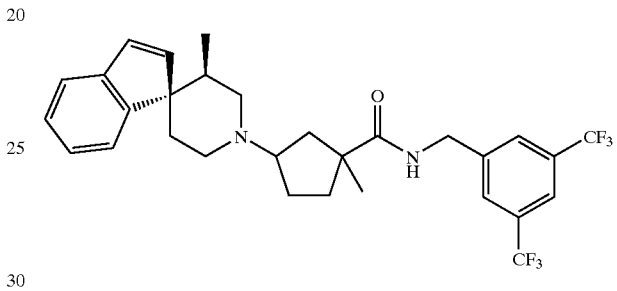

A solution of the olefin 3,5-bis(trifluoromethyl)benzyl 3-methylene-1-methylcyclopentane-carboxamide (Intermediate 25, 255 mg, 0.698 mmol) in dichloromethane (20 mL) was ozonized at −78° C. The excess ozone was removed with a stream of nitrogen. Intermediate 1 (165 mg, 0.698 mmol), diisopropylethylamine (121 µL, 0.698 mmol) and 400 mg of molecular sieves (4A, crushed) were added, followed by sodium triacetoxyborohydride (444 mg, 2.094 mmol). The reaction mixture was stirred at room temperature for 48 hrs after which it was diluted with dichloromethane (50 mL). The sieves were filtered off (Celite), the filtrate was washed with a saturated solution of sodium bicarbonate (1×50 mL), water (2×50 mL) and brine (1×50 mL). After drying (anh. sodium sulfate), the solvent was evaporated under reduced pressure, and the residue (216 mg) was further purified by preparative thin layer chromatography (Analtech, Silica Gel GF, 1000µ, 100% ethyl acetate) to yield 68 mg (18%) of the higher eluting (1,3-cis-cyclopentane) diastereoisomeric pair and 92 mg (24%) of the lower eluting trans-diastereoisomeric pair. The higher eluting diastereoisomeric pair was separated into single enantiomers using Diacel's Chiralcel OD chiral preparative HPLC column, eluent hexane:ethanol (97:3) at flowrate of 9 mL/min. The retention times of the individual isomers (analytical 250×4.6 mm column, 1.0 mL/min) were 6.93 min (40%), 7.91 (45%), 9.63 (9%) and 12.04 (4%). $^1$H NMR (500 MHz, CDCl$_3$) 9.22 (bs, 1H), 7.82 (bs, 2H), 7.78 (bs, 1H), 7.27 (m, 1H), 7.24 (dt, 7.3 Hz, 0.7 Hz, 1H), 7.14 (t, 7.3 Hz, 1H), 6.80 (m, 2H), 6.60 (d, 5.7 Hz, 1H), 4.68 (m, 2H), 3.15 (bd, 11.4 Hz, 1H), 3.02 (bd, 10.5 Hz, 1H), 2.93 (bs, 1H), 2.35 (bd, 14 Hz, 1H), 2.20 (m, 2H), 1.7–2.1 (m, 9, 1.37 (s, 3H), 1.32 (bdt, 13.7 Hz, 2.5 Hz, 2H).

INTERMEDIATE 26

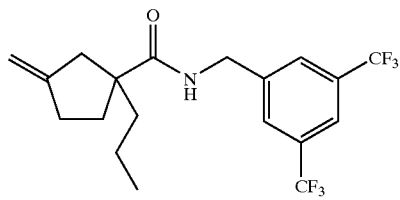

A suspension of crude methyl 3-methylene-1-propan-1-ylcyclopentane carboxylate (see Intermediate 5, Step A, 773 mg, no more than 4.10 mmol) in dioxane (4 mL) and water (4 mL) containing lithium hydroxide monohydrate (344 mg, 8.20 mmol) was homogenized with methanol and heated to 80° C. for 1 hour. The solvents were removed under reduced pressere, the residue was dissolved in water 10 mL and the non-acidic components were extracted into diethyl ether. The pH of the aqueous phase was set acidic, the crude product was extracted with chloroform (6×30 mL). The combined organic extracts were dried with anhydrous sodium sulfate, the solvent was evaporated under reduced pressure to leave 535 mg (3.18 mmol) of the crude product. This was dissolved in methylene chloride (20 mL) and 3,5-bistrifluoromethylbenzylamine hydrochloride (878 mg, 3.18 mmol) was added, followed by diisopropylethylamine (555 μL, 3.18 mmol), 1-hydroxy-7-azabenzotriazole (432 mg, 3.18 mmol) and 1-[3-(dimethylamino)propyl]-3-ethylcarbodiimide hydrochloride (EDC, 915 mg, 4.77 mmol). The reaction mixture was stirred at ambient temperature overnight, more methylene chloride was added and extracted with sodium bicarbonate, water and brine. The organic phase was dried over anhydrous magnesium sulfate to yield 686 mg of crude product, which was further purified by mplc (silica gel, ethyl acetate:hexanes/(25:75) to give 480 mg 30% for two steps) of pure product. $^1$H NMR (500 MHz, CDCl$_3$): 7.79 (s, 1H), 7.71 (s, 2H), 6.18 (bs, 1H), 4.98 (bs, 1H)m 4.91 (bs, 1H), 4.62 (dd, J=15.56, 6.18 Hz, 1H), 4.56 (dd, J=15.56, 5.95 Hz, 1H), 2.74 (bd, J=16.25 Hz, 1H), 2.40 (m, 3H), 2.15 (m, 1H), 1.73 (m, 2H), 1.52 (m, 1H), 1.27 (m, 1H), 0.9 (t, J=7.1 Hz, 3H).

EXAMPLE 96

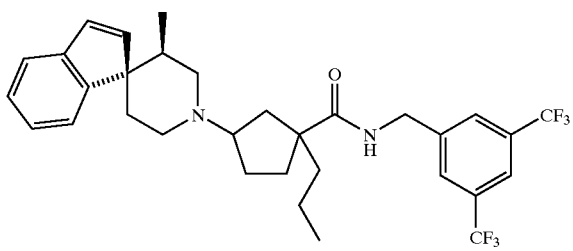

The title compound was prepared using a synthetic sequence analogous to that described in Example 95, except that Intermediate 25 was replaced by Intermediate 26. Single enantiomers were obtained via chiral HPLC, using Diacel's Chiralcel OD semipreparative column, eluent hexane/ethanol (97:3). The observed retention times(area %) on a identical analytical column (250×4.6 mm, 1.0 mL/min flow) were 5.40 (27%), 5.6, (33%) 7.0 (21%) and 8.5 minutes (19%), respectively. MS for $C_{32}H_{37}F_6N_2O$ [M+H]$^+$ calculated 579.27, found 579.25.

INTERMEDIATE 27

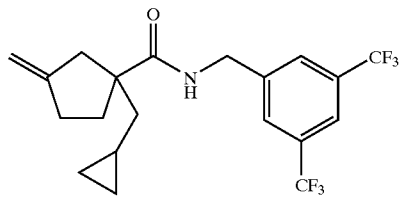

The title compound was synthesized starting from methyl 3-methylene-1-cyclopropylmethylcyclopentane carboxylate (see Intermediate 7, Step A) according to the procedure described for Intermediate 26. $^1$H NMR (500 MHz, CDCl$_3$): 7.79 (s, 1H), 7.74 (s, 2H), 6.24 (bs, 1H), 5.0 (bs, 1H), 4,92 (bs, 1H), 4.63 (dd, J=15.79, 6.4 Hz, 1H), 4.57 (dd, J=15.56, 5.95 Hz, 1H), 2.78 (bd, J=16.25 Hz, 1H), 2.48 (bd, J=15.0 Hz, 1H), 2.40 (m, 2H), 2.15 (m, 1H), 1.78 (m, 2H), 1.44 (dd, J=14.19, 7.10 Hz, 1H), 0.63 (m, 1H), 0.42 (m, 2H), 0.05 (m, 2H).

EXAMPLE 97

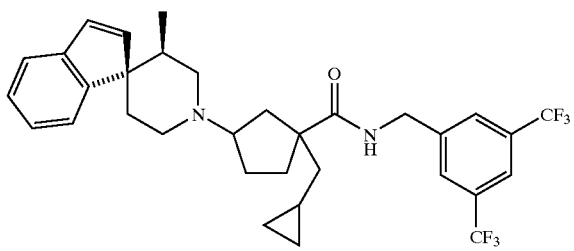

The title compound was prepared using a synthetic sequence analogous to that described in Example 95, except that Intermediate 25 was replaced by Intermediate 27. Single enantiomers were obtained via chiral HPLC, using Diacel's Chiralcel OD semipreparative column, eluent hexane/ethanol (97:3). The observed retention times(areas %) on a identical analytical column (250×4.6 mm, 1.0 mL/min flow) were 5.82 (21%), 6.21, (25%) 8.14, (25%) and 9.81 (26%) minutes, respectively. MS for $C_{33}H_{37}F_6N_2O$ [M+H]$^+$ calculated 591.27, found 591.26.

INTERMEDIATE 28

Step A

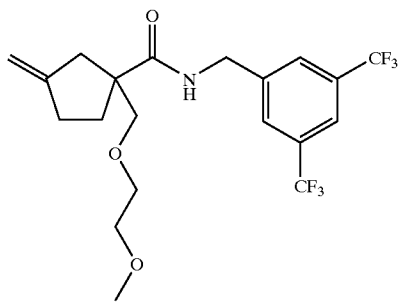

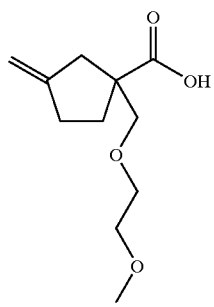

A solution of diisopropylamine (662 μL, 4.72 mmol) in THF (10 mL) was cooled to −78° C. and treated with nbutyl lithium (1.88 mL of 2.5M solution in hexanes, 4.72 mmol). After stirring at −78° C. for 15 minutes, the neat methyl 3-methylenecyclopentane carboxylate (Trost, B. M., Chan, M. T., *J. Am. Chem. Soc.*, 1983, 105, 2315) (500 μL, 4.102 mmol) was added via syringe, and the reaction mixture was stirred at −78° C. for 2 hrs. Neat methoxyethoxymethyl chloride (1.405 mL, 12.31 mmol) was added via syringe, the reaction mixture was stirred at −78° C. for 1 hour, than allowed to stand at +5° C. overnight. The reaction was quenched by pouring onto an aqueous solution of citric acid (10%, 50 mL) and the product was extracted into diethyl ether (6×30 mL). The combined organic extracts were dried with magnesium sulfate, and the solvent was evaporated in vacuo (150 torr). The volatile crude product (1.96 g) was used in the subsequent reaction step as obtained.

Step B

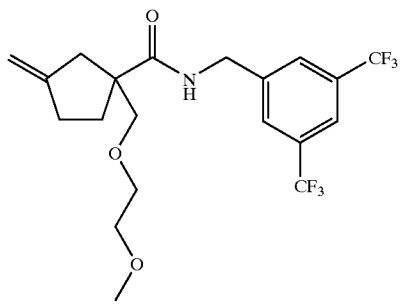

The title compound was synthesized starting from methyl 3-methylene-1-methoxyethoxymethylmethylcyclopentane carboxylate (see previous step) according to the procedure described for Intermediate 26. LC-MS for $C_{20}H_{24}F_6N_2O_3$ $[M+H]^+$ calculated 440.16, found 440.20.

EXAMPLE 98

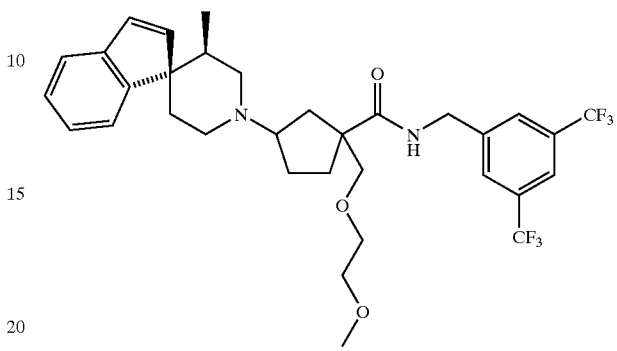

The title compound was prepared using a synthetic sequence analogous to that described in Example 95, except that Intermediate 25 was replaced by Intermediate 28. Single enantiomers were obtained via chiral HPLC, using Diacel's Chiralcel OD semipreparative column, eluent hexane/ethanol (97:3). The observed retention times (area %) on a identical analytical column (250×4.6 mm, 1.0 mL/min flow) were 9.40 (15%), 10.90 (34%), 12.40 (35%) and 16.60 minutes (15%), respectively. MS for $C_{33}H_{37}F_6N_2O$ $[M+H]^+$ calculated 591.27, found 591.26. MS for $C_{33}H_{39}F_6N_2O_3$ $[M+H]^+$ calculated 625.28, found 625.28.

INTERMEDIATE 29

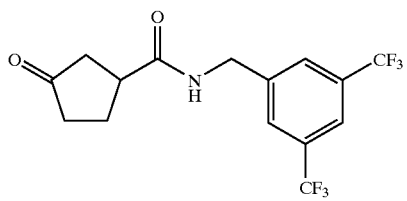

A solution of 3-oxo-cyclopentanecarboxylic acid (1.0 g, 7.80 mmol), 3,5-bis(trifluoromethyl)benzylamine hydrochloride (2.18 g, 7.80 mmol), 1-hydroxy-7-azabenzotriazole (1.06 g, 7.80 mmol) in dichloromethane (40 mL) was treated with 1-[3-(dimethylamino)propyl]-3-ethylcarbodiimide hydrochloride (EDC, 2.24 g, 11.7 mmol) and the solution was stirred at r.t. overnight. The reaction mixture was washed with water (3×50 mL), brine (1×50 mL), dried (anhydrous magnesium sulfate) and evaporated to dryness. The crude product was further purified via MPLC (7.5% of methanol in dichloromethane) to give 2.37 g (86%) of pure ketone. $^1$H NMR (500 MHz, CDCl$_3$): 7.82 (s, 1H), 7.74 (s, 2H), 6.23 (bs, 1H), 4.63 (dd, 15.3, 6.1 Hz, 1H), 4.56 (dd, 15.3, 6.0 Hz, 1H), 2.99 (p, 8.1 Hz, 1H), 2.60 (ddd, 18.3, 8.4, 1.1 Hz, 1H), 2.46 (m, 2H), 2.24 (m, 3H),

EXAMPLE 99

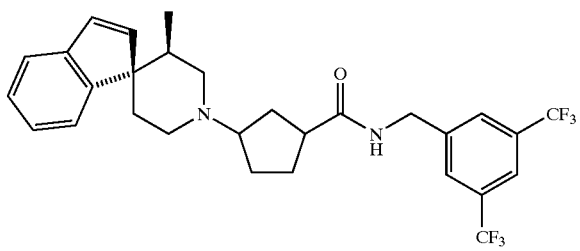

A solution of 3,5-bis(trifluoromethyl)benzyl 3-oxo-cyclopentane-carboxamide (Intermediate 29, 172.8 mg, 0.489 mmol), Intermediate 1 (115.3 mg, 0.489 mmol), diisopropylethylamine (85 µL, 0.489 mmol) and crushed molecular sieves (4A, 300 mg) in dichloroethane (10 mL) was treated with sodium triacetoxyborohydride (311 mg, 1.467 mmol) and stirred at r.t. 24 hrs. The sieves were filtered off (plug of Celite), washed with dichloromethane and the combined organic washings were extracted with a saturated solution of sodium bicarbonate (1×50 mL), water (3×50 mL), brine (1×50 mL) and dried over anhydrous sodium sulfate. Solvent was evaporated to dryness to yield 239.5 mg of product as a mixture of four diastereoisomers in a ratio of 1:1:4:4. Single enantiomers could be obtained using chiral HPLC (Chiralcel OD, 20×200 mm, using a mixture of hexane/ethanol (96:4) as eluent). The observed retention times (area %) on an identical analytical column (250×4.6 mm, 1.0 mL/min) for the respective enantiomers were 9.18 (10%), 9.69 (12%), 10.82 (39%) and 12.14 minutes (37%), respectively. MS for $C_{29}H_{31}F_6N_2O$ $[M+H]^+$ calculated 537.23, found 537.24.

EXAMPLE 100

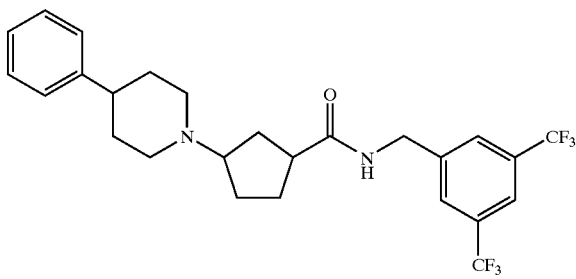

The title compound was prepared starting from 3,5-bis(trifluoro-methyl)benzyl 3-oxo-1-methylcyclopentane-carboxamide (Intermediate 29) and 4-phenylpiperidine using a synthetic sequence analogous to that described in Example 99. Single enantiomers were obtained via chiral HPLC, using Diacel's Chiralcel OD semipreparative column, eluent hexane/ethanol (96:4). The observed retention times (area %) on an identical analytical column (250× 4.6 mm, 1.0 mL/min) for the respective enantiomers were 10.03 (9%), 10.50 (13%), 12.26 (39%) and 14.02 minutes (39%), respectively. MS for $C_{26}H_{29}F_6N_2O$ $[M+H]^+$ calculated 499.21, found 499.20.

EXAMPLE 101

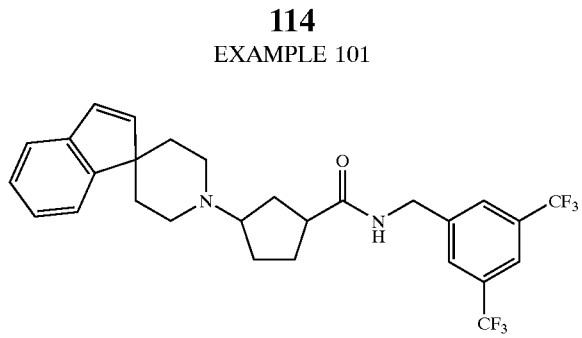

The title compound was prepared starting from 3,5-bis(trifluoro-methyl)benzyl 3-oxocyclopentane-carboxamide and the spiroindenylpiperidine using a synthetic sequence analogous to that described in Example 99. Single enantiomers were obtained via chiral HPLC, using Diacel's Chiralcel OD semipreparative column, eluent hexane/ethanol (96:4). The observed retention times (area %) on an identical analytical column (250×4.6 mm, 1.0 mL/min) for the respective enantiomers were 9.54 (10%), 9.87 (14%), 11.86 (39%) and 13.25 minutes (38%), respectively. MS for $C_{28}H_{29}F_6N_2O$ $[M+H]^+$ calculated 522.21, found 522.22.

INTERMEDIATE 30

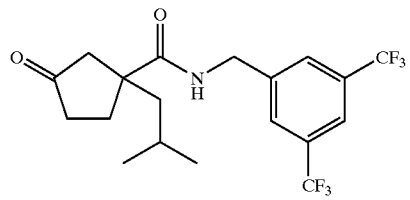

Step A
3-Methylene-1-isobutyl-cyclopentanecarboxylic acid

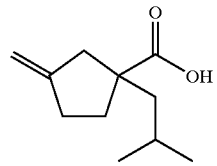

A solution of methyl 3-methylene-1-isobutyl-cyclopentanecarboxylate (see Intermediate 6, Step A, 3.92 g, 19.98 mmol) in a mixture of dioxane (50 mL) and water (50 mL) containing 2.79 g (116.4 mmol) of lithium hydroxide monohydrate was heated to gentle reflux overnight. The solvent was removed in vacuo, the residue was dissolved in water and the pH was adjusted to acidic with 2N HCl. The product was extracted from the aqueous phase with chloroform (6×30 mL). The combined organic extracts were dried (anhydrous magnesium sulfate) and the solvent was removed in vacuo to yield 3.10 g (85%) of the desired product.

Step B
3-Oxo-1-isobutyl-cyclopentanecarboxylic acid

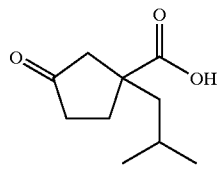

A solution of the 3-methylene-1-isobutyl-cyclopentanecarboxylate (3.10 g, 17.0 mmol) in dichloromethane was cooled to −78° C. and stream of ozone was passed through the stirred solution until a permanent blue color indicated complete consumption of the olefin. The excess ozone was purged with nitrogen, and triphenylphosphine (4.90 g, 18.70 mmol) was added. The cooling bath was removed, and the reaction mixture was stirred at ambient temperature overnight. The solvent was evaporated in vacuo, the residue was diluted with diethyl ether, and the triphenylphosphine oxide was filtered off. The organic solution was washed with aqueous 10% potassium carbonate (1×150 mL). The aqueous phase was washed with diethyl ether (3×50 mL), and set acidic with 2N HCl. The desired acid was extracted into diethyl ether (4×50 mL), dried (anhydrous magnesium sulfate) and the solvent was removed in vacuo to yield 2.72 g (87%) of the desired acid of sufficient purity. $^1$H NMR (CDCl$_3$, 500 MHz): 2.87 (dd, J=18.31, 1.83 Hz, 1H), 2.43 (dp, J=6.64, 1.83 Hz), 2.30 (d, J=16.0 Hz, 1H), 2.30 (d, 2.74 Hz, 1H), 2.15 (d, J=18.07 Hz, 1H), 1.94 (m, 2H), 1.70 (h, J=6.40 Hz, 1H), 1.57 (dd, J=13.96, 6.64 Hz, 1H), 0.93 (d, 6.63 Hz, 3H), 0.92 (d, J=6.63 Hz, 1H).

Step C
3,5-Bis(trifluoromethyl)benzyl 3-oxo-1-isobutylcyclopentane-carboxamide

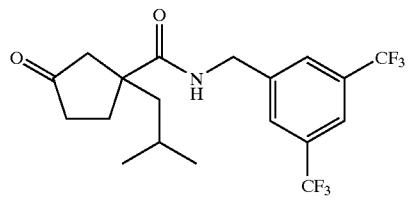

A mixture of the acid from previous step (750 mg, 4.071 mmol), 3,5-bistrifluoromethylbenzylamine hydrochloride (1.138 g, 4.071 mmol), diisopropylethylamine (710 µL, 4.071 mmol), dimethylaminopyridine (60.0 mg 0.491 mmol) in dichloromethane (15 mL) was treated with 1-[3-(dimethylamino)propyl]-3-ethylcarbodiimide hydrochloride (EDC, 1.56 g, 8.14 mmol) and stirred at r.t. for 24 hrs. The reaction mixture was diluted with dichloromethane (20 mL), washed with water (3×30 mL), brine (1×30 mL), dried over anhydrous sodium sulfate and the solvent was evaporated under reduced pressure to yield 1.25 g (75%) of the desired product which was further purified by column chromatography (silica gel, ethyl acetate:hexanes (1:1)) to yield 583 mg (35%) of the pure desired product. LC-MS for C$_{19}$H$_{22}$F$_6$NO$_2$ [M+H]$^+$ calculated 410.15, found 410.20.

EXAMPLE 102

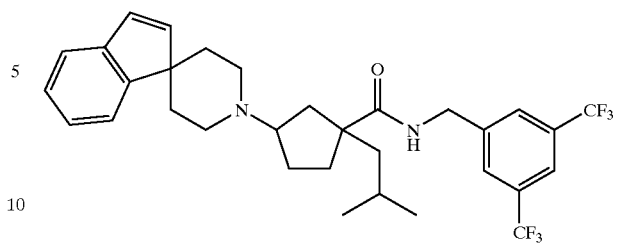

A solution of 3,5-bis(trifluoromethyl)benzyl 3-oxo-1-isobutyl-cyclopentane-carboxamide (Intermediate 30, 82 mg, 0.20 mmol), 4-(spiroindenyl)-piperidine hydrochloride (53 mg, 0.24 mmol), diisopropylethylamine (42 µL, 0.489 mmol) and crushed molecular sieves (4A, 100 mg) in dichloroethane (5 mL) was treated with sodium triacetoxyborohydride (212 mg, 1.0 mmol) and stirred at r.t. 24 hrs. The sieves were filtered off (plug of Celite), washed with dichloromethane and the combined organic washings were extracted with a saturated solution of sodium bicarbonate (1×20 mL), water (3×20 mL), brine (1×20 mL) and dried over anhydrous sodium sulfate. Solvent was evaporated to dryness to yield 95.4 mg of product as a mixture of cis- and trans-diastereoisomers, which were separated using chiral HPLC (Chiralcel OD, 20×200 mm, using a mixture of hexane/ethanol (97:3) as eluent. The retention times of the respective diastereoisomeric pairs on a analytical (250×4.6 mm column) at 1.0 mL/min flow rate were 6.41 (68%) minutes and 8.83 (30%) minutes respectively. LC-MS for C$_{32}$H$_{37}$F$_6$N$_2$O [M+H]$^+$ calculated 579.27, found 579.35.

EXAMPLE 103

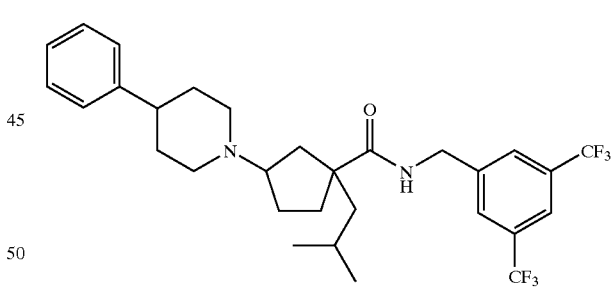

The title compound was prepared starting from 3,5-bis (trifluoromethyl)benzyl 3-oxo-1-isobutylcyclopentane-carboxamide (Intermediate 30) and 4-phenylpiperidine using a synthetic sequence analogous to that described in Example 102. Single enantiomers were obtained via chiral HPLC, using Diacel's Chiralcel OD semipreparative column, eluent hexane/ethanol (97:3). The observed retention times (area %) of the respective enantiomers under analytical conditions (250×4.6 mm column, 1.0 mL/min) were 5.90 (30%), 6.44 (35%), 7.91 (15%) and 8.58 minutes (20%), respectively. LC-MS for C$_{30}$H$_{37}$F$_6$N$_2$O [M+H]$^+$ calculated 555.27, found 555.25.

EXAMPLE 104

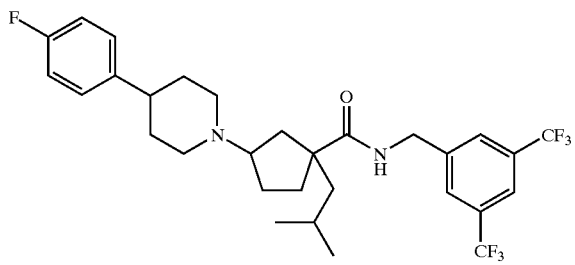

The title compound was prepared starting from 3,5-bis (trifluoromethyl)benzyl 3-oxo-1-isobutylcyclopentane-carboxamide (Intermediate 30) and 4-(4-fluorophenyl)piperidine as described in Example 102. The respective cis- and trans-diastereoisomeric pairs were obtained via chiral HPLC, using Diacel's Chiralcel OD semipreparative column, eluent hexane/ethanol (97:3). The observed retention times (area %) under analytical conditions (250×4.6 mm column, 1.0 mL/min) were 5.92 (70%) and 6.77 minutes (30%), respectively. LC-MS for $C_{30}H_{36}F_7N_2O$ $[M+H]^+$ calculated 573.26, found 573.30.

EXAMPLE 105

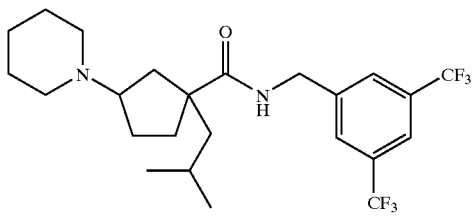

The title compound was prepared starting from 3,5-bis (trifluoromethyl)benzyl 3-oxo-1-isobutylcyclopentane-carboxamide (Intermediate 30) and piperidine as described in Example 102. The respective 1,3-cis- and 1,3-trans diastereoisomeric pairs were obtained via chiral HPLC, using Diacel's Chiralcel OD semipreparative column, eluent hexane/ethanol (97:3). The observed retention times (area %) under analytical conditions (250×4.6 mm column, 1.0 mL/min) were 4.62 (72%) and 5.31 minutes (28%), respectively. LC-MS for $C_{24}H_{33}F_6N_2O$ $[M+H]^+$ calculated 479.24, found 479.20.

EXAMPLE 106

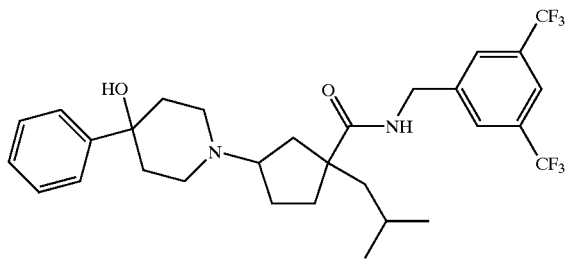

The title compound was prepared starting from 3,5-bis (trifluoromethyl)benzyl 3-oxo-1-isobutylcyclopentane-carboxamide (Intermediate 30) and 4-phenyl-4-hydroxypiperidine as described in Example 102. The respective 1,3-cis and 1,3-trans diastereoisomeric pairs were separated using preparative TLC. LC-MS for $C_{30}H_{37}F_6N_2O_2$ $[M+H]^+$ calculated 571.27, found 571.30.

INTERMEDIATE 31

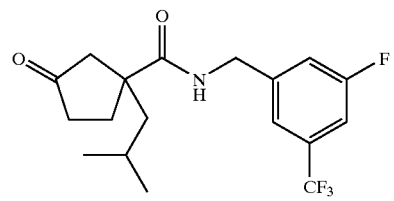

The title compound was synthesized according to a procedure described for preparation of Intermediate 30, except that in Step C 3-fluoro-5-trifluoromethylbenzylamine was used instead of the 3,5-bistrifluoromethylbenzylamine. LC-MS for $C_{18}H_{22}F_4NO_2$ $[M+H]^+$ calculated 360.15, found 360.20.

EXAMPLE 107

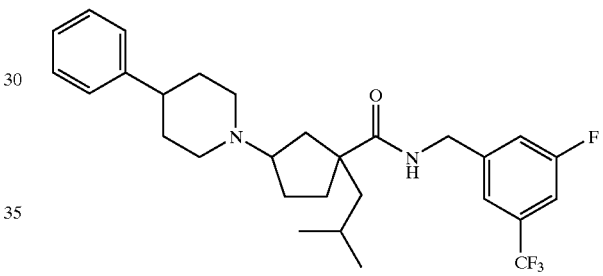

The title compound was prepared starting from 3-fluoro-5-trifluoromethylbenzyl 3-oxo-1-isobutylcyclopentane-carboxamide (Intermediate 31) and 4-phenylpiperidine as described in Example 102. Single enantiomers were obtained via chiral HPLC, using Diacel's Chiralcel OD semipreparative column, eluent hexane/ethanol (98:2). The observed retention times of the respective enantiomers under analytical conditions (250×4.6 mm column, 1.0 mL/min) were 8.69, 9.61, 16.70 and 18.0 minutes, respectively. LC-MS for $C_{29}H_{37}F_4N_2O$ $[M+H]^+$ calculated 505.28, found 505.30.

EXAMPLE 108

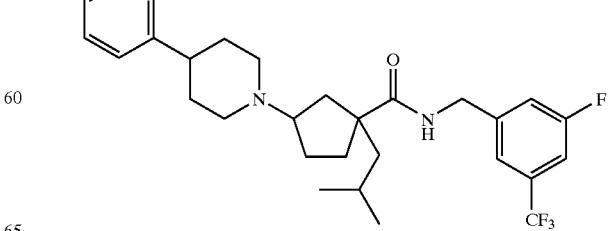

The title compound was prepared starting from 3-fluoro-5-trifluoromethylbenzyl 3-oxo-1-isobutylcyclopentane-carboxamide (Intermediate 31) and 4-(4-fluorophenyl)piperidine as described in Example 102. Single enantiomers were obtained via chiral HPLC, using Diacel's Chiralcel OD semipreparative column, eluent hexane/ethanol (98:2). The observed retention times (area %) of the respective enantiomers under analytical conditions (250×4.6 mm column, 1.0 mL/min) were 8.02 (cis-, enantiomer, 30%), 9.18 (cis-enantiomere, 36%) and 12.62 (trans-racemate, 33%), respectively. LC-MS for $C_{29}H_{36}F_5N_2O$ $[M+H]^+$ calculated 523.27, found 523.25.

EXAMPLE 109

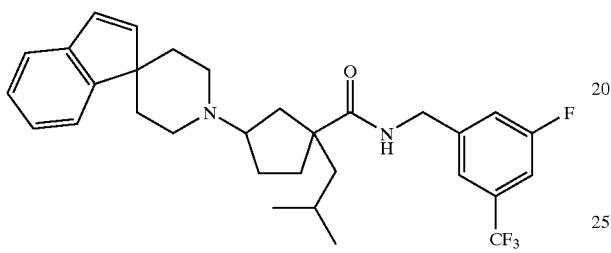

The title compound was prepared starting from 3-fluoro-5-trifluoromethylbenzyl 3-oxo-1-isobutylcyclopentane-carboxamide (Intermediate 31) and 4-spiroindenylpiperidine as described in Example 102. Single enantiomers were obtained via chiral HPLC, using Diacel's Chiralcel OD semipreparative column, eluent hexane/ethanol (97:3). The observed retention times of the respective enantiomers under analytical conditions (250×4.6 mm column, 1.0 mL/min) were 8.89, 9.28, 16.63 and 17.55 minutes, respectively. LC-MS for $C_{32}H_{37}F_4N_2O$ $[M+H]^+$ calculated 523.28, found 523.30.

EXAMPLE 110

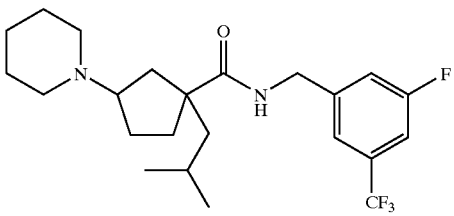

The title compound was prepared starting from 3-fluoro-5-trifluoromethylbenzyl 3-oxo-1-isobutylcyclopentane-carboxamide (Intermediate 31) and piperidine as described in Example 102. The respective 1,3-cis- and 1,3-trans diastereoisomeric pairs were obtained via chiral HPLC, using Diacel's Chiralcel OD semipreparative column, eluent hexane/ethanol (97:3). The observed retention times (area %) were 5.29 (70%) and 7.09 minutes (30%), respectively. LC-MS for $C_{23}H_{33}F_4N_2O$ $[M+H]^+$ calculated 423.25, found 423.30.

EXAMPLE 111

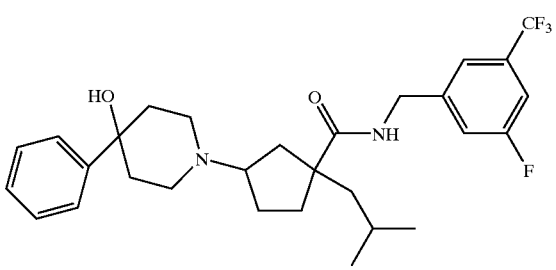

The title compound was prepared starting from 3-fluoro-5-trifluoromethylbenzyl 3-oxo-1-isobutylcyclopentane-carboxamide (Intermediate 31) and 4-phenyl-4-hydroxypiperidine as described in Example 102. LC-MS for $C_{29}H_{37}F_4N_2O_4$ $[M+H]^+$ calculated 521.27, found 521.30.

INTERMEDIATE 32

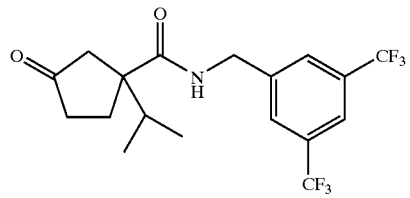

Step A: 3-Methylene-1-isopropylcyclopentanecarboxylic acid

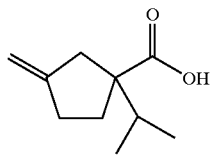

A solution of the methyl 3-methylene-1-isopropylcyclopentanecarboxylate (see Intermediate 3, Step A, 1.21 g, 6.64 mmol) in a mixture of dioxane (4 mL) and water (4 mL) containing 1.114 g (26.56 mmol) of lithium hydroxide monohydrate was homogenized with methanol, and stirred at 80° C. for 48 hrs. The solvent was removed in vacuo, the residue was dissolved in water and the non-acidic components were extracted with diethyl ether (3×30 mL), combined ethers were back-washed with water (1×30 mL). The combined aqueous phases were acidified with 2N HCl and extracted with chloroform (6×30 mL), dried (anhydrous magnesium sulfate) and evaporated to dryness to leave 1.25 g of crude acid. It was used in the next reaction step without any further purification.

Step B: 3,5-Bis(trifluoromethyl)benzyl 3-methylene-1-isopropylcyclopentanecarboxamide

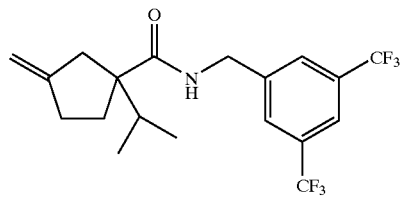

The solution of 3-methylene-1-isopropylcyclopentanecarboxylic acid from the previous step (1.25 g, 7.44 mmol) 3,5-bis(trifluoromethyl)benzylamine hydrochloride (2.08 g, 7.44 mmol), dimethylaminopyridine (111.0 mg, 0.91 mmol) and diisopropylethylamine (1.29 mL, 7.44 mmol) and 1-[3-(dimethylamino)propyl]-3-ethylcarbodiimide hydrochloride (EDC, 2.85 g, 14.9 mmol) in dichloromethane (50 mL) was stirred at room temperature for 24 hrs. The reaction mixture was diluted with dichloromethane (100 mL) and washed with water (3×50 mL), brine (1×50 mL), dried (anhydrous sodium sulfate) and the solvent was evaporated under reduced pressure. The crude product was purified via mplc (Lobar Fertigsaule, LiChroprep, 40–63 μm, ethyl acetate/hexanes (1:4)) yielding 910 mg (31%) of pure product. $^1$H NMR (500 MHz, CDCl$_3$): 7.76 (s, 1H), 7.70 (s, 2H), 6.20 (bs, 1H), 4.95 (bs, 1H), 4.88 (bs, 1H), 4.65 (dd, J=15.70, 6.40 Hz, 1H), 4.50 (dd, J=15.50, 5.70 Hz, 1H), 2.68 (bd, J=16.20 Hz, 1H), 2.50 to 2.10 (bm, 4H), 1.96 (h, J=6.9 Hz, 1H), 1.74 (m, 1H), 0.87 (d, J=6.9 Hz, 3H), 0.85 (d, J=7.3 Hz, 3H).

Step C: 3,5-Bis(trifluoromethyl)benzyl 3-oxo-1-isopropylcyclopentanecarboxamide

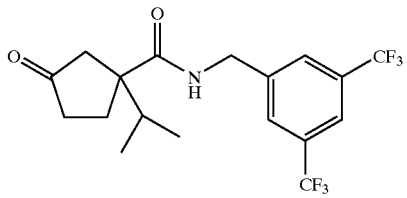

A solution of 3,5-bis(trifluoromethyl)benzyl 3-methylene-1-isopropylcyclopentane-carboxamide (910 mg, 2.31 mmol) in dichloromethane (50 mL) was cooled to −78° C. and a stream of ozone was passed through until the permanent blue color indicated complete consumption of the olefin. The excess ozone was purged with a stream of nitrogen, and triphenylphosphine (729 mg, 2.78 mmol) was added. The cooling bath was removed, and the reaction mixture was allowed to stir at ambient temperature overnight. The solvent was removed in vacuo, the residue was purified by column chromatography (silica gel, ethyl acetate hexane/1:2) to give 760.7 mg (83%) of the desired product. $^1$H NMR (500 MHz, CDCl$_3$): 7.81 (s, 1H), 7.74 (s, 2H), 6.16 (bs, 1H), 6.61 (m, 2H), 2.78 (bd, J=18.07 Hz, 1H), 2.40 to 2.20 (bm, 4H), 2.08–1.98 (m, 2H), 0.99 (d, J=6.86 Hz, 3H), 0.97 (d, J=6.87 Hz, 3H).

EXAMPLE 112

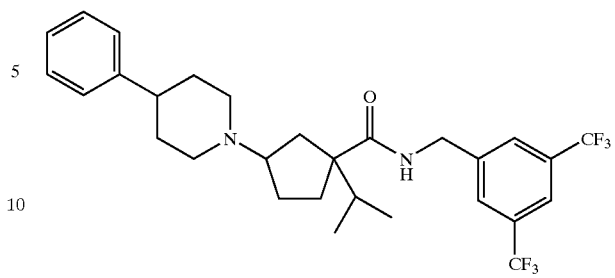

A solution of 3,5-bis(trifluoromethyl)benzyl 3-oxo-1-isopropylcyclopentane-carboxamide (Intermediate 32, 40.0 mg, 0.1 mmol) 4-phenylpiperidine hydrochloride (20.0 mg, 0.1 mmol), diisopropylethylamine (18 μL, 0.1 mmol) and crushed molecular sieves (4A, 70 mg) in dichloroethane (5 mL) was treated with sodium triacetoxyborohydride (65 mg, 0.3 mmol) and stirred at r.t. 24 hrs. The sieves were filtered off (plug of Celite), washed with dichloromethane and the combined organic washings were extracted with a saturated solution of sodium bicarbonate (1×10 mL), water (3×10 mL), brine (1×10 mL) and dried over anhydrous sodium sulfate. Solvent was evaporated to dryness to yield 37.6 mg (70%) of product as a mixture of cis- and trans-diastereoisomers. These were separated using chiral HPLC (Chiralcel OD, 20×200 mm, using a mixture of hexane/ethanol (98:2) as eluent. The retention times of the respective diastereoisomeric pairs on a analytical (250×4.6 mm column) at 1.0 mL/min flow rate were 8.47 minutes 9.25 minutes, 12.08 minutes, and 14.32 minutes, respectively. LC-MS for $C_{29}H_{35}F_6N_2O$ [M+H]$^+$ calculated 541.26, found 541.30.

EXAMPLE 113

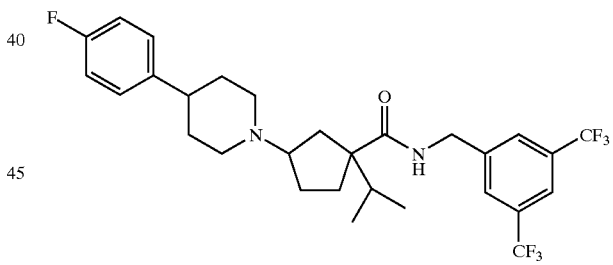

The title compound was prepared by a synthetic sequence analogous to that described in Example 112 except that 4-(4-fluorophenyl)piperidine hydrochloride was used instead of 4-phenylpiperidine hydrochloride. The respective cis- and trans diastereoisomeric pairs were obtained via chiral HPLC, using Diacel's Chiralcel OD semipreparative column, eluent hexane/ethanol (98:2). The retention times observed on a analogous analytical (250×4.6 mm) column at a flow rate of 1.0 mL/min were 8.2 minutes and 10.8 minutes, respectively. The cis-diastereoisomeric pair (eluting first on the OD column) was separated into single enantiomers using the Chiralpak AD semipreparative column, eluent hexane:ethanol/95:5. The retention times observed on a analogous analytical (250×4.6 mm) column at a flow rate of 1.0 mL/min were 7.3 minutes and 11.2 minutes, respectively. LC-MS for $C_{32}H_{37}F_6N_2O$ [M+H]$^+$ calculated 579.27, found 579.35.

EXAMPLE 114

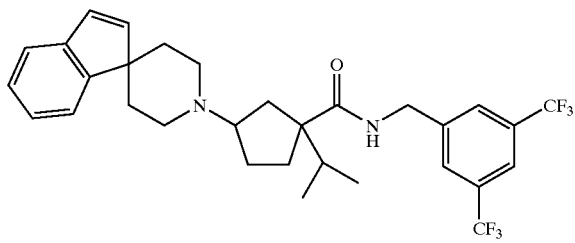

The title compound was prepared by a synthetic sequence analogous to that described in Example 112 except that spiroindenylpiperidine hydrochloride was used instead of 4-phenylpiperidine hydrochloride. Single enantiomers were obtained via chiral HPLC, using Diacel's Chiralcel OD semipreparative column, eluent hexane/ethanol (98:2). The observed retention times (area %) of the respective enantiomers under analytical conditions (250×4.6 mm column, 1.0 mL/min) were 8.60 (27%), 10.08 (27%), 13.14 (22%) and 17.77 minutes (23%), respectively. LC-MS for $C_{31}H_{35}F_6N_2O$ $[M+H]^+$ calculated 565.26, found 565.30.

EXAMPLE 115

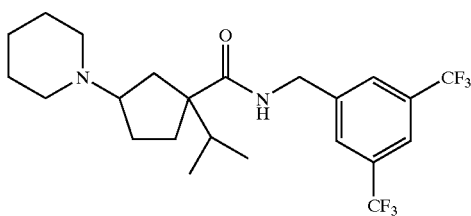

The title compound was prepared by a synthetic sequence analogous to that described in Example 112 except that piperidine was used instead of 4-phenylpiperidine hydrochloride. The respective cis- and trans diastereoisomeric pairs were obtained via chiral HPLC, using Diacel's Chiralcel OD semipreparative column, eluent hexane/ethanol (98:2). The observed retention times under analytical conditions (250×4.6 mm column, 1.0 mL/min) were 5.88 (72%) and 7.59 (27%), respectively. LC-MS for $C_{23}H_3OF_6N_2O$ $[M+H]^+$ calculated 465.23, found 465.25.

EXAMPLE 116

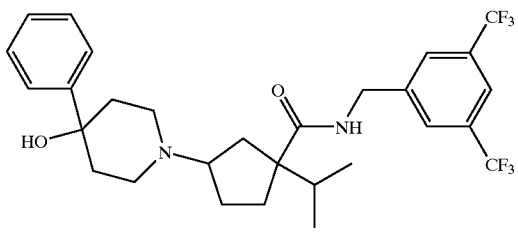

The title compound was prepared by a synthetic sequence analogous to that described in Example 112 except that 4-hydroxy-4-phenylpiperidine hydrochloride was used instead of 4-phenylpiperidine hydrochloride. Single enantiomers were obtained via chiral HPLC, using Diacel's Chiralcel OD semipreparative column, eluent hexane/ethanol (97:3). LC-MS for $C_{29}H_{35}F_6N_2O_2$ $[M+H]^+$ calculated 557.25, found 557.35.

EXAMPLE 117

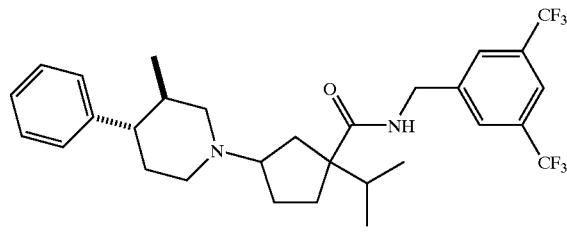

The title compound was prepared by a synthetic sequence analogous to that described in Example 112 except that 4-(3R,S 4S,R,)-4-phenyl-3-methylpiperidine hydrochloride was used instead of 4-phenylpiperidine hydrochloride. LC-MS for $C_{30}H_{37}F_6N_2O_2$ $[M+H]^+$ calculated 555.27, found 555.25.

EXAMPLE 118

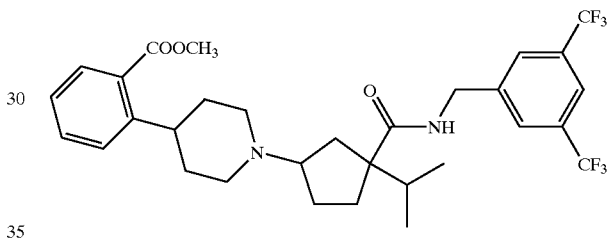

The title compound was prepared by a synthetic sequence analogous to that described in Example 112 except that 4-(2-methoxycarbonylphenyl)piperidine hydrochloride was used instead of 4-phenylpiperidine hydrochloride. LC-MS for $C_{31}H_{37}F_6N_2O$ $[M+H]$ calculated 599.26, found 599.35.

EXAMPLE 119

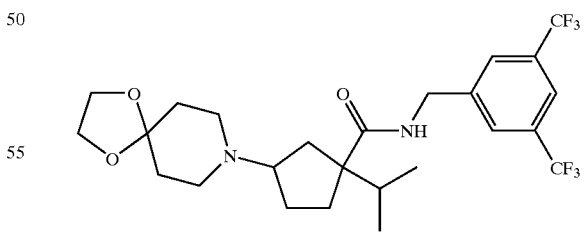

The title compound was prepared by a synthetic sequence analogous to that described in Example 112 except that 4-ethylenedioxy-piperidine hydrochloride was used instead of 4-phenylpiperidine hydrochloride. LC-MS for $C_{25}H_{33}F_6N_2O_3$ $[M+H]^+$ calculated 523.23, found 523.30.

EXAMPLE 120

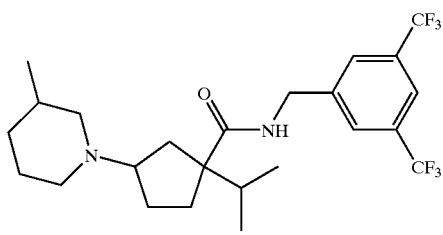

The title compound was prepared by a synthetic sequence analogous to that described in Example 112 except that 3-methylpiperidine hydrochloride was used instead of 4-phenylpiperidine hydrochloride. LC-MS for $C_{24}H_{33}F_6N_2O$ [M+H]$^+$ calculated 479.24, found 479.20.

EXAMPLE 121

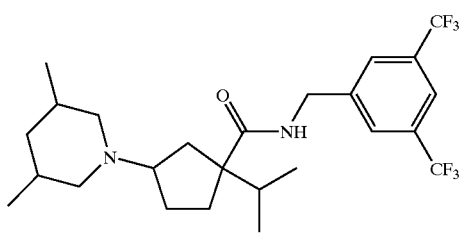

The title compound was prepared by a synthetic sequence analogous to that described in Example 112 except that 3,5-dimethylpiperidine hydrochloride was used instead of 4-phenylpiperidine hydrochloride. LC-MS for $C_{25}H_{35}F_6N_2O$ [M+H]$^+$ calculated 493.26, found 493.30.

EXAMPLE 122

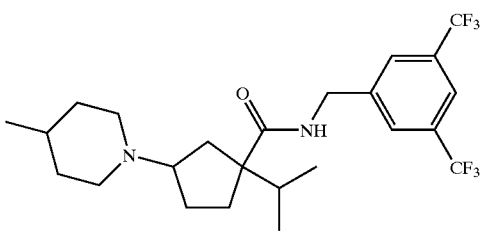

The title compound was prepared by a synthetic sequence analogous to that described in Example 112 except that 4-methylpiperidine hydrochloride was used instead of 4-phenylpiperidine hydrochloride. LC-MS for $C_{24}H_{33}F_6N_2O$ [M+H]$^+$ calculated 479.24, found 479.20.

EXAMPLE 123

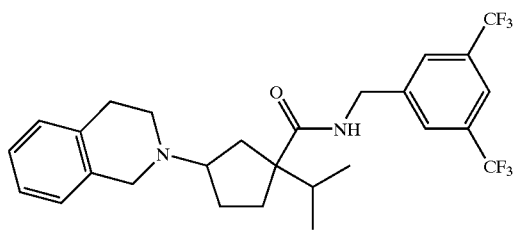

The title compound was prepared by a synthetic sequence analogous to that described in Example 112 except that 1,2,3,4-tetrahydroisoquinoline hydrochloride was used instead of 4-phenylpiperidine hydrochloride. LC-MS for $C_{27}H_{31}F_6N_2O$ [M+H]$^+$ calculated 513.23, found 513.25.

EXAMPLE 124

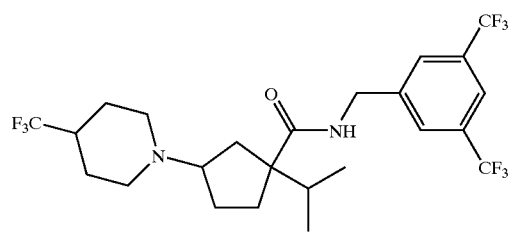

The title compound was prepared by a synthetic sequence analogous to that described in Example 112 except that 4-trifluoromethylpiperidine hydrochloride was used instead of 4-phenylpiperidine hydrochloride. LC-MS for $C_{24}H_{30}F_9N_2O$ [M+H]$^+$ calculated 533.21, found 533.20.

EXAMPLE 125

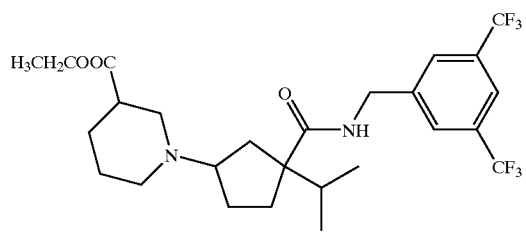

The title compound was prepared by a synthetic sequence analogous to that described in Example 112 except that 3-ethoxycarbonylpiperidine hydrochloride was used instead of 4-phenylpiperidine hydrochloride. LC-MS for $C_{26}H_{35}F_6N_2O_3$ [M+H]$^+$ calculated 537.25, found 537.25.

EXAMPLE 126

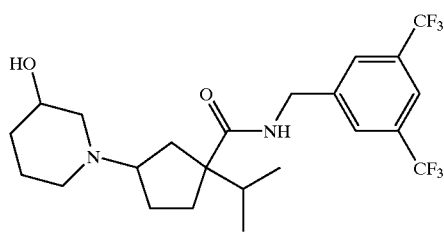

The title compound was prepared by a synthetic sequence analogous to that described in Example 112 except that 3-hydroxypiperidine hydrochloride was used instead of 4-phenylpiperidine hydrochloride. LC-MS for $C_{23}H_{31}F_6N_2O_2$ [M+H]$^+$ calculated 481.22, found 481.15.

EXAMPLE 127

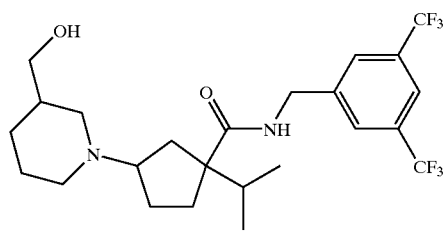

The title compound was prepared by a synthetic sequence analogous to that described in Example 112 except that 3-hydroxymethylpiperidine hydrochloride was used instead of 4-phenylpiperidine hydrochloride. LC-MS for $C_{24}H_{33}F_6N_2O_2$ [M+H]$^+$ calculated 495.24, found 495.25.

EXAMPLE 128

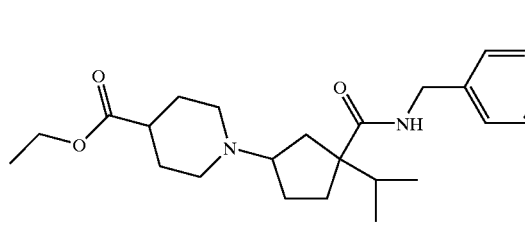

The title compound was prepared by a synthetic sequence analogous to that described in Example 112 except that 4-ethoxycarbonylpiperidine hydrochloride was used instead of 4-phenylpiperidine hydrochloride. LC-MS for $C_{26}H_{35}F_6N_2O_3$ [M+H]$^+$ calculated 49537.25, found 537.25.

EXAMPLE 129

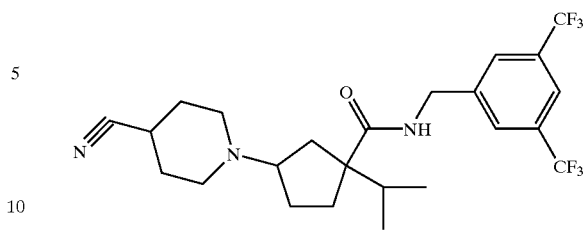

The title compound was prepared by a synthetic sequence analogous to that described in Example 112 except that 4-cyanopiperidine hydrochloride was used instead of 4-phenylpiperidine hydrochloride. LC-MS for $C_{24}H_{30}F_6N_3O$ [M+H]$^+$ calculated 490.22, found 490.30.

EXAMPLE 130

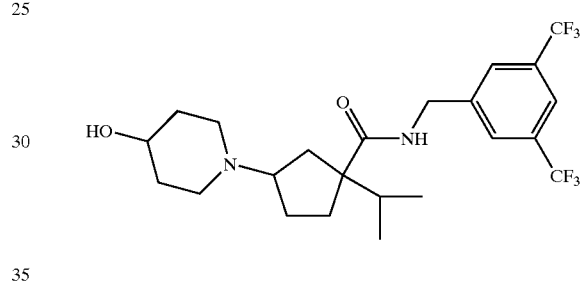

The title compound was prepared by a synthetic sequence analogous to that described in Example 112 except that 4-hydroxypiperidine hydrochloride was used instead of 4-phenylpiperidine hydrochloride. LC-MS for $C_{23}H_{31}F_6N_2O_2$ [M+H]$^+$ calculated 481.22, found 481.30.

EXAMPLE 131

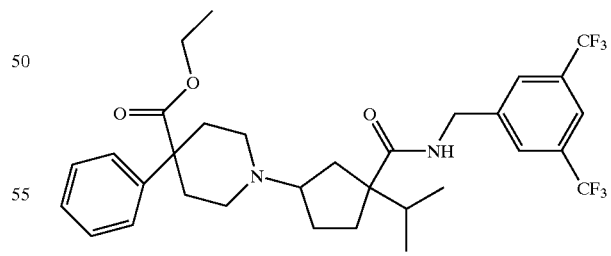

The title compound was prepared by a synthetic sequence analogous to that described in Example 112 except that 4-ethoxy-4-phenylcarbonylpiperidine hydrochloride was used instead of 4-phenylpiperidine hydrochloride. LC-MS for $C_{32}H_{39}F_6N_2O_3$ [M+H]$^+$ calculated 613.28, found 613.25.

EXAMPLE 132

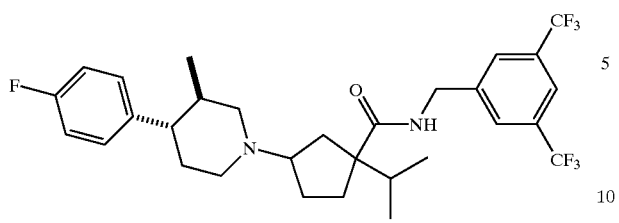

The title compound was prepared by a synthetic sequence analogous to that described in Example 112 except that trans-(4-fluorophenyl)-3-methylpiperidine hydrochloride was used instead of 4-phenylpiperidine hydrochloride. LC-MS for $C_{30}H_{37}N_2OF_7$ [M+H]$^+$ calculated 573.26, found 573.25.

INTERMEDIATE 33

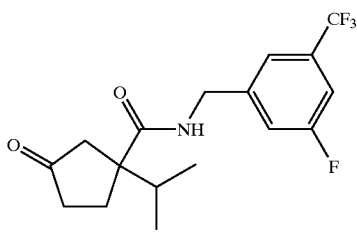

Step A: 3-Oxo-1-isopropylcyclopentanecarboxylic acid

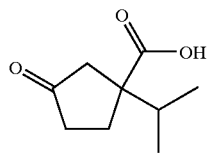

A solution of methyl 3-oxo-1-isopropylcyclopentanecarboxylate (see Intermediate 12, Step D, 27 g, 146.6 mmol) in dioxane (300 mL) and conc HCl (100 mL) was heated to reflux overnight. The crude product was extracted into diethyl ether (4×200 mL) and the combined organic extracts were washed with an aqueous solution of sodium hydroxide (5N, 2×150 mL). The combined aqueous extracts were cooled to 0° C. and acidified with conc HCl. The product was extracted with ether (3×200 mL), dried with magnesium sulfate and the solvent was evaporated in vacuo. The weight of the product was 20 g (98%). $^1$H NMR (500 MHz, CDCl$_3$): 2.81 (d, J=8.54 Hz, 1H), 2.48 (m, 1H), 2.32 (m, 2H), 2.15 (d, J=18.53 Hz, 1H), 2.08 (m, 1H), 1.95 (m, 1H), 1.03 (d, J=6.86 Hz, 3H), 0.96 (d, J=6.87 Hz, 1H).

Step B: 1-Isopropyl-3-oxocyclopentanoyl chloride

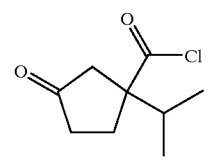

A solution of 1-isopropyl-3-oxocyclopentylcarboxylic acid (20.1 g, 118.9 mmol) in benzene (150 mL) was slowly treated with thionyl chloride (23.5 mL, 322.1 mmol) and the resulting solution was stirred at 45° C. for 3 hours. The solvent and the volatile components were evaporated under reduced pressure (100 torr) and the residue was distilled to obtain 6.727 g (30%) of the desired product, B.P.: 110–114° C. at 5 torr. $^1$H NMR (500 MHz, CDCl$_3$): 2.82 (dd, J=18.36, 1.76 Hz, 1H), 2.50 (m, 1H), 2.35 (m, 2H), 2.20 to 190 (bm, 3H), 1.03 (bd, J=8.2 Hz, 6H).

Step C: 3-Fluoro-5-trifluoromethylbenzyl 3-oxo-1-isopropylpentane-carboxamide

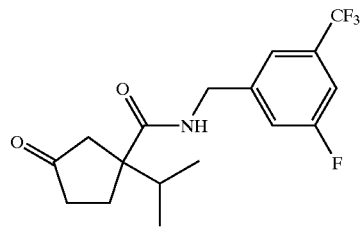

A solution of 3-fluoro-5-trifluoromethylbenzylamine (3.07g, 15.9 mmol) and diisopropylethylamine (2.77 mL, 15.9 mmol) in dichloromethane (60 mL) was slowly treated with 1-isopropyl-3-oxocyclopentanoyl chloride (3.0 g, 15.9 mmol) and stirred at ambient temperature overnight. The mixture was diluted with dichloromethane washed with a saturated solution of sodium bicarbonate, 2N HCl, water and brine. The organic phase was dried with anhydrous magnesium sulfate and the solvent was evaporated in vacuo to yield 6.0 g of crude product. This was further purified by column chromatography (silica gel, ethyl acetate hexane (40:60%) to yield 4.10 g (85%) of the pure product. $^1$H NMR (500 MHz, CDCl$_3$): 7.32 (s, 1H), 7.23 (d, J=8.23 Hz, 1H), 7.19 (d, J=8.93 Hz, 1H), 4.52 (m, 2H), 2.79 (d, J=18.53 Hz, 1H), 2.40 to 2.18 (bm, 4H), 2.0 (m, 2H), 0.98 (d, J=6.63 Hz, 3H), 0.96 (d, 6.60 Hz, 3H).

EXAMPLE 133

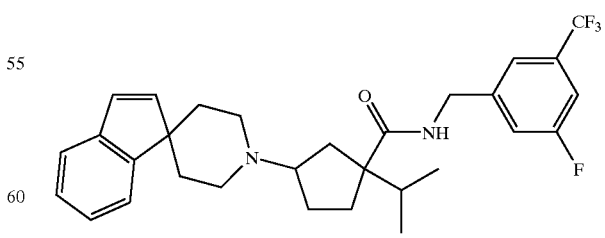

A solution of 3-fluoro-5-trifluoromethylbenzyl 3-oxo-1-isopropylpentane-carboxamide (Intermediate 33, 66.0 mg, 0.2 mmol), 4-spiroindenylpiperidine hydrochloride (44.0 mg, 0.2 mmol), diisopropylethylamine (35 µL, 0.2 mmol)

and crushed molecular sieves (4A, 90 mg) in dichloroethane (3 mL) was treated with sodium triacetoxyborohydride (127 mg, 0.6 mmol) and stirred at r.t. 24 hrs. The sieves were filtered off (plug of Celite), washed with dichloromethane and the combined organic washings were washed with a saturated solution of sodium bicarbonate (1×10 mL), water (3×10 mL), brine (1×10 mL) and dried over anhydrous sodium sulfate. The eluent was evaporated in vacuo and the residue was further purified by preparative TLC (ethyl acetate as eluent) to yield 52.6 mg (51%) of product as a mixture of cis- and trans-diastereoisomers. These were separated using chiral HPLC (Chiralcel OD, 20×200 mm, using a mixture of hexane/ethanol (97:3) as eluent. The retention times of the respective enantiomers on a analytical (250×4.6 mm column) at 1.0 mL/min flow rate were 7.60, 8.40, 11.2 and 14.5 minutes, respectively. LC-MS for $C_{30}H_{35}F_4N_2O$ $[M+H]^+$ calculated 515.26, found 515.20.

EXAMPLE 134

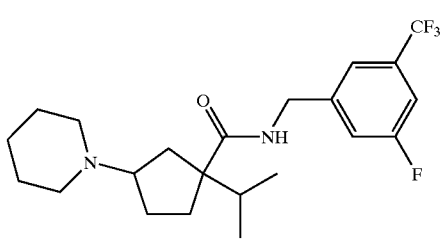

The title compound was prepared by a synthetic sequence analogous to that described in Example 133 except that piperidine was used instead of 4-spiroindenylpiperidine hydrochloride. Single enantiomers were obtained via chiral HPLC, using Diacel's Chiralcel OD semipreparative column, eluent hexane/ethanol (97:3). The observed retention times under analytical conditions (250×4.6 mm column, 1.0 mL/min) were 5.50 (cis-enantiomer), 5.90 (cis-enantiomer) and 6.90 (trans-racemate), respectively. LC-MS for $C_{22}H_{31}F_4N_2O$ $[M+H]^+$ calculated 415.23, found 415.30.

EXAMPLE 135

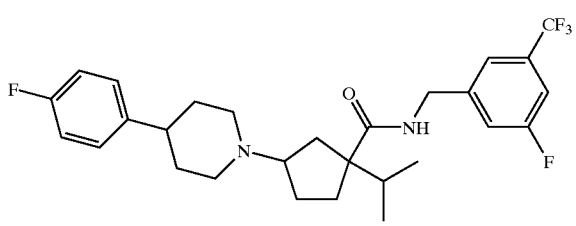

The title compound was prepared by a synthetic sequence analogous to that described in Example 133 except that 4-(4-Fluorophenyl)piperidine was used instead of 4-spiroindenylpiperidine hydrochloride. Single enantiomers were obtained via chiral HPLC, using Diacel's Chiralcel OD semipreparative column, eluent hexane/ethanol (97:3). The observed retention times under analytical conditions (250× 4.6 mm column, 1.0 mL/min) were 7.90 (cis-racemate) and 9.50 (trans-racemate), respectively. LC-MS for $C_{28}H_{34}F_5N_2O$ $[M+H]^+$ calculated 509.25, found 509.30.

INTERMEDIATE 34

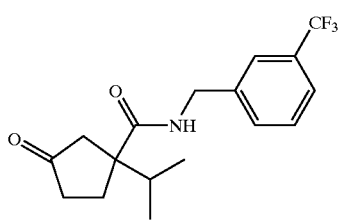

The title compound was synthesized as described for Intermediate 32, except that in Step C 3,5-bisrifluoromethylbenzylamine was replaced by 3-trifluoromethylbenzylamine.

EXAMPLE 136

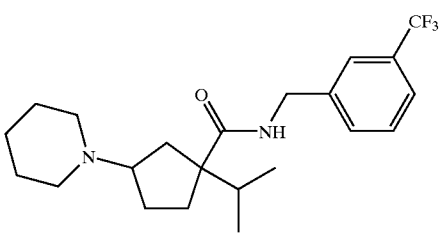

The title compound was prepared by a synthetic sequence analogous to that described in Example 133 except that Intermediate 33 was replaced by Intermediate 34 and 4-spiroindenylpiperidine was replaced with piperidine. The respective 1,3-cis- and 1,3-trans-diastereoisomeric pairs were obtained via chiral HPLC, using Diacel's Chiralcel OD semipreparative column, eluent hexane/ethanol (98:2). The observed retention times under analytical conditions (250× 4.6 mm column, 1.0 mL/min) were 5.90 and 7.30 minutes, respectively. LC-MS for $C_{22}H_{32}F_3N_2O$ $[M+H]^+$ calculated 397.24, found 397.30.

EXAMPLE 137

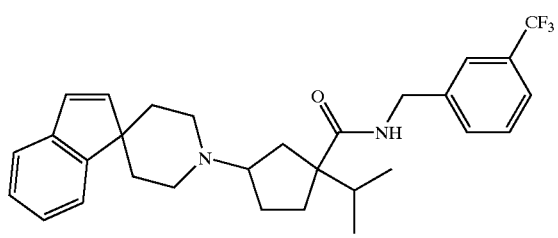

The title compound was prepared by a synthetic sequence analogous to that described in Example 133 except that Intermediate 33 was replaced by Intermediate 34. Single enantiomers were obtained via chiral HPLC, using Diacel's Chiralcel OD semipreparative column, eluent hexane/ethanol (97:3). The observed retention times under analytical conditions (250×4.6 mm column, 1.0 mL/min) were 9.10, 9.90, 14.0 and 17.0 minutes, respectively. LC-MS for $C_{30}H_{36}F_3N_2O$ $[M+H]^+$ calculated 497.27, found 497.30.

EXAMPLE 138

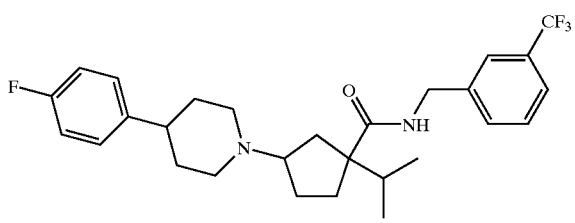

The title compound was prepared by a synthetic sequence analogous to that described in Example 133 except that Intermediate 33 was replaced by Intermediate 34 and 4-spiroindenylpiperidine was replaced with 4-(4-fluorophenyl)piperidine. The respective 1,3-cis- and 1,3-trans-diastereoisomeric pairs were obtained via chiral HPLC, using Diacel's Chiralcel OD semipreparative column, eluent hexane/ethanol (97:3). The observed retention times under analytical conditions (250×4.6 mm column, 1.0 mL/min) were 8.0 and 10.9 minutes, respectively. LC-MS for $C_{28}H_{35}F_4N_2O$ $[M+H]^+$ calculated 491.26, found 491.30.

EXAMPLE 139

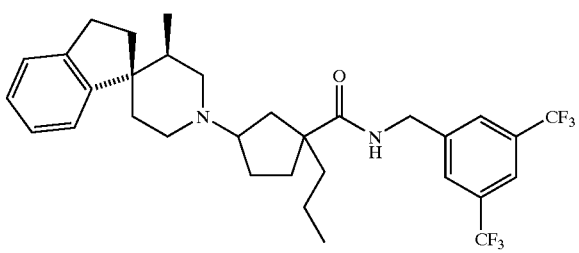

A solution of olefin listed under Example 96 (single isomer, the first eluting enantiomer, as a hydrochloride, 12.2 mg, 0.0198 mmol) in ethyl alcohol (5 mL) was treated with palladium on charcoal (10 mg, 10%) and hydrogenated (balloon pressure) at ambient temperature for 15 minutes. LC-MS indicated complete conversion and the catalyst was filtered off through Celite. Evaporation of the solvent gave the desired product (7.9 mg, 65%) in a form of the respective hydrochloride salt LC-MS for $C_{32}H_{39}F_6N_2O$ $[M+H]^+$ calculated 581.29, found 581.35.

EXAMPLE 140

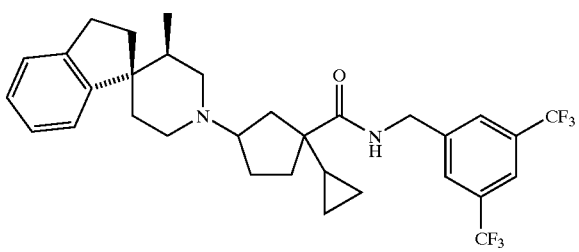

The title compound was prepared by a hydrogenation analogous to that described in Example 139 starting from olefin listed under Example 67, single isomer, the second eluting enantiomer. LC-MS for $C_{32}H_{39}F_6N_2O$ $[M+H]^+$ calculated 581.29, found 581.35.

EXAMPLE 141

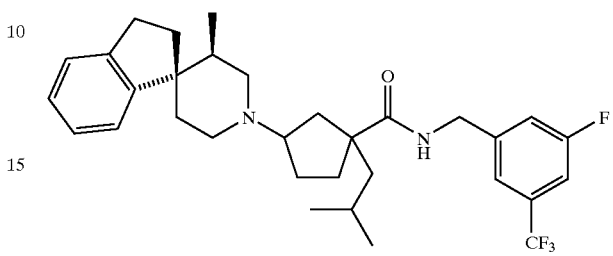

The title compound was prepared by a hydrogenation analogous to that described in Example 139 starting from olefin listed under Example 32, single isomer, the first eluting enantiomer. LC-MS for $C_{32}H_{41}F_4N_2O$ $[M+H]^+$ calculated 545.31, found 545.50.

EXAMPLE 142

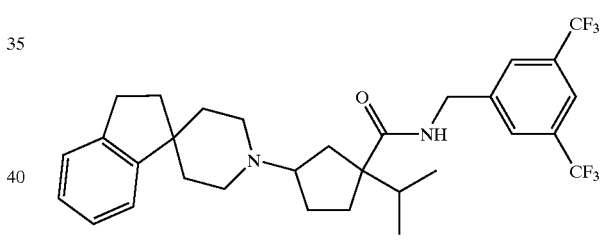

The title compound was prepared by a hydrogenation analogous to that described in Example 139 starting from the olefin described in Example 114. LC-MS for $C_{31}H_{37}F_6N_2O$ $[M+H]^+$ calculated 567.27, found 567.25.

EXAMPLE 143

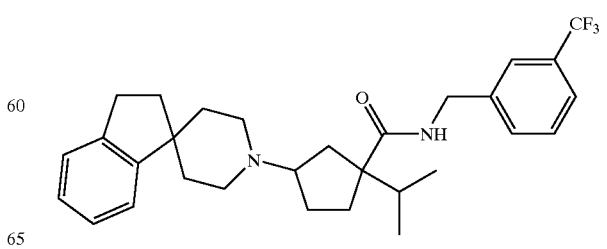

The title compound was prepared by a hydrogenation analogous to that described in Example 139 starting from the olefin described in Example 137. LC-MS for $C_{30}H_{38}F_3N_2O$ [M+H]$^+$ calculated 499.29, found 499.30.

EXAMPLE 144

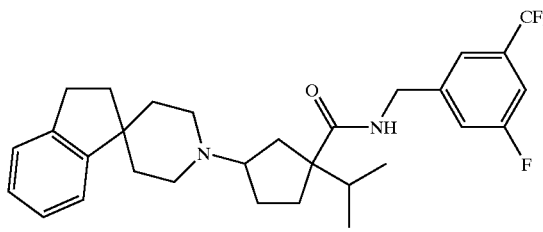

The title compound was prepared by a hydrogenation analogous to that described in Example 139 starting from the olefin described in Example 133. LC-MS for $C_{30}H_{37}F_4N_2O$ [M+H]$^+$ calculated 517.28, found 517.30.

EXAMPLE 145

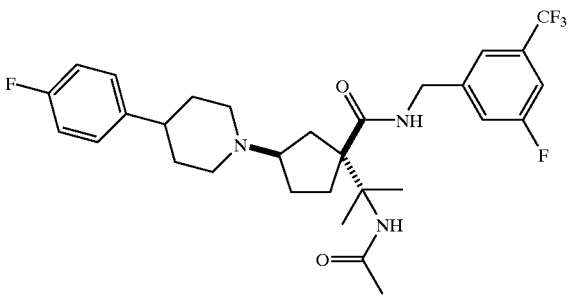

A solution of the alcohol from Example 87 (70.3 mg, 0.125 mmol) in acetonitrile (2.0 mL) was cooled to 0° C. and sulfuric acid (4.0 mL, conc.) was slowly added. The cooling bath was removed, and the stirring was continued at ambient temperature for 6 hrs. The reaction mixture was poured onto ice, and the pH was adjusted to basic (aq. NaOH, 50%). The crude product was extracted with a mixture of chloroform and isopropyl alcohol (85:15, 3×30 mL), dried (anhydrous sodium sulfate) and evaporated to dryness. The residue was further purified via preparative TLC (ethyl acetate:ethyl alcohol:ammonium hydroxide/90:8:2) to yield 11.2 mg (16%). $^1$H NMR (500 MHz, CDCl$_3$): 8.99 (bs, 1H), 7.96 (s, 1H), 7.38 (bs, 1H), 7.24 (m, 2H), 6.98 (m, 4H), 4.52 (dd, J=15.33, 5.95 Hz, 1H), 4.48 (dd, J=15.56, 5.27 Hz, 1H), 3.22 (bd, J=11.0 Hz, 1H), 3.80 (bd, J=11.0 Hz, 1H), 2.76 (m, 1H), 2.48 (bt, J=12.13 Hz, 1H), 2.16 (dd, J=15.10, 8.47 Hz, 1H), 2.02 (m, 5H), 1.94 (s, 3H), 1.90 m (1H), 1.82 (m, 2H), 1.70 (m, 1H), 1.58 (s, 3H), 1.40 (s, 3H). LC-MS for $C_{30}H_{37}F_5N_3O_2$ [M+H]$^+$ calculated 566.27, found 566.35.

EXAMPLE 146

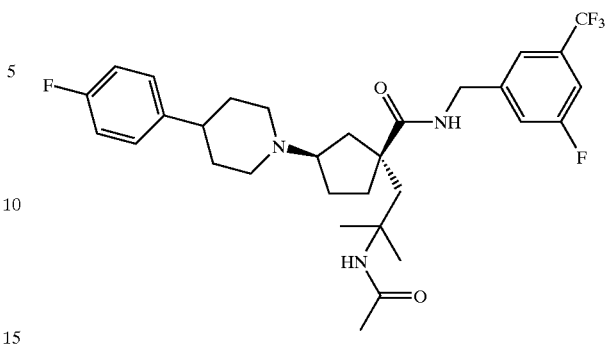

The title compound was prepared starting with the olefin from Example 89 by a Ritter reaction analogous to that described in Example 145. $^1$H NMR (500 MHz, CDCl$_3$): 9.46 (bt, J=4.81 Hz, 1H), 7.37 (s, 1H), 7.25 (m, 2H), 6.97 (m, 4H), 5.5 (bs, 1H), 4.52 (dd, J=15.10, 5.72 Hz, 1H), 4.47 (dd, J=15.10, 5.26 Hz, 1H), 3.28 (bd, J=10.98 Hz) 3.05 (bd, J=10.76 Hz, 1H), 2.85, (m, 1H), 2.63 (d, J=14.64 Hz, 1H), 2.48 (bt, J=12.13 Hz, 1H), 2.34 (d, J=14.87 Hz, 1H), 2.10 (bd J=6.18 Hz, 1H), 1.85 to 2.0 (m, 6H), 1.82 (s, 3H), 1.60 (m, 2H), 1.46 (s, 3H), 1.38 (s, 3H), 1.2 to 1.30 (m, 2H). LC-MS for $C_{31}H_{39}N_3O_2F_5$ [M+H]$^+$ calculated 580.29, found 580.30.

INTERMEDIATE 35

Step A

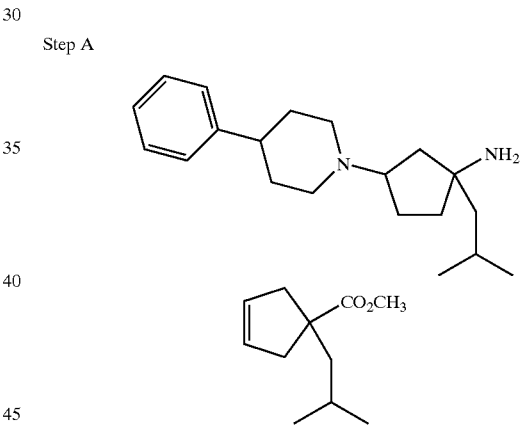

To a cooled (−78° C.) solution of diisopropylamine (38.7 mL, 0.295 Mol) in anhydrous tetrahydrofuran (300 mL) under an atmosphere of nitrogen was added slowly butyl lithium (118 mL of a 2.5M solution in hexanes, 0.295 Mol), and the resulting mixture stirred at −78° C. for 10 min. To this mixture was added methyl-3-cyclopentenecarboxylate (31 g, 0.246 Mol), after stirring for a further 15 min 2-bromo-3-methylpropane (53 mL, 0.49 Mol) was added, and the mixture continued stirring at −78° C. for 30 min then allowed to rise to +4° C. and left standing at this temperature overnight. The reaction mixture was poured in 5% citric acid (1 liter) and extracted with diethyl ether (3×300 mL). The combined diethyl ether layers were washed with water (2×500 mL), saturated NaCl (1×100 ml), dried over MgSO$_4$, filtered and concentrated in vacuo. The residue was purified by vacuum distillation (bp 56° C. @ 5 mm Hg) to provide 30 g (68%) of product.

H NMR (CDCl$_3$, 400 MHz): δ 5.59 (s, 2H), 3.61 (s, 3H), 2.90 (dd, J=16.8, 2.8 Hz, 2H), 2.30 (dd, J=16.8, 2.4 Hz, 2H), 1.66 (m, 3H), 0.85 (d, J=6.4 Hz, 6H).

Step B

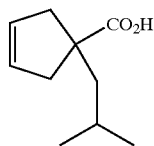

To a solution of the ester prepared in Step A (6 g, 33 mmol) in ethanol (100 mL), was added a solution of potassium hydroxide (6 g, 107 mmol) in water (30 mL), and the resulting mixture heated at reflux for 12 hr. After cooling the ethanol was removed by concentration in vacuo, and the residue was diluted with more water (50 mL). The aqueous mixture was washed with diethyl ether (3×100 mL), then acidified to pH=1 with concentrated hydrochloric acid. The resulting mixture was extracted with diethyl ether (3×100 mL), the combined ethereal layers were washed with water (1×100 mL), saturated NaCl (1×50 mL), dried over MgSO$_4$, filtered and concentrated in vacuo to give 5.29 g (97%) of product.

H NMR (CDCl$_3$, 500 MHz): δ 5.63 (s, 2H), 2.96 (d, J=15.0 Hz, 2H), 2.35 (d, J=15.0 Hz, 2H), 1.73 (m, 3H), 0.91 (d, J=6.5 Hz, 6H).

Step C

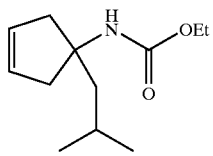

To a solution of the cyclopentene acid prepared in step B (5.29 g, 31.9 mmol) in anhydrous toluene (100 mL) under an atmosphere of nitrogen, was added diphenylphosphoryl azide (13.7 mL, 63.7 mmol), and triethylamine (8.88 mL, 63.7 mmol), and the resulting mixture stirred at 80° C. for 2 hours. The cooled reaction mixture was concentrated in vacuo, and the residue was partitioned between ethyl acetate (100 mL) and saturated NaHCO$_3$, the organic layer was washed with water (100 mL), saturated NaCl (50 mL), dried over MgSO$_4$, filtered and concentrated in vacuo. The residue was purified by MPLC (silica, elution with 20% EtOAc/hexanes). The purified material was dissolved in ethanol (50 mL) and sodium hydride (500 mg of a 60% dispersion in mineral oil, 12.5 mmol) was added, and the resulting mixture stirrred at room temperature for 1 hour. The reaction mixture was concentrated in vacuo, and the resulting residue partitioned between diethyl ether (100 mL) and water (100 mL), the organic layer was separated and washed with saturated NaCl (50 mL), dried over MgSO$_4$, filtered and concentrated in vacuo. The residue was purified by MPLC (silica, 20% EtOAc/hexanes) to provide 3.4 g (50%) of product.

H NMR (CDCl$_3$, 500 MHz): δ 5.64 (s, 2H), 4.76 (br s, 1H), 4.06 (br d, J=6.0 Hz, 2H), 2.58 (br d, J=16.0 Hz, 2H), 2.45 (d, J=15.5 Hz, 2H), 1.80 (br d, J=5.0 Hz, 2H), 1.70 (septet, J=6.5 Hz, 1H), 1.22 (br t, J=6.5 Hz, 3H), 0.94 (d, J=6.5 Hz, 6H).

Step D

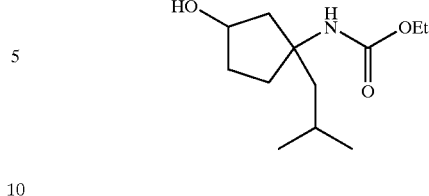

To a cooled (0° C.) solution of the ethyl carbamate prepared in step C (3.4 g, 16 mmol), in anhydrous tetrahydrofuran (100 mL) under an atmosphere of nitrogen, was added borane-methyl sulfide complex (1 mL, 9.7 mmol), and the resulting mixture stirred at room temperature for 3 hours. A further portion of borane-methyl sulfide complex (0.6 mL, 6 mmol) was added and stirring continued for a further 90 mins. The reaction mixture was cooled in an ice bath and sodium hydroxide (5.9 mL of a 3N solution, 17.7 mmol) added in a dropwise fashion, followed by addition of hydrogen peroxide (6.1 mL of a 30% aqueous solution). The resulting reaction mixture was heated at 40° C. with stirring for 1 hour. After cooling the mixture was partitioned between diethyl ether (100 mL) and water (200 mL), the organic layer was separated and the aqueous layer was extracted with further portions of diethyl ether (2×100 mL). The combined diethyl ether layers were washed with saturated NaCl (100 ml), dried over MgSO$_4$, filtered and concentrated in vacuo to give 3.25 g of crude product used in step E without further purification.

Step E

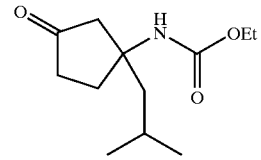

To a (−78° C.) solution of oxalyl chloride (1.36 mL, 15.6 mmol) in anhydrous dichloromethane (50 mL) under an atmosphere of nitrogen was added in a dropwise manner dimethyl sulfoxide (2.22 mL, 31.2 mmol), and the resulting mixture stirred at −78° C. for 10 mins. To this mixture was added, using a canula a solution of the product from step D (3.25 g, 14.2 mmol) in anhydrous dichloromethane (50 mL). The reaction mixture was stirred at −78° C. for a further 15 mins, then triethylamine (9.9 mL, 71 mmol) was added and the resulting mixture was allowed to rise to room temperature over 1 hour. The reaction mixture was washed with water (3×100 mL), saturated NaCl (50 mL), dried over MgSO$_4$, filtered and concentrated in vacuo. The residue was purified by MPLC (silica, elution 30% EtOAc/hexanes) to provide 2.6 g (81%) of product.

H NMR (CDCl$_3$, 500 MHz): δ 4.91 (br s, 1H), 4.23 (br d, J=6.2 Hz, 2H), 2.71 (br d, J=18.1 Hz, 1H), 2.49 (br m, 1H), 2.32 (q, J=9.6 Hz, 1H), 2.21 (m, 2H), 1.93–1.85 (m, 1H), 1.81–1.65 (m, 3H), 1.18 (br t, J=6.9 Hz, 3H), 0.92 (dd, J=7.0, 8.5 Hz, 6H).

Step F

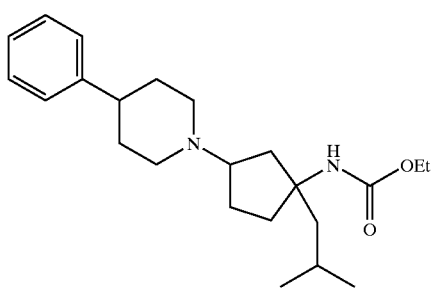

The ketone prepared in step E above (2.6 g, 11.5 mmol) was combined with 4-phenyl piperidine hydrochloride (2.26 g, 11.5 mmol), diisopropylethylamine (2.1 mL, 11.5 mmol), 4 Å molecular sieves (powder 2 g), and sodium triacetoxyborohydride (12.1 g, 57 mmol), in anhydrous 1,2-dichloroethane (100 mL) under an atmosphere of nitrogen, and the resulting mixture stirred at room temperature for 48 hours. The reaction mixture was filtered through celite. The filtrate was diluted with dichloromethane (100 mL) and washed with saturated $NaHCO_3$ solution (2×150 mL), water (100 mL), saturated NaCl (50 mL), dried over $MgSO_4$, filtered and concentrated in vacuo to afford 3.7 g (87%) of product used without further purification. ESI-MS calc for C23H36N2O2: 372; Found: 373 (M+H).

Step G

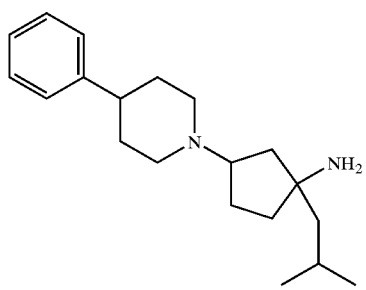

To a solution of the ethyl carbamate prepared in step F (3.6 g, 9.7 mmol) in ethanol (100 mL) was added a solution of potassium hydroxide (5 g, 89 mmol) in water (5 mL), and the resulting mixture heated at reflux for 120 hours. The cooled reaction mixture was evaporated to dryness, and the resulting residue partitioned between $CH_2Cl_2$ (100 mL) and water (100 mL). The organic layer was separated, and the aqueous layer extracted with further portions of $CH_2Cl_2$ (2×100 mL), the combined $CH_2Cl_2$ layers were washed with saturated NaCl (100 mL), dried over $MgSO_4$, filtered and concentrated in vacuo. The residue was purified by MPLC (silica, elution with a gradient rising from 0.5/2/97.5 concentrated ammonium hydroxide/methanol/dichloromethane to 0.5/10/89.5 concentrated ammonium hydroxide/methanol/dichloromethane), to give 1.5 g (52%) of product as a mixture of cis and trans isomers.

ESI-MS calc for C20H32N2: 300; Found: 301 (M+H).

EXAMPLE 147

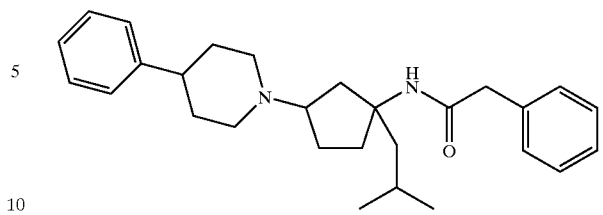

Intermediate 35 (100 mg, 0.3 mmol) was combined with EDC (128 mg, 0.6 mmol), HOAt (45.4 mg, 0.3 mmol), and phenyl acetic acid (45 mg, 0.3 mmol) in dichloromethane (15 mL), and the resulting mixture stirred at room temperature for 1 hour. The mixture was washed with water (50 mL), and the aqueous layer back-extracted with dichloromethane (2×25 mL). The combined dichloromethane layers were washed with water (2×50 mL), saturated NaCl (30 mL), dried over $MgSO_4$, filtered and concentrated in vacuo. The residue was applied to 2 preparative TLC plates (silica, 1.0 mm) and eluted with EtOAc. The purified product (mixture of 4 compounds cis and trans racemates) was converted to its hydrochloride salt by dissolving in methanol (2 mL) and adding 4 N HCl in dioxane (1 mL) and concentrating. The residue was suspended in 1:2 $CH_2Cl_2$:hexanes (5 mL) and evaporated to give a white powder 51.4 mg (38%). ESI-MS calc for C28H38N2O: 418; Found: 419 (M+H).

EXAMPLE 148

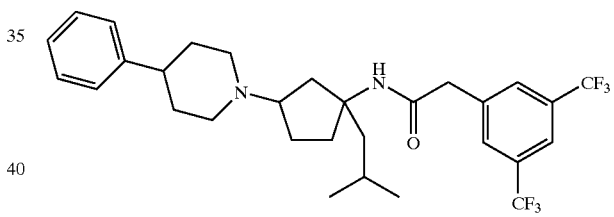

Example 148 was prepared using the same procedure used to prepare Example 147, substituting 3,5 bis trifluoromethyl phenyl acetic acid for phenyl acetic acid. ESI-MS calc for $C_{30}H_{36}F_6N2O$: 554; Found: 555 (M+H).

EXAMPLE 149

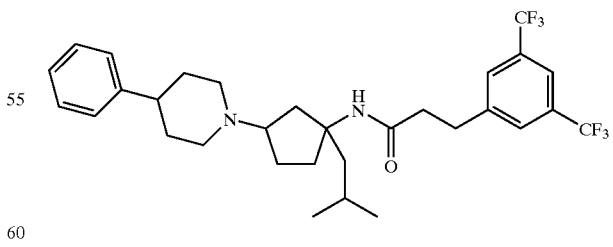

Example 149 was prepared using the same procedure used to prepare Example 147 substituting 3,5-bis-(trifluoromethyl)hydrocinnamic acid for phenyl acetic acid.

ESI-MS calc for C31H38F6N2O: 568; Found: 569 (M+H).

EXAMPLE 150

Step A

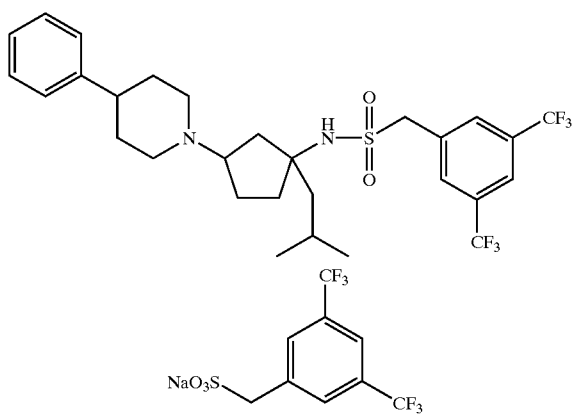

To a solution of 3,5-bis(trifluoromethyl)benzyl bromide (10 g, 32.6 mmol) in acetone (20 mL), was added a solution of sodium sulfite (4.11 g, 32.6 mmol) in water (40 mL), and the resulting mixture heated at reflux for 3 hours. The cooled reaction mixture was concentrated in vacuo, and the residue was azeotroped with two portions of ethanol (2×100 ml) to give the crude product 13.5 g containing some residual ethanol, which was used in step B without further purification.

Step B

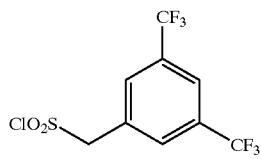

To a solution of the sulfonate salt formed in step A (13.5 g crude, ca 32.6 mmol) in a mixture of sulfalone (20 mL), and anhydrous acetonitrile (20 mL) under an atmosphere of nitrogen, was added phosphorous oxychloride (15.6 mL, 168 mmol), and the resulting mixture heated at 70° C. for 40 mins. The reaction mixture was cooled in an ice bath and water (100 mL) added dropwise. After complete addition the mixture was stirred at <10° C. for 10 mins, and the precipitate removed by filtration. The solid was washed with further portions of water (2×100 mL), and air dried to give 10 g (94% over 2 steps) of product.

Step C

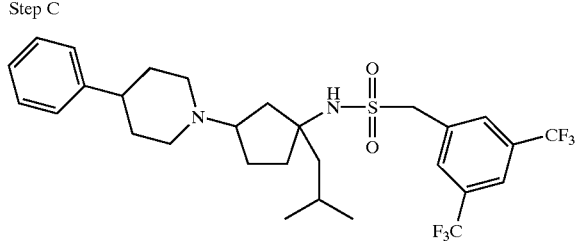

To a solution of intermediate 35 (100 mg, 0.33 mmol) in anhydrous dichloromethane (5 mL) under an atmosphere of nitrogen, was added diisopropylethylamine (64 μl, 0.36 mmol) followed by the benzyl sulfonyl chloride prepared in step B (109 mg, 0.33 mmol), and the resulting mixture stirred at room temperatue for 16 hours. The reaction mixture was diluted with more dichloromethane (50 mL) and washed with water (50 mL), saturated NaHCO₃ (50 mL), and saturated NaCl (30 mL), dried over MgSO₄, filtered and concentrated in vacuo. The residue was applied to 2 preparative TLC plates (silica, 1.0 mm) and eluted with 50% EtOAc/hexanes. The purified product (mixture of 4 compounds cis and trans racemates) was converted to its hydrochloride salt by dissolving in 2 mL methanol and adding 4 N HCl in dioxane (1 mL) and concentrating. The residue was suspended in 1:2 CH₂Cl₂:hexanes (5 mL) and evaporated to give a white powder 29.5 mg (14%). ESI-MS calc for C29H36F6N2O2S: 590; Found: 591 (M+H).

INTERMEDIATE 36

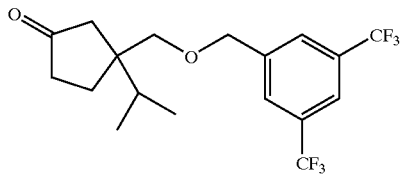

Step A

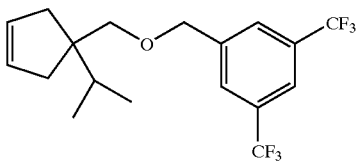

To a cooled (0° C.) suspension of lithium aluminum hydride (1.13 g, 29.8 mmol) in anhydrous tetrahydrofuran (75 mL), was added slowly using a canula, a solution of methyl-3-isopropyl cyclopentene-3-carboxylate (5 g, 29.8 mmol) in anhydrous tetrahydrofuran (75 mL). After complete addition the mixture was stirred at room temperature for 15 hours. The reaction mixture was cooled in an ice bath and quenched by the successive dropwise addition of water (1.2 mL), 4N NaOH (1.2 mL), and water (3.6 mL). The resulting mixture was stirred for 10 mins then filtered through celite and concentrated in vacuo to give 3.7 g (89%) of product. $^1$H NMR (CDCl₃, 500 MHz): δ 5.62 (s, 2H), 3.54 (s, 2H), 2.27 (d, J=14.6 Hz, 2H), 2.14 (d, J=14.6 Hz, 2H), 1.85 (septet, J=6.6 Hz, 1H), 0.89 (d, J=6.6 Hz, 6H).

Step B

To a solution of the cyclopentene methanol prepared in step A (1 g, 7.14 mmol), in anhydrous N,N-dimethylformamide (25 mL) which was heated at 80° C. under an atmosphere of nitrogen, was added sodium hydride (371 mg of a 60% dispersion in mineral oil, 9.29 mmol), and the resulting mixture continued heating at 80° C. for 10 mins. To this mixture was added 3,5-bis(trifluoromethyl) benzyl bromide (1.57 mL, 8.53 mmol), and tetrabutyl ammonium iodide (100 mg, 0.27 mmol), and the reaction mixture continued heating at 80° C. for 17 hours. The cooled reaction mixture was poured into water (150 mL) and extracted with diethyl ether (3×75 mL), the combined diethyl ether layers were washed with water (2×200 mL), and saturated NaCl (100 mL), dried over MgSO$_4$, filtered and concentrated in vacuo. The residue was purified by MPLC (silica, elution 10% diethyl ether/hexanes) to afford 1 g (38%) of product. $^1$H NMR (CDCl$_3$, 500 MHz): δ 7.80 (s, 3H), 5.62 (s, 2H), 4.62 (s, 2H), 3.40 (s, 2H), 2.30 (d, J=15.1 Hz, 2H), 2.17 (d, J=1.6 Hz, 2H), 1.95 (septet, J=6.6 Hz, 1H), 0.89 (d, J=6.6 Hz, 6H).

Step C

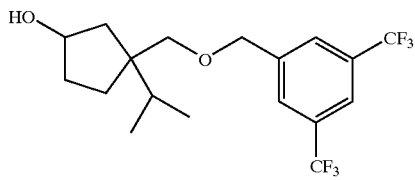

To a cooled (0° C.) solution of the benzyl ether prepared in step B (1 g, 2.7 mmol), in anhydrous tetrahydrofuran (20 mL) under an atmosphere of nitrogen, was added borane-methyl sulfide complex (273 μl, 2.7 mmol). After complete addition the reaction was allowed to stir at room temperature for 72 hours. The reaction was cooled in an ice bath and sodium hydroxide (1.0 mL of a 3N solution, 3.0 mmol) was added dropwise, followed by addition of hydrogen peroxide (1.1 mL of a 30% aqueous solution), and the resulting mixture heated at 45° C. for 1 hour. The reaction mixture was diluted with water (100 mL) and extracted with diethyl ether (3×50mL), the combined diethyl ether layers were washed with water (2×100 mL), saturated NaCl (50 mL), dried over MgSO$_4$, filtered and concentrated in vacuo to give the crude product 850 mg (82%), which was used in the next step without further purification.

Step D

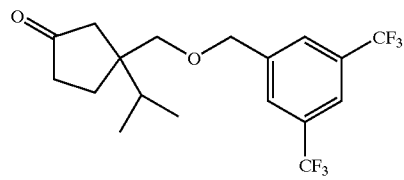

To a cooled (−78° C.) solution of oxalyl chloride (260 μl, 3 mmol) in anhydrous dichloromethane (10 mL) under an atmosphere of nitrogen, was added dropwise dimethyl sulfoxide (422 μl, 6 mmol). The reaction mixture was stirred for a further 10 mins at −78° C. then a solution of the cyclopentanol prepared in step C (850 mg, 2.2 mmol), in anhydrous dichloromethane (10 mL) was added. After stirring at −78° C. for a further 15 mins, triethylamine (1.88 mL, 13.5 mmol) was added and the reaction allowed to warm up to room temperature over 2 hours. The reaction mixture was washed with water (40 mL), the aqueous layer was back-extracted with dichloromethane (2×20 mL); the combined organic layers were washed with water (2×50 mL), saturated NaCl (30 mL), dried over MgSO$_4$, filtered and concentrated in vacuo. The residue was purified by MPLC (silica, elution with 10% EtOAc/hexanes) to give 550 mg (65%) of product.

H NMR (CDCl$_3$, 500 MHz): δ 7.81 (s, 1H), 7.74 (s, 2H), 4.60 (s, 2H), 3.52 (d, J=8.9 Hz, 1H), 3.47 (d, J=8.9 Hz, 1H), 2.41–2.23 (m, 3H), 2.16 (dd, J=1.1, 18.0 Hz, 2H), 2.10–2.04 (m, 1H), 1.93–1.87 (m, 1H), 1.83 (septet, J=7.1 Hz, 1H), 0.96 (dd, J=0.9, 7.1 Hz, 6H).

EXAMPLE 151

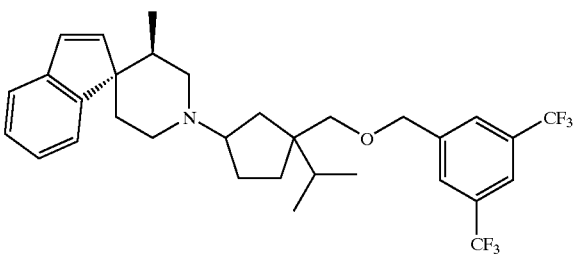

Cyclopentanone Intermediate 36 (100 mg, 0.26 mmol) was combined with 3-methyl-4-spiroindenylpiperidine hydrochloride (Intermediate 1) (61.5 mg, 0.26 mmol), diisopropylethylamine (50 1, 0.28 mmol), 4 Å molecular sieves (powder 100 mg), and sodium triacetoxyborohydride (166 mg, 0.79 mmol) in anhydrous 1,2-dichloroethane (10 mL), under an atmosphere of nitrogen, and the resulting mixture stirred at room temperature for 96 hours. The reaction mixture was filtered through celite. The filtrate was diluted with dichloromethane (10 mL) and washed with saturated NaHCO$_3$ solution (2×25 mL), water (20 mL), saturated NaCl (15 mL), dried over MgSO$_4$, filtered and concentrated in vacuo. The residue was applied to 2 preparative TLC plates (silica, 1.0 mm) and eluted with 0.5/5/94.5 concentrated ammonium hydroxide/methanol/dichloromethane. The purified product (mixture of cis and trans racemates) was converted to its hydrochloride salt by dissolving in methanol (2 mL) and adding 4 N HCl in dioxane (1 mL) and concentrating. The residue was suspended in 1:2 CH$_2$Cl$_2$:hexanes (5 mL) and evaporated to give a white powder 57.6 mg (37%). ESI-MS calc. for C32H37F6NO: 565; Found: 566 (M+H).

EXAMPLE 152

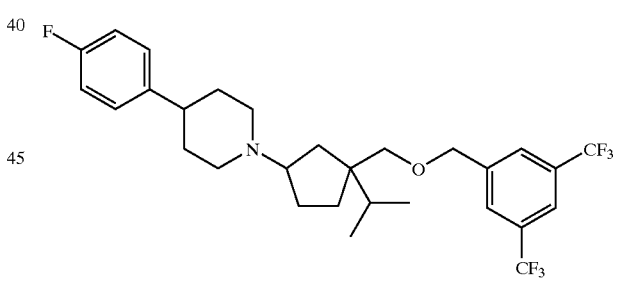

Example 152 was prepared in a similar manner to example 151 by substituting 4-(4-fluoro)phenyl piperidine hydrochloride for methyl spiroindene piperidine hydrochloride, Intermediate 1. ESI-MS calc for C29H34F7NO: 545; Found: 546 (M+H).

INTERMEDIATE 37

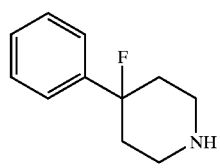

Step A

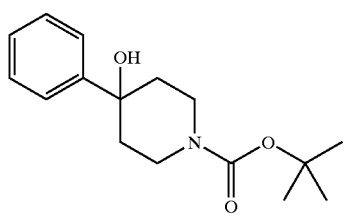

To a solution of 4-hydroxy-4-phenylpiperidine (3 g, 16.9 mmol) in dichloromethane (25 mL) was added di-tert-butyl dicarbonate (4.43 g, 20.3 mmol), and the resulting mixture stirred at room temperature for 2 hours. N,N-dimethylethylenediamine (0.5 mL, 4.6 mmol) was added and stirring continued for a further 30 mins. The reaction mixture was washed with 5% citric acid solution (25 mL), water (2×25 mL), saturated NaCl (15 mL), dried over $MgSO_4$, filtered and concentrated in vacuo to give 4.6 g (98%) of product. This material was used without further purification in step B.

Step B

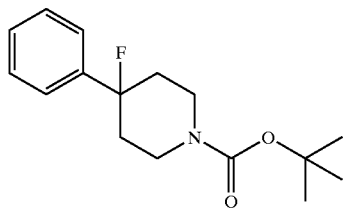

To a cooled (−78° C.) solution of (diethylamino)sulfur trifluoride (2.3 mL, 17.3 mmol) in anhydrous dichloromethane (100 mL) under an atmosphere of nitrogen, was added using a canula, a solution of the BOC piperidine prepared in step A (4.6 g, 16.6 mmol) in anhydrous dichloromethane (100 mL). After the addition was complete the reaction mixture was stirred at −78° C. for a further 1 hour and then allowed to rise to room temperature, and stirred for a further 30 mins. Saturated $NaHCO_3$ solution (150 mL) was added and the mixture stirred for 15 mins, then the organic layer was separated. To this solution was added 57–86% 3-chloroperoxybenzoic acid (1 g, approx 3.8 mmol), and the mixture stirred for 30 mins. The reaction mixture was washed with saturated $NaHCO_3$ (200 mL), water (200 mL), saturated NaCl (100 mL), dried over $MgSO_4$, filtered and concentrated in vacuo. The residue was purified by MPLC (silica, elution with 10% EtOAc/hexanes) to give 3.43 g (74%) of product.

H NMR ($CDCl_3$, 500 MHz): δ 7.39 (d, J=3.5 Hz, 4H), 7.33 (m, 1H), 4.14 (br m, 2H), 3.20 (br m, 2H), 2.00 (m, 4H),1.51 (s, 9H).

Step C

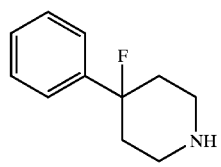

A solution of the BOC piperidine prepared in step B (500 mg, 1.8 mmol) in methanol (20 mL) was saturated with anhydrous hydrogen chloride gas, and the resulting mixture left standing at room temperature for 16 hours. The mixture was concentrated in vacuo, and the residue partitioned between saturated $NaHCO_3$ (30 mL) and dichloromethane (20 mL). The organic layer was separated, and the aqueous layer extracted with further portions of dichloromethane (2×20 mL). The combined dichloromethane layers were dried over $MgSO_4$, filtered and concentrated in vacuo to give 275 mg (85%) of product. H NMR ($CDCl_3$, 400 MHz): δ 7.45–7.27 (m, 5H), 2.09–1.88 (m, 4H), 3.16–2.97 (m, 5H). ESI-MS calc. for C11H14FN: 179; Found: 160 100% (M-19), 180 50% (M+H).

INTERMEDIATE 38

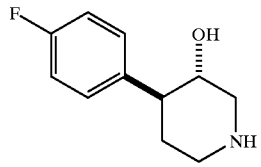

Step A

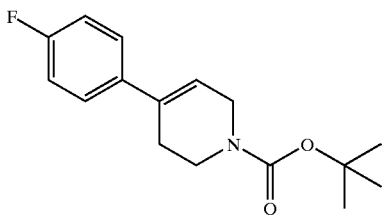

To a suspension of 4-(4-fluorophenyl)-1,2,3,6-tetrahydropyridine hydrochloride (10 g, 46.8 mmol) in dichloromethane (150 mL) was added diisopropylethylamine (8.97 mL, 51.5 mmol), followed by di-tert-butyl dicarbonate (12.27 g, 56.2 mmol), and the resulting mixture stirred at room temperature for 2 hours. N,N-dimethylethylenediamine (1 mL, 9 mmol) was added and stirring continued for a further 30 mins. The reaction mix ture was washed with 5% citric acid solution (100 mL), water (2×100 mL), saturated NaCl (50 mL), dried over MgSO₄, filtered and concentrated in vacuo to give 13.5 g crude product, which was used without further purification in step B.

Step B

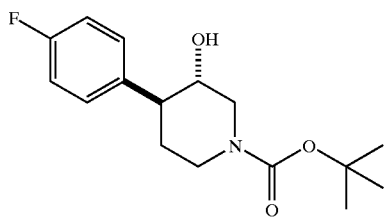

To a cooled (0° C.) solution of borane-methyl sulfide complex (5.9 mL, 59 mmol) in anhydrous tetrahydrofuran (100 mL) under an atmosphere of nitrogen, was added using a canula, a solution of the BOC tetrahydropyridine prepared in step A (13.5 g, 49 mmol) in tetrahydrofuran (100 mL). The resulting mixture was stirred at room temperature for 17 hours, then cooled in an ice bath and sodium hydroxide (18 mL of a 3N solution, 53.8 mmol) added in a dropwise manner, followed by hydrogen peroxide (20 mL of a 30% solution). The resulting mixture was stirred at 45° C. for 1 hour, then poured into water (500 mL) and extracted with diethyl ether (3×100 mL). The combined diethyl ether layers were washed with water (500 mL), saturated NaHCO₃ (200 mL), saturated NaCl (150 mL), dried over MgSO₄, filtered and concentrated in vacuo to give 12.1 g (84%) of product. This material was used in step C without further purification. H NMR (CDCl₃, 500 MHz): δ 7.26 (dd, J=5.5, 8.7 Hz, 2H), 7.03 (t, J=8.7 Hz, 2H), 4.40 (br m, 1H), 4.20 (br m, 1H), 3.64 (m, 1H), 2.76 (br m, 1H), 2.63 (br m, 1H), 2.53 (m, 1H), 1.86–1.64 (m, 3H), 1.48 (s, 9H).

Step C

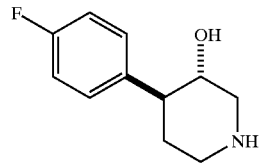

A solution of the BOC piperidine prepared in step B (500 mg, 1.7 mmol) in methanol (20 mL) was saturated with anhydrous hydrogen chloride gas, and the resulting mixture left standing at room temperature for 7 hours. The mixture was concentrated in vacuo, and the residue partitioned between saturated NaHCO₃ (30 mL) and dichloromethane (20 mL). The organic layer was separated, and the aqueous layer extracted with further portions of dichloromethane (2×20 mL). The combined dichloromethane layers were dried over MgSO₄, filtered and concentrated in vacuo to give 260 mg (78%). ESI-MS calc. for C11H14FNO: 195; Found: 196 (M+H).

INTERMEDIATE 39

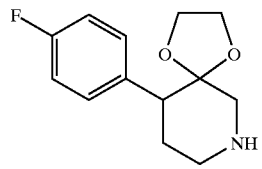

Step A

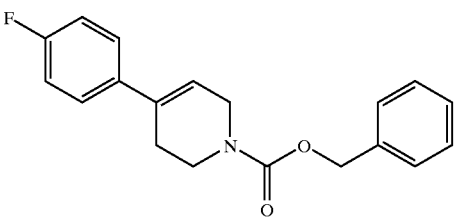

To a suspension of 4-(4-fluorophenyl)-1,2,3,6-tetrahydropyridine hydrochloride (5 g, 23.4 mmol) and triethylamine (7.7 mL, 56.5 mmol), in anhydrous tetrahydrofuran (150 mL) under an atmosphere of nitrogen, was added benzyl chloroformate (4.4 mL, 30.8 mmol), and the resulting mixture stirred at room temperature for 72 hours. N,N-dimethylethylenediamine (2 mL, 28 mmol) was added and the mixture stirred for a further 2 hours. The mixture was diluted with EtOAc (200 mL) and washed with 5% citric acid solution (200 mL), water (100 mL), saturated NaCl (100 mL), dried over MgSO₄, filtered and concentrated in vacuo to give 7 g (96%) of crude product. This material was used without further purification in step B.

Step B

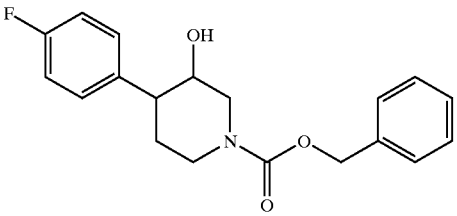

To a cooled (0° C.) solution of the tetrahydropyridine prepared in step A (7 g, 22.5 mmol) in anhydrous tetrahydrofuran (150 mL) under an atmosphere of nitrogen, was added borane-methyl sulfide (2.25 mL, 22.5 mmol). The resulting mixture was stirred at room temperature for 17 hours, then cooled in an ice bath and sodium hydroxide (7.9 mL of a 3N solution, 23.6 mmol) added in a dropwise manner, followed by hydrogen peroxide (8 mL of a 30% solution). The resulting mixture was stirred at 45° C. for 1 hour, then poured into water (300 mL) and extracted with diethyl ether (3×100ml). The combined diethyl ether layers were washed with water (500 mL), saturated NaCl (100 mL), dried over MgSO₄, filtered and concentrated in vacuo to give 5.96 g (81%) of product. This material was used in step C without further purification.

Step C

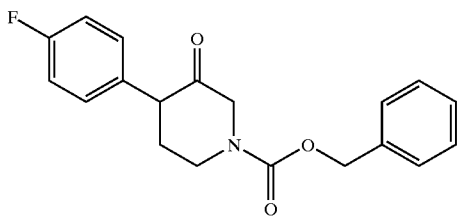

To a cooled (−78° C.) solution of oxalyl chloride (2.5 mL, 28 mmol) in anhydrous dichloromethane (100 mL) under an atmosphere of nitrogen, was added dropwise dimethyl sulfoxide (4.06 mL, 57 mmol). After stirring at −78° C. for 10 mins a solution of the piperidinol prepared in step B (5.96 g, 26 mmol) in dichloromethane (50 ml) was added using a double ended needle. After a further 15 mins at −78° C. triethylamine (18 mL, 130 mmol) was added, and the resulting mixture allowed to warm to room temperature. Washed with water (3×150 mL), saturated NaCl (100 mL), dried over MgSO$_4$, filtered and concentrated in vacuo. The residue was purified by MPLC (silica, elution with 20% EtOAc/hexanes) to give 3.9 g (65%) of product.

H NMR (CDCl$_3$, 500 MHz): δ 7.40 (m, 5H), 7.01 (m, 4H), 5.19 (s, 2H), 4.37 (d, J=18.0 Hz, 1H), 4.01 (br m, 2H), 3.60 (m, 2H), 2.35 (m, 1H), 2.21 (m, 1H).

Step D

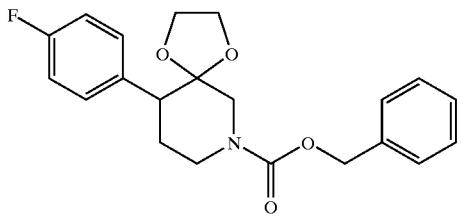

To a solution of the piperidone prepared in step C (3.9 g, 11.9 mmol), and ethylene glycol (10 mL, 179 mmol) in toluene (150 mL) was added p-toluene sulfonic acid (500 mg, 2.6 mmol), and the resulting mixture heated to reflux under Dean and Stark conditions for 16 hours. The cooled reaction mixture was concentrated in vacuo. The residue was partitioned between saturated NaHCO$_3$ (100 mL) and dichloromethane (100 mL), the organic layer was separated, dried over MgSO$_4$, filtered and concentrated in vacuo. The residue was purified by MPLC (silica, elution with 20% EtOAc/hexanes) to give 3.5 g (79%) of product. H NMR (CDCl$_3$, 500 MHz): δ 7.39 (m, 5H), 7.28 (dd, J=5.0, 8.7 Hz, 2H), 6.98 (t, J=8.7 Hz, 2H), 5.23 (d, J=12.4 Hz, 1H), 5.14 (d, J=12.4 Hz, 1H), 4.36 (dd, J=13.0, 42.8 Hz, 1H), 4.16 (dd, J=12.1, 74.6 Hz, 1H), 3.90–3.50 (br m, 3H), 3.13–2.79 (br m, 4H), 2.24 (br m, 1H), 1.79 (br d, J=11.2 Hz, 1H).

Step E

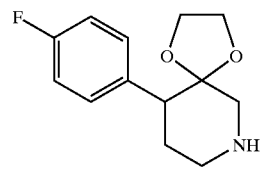

To a nitrogen flushed solution of the Cbz protected piperidine prepared in step D (3.5 g, 9.3 mmol) in ethyl alcohol (75 mL) was added 10% palladium on carbon (500 mg), and the resulting mixture shaken under an atmosphere of hydrogen at 50 psi for 4 hours. The palladium on carbon was removed by filtration through celite, and the filtrate concentrated in vacuo to give 2.2 g (99%) of crude material which was used without further purification. H NMR (CDCl$_3$, 500 MHz): δ 7.29 (dd, J=5.7, 8.5 Hz, 2H), 6.98 (t, J=8.7 Hz, 2H), 3.75 (m, 3H), 3.51 (m, 1H), 3.21 (d, J=13.1 Hz, 1H), 3.03 (m, 1H), 2.94 (d, J=13.0 Hz, 1H), 2.73 (d, J=13.0 Hz, 1H), 2.17 (quartet of doublets, J=4.4, 13.3 Hz, 1H), 1.83 (d, J=13.3 Hz, 1H). ESI-MS calc. for C13H16FNO2: 237; Found: 238 (M+H).

EXAMPLE 152

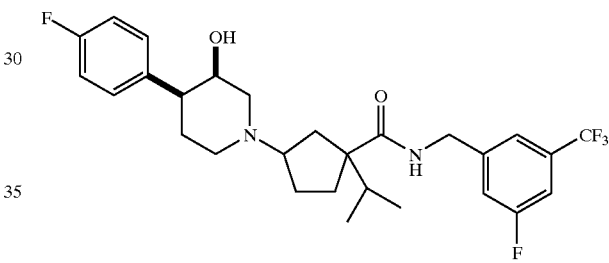

Step A

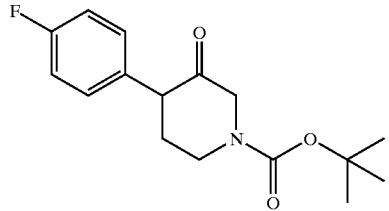

To a cooled (−78° C.) solution of oxalyl chloride (1.63 mL, 18.6 mmol) in anhydrous dichloromethane (50 mL) under an atmosphere of nitrogen, was added dropwise dimethyl sulfoxide (2.65 mL, 37.2 mmol). After stirring at −78° C. for 10 mins, a solution of the BOC piperidinol prepared in step B of intermediate 38 (5 g, 17 mmol) in dichloromethane (50 ml), was added using a double ended needle. After a further 15 mins at −78° C., triethylamine (11.8 mL, 85 mmol) was added, and the resulting mixture allowed to warm to room temperature. The mixture was washed with water (3×100 mL), saturated NaCl (50 mL), dried over MgSO$_4$, filtered and concentrated in vacuo. The residue was purified by MPLC (silica, elution with 20% EtOAc/hexanes) to give 3.0 g (60%) of product. H NMR (CDCl$_3$, 500 MHz): δ 7.26 (dd, J=5.5, 9.0 Hz, 2H), 7.03 (t, J=9.0 Hz, 2H), 4.24 (d, J=18.0 Hz, 1H), 4.03 (br m, 2H), 3.63 (dd, J=5.5, 12.5 Hz, 1H), 3.51 (br m, 1H), 2.30 (m, 1H), 2.20 (m, 1H), 1.49 (s, 9H).

Step B

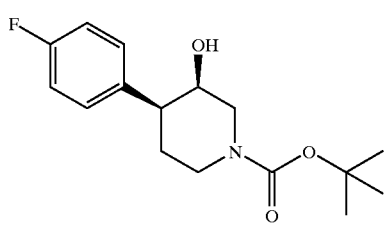

To a cooled (−78° C.) solution of the piperidone prepared in step A (3.0 g, 10.2 mmol) in anhydrous tetrahydrofuran (100 mL) under an atmosphere of nitrogen, was added slowly K-Selectride (10.2 mL of a 1.0M solution, 10.2 mmol). After stirring at −78° C. for 30 mins the reaction mixture was allowed to warm to room temperature. Saturated NH$_4$Cl solution (50 mL) was added followed by water (200 mL) and the resulting mixture extracted with diethyl ether (200 mL), the organic layer was washed with saturated NaCl (100 mL), dried over MgSO$_4$, filtered and concentrated in vacuo. On standing a solid formed in the residue which was purified by adding hexanes (10 mL), and filtering to give 1.1 g (37%) of product.

H NMR (CDCl$_3$, 500 MHz): δ 7.26 (dd, J=5.5, 8.7 Hz, 2H), 7.03 (t, J=8.7 Hz, 2H), 4.31 (br m, 2H), 3.94 (br s, 1H), 3.01 (br d, J=12.8 Hz, 1H), 2.81 (br m, 2H), 2.23 (quartet of doublets, J=4.6, 13.0 Hz, 1H), 1.77 (br m, 1H), 1.61 (br m, 1H), 1.49 (s, 9H).

Step C

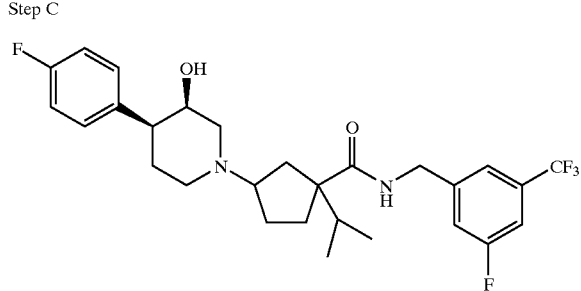

To a solution of the intermediate prepared in step B (500 mg, 0.5 mmol) in dichloromethane (10 mL) was added trifluoroacetic acid (1 mL, 13 mmol), and the resulting mixture stirred at room temperature for 2 hours. The mixture was concentrated in vacuo, and the residue dissolved in 1,2-dichloroethane (10 mL). To this mixture was added intermediate 33 (175 mg, 0.5 mmol), diisopropylethylamine (89 μl, 0.5 mmol), sodium triacetoxyborohydride (500 mg, 2.4 mmol), and 4 Å molecular sieves (powder 100 mg). The resulting mixture was stirred at room temperature for 48 hours. The reaction mixture was filtered through celite. The filtrate was diluted with dichloromethane (10 mL) and washed with saturated NaHCO$_3$ solution (2×15 mL), water (15 mL), saturated NaCl (10 mL), dried over MgSO$_4$, filtered and concentrated in vacuo. The residue was applied to 2 preparative TLC plates (silica, 1.0 mm) and eluted with 100% EtOAc The purified product (mixture of 8 isomers) was converted to the hydrochloride salt by dissolving in methanol (2 mL) and adding 4 N HCl in dioxane (1 mL) and concentrating. The residue was suspended in 1:2 CH$_2$Cl$_2$:hexanes (5 mL) and evaporated to give a white powder 84 mg (30%).

ESI-MS calc. for C28H33F5N2O2: 524; Found: 525 (M+H).

EXAMPLE 153

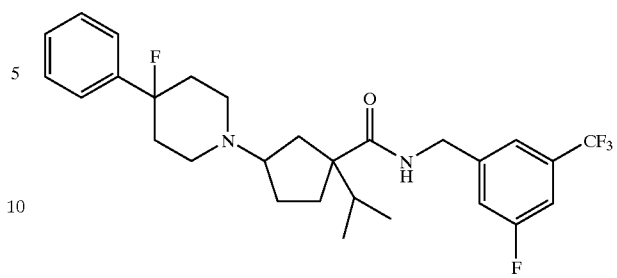

The piperidine Intermediate 37 (135 mg, 0.75 mmol) was combined with Intermediate 33 (260 mg, 0.75 mmol), 4 Å molecular sieves (powder 100 mg), and sodium triacetoxyborohydride (800 mg, 3.76 mmol) in anhydrous 1,2-dichloroethane (10 mL), under an atmosphere of nitrogen, and the resulting mixture stirred at room temperature for 48 hours. The reaction mixture was filtered through celite. The filtrate was diluted with dichloromethane (10 mL) and washed with saturated NaHCO$_3$ solution (2×15 mL), water (15 mL), saturated NaCl (10 mL), dried over MgSO$_4$, filtered and concentrated in vacuo. The residue was purified at first by MPLC (silica, elution with 100% EtOAc), and then was applied to 2 preparative TLC plates (silica, 1.0 mm) and eluted with 50% EtOAc/hexanes, whereupon two mixtures of isomers were separated. The purified products (cis and trans racemates) were converted to the hydrochloride salts by dissolving in methanol (2 mL) and adding 4 N HCl in dioxane (1 mL) and concentrating. The residue was suspended in 1:2 CH$_2$Cl$_2$:hexanes (5 mL) and evaporated to give white powders; top spot 84 mg, bottom spot 41 mg giving a combined yield of 31%.

ESI-MS top spot calc. for C28H33F5N2O: 508; Found: 509 (M+H). ESI-MS bottom spot calc. for C28H33F5N2O: 508; Found: 509 (M+H).

EXAMPLE 154

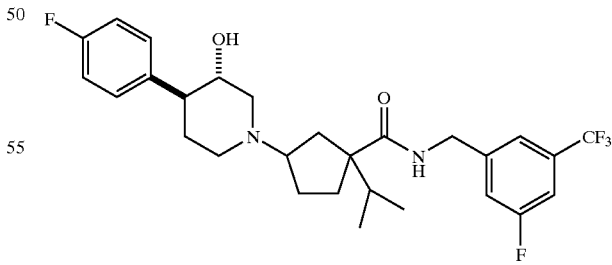

Example 154 was prepared in a similar manner to example 153 substituting intermediate 38 for intermediate 37. ESI-MS calc. for C28H33F5N2O2: 524; Found: 525 (M+H).

EXAMPLE 155

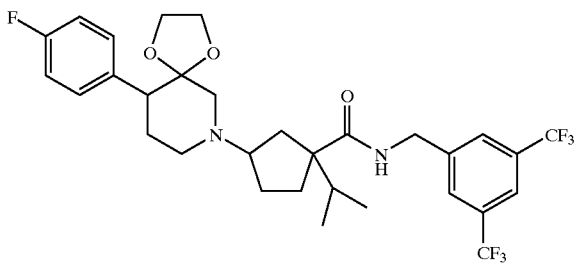

Example 155 was prepared in a similar manner to example 153 substituting intermediate 39 for intermediate 37, and intermediate 32 for intermediate 33. ESI-MS top spot calc. for C31H35F7N2O3: 616; Found: 617 (M+H). ESI-MS bottom spot calc. for C31H35F7N2O3: 616; Found: 617 (M+H).

INTERMEDIATE 40

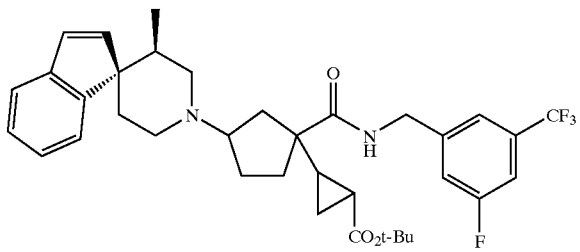

Step A

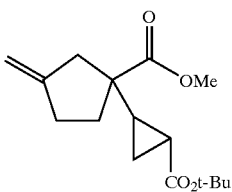

A solution of methyl (3-methylenecyclopentane) carboxylate (1.0 g, 7.1 mmol) in THF (6 mL) was added dropwise to a precooled (−78° C.) 1.5 M cyclohexane solution of LDA (5.7 mL, 8.6 mmol) in THF (18 mL). After stirring at −78° C. for 0.5 h, a solution of tertbutyl 4-bromocrotonate (1.73 g, 7.84 mmol) in THF (6 mL) was added dropwise. The resulting reaction mixture was stirred at −78° C. for 1 h, warmed to rt over 30 min, then poured into 1 N HCl (100 mL). The aqueous layer was extracted twice with ether (2×100 mL) and the combined ethereal layers were washed with brine, dried over anhydrous MgSO$_4$, filtered, and concentrated. The crude product was purified by MPLC (silica, 15% EtOAc/hexane), to afford 1.8 g of a colorless oil (90% yield). $^1$H NMR identified the product as a mixture of stereoisomers (erythro/threo), all possessing the trans-cyclopropyl arrangement.

1H NMR (CDCl$_3$, 500 MHz) δ 4.84–4.87 (m, 2H), 3.68 (s, 3H), 2.75 (dd, J=10, 16 Hz, 1H), 2.37 (m, 2H), 2.04–2.17 (m, 2H), 1.60–1.69 (m, 2H), 1.45–1.50 (m, 1H), 1.43 (s, 9H), 1.07 (m, 1H), 0.86 (m, 0.6H), 0.80 (m, 0.4H).

Step B

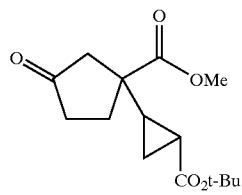

A solution of exocyclic olefin prepared in step A (7.94 g, 28.3 mmol) in DCM (100 mL) was treated at −78° C. with ozone gas. When the reaction mixture changed from colorless to blue/green, ozone bubbling was terminated and nitrogen gas was passed through the solution until it was again colorless. Then triphenylphosphine (8.17 g, 31.1 mmol) was added and the reaction mixture was permitted to warm to rt and stir for 3 h. The solvent was removed under reduced pressure and the resulting oil was combined with 1:1 ethyl acetate/hexane (75 mL). The precipitated triphenylphosphine oxide was filtered off and the filtrate was concentrated and purified by MPLC (silica, eluted with 50% EtOAc/hexane) to afford 6.33 g of the product as a clear oil (79% yield). 1H NMR (CDCl$_3$, 500 MHz) δ 3.74 (s, 3H), 2.66 (dd, J=12.5, 18.5 Hz, 1H), 2.30–2.40 (m, 3H), 1.90–2.00 (m, 2H), 1.79 (m, 1H), 1.45–1.54 (m, 1H), 1.44 (overlapping singlets, 9H), 1.11–1.18 (m, 1H), 0.78–0.84 (m, 1H).

Step C

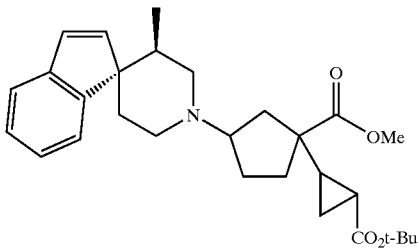

The ketone prepared in Step B above (1.22 g, 4.32 mmol) was combined with Intermediate 1, (1.22 g, 5.18 mmol), triethylamine (520 mg, 5.2 mmol), 4 Å Molecular sieves (powder, 2 g), and sodium triacetoxyborohydride (3.66 g, 17.3 mmol) in DCM (50 mL). The resulting mixture was stirred at room temperature for 96 h, then filtered through celite. The filtrate was diluted with DCM (100 mL) and washed with saturated NaHCO$_3$ solution, then brine, dried over anhydrous MgSO$_4$, filtered, and concentrated. Purification by MPLC (silica, ethyl acetate, then 10% MeOH/ ethyl acetate) afforded 1.53 g (76% yield) of product as a mixture of isomers. ESI-MS calc. for C29H39NO4: 465; Found 466 (M+H).

Step D

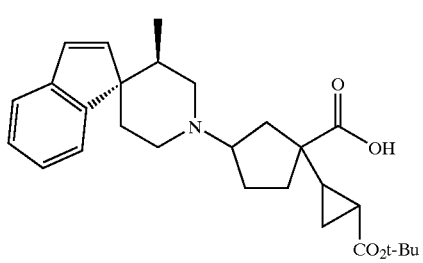

The methyl ester prepared as described in the previous step (315 mg, 0.676 mmol) was dissolved in 1:1 THF/MeOH (6 mL) and treated with a solution of LiOH.H$_2$O (142 mg, 3.38 mmol) in water (3 mL). The resulting mixture was stirred at room temperature for 6 h. The reaction mixture was concentrated to remove the organic solvents, diluted with brine (5 mL) and treated dropwise wih 1N HCl solution until the pH was 7. The mixture was then extracted twice with chloroform (25 mL). The combined organic layers were washed once with brine (10 mL), dried over anhydrous MgSO$_4$, filtered, and concentrated. The crude product was submitted to purification by preparative TLC (silica, 10% MeOH/DCM), whereupon two mixtures of isomers were separated (153 mg top spot: cis-cyclopentyl, 108 mg bottom spot: trans-cyclopentyl), giving a combined yield of 86%. ESI-MS top spot calc. for C28H37NO4: 451; Found 452 (M+H). ESI-MS bottom spot calc. for C28H37NO4: 451; Found 452 (M+H).

Step E

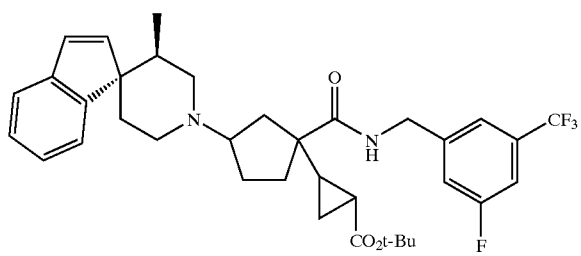

The cis-cyclopentyl carboxylic acid prepared as described above (150 mg, 0.332 mmol), was combined with 3-fluoro-5-trifluoromethylbenzylamine (96 mg, 0.50 mmol), EDC (95 mg, 0.50 mmol), and DMAP (~10 mg) in DCM (3 mL). The reaction mixture was stirred at room temperature for 16 h. The reaction mixture was diluted with more DCM (10 mL) and washed with water, then brine, dried over anhydrous MgSO$_4$, filtered, and concentrated. The crude product was purified by preparative TLC (silica, 5% MeOH/EtOAc) to give 200 mg (96%) of product as a mixture of four isomers. ESI-MS calc. for C36H42F4N2O3: 626; Found: 627 (M+H).

INTERMEDIATE 41

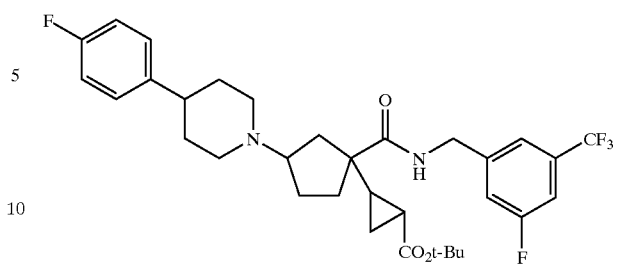

Intermediate 41 was prepared using the same protocols as for Intermediate 40, except that 4-(4-fluorophenyl)piperidine was used in the reductive amination step. ESI-MS calc. for C33H39F5N2O3: 606; Found 607 (M+H).

Intermediate 41 may be further resolved by chiral HPLC (ChiralPak AD column, 25% ethanol/hexane) into one mixture of two isomers (peak 1) and two single isomers (peaks 2 and 3).

EXAMPLE 156

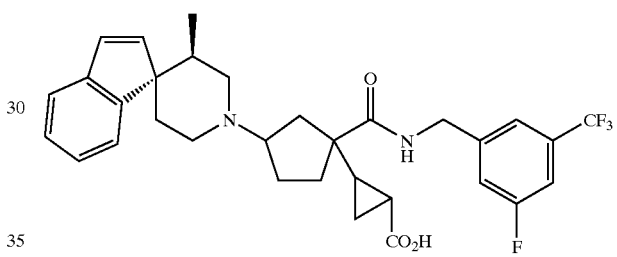

Intermediate 40 (200 mg, 0.319 mmol) was dissolved in DCM (2.5 mL) and treated with TFA (2.5 mL). The resulting mixture was stirred at room temperature for 3.5 h, then concentrated at 40° C. under reduced pressure. The residue was partitioned between CHCl$_3$ and brine. The aqueous layer was adjusted to pH 7 with saturated NaHCO$_3$ solution and the phases were separated. The aqueous layer was washed an additional two times with CHCl$_3$, the organic layers were combined, washed with brine, and concentrated to afford 138 mg of the free amino acid as a mixture of 4 isomers (cis-cyclopentyl, trans cyclopropyl).

ESI-MS calc. for C32H34F4N2O3: 570; Found 571 (M+H).

EXAMPLE 157

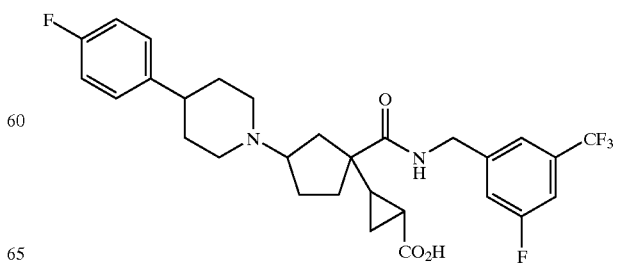

Compound 157, as a mixture of 4-isomers (cis-cyclopentyl, trans-cyclopropyl), was prepared from Intermediate 41 in the same fashion as in Example 156. ESI-MS calc. for C29H31F5N2O3: 550; Found 551 (M+H).

EXAMPLE 158

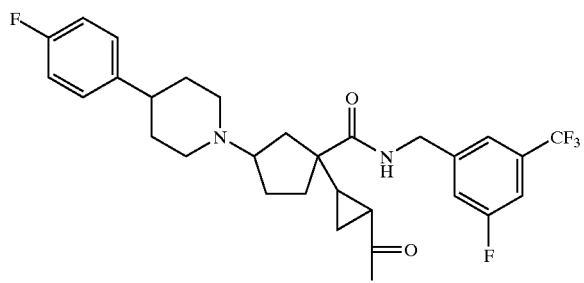

The carboxylic acid from Example 157 (20 mg, 0.036 mmol) was combined with EDC (21 mg, 0.11 mmol), HOAt (15 mg, 0.11 mmol), and ethylamine (2.0 M in THF, 0.091 mL, 0.18 mmol) in DCM (1 mL) and stirred at room temperature for 19 h. The reaction mixture was applied directly to a preparative TLC plate (silica, 0.5 mm) and eluted with 1/9/90 concentrated ammonium hydroxide/methanol/DCM. Two sets of two isomers were recovered from the purification (i.e., mixture of four isomers was separated into two mixtures of two isomers). Each two isomer mixture was converted to its hydrochloride salt by dissolving in 1 mL DCM, adding 4 N HCl in dioxane (1 drop) and concentrating, giving a white powder (top spot mixture: 7.9 mg, bottom spot mixture: 12.3 mg, combined yield=20.2 mg, 91%). ESI-MS top spot mixture calc. for C31H36F5N3O2: 577; Found 578.3 (M+H). ESI-MS bottom spot mixture calc. for C31H36F5N3O2: 577; Found 578.3 (M+H).

A variety of other amides were prepared starting from the carboxylic acids prepared in Examples 156 and 157 in an analogous fashion to that shown in Example 158. Some of those products also separated into two mixtures of two isomers and others were inseparable and were evaluated as mixtures of four isomers. The Table below shows some of the additional amides prepared.

TABLE 1

OTHER AMIDES

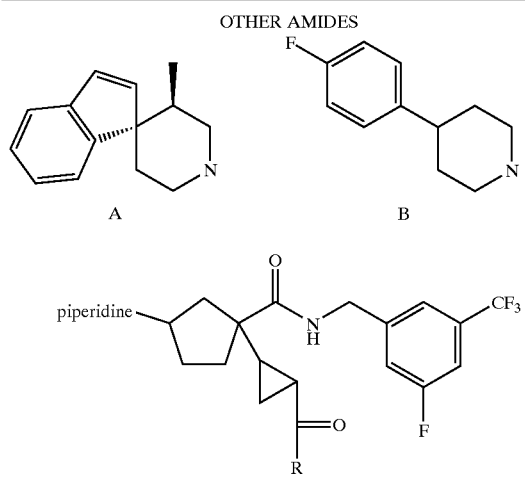

| Example | piperidine | R | MF ESI-MS found M + 1 |
|---|---|---|---|
| 159 | A | NHPh top 2 isomers<br>NHPh bottom 2 isomers | C38H39F4N3O2<br>Top: 646<br>Bottom: 646 |
| 160 | A | 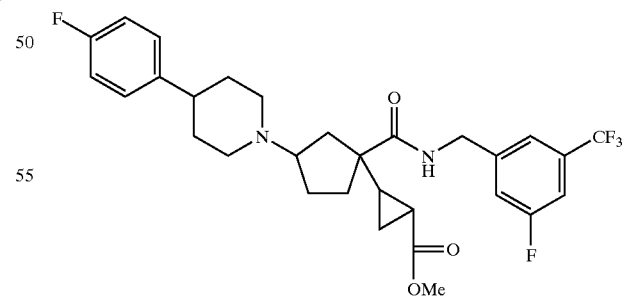 | C36H41F4N3O3<br>640 |
| 161 | A | NMe2 | C34H39F4N3O2<br>598 |
| 162 | A | NH-t-Bu | C36H43F4N3O2<br>626 |
| 163 | A | NHCH2CO2Et | C36H41F4N3O4<br>656 |
| 164 | A | NH2 | C32H35F4N3O2<br>570 |
| 165 | A | NHMe | C33H37F4N3O2<br>584 |
| 166 | A | NHCH2CO2H | C34H37F4N3O4<br>628 |
| 167 | A | NHEt top two isomers<br>NHEt bottom two isomers | C34H39F4N3O2<br>Top: 598<br>Bottom: 598 |
| 168 | B | NMe2 | C31H36F5N3O2<br>578 |
| 169 | B | (pyrrolidine) | C33H38F5N3O2<br>604 |
| 170 | B | NH-i-Pr top two isomers<br>NH-i-Pr bottom two isomers | C32H38F5N3O2<br>Top: 592<br>Bottom: 592 |
| 171 | B | NH2 | C29H32F5N3O2<br>549 |

EXAMPLE 172

The carboxylic acid from Example 157 (222 mg, 0.403 mmol) was combined with EDC (232 mg, 1.21 mmol), methanol (0.16 mL, 4.0 mmol), and catalytic DMAP (~15 mg) in DCM (5 mL). The reaction mixture was stirred at room temperature overnight, then diluted with more DCM and washed with water followed by brine. The organic layer was dried over anhydrous MgSO₄, filtered, and concentrated. Purification by preparative TLC (silica, 0.5/4.5/95 of concentrated ammonium hydroxide/methanol/DCM) provided 157 mg of product as a mixture of 4 stereoisomers. ESI-MS calc. for C30H33F5N2O3: 564; Found 565 (M+H).

EXAMPLE 173

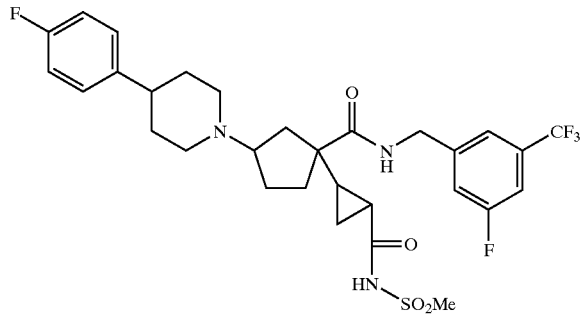

The carboxylic acid from Example 157 (20 mg, 0.036 mmol) was combined with EDC (21 mg, 0.11 mmol), methanesulfonamide (17 mg, 0.18 mmol), and DMAP (~10 mg) in 1 mL of DCM. The reaction mixture was stirred at room temperature overnight and then applied directly onto a preparative TLC plate (silica) and eluted with 1/9/90 concentrated ammonium hydroxide/methanol/DCM. A second preparative TLC (silica, 12% methanol/DCM) afforded the pure product which was converted to its hydrochloride salt by dissolving in 1 mL of DCM, adding 1 drop of 4 N HCl in dioxane, and concentrating (7.2 mg). ESI-MS calc. for C30H34F5N3O4S: 627; Found 628 (M+H).

EXAMPLE 174

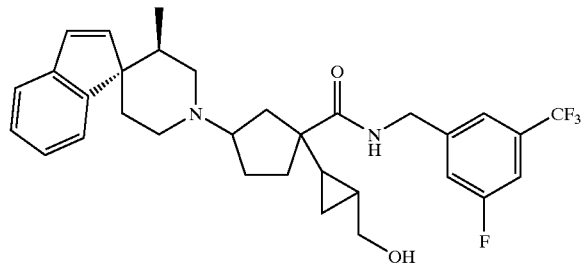

Step A

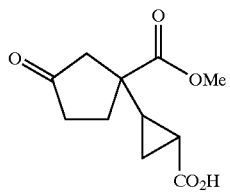

The ketodiester prepared as described in Step B of the synthesis of Intermediate 40 (5.33 g, 18.9 mmol) was stirred for 1.5 h. at room temperature in a 1:1 mixture of TFA/DCM (50 mL). The reaction mixture was concentrated. The resulting residue was dissolved in ethyl acetate and washed four times with water, once with brine, then dried over anhydrous MgSO₄, filtered and concentrated to give 3.73 g of crude product which was used without purification.

1H NMR (CDCl₃, 500 MHz) δ 7.53 (br s, 1H), 3.75 (s, 3H), 2.71 (d, J=18.5 Hz, 0.4H), 2.66 (d, J=19 Hz, 0.6H), 2.40 (m, 1H), 2.35 (m, 2H), 1.88–1.99 (m, 3H), 1.65 (m, 0.4H), 1.59 (m, 0.6H), 1.31 (m, 1H), 0.98 (m, 1H).

Step B

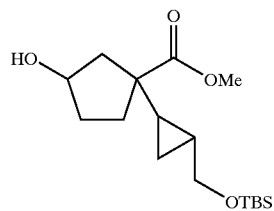

The product from Step A above (1.55 g, 6.85 mmol) was dissolved in THF (20 mL), cooled to 0° C., and treated dropwise under nitrogen with BH₃.DMS (0.72 mL, 7.5 mmol). Following the addition, the reaction mixture was stirred at 0° C. for another 4 h., then was quenched by addition of methanol (5 mL). The reaction mixture was concentrated and the resulting residue purified by MPLC (silica, 10% MeOH/DCM) to give 854 mg of the fully reduced diol as a complex mixture of isomers. Most of this mixture (818 mg, 3.82 mmol) was dissolved in DMF (10 mL) and treated with imidazole (780 mg, 11.5 mmol), followed by TBSCl (576 mg, 3.82 mmol). The resulting reaction mixture was stirred overnight at room temperature. The crude product was purified by MPLC (silica 40% ethyl acetate/hexane), giving two major products which by 1HNMR appeared to be the product, cis-cyclopentyl and trans-cyclopentyl isomer mixtures. ESI-MS of cis/trans mixture calc. for C17H32O4Si: 328; Found: 329 (M+H) and 351 (M+Na).

Step C

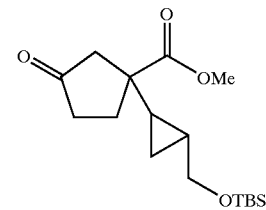

Oxalyl chloride (277 mg, 2.19 mmol) was added to 10 mL of DCM precooled to −78° C. Then a solution of DMSO (342 mg, 4.38 mmol) in DCM (1 mL) was added dropwise. After an additional 3 min, the alcohol prepared as described in Step B above (360 mg, 1.10 mmol, top spot isomer mixture) was added dropwise in 4 mL DCM. After stirring for another 15 min., triethylamine (1.22 mL, 8.76 mmol) was added dropwise. After 5 min., the reaction mixture was allowed to warm to room temperature and stir for 15 minutes. Then the reaction mixture was diluted with DCM and washed with 1N HCl solution, saturated NaHCO₃ solution, and brine. The organic layer was then dried over anhydrous MgSO₄, filtered and concentrated. This same procedure was carried out with the bottom spot isomer mixture from Step B (352 mg, 1.07 mmol). ¹H NMR analysis of both products established that they were identical, confirming that the starting material mixtures were related as cis/trans alcohol mixtures. The two batches were combined to afford 689 mg of ketone as a mixture of four isomers (97%).

Step D

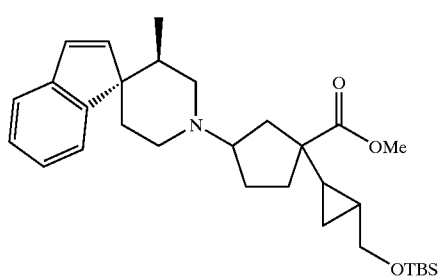

The mixture of ketone isomers prepared as described in the previous step (689 mg, 2.11 mmol) was combined with Intermediate 1 (597 mg, 2.53 mmol), triethylamine (0.35 mL, 2.5 mmol), NaBH(OAc)₃ (1.79 g, 8.44 mmol), and 4 Å molecular sieves (~2 g) in DCM (10 mL). The resulting mixture was stirred at room temperature for four days. After filtration through a celite plug, the reaction mixture was diluted with DCM, washed with saturated NaHCO₃ solution, followed by brine, dried over anhydrous MgSO₄, filtered, and concentrated. Purification by MPLC (silica, 10% methanol/ethyl acetate) gave 1.01 g (94%) of aminoester as a mixture of isomers. ESI-MS calc. for C31H47NO3Si: 509; Found 510 (M+H).

Step E

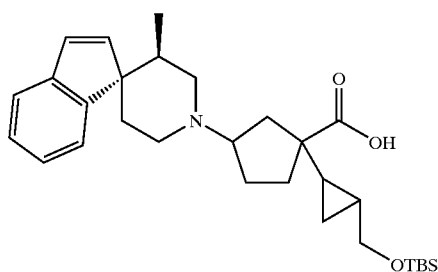

The aminoester prepared as described in Step D above (997 mg, 1.96 mmol) was dissolved in 1:1 THF/methanol (14 mL). Then a solution of LiOH.H₂O (410 mg, 9.78 mmol) in water (7 mL) was added and the resulting reaction mixture was stirred at room temperature for three days. The reaction mixture was concentrated and used as is in the subsequent step. HPLC-MS analysis revealed two peaks (2:1 ratio) with the major peak having M=382 and the minor peak having M=496 (M+H). The products were thus identified as being a 2:1 mixture of silyl-deprotected products and desired products.

Step F

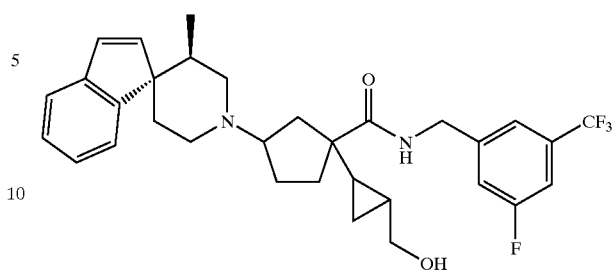

The acid mixture from Step E above (no more than 1.96 mmol) was dissolved in DCM (10 mL) and treated with 3-fluoro-5-trifluoromethylbenzylamine (568 mg, 2.94 mmol), EDC (751 mg, 3.92 mmol) and DMAP (~20 mg). The reaction mixture was stirred at room temperature overnight, then diluted with DCM and washed with saturated NaHCO₃ solution, water, and brine. The organic layer was dried over anhydrous MgSO₄, filtered, and concentrated. The crude product was dissolved in THF (10 mL) and treated with a THF solution of TBAF (1.0M, 2.35 mL, 2.35 mmol). The mixture was stirred at room temperature for 2 h., then was diluted with ethyl acetate and washed with water, followed by brine. The organic layer was dried over anhydrous MgSO₄, filtered, and concentrated. The crude product was purified and separated into two isomer mixtures (presumably cis-cyclopentyl and trans-cyclopentyl) by a sequence of steps including preparative TLC (silica, 10% methanol/ethyl acetate), repeated a second time (silica, 10% methanol/DCM), and MPLC (silica, 12–15% gradient methanol/ethyl acetate). The "top spot" mixture afforded 181 mg (trans) and the "bottom spot mixture" resulted in 275 mg (cis). ESI-MS top spot calc. for C32H36F4N2O2: 556; Found: 557 (M+H). ESI-MS bottom spot calc. for C32H36F4N2O2: 556; Found: 557 (M+H).

INTERMEDIATE 42

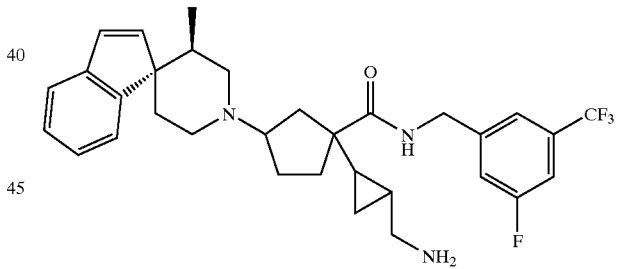

Step A

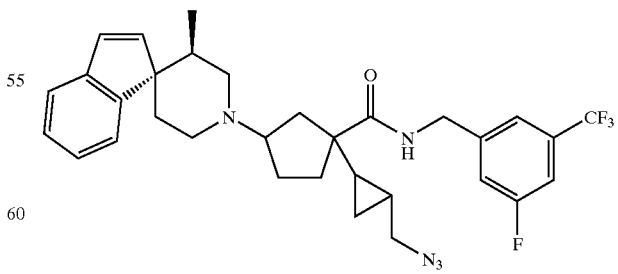

To a DCM (5 mL) solution of the mixture of isomers obtained from the top spot in Example 174 (162 mg, 0.291 mmol) at 0° C. was added triethylamine (59 mg, 0.58 mmol), followed in turn, by methanesulfonyl chloride (37 mg, 0.32 mmol). Then DMAP (~10 mg) was added and the reaction mixture was stirred at 0° C. for 1 h. The reaction mixture was diluted with more DCM, and was washed with water, saturated NaHCO$_3$ solution, and brine. The organic layer was dried over anhydrous MgSO$_4$, filtered and concentrated. The resulting crude mesylate mixture was dissolved in DMF (5 mL) and treated with sodium azide (95 mg, 1.46 mmol). The resulting mixture was stirred at 60° C. for 4 h., cooled to room temperature, diluted with ether, and washed with water five times. The ethereal layer was washed one final time with brine, dried over anhydrous MgSO$_4$, filtered and concentrated to give 122 mg of crude product, which was used as is in the next step. ESI-MS calc. for C32H35F4N5O: 581; Found 582 (M+H). The mixture of alcohol isomers obtained from the bottom spot in Example 174 was converted to its azide mixture in the same fashion as just described for the top spot isomers. ESI-MS calc. for C32H35F4N5O: 58 1; Found 582 (M+H).

Step B

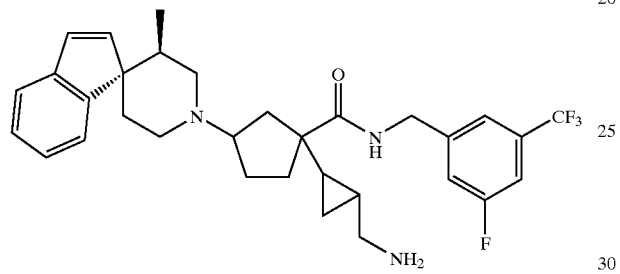

The mixture of 4 azide isomers obtained as described in Step A above (113 mg, 0.194 mmol) was combined with triphenylphosphine (510 mg, 1.94 mmol), and water (0.5 mL) in 10 mL of THF. The resulting mixture was stirred in a nitrogen atmosphere for 16 h. An additional 0.5 mL of water was added and the reaction mixture was stirred for one more hr. The organic solvent was removed at 50° C. under reduced pressure and the crude product was purified by preparative TLC (silica, first with 1/9/90 NH$_4$OH/methanol/DCM, then a second time with 1.5/13.5/85 NH$_4$OH/methanol/DCM) to afford 77 mg of a mixture of 4 diastereomeric amine isomers (Intermediate 42A). ESI-MS calc. for C32H37F4N3O: 555; Found: 556 (M+H). The other four amine diastereomers (see Step A) were prepared in the same fashion (from the bottom spot collected in Example 174) giving Intermediate 42B.

ESI-MS calc. for C32H37F4N3O: 555; Found: 556 (M+H).

EXAMPLE 175

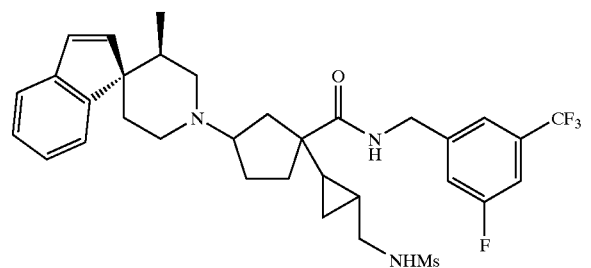

Intermediate isomer mixture 42A (19.5 mg, 0.035 mmol) was combined with triethylamine (73 µL, 0.53 mmol) in DCM (3 mL) and treated with methanesulfonyl chloride (40 mg, 0.35 mmol). The reaction mixture was stirred at room temperature overnight. After partially concentrating the reaction mixture to <1 mL, it was directly applied to a preparative TLC plate and eluted with 0.5/4.5/95 NH$_4$OH/methanol/DCM. The mixture of four diastereomers was thus separated into two sets of two isomers, presumably threo and erythro, respectively. These were then converted to their hydrochloride salts by dissolving in DCM, adding 2 drops (excess) of 4 N HCl in dioxane, and concentrating. ESI-MS calc for top spot C33H39F4N3O3S: 633; Found: 634 (M+H). ESI-MS calc for bottom spot C33H39F4N3O3S: 633; Found: 634 (M+H).

This same procedure was carried out with the other mixture of four amine isomers, Intermediate 42B. This also resulted in separation of the product mixture into two sets of two isomers, leading in total to four sets of two diastereomeric methanesulfonamides. ESI-MS calc for top spot C33H39F4N3O3S: 633; Found: 634 (M+H). ESI-MS calc for bottom spot C33H39F4N3O3S: 633; Found: 634 (M+H).

EXAMPLE 176

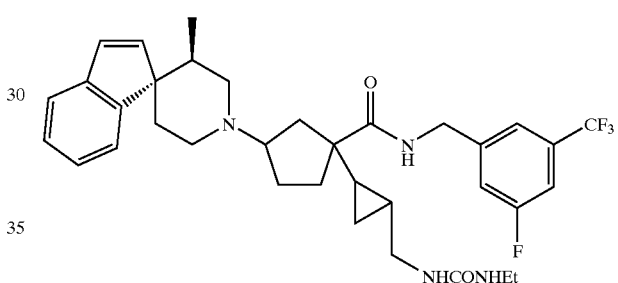

Intermediate isomer mixture 42A (8.3 mg, 0.015 mmol) was combined with triethylamine (13 µL, 0.089 mmol), and disuccidimidyl carbonate (10 mg, 0.037 mmol) in DCM (3 mL). After one h., a 2N THF solution of ethylamine (75 µL, 0.15 mmol) was added and the reaction mixture was stirred overnight. After concentrating the reaction mixture to <1 mL, it was applied directly to a preparative TLC plate and eluted with 0.5/4.5/95 NH$_4$OH/methanol/DCM. The mixture of four diastereomers was thus separated into two sets of two isomers, presumably threo and erythro, respectively. These were then converted to their hydrochloride salts by dissolving in DCM, adding 2 drops (excess) of 4 N HCl in dioxane, and concentrating.

ESI-MS calc for top spot C35H42F4N4O2: 626; Found: 627 (M+H). ESI-MS calc for bottom spot C35H42F4N4O2: 626; Found: 627 (M+H).

This same procedure was carried out with the other mixture of four amine isomers, Intermediate 42B. The resulting four isomeric ureas were not separable in this case.

ESI-MS calc for C35H42F4N4O2: 626; Found: 627 (M+H).

EXAMPLE 177

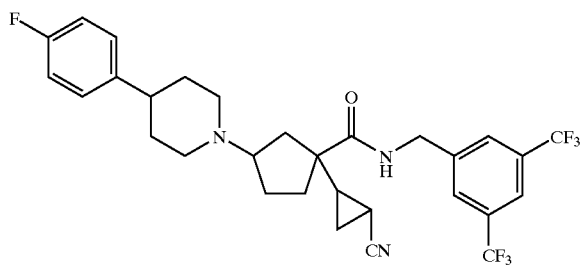

Step A

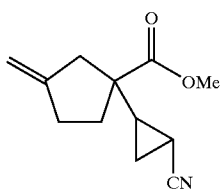

A precooled (−78° C.) THF (80 mL) solution of commercially available methyl-(3-methylenecyclopentane) carboxylate (3.90 g, 27.8 mmol) was treated dropwise with 1.5 M LDA in cyclohexane (22.3 mL, 33.4 mmol) over 10 min. The reaction mixture was stirred for an additional 35 min., then a solution of 4-bromocrotononitrile (1:2 trans/cis, prepared according to Zindel, J.; de Meijere, A., *Synthesis* (1994), 190–194. 4.26 g, 29.2 mmol) in THF (5 mL) was added dropwise over 10 min. The reaction mixture was stirred at −78° C. for 1.5 h., then poured into 10% citric acid solution. This mixture was extracted twice with ether (300 mL), the ethereal layers were combined, and these in turn were washed with saturated NaHCO₃ solution, followed by brine. The ethereal layer was then dried over anhydrous MgSO₄, filtered, and concentrated. Purification by MPLC (silica, 40% ether/hexane) afforded two product mixtures (6:1 ratio), corresponding to the four isomers with trans-cyclopropyl stereochemistry (3.07 g) and the four with cis-cyclopropyl stereochemistry (504 mg), respectively.

Step B

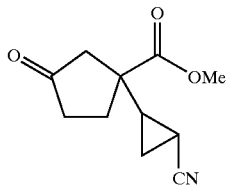

Ozone gas was bubbled through a cooled solution (−78° C.) of the olefin prepared as described in Step A above (top spot, trans-cyclopropyl, 3.07 g, 15.0 mmol) in DCM (50 mL) until the reaction mixture became blue in color. Then nitrogen gas was bubbled through the solution until it was colorless again. Triphenylphosphine (4.33 g, 16.5 mmol) was then added and the reaction mixture was permitted to warm to room temperature and stir for three hours. The reaction mixture was then concentrated and purified by flash chromatography (silica, eluted with DCM, then 1% methanol/DCM, then 3% methanol/DCM) to give 1.31 g of product as a mixture of 4 diastereomers (trans cyclopropyl). The olefin prepared in Step A having the cis-cyclopropyl stereochemistry (bottom spot) was converted to its corresponding ketone in the same fashion as that described immediately above.

Step C

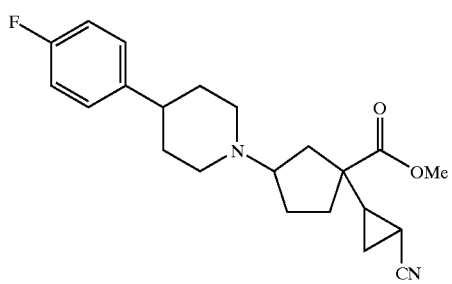

The trans-cyclopropyl ketone from Step B above (1.31 g, 6.32 mmol) was combined with 4-(p-fluorophenyl) piperidine hydrochloride (1.64 g, 7.59 mmol), triethylamine (1.06 mL, 7.59 mmol), 4 Å powdered molecular sieves (~2 g), and sodium triacetoxyborohydride (5.36 g, 25.3 mmol) in 50 mL DCM. The reaction mixture was stirred at room temperature for 3 days, then filtered through celite, diluted with DCM, and washed with saturated NaHCO₃ solution and brine. The organic layer was dried over anhydrous MgSO₄, filtered and concentrated. Flash chromatography (silica, 3–4% gradient of a 10% NH₄OH solution in methanol in DCM) furnished 2.02 g of product, now as a mixture of 8 isomers (cis/trans cyclopentyl). ESI-MS calc. for C22H27FN2O2: 370; Found: 371 (M+H). This same procedure was carried out with the ketone having the cis-cyclopropyl stereochemistry (389 mg, 1.88 mmol), giving after purification 438 mg of a mixture of eight diastereomers (cis cyclopropyl, and a mixture of cis and trans cyclopentyl). ESI-MS calc. for C22H27FN2O2: 370; Found: 371 (M+H).

Step D

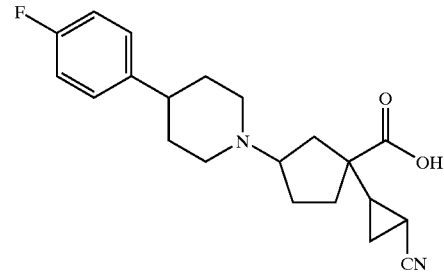

The aminoester isomer mixture (trans-cyclopropyl, cis/trans-mixture cyclopentyl) prepared in Step C above (1.98 g, 5.34 mmol) was dissolved in 1:1 THF/methanol (18 mL) and treated with a solution of LiOH.H₂O (1.12 g, 26.7 mmol) in 9 mL of water. The resulting reaction mixture was stirred at room temperature for 1 h, then neutralized with 1 N HCl solution, and concentrated to remove the organic solvents. The aqueous product mixture was then extracted three times with chloroform, the organic layers were combined and dried over anhydrous MgSO₄, filtered, and concentrated. The crude product was purified by flash chromatography (silica, 10–20% gradient of methanol/DCM) to give 1.17 g of carboxylic acid product as an inseparable mixture of eight isomers. ESI-MS calc. for C21H25FN2O2: 356; Found 357 (M+H). This same procedure was carried out with the aminoester mixture having the cis-cyclopropyl stereochemistry (389 mg, 1.88 mmol), giving after purification a mixture of eight diastereomers (cis cyclopropyl, and a mixture of cis and trans cyclopentyl). ESI-MS calc. for C21H25FN2O2: 356; Found 357 (M+H).

Step E

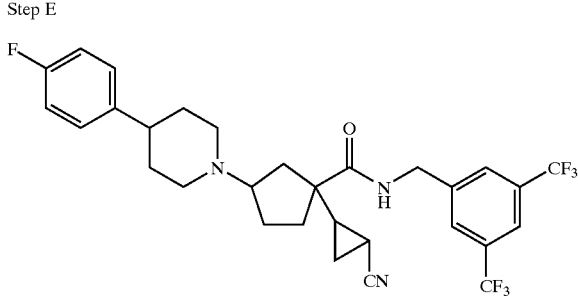

The carboxylic acid mixture (trans-cyclopropyl, cis/trans-cyclopentyl) prepared as described in Step D (732 mg, 2.05 mmol) was combined with 3,5-Bis(trifluoromethyl)benzylamine hydrochloride (861 mg, 3.08 mmol), EDC (589 mg, 3.08 mmol), and DMAP (~25 mg) in DCM (20 mL). The resulting mixture was stirred at room temperature for 2 h., then diluted with more DCM and washed with water, followed by brine. The organic layer was dried over anhydrous $MgSO_4$, filtered, and concentrated. Purification by MPLC (silica, 10–15% stepwise gradient of methanol/ethyl acetate) afforded two mixtures of four isomers each, presumably by separation of the cis and trans-cyclopentyl isomers. The top spot mixture gave 708 mg (cis-cyclopentyl) and the bottom spot mixture gave 591 mg (trans-cyclopentyl).

ESI-MS top spot mixture calc. for C30H30F7N3O: 581; Found 582 (M+H). ESI-MS bottom spot mixture calc. for C30H30F7N3O: 581; Found 582 (M+H).

This same procedure was carried out on the mixture of isomers having the cis-cyclopropyl arrangement (see Step A). This product mixture also was separable into two sets of four isomers, again presumed to be the 4 cis-cyclopentyl and the 4-trans-cyclopentyl isomers. ESI-MS top spot mixture calc. for C30H30F7N3O: 581; Found 582 (M+H).

ESI-MS bottom spot mixture calc. for C30H30F7N3O: 581; Found 582 (M+H). The four cis isomer mixture could be further separated by chiral HPLC separation (ChiralPak AD column, 5% ethanol/hexane) into two single isomers (peaks one and three) and one mixture of two isomers (peak 2).

EXAMPLE 178

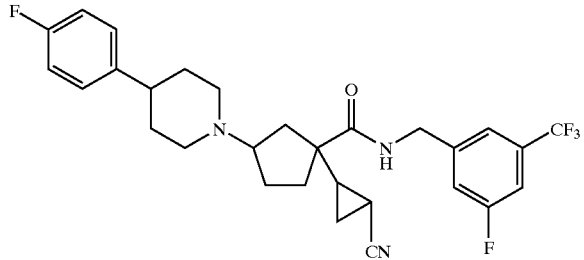

A solution of the primary amide from Example 171, Table 1 above (403 mg, 0.733 mmol, mixture of 4-diastereomers) in THF (5 mL) under $N_2$ was treated with pyridine (178 μL, 2.20 mmol), followed by trifluoroacetic anhydride (dropwise, 176 μL, 1.25 mmol). The reaction mixture was stirred at room temperature overnight, however HPLC-MS indicated that the reaction had only gone to 60% conversion. Second portions of pyridine and trifluoroacetic anhydride were added, as above, and the reaction was stirred for 2 more h. HPLC-MS now showed the reaction to be complete. The reaction mixture was quenched with water, then partially concentrated to remove the THF. The resulting mixture was diluted with DCM and washed with water. The aqueous layer was back-washed with more DCM, and the organic layers were combined, washed with brine, dried over anhydrous $MgSO_4$, filtered, and concentrated. Purification by preparative TLC (silica, 10% methanol/DCM) gave 282 mg of nitrile as a mixture of four isomers (72%).

1H NMR ($CDCl_3$, 500 MHz) δ 9.17 (br s, 1H), 7.36 (s, 1H), 7.23 (t, J=8 Hz, 2H), 6.98 (br s, 4H), 4.57 (m, 1H), 4.43 (m, 1H), 3.19 (m, 1.5H), 2.84 (m, 0.5H), 2.49 (m, 1H), 1.7–2.1 (m, 8H), 1.48–1.62 (m, 3H), 1.08–1.28 (overlapping m, 6H).

INTERMEDIATE 43

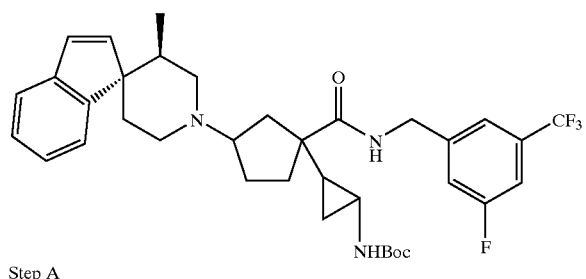

Step A

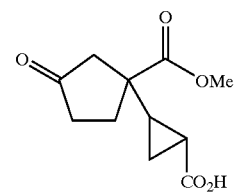

The intermediate ketodiester prepared as described in the synthesis of Intermediate 40, Step B (945 mg, 3.35 mmol) was dissolved in 1:1 TFA/DCM (10 mL) and stirred at room temperature for 3 h. The reaction mixture was then concentrated. The residue was partitioned between water and ethyl acetate. The organic layer was washed again with water, then with brine, then was dried over anhydrous $MgSO_4$, filtered, and concentrated. The crude product was purified by MPLC (silica, 1/49/50 acetic acid/ethyl acetate/hexane) to afford 654 mg of product as a yellow oil (inseparable mixture of 4 isomers, 86%). 1H NMR ($CDCl_3$, 500 MHz) δ 3.77 (s, 3H), 2.70 (m, 1H), 2.41 (m, 1H), 2.35 (m, 2H), 1.94–2.06 (m, 3H), 1.59–1.67 (m, 1H), 1.33 (m, 1H), 0.99 (m, 1H).

Step B

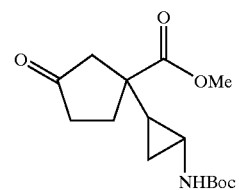

The carboxylic acid prepared as described in Step A above (511 mg, 2.26 mmol) was combined with diphenylphosphoryl azide (535 μL, 2.48 mmol), and triethylamine (378 μL, 2.71 mmol) in toluene (10 mL). The resulting mixture was heated at 90° C. under nitrogen for 2 h. The reaction mixture was then cooled and t-butanol (20 mL) was added, then the temperature was raised again to 90° C. and the mixture was stirred overnight. After cooling to room temperature, the reaction mixture was concentrated, then purified directly by MPLC (silica, 50% ethyl acetate/hexane), giving 198 mg of a yellow oil (29%). 1H NMR (CDCl$_3$, 500 MHz) δ 4.70 (br s, 1H), 3.75 (overlapping s, 3H), 2.60–2.71 (m, 1H), 2.51 (m, 1H), 2.32 (m, 2H), 2.16 (m, 1H), 1.98 (m, 1H), 1.45 (s, 9H), 1.28–1.38 (m, 1H), 0.70–0.92 (m, 2H).

Step C

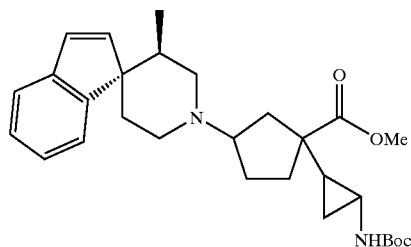

The ketone intermediate prepared as described in Step B above (198 mg, 0.666 mmol) was combined with 3-methylspiroindenepiperidine hydrochloride (Intermediate 1, 235 mg, 0.999 mmol), triethylamine (139 µL, 0.999 mmol), and powdered molecular sieves (~1 g) in DCM (5 mL) and treated with sodium triacetoxyborohydride (282 mg, 1.33 mmol). The reaction mixture was stirred at room temperature for 48 h, then was filtered through celite. The filtrate was concentrated, then partitioned between ethyl acetate and water. The organic layer was washed with saturated NaHCO$_3$, then brine, dried over anhydrous MgSO$_4$, filtered, and concentrated. Purification by MPLC (silica, 55% ethyl actetate/hexane) afforded 273 mg of a white solid (85%). Since this reaction generated cis/trans-amine isomers, the total number of isomers present was eight. ESI-MS calc. for C29H40N2O4: 480; Found: 481 (M+H).

Step D

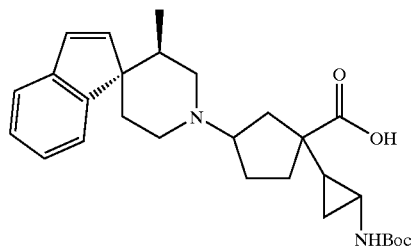

The aminoester prepared as described in Step C above (273 mg, 0.568 mmol) was dissolved in 1:1 THF/methanol (6 mL) and treated with a solution of LiOH.H$_2$O (119 mg, 2.84 mmol) in water (3 mL). The reaction mixture was stirred at room temperature for 4 h., then was cooled to 0° C. and treated with 10% citric acid until the pH was 7. The reaction mixture was then concentrated to remove the organic solvents and the resulting aqueous mixture was extracted three times with ethyl acetate. The aqueous phase was then treated with 1 N HCl solution until the pH was 4, and then extracted two more times with ethyl acetate. The organic layers were combined and washed with 1 N HCl solution, then brine. The organic phase was dried over anhydrous MgSO$_4$, filtered, and concentrated. The crude product was purified by preparative TLC (silica, 5% MeOH/DCM) to provide 116 mg of a top spot (four "cis" isomers), and 130 mg of a bottom spot (four "trans" isomers). ESI-MS calc. for C28H38N2O4: 466; Found: 467 (M+H).

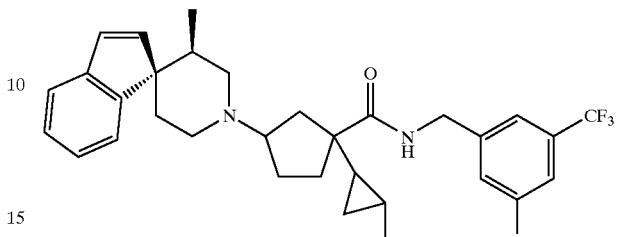

The four isomers of amino acid obtained from the top spot (cis) in Step D above (114 mg, 0.244 mmol) were combined with 3-fluoro-5-trifluoromethylbenzylamine (54 µL, 0.37 mmol), EDC (70 mg, 0.37 mmol), and DMAP (3.0 mg, 0.024 mmol) in DCM (5 mL). The reaction mixture was allowed to stir at room temperature over the weekend. The reaction mixture was then poured into water and extracted with DCM. The organic layer was washed with brine, dried over anhydrous MgSO$_4$, filtered, and concentrated. Purification by preparative TLC (silica, 0.5/4.5/95 NH$_4$OH/methanol/DCM, then a second purification using 0.3/2.7/97 NH$_4$OH/methanol/DCM) resulted in separation of the product mixture into two sets of two isomers (top spot 82.1 mg, bottom spot 34 mg). Intermediate 43A, ESI-MS top spot calc. for C36H43F4N4O3: 641; Found: 642 (M+H). Intermediate 43B, ESI-MS bottom spot calc. for C36H43F4N4O3: 641; Found: 642 (M+H).

EXAMPLE 179

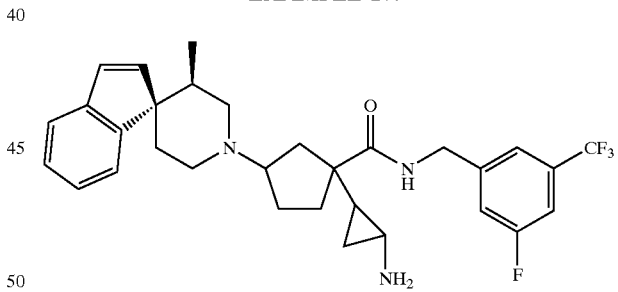

The two isomers obtained from the top spot in the synthesis of Intermediate 43 (Step E, 43A) (79 mg, 0.123 mmol) were dissolved in 4N HCl in dioxane (3 mL) and stirred at room temperature for 4 h. The reaction mixture was then concentrated to give 74 mg of a yellow solid (98%), Example 179A.

ESI-MS calc. for C31H35F4N3O: 541; Found: 542 (M+H).

This same procedure was carried out on the two isomers obtained from the bottom spot in the synthesis of Intermediate 43 (Step E, 43B) (31 mg, 0.0483 mmol) giving 28 mg of a yellow solid (94%), Example 179B. ESI-MS calc. for C31H35F4N3O: 541; Found: 542 (M+H).

EXAMPLE 180

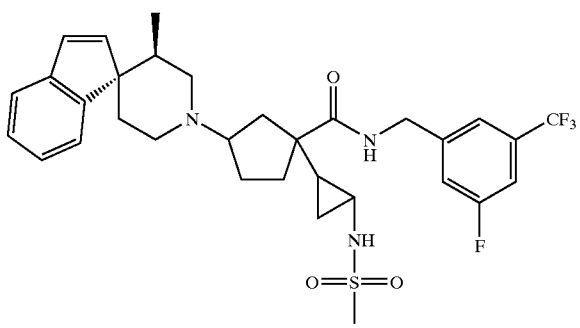

To a solution of the product obtained in Example 179A (top spot-two isomers, 23 mg, 0.043 mmol) in DCM (3 mL), was added triethylamine (89 µL, 0.64 mmol), followed by methanesulfonyl chloride (33 µL, 0.43 mmol). The reaction mixture was stirred overnight at room temperature. The reaction mixture was concentrated, loaded directly onto a preparative TLC plate (silica), and eluted with 0.5/4.5/95 NH$_4$OH/methanol/DCM. A white solid (16 mg, 60%) was collected.

ESI-MS calc. for C32H37F4N3O3S: 619; Found: 620 (M+H).

This same procedure was carried out using the product obtained in Example 179B (bottom spot-two isomers, 13 mg, 0.024 mmol) giving 8.0 mg (55%) of a white solid.

ESI-MS calc. for C32H37F4N3O3S: 619; Found: 620 (M+H).

EXAMPLE 181

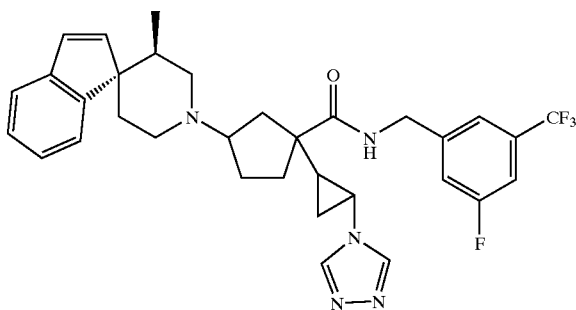

To a solution of the product obtained in Example 179B (bottom spot-two isomers, 13 mg, 0.024 mmol) in toluene (3 mL) was added N,N-dimethylformamide azine (10 mg, 0.072 mmol, prepared according to Bartlett, R. K.; Humphrey, I. R., *J. Chem. Soc. C* (1967), 1664.) and TsOH (1 mg). The resulting mixture was stirred at reflux for 24 h., concentrated, and applied directly to a reparative TLC plate (silica, eluted with 1/9/90 NH$_4$OH/methanol/DCM). A white powder (8 mg, 57%) was collected. ESI-MS calc. for C33H35F4N5O: 593; Found: 94 (M+H).

EXAMPLE 182

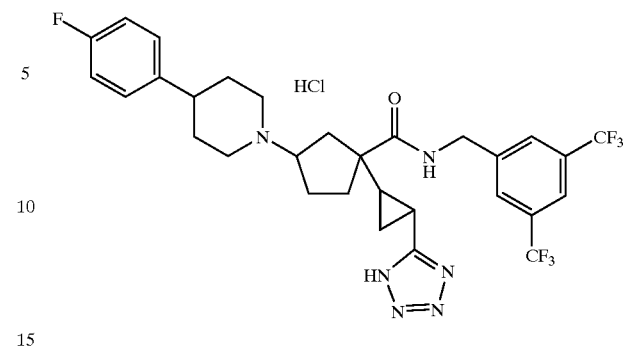

The product from Example 177 above (top spot, cis-cyclopentyl, trans-cyclopropyl, a mixture of four isomers, 101 mg, 0.174 mmol) was combined under a nitrogen atmosphere with sodium azide (34 mg, 0.52 mmol), and triethylamine hydrochloride (36 mg, 0.26 mmol) in 1-methyl-2-pyrrolidinone (3 mL). The resulting mixture was stirred at reflux for 2.5 h, then at room temperature overnight. The reaction mixture was diluted with ethyl acetate and washed with water. The aqueous layer was back washed with ethyl acetate, the organic layers were combined, and washed an additional 3 times with water and once with brine. The organic layer was then dried over anhydrous MgSO$_4$, filtered, and concentrated. Purification was accomplished by reverse phase HPLC (Column: YMC ProC18, 20×100 mm, ODS-A 5 µM; Gradient 10–70% of 0.1% TFA/MeCN in 0.1% TFA/water over 10 min., followed by ramp to 100% of 0.1% TFA/MeCN over 2 min.) to give the TFA salt, which was taken up in DCM and treated with excess 4 N HCl in dioxane and concentrated (repeat twice). ESI-MS calc. for C30H31F7N6O: 624; Found: 625 (M+H).

EXAMPLE 183

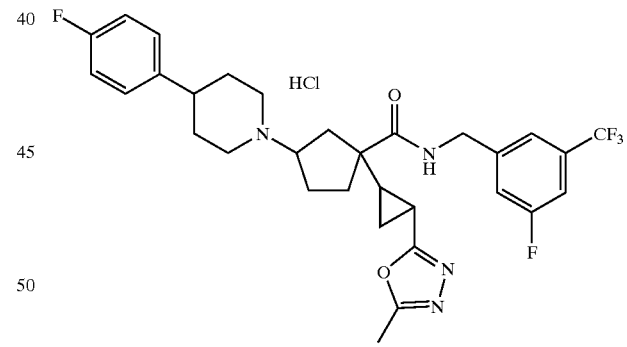

The carboxylic acid from Example 157 above (122 mg, 0.222 mmol) was combined with acetic hydrazide (20 mg, 0.27 mmol) in phosphorus oxychloride (1 mL) and stirred at reflux for two h. The mixture was stirred at room temperature overnight then concentrated. The residue was purified by reverse phase HPLC, (Column: YMC ProC18, 20×100 mm, ODS-A 5 µM; Gradient 10–70% of 0.1% TFA/MeCN in 0.1% TFA/water over 10 min., followed by ramp to 100% of 0.1% TFA/MeCN over 2 min.) giving the TFA salt, which was taken up in DCM and treated with excess 4 N HCl in dioxane and concentrated (repeat twice) to afford 7 mg of product (mixture of 4 diastereomers) as its HCl salt. ESI-MS calc. for C31H33F5N4O2: 588; Found: 589 (M+H).

EXAMPLE 184

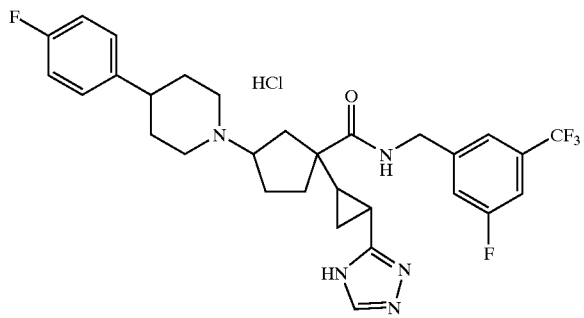

A solution of the primary amide from Example 171, Table 1 above (117 mg, 0.213 mmol, mixture of 4-diastereomers) in N,N-dimethylformamide dimethylacetal (1 mL) was stirred at 120° C. for 2 h. The N,N-dimethylformamide dimethylacetal was distilled off (120° C., house vacuum, short path distillation apparatus). The residue was dissolved in glacial acetic acid (1 mL), treated with hydrazine hydrate (13 mg, 0.26 mmol), and stirred at 90° C. for 2 h. The reaction mixture was concentrated to remove the acetic acid. The residue was partitioned between ethyl acetate and saturated NaHCO$_3$ solution. The organic layer was washed a second time with saturated NaHCO$_3$ solution, then with brine, then was dried over MgSO$_4$, filtered, and concentrated. The crude product was purified by reverse phase HPLC (Column: YMC ProC18, 20×100 mm, ODS-A 5 μM; Gradient 10–70% of 0.1% TFA/MeCN in 0.1% TFA/water over 10 min., followed by ramp to 100% of 0.1% TFA/MeCN over 2 min.) to give the TFA salt, which was taken up in DCM and treated with excess 4 N HCl in dioxane and concentrated (repeat twice). 51 mg of the product, as a mixture of four diastereomers, was obtained.

ESI-MS calc. for C30H32F5N5O: 573; Found: 574 (M+H).

EXAMPLE 185

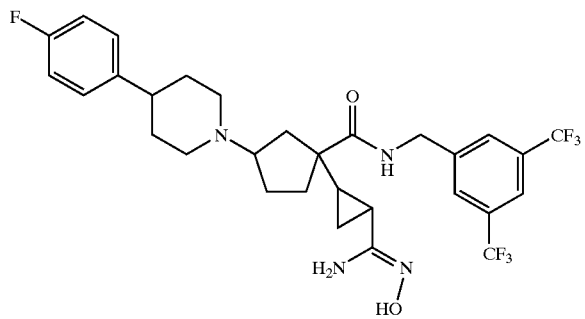

The nitrile from Example 177 above (mixture of four diastereomers, 197 mg, 0.338 mmol) was combined with hydroxylamine hydrochloride (65.4 mg, 1.01 mmol) and potassium carbonate powder (93 mg, 0.68 mmol) in ethanol (2 mL) and stirred at reflux overnight. HPLC-MS analysis indicated that the reaction was incomplete, so second portions of hydroxylamine hydrochloride and potassium carbonate were added and the mixture was stirred at reflux for an 24 h. The mixture was then concentrated and partitioned between DCM and brine. After washing the aqueous layer a second time with DCM, the organic layers were combined, dried over Na$_2$CO$_3$, filtered and concentrated. Purification by preparative TLC (eluting with 1:9:90 NH$_4$OH solution/methanol/DCM) gave 155 mg of product as a mixture of 4 diastereomers. ESI-MS calc. For C30H33F7N4O2: 614; Found: 615 (M+H).

EXAMPLE 186

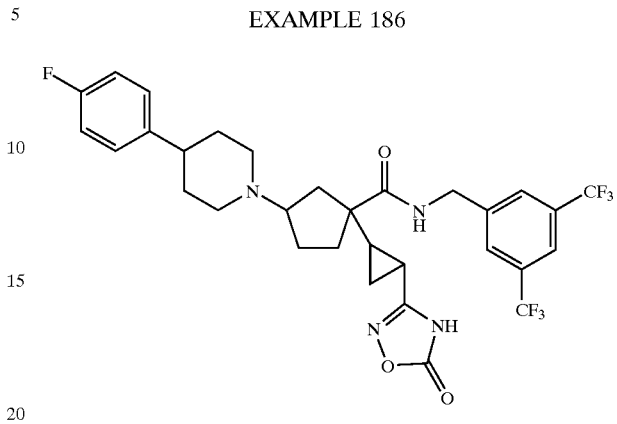

The product from Example 185 above (74.4 mg, 0.121 mmol) was dissolved in DCM (5 mL) and treated with triethylamine (20 μL, 0.15 mmol), followed by isobutyl-chloroformate (17 μL, 0.13 mmol). The reaction mixture was stirred at room temperature for 1.5 h, then diluted with DCM and washed with water followed by brine. The organic phase was dried over MgSO$_4$, filtered and concentrated. The resulting crude ester was dissolved in m-xylene and stirred at reflux for 2 h. The reaction mixture was concentrated and the crude product was purified by reverse phase HPLC (Column: YMC ProC18, 20×100 mm, ODS-A 5 μM; 10 Gradient 10–70% of 0.1% TFA/MeCN in 0.1% TFA/water over 10 min., followed by ramp to 100% of 0.1% TFA/MeCN over 2 min.). Further purification by preparative TLC (eluted with 1:9:90 of NH$_4$OH solution/MeOH/DCM) gave 12.1 mg of the desired product. ESI-MS calc. for C31H31F7N4O3: 640; Found: 641 (M+H).

EXAMPLE 187

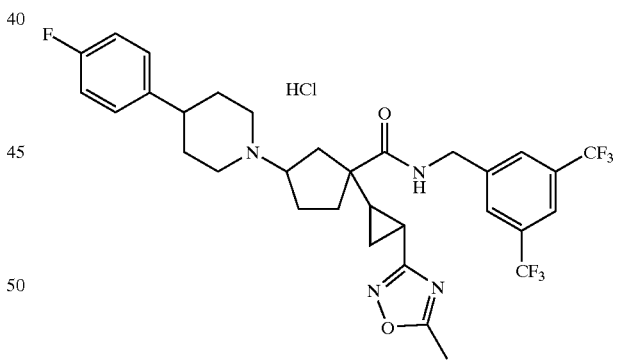

The product from Example 185 above (70.5 mg, 0.115 mmol) was dissolved in acetic anhydride (2 mL) and stirred at reflux for 3 h. The reaction mixture was concentrated and purified by reverse phase HPLC (Column: YMC ProC18, 20×100 mm, ODS-A 5 μM; Gradient 10–70% of 0.1% TFA/MeCN in 0.1% TFA/water over 10 min., followed by ramp to 100% of 0.1% TFA/MeCN over 2 min.). Further purification by preparative TLC (eluted with 1.5:13.5:85 of NH$_4$OH solution/MeOH/DCM) and conversion of the resultant free base to its hydrochloride salt with 4 N HCl in dioxane (excess) gave 31.2 mg of the desired product. ESI-MS calc. for C32H33F7N4O2: 638; Found: 639 (M+H).

EXAMPLE 188

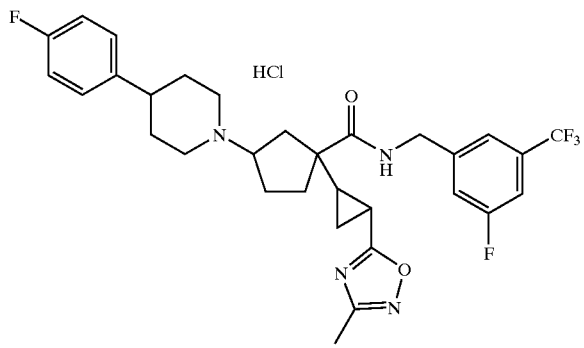

A solution of the primary amide from Example 171, Table 1 above (29 mg, 0.053 mmol, mixture of 4-diastereomers) in N,N-dimethylacetamide dimethylacetal (1 mL) was stirred at 120° C. for 3 h, then concentrated using a short path distillation apparatus. A solution of hydroxylamine hydrochloride (5.5 mg, 0.079 mmol) and 5 N NaOH (16 µL, 0.079 mmol) in 7:3 acetic acid/water (1.5 mL) was added to the intermediate residue and the resulting mixture was stirred at room temperature for 3 h. The reaction mixture was then diluted with ethyl acetate and washed with 2 N NaOH solution twice, with water once, and with brine once. The organic layer was dried over MgSO$_4$, filtered, and concentrated. The crude product was purified by reverse phase HPLC (Column: YMC ProC18, 20×100 mm, ODS-A 5 µM; Gradient 10–70% of 0.1% TFA/MeCN in 0.1% TFA/water over 10 min., followed by ramp to 100% of 0.1% TFA/MeCN over 2 min.). Further purification by preparative TLC (eluted with 0.5:4.5:95 of NH$_4$OH solution/MeOH/DCM) resulted in isolation of two spots, each identified as product (mixtures of two diastereomers) by HPLC-MS. The resultant free bases were converted to the corresponding hydrochloride salts with 4 N HCl in dioxane (excess) giving 7.2 mg (top spot) and 1.5 mg (bottom spot) of the desired products.

INTERMEDIATE 44

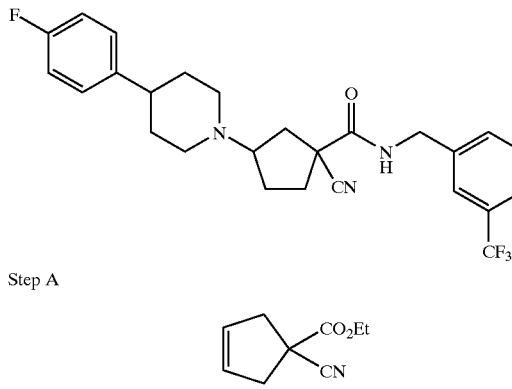

Step A

A solution of ethyl cyanoacetate (40.9 g, 0.361 mol) in 400 mL DMF was cooled to 0° C. and treated under a steady stream of N$_2$ with lithium hydride (7.18 g, 0.903 mol) in multiple portions. After hydrogen evolution subsided, cis-1,4-dichloro-2-butene (51.9 g, 0.415 mol) was added dropwise by addition funnel. The reaction became very thick during the addition, requiring the addition of 200 mL of DMF to aid in stirring. The reaction mixture was permitted to warm to room temperature and was stirred for 1 h. The reaction mixture was then poured into a 1:1 mixture of water/ice, which was in turn extracted twice with ether. The ethereal layers were combined and washed five times with water, and once with brine. The ethereal phase was then dried over MgSO$_4$, filtered and concentrated. The resulting crude product was distilled using a short path distillation apparatus (1 mm Hg, bath temperature=100° C., head temperature=75° C.), giving 25.8 g of the desired product (43%). 1H NMR (CDCl$_3$, 500 MHz) δ 5.70 (s, 2H), 4.27 (q, J=7 Hz, 2H), 3.10 (m, 4H), 1.34 (t, J=7 Hz, 3H).

Step B

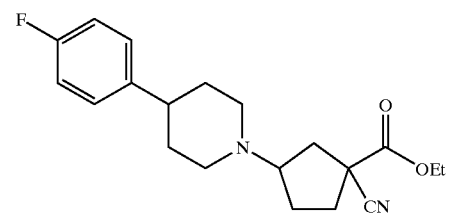

A solution of the cyclopentene prepared in Step A above (17.5 g, 0.106 mol) in 100 µL of THF was cooled to −78° C. and treated with BH$_3$.THF (1 M solution in THF, 63.5 mL, 63.5 mmol) dropwise. The reaction mixture was stirred at −78° C. for 0.5 h, then warmed to room temperature and stirred for an additional 1 h. TLC indicated that the reaction was incomplete so the mixture was cooled back to −78° C. and treated with more BH$_3$.THF solution (1 M solution in THF, 42 mL, 42 mmol). The reaction mixture was then warmed to room temperature and stirred for 2 h. After storing overnight in a freezer, the reaction mixture was concentrated at room temperature and redissolved in DCM (500 mL). Then while stirring with an overhead mechanical stirring apparatus, premixed PCC (137 g, 0.635 mol) and magnesium sulfate (130 g) were added in portions over 15 minutes. The resulting exothermic reaction was controlled with an ice bath. After stirring at room temperature for 3 h, the reaction mixture was filtered through a 3" plug of silica, washing the remaining solids three times with acetone. The filtrate was concentrated and filtered a second time through a 3" silica plug washing through with 50% ethyl acetate/hexane. The filtrate was concentrated and the residue was purified by flash chromatography (silica, 50% ethyl acetate/hexane) giving 4.63 g (24%) of product.

1H NMR (CDCl$_3$, 500 MHz) δ 4.35 (q, J=8.5 Hz, 2H), 2.94 (d, J=23 Hz, 1H), 2.78 (d, J=23 Hz, 1H), 2.51–2.70 (m, 4H), 1.38 (t, J=9 Hz, 3H).

Step C

A solution of the ketone prepared as described in Step B above (3.57 g, 19.7 mmol) in DCM (75 mL) was treated with triethylamine (3.29 mL, 23.6 mmol), 4-(4-fluorophenyl)piperidine hydrochloride (5.10 g, 23.6 mmol), 4 Å powdered molecular seives (5 g), and sodium triacetoxyborohydride (16.7 g, 78.8 mmol). The resulting mixture was stirred at room temperature for 72 h. The reaction mixture was then filtered through celite, washing with additional DCM. The filtrate was washed with saturated NaHCO₃ solution, water, and brine. The organic layer was dried over anhydrous MgSO₄, filtered, and concentrated. The crude product was purified by MPLC (silica, ethyl acetate, then 5% methanol/ ethyl acetate, then 10% methanol/ethyl acetate) to give 4.45 g of product as a colorless oil (66%). ESI-MS calc. for C20H25FN2O2: 344; Found: 345 (M+H).

Step D

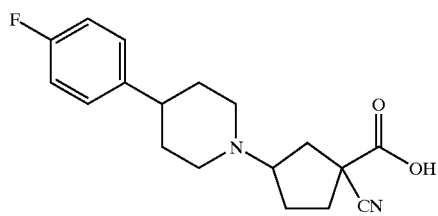

A solution of the aminoester prepared as described in Step C above (4.34 g, 12.6 mmol) in 1:1 THF/methanol (50 mL) was treated over a period of 5 min with a solution of LiOH.H₂O (2.64 g, 63.0 mmol) in water (25 mL). The reaction mixture was stirred at room temperature for 1 h, then neutralized with 3N HCl solution, and concentrated to remove the organic solvents. The aqueous mixture was diluted with brine and extracted three times with chloroform. The combined organic layers were dried over anhydrous MgSO₄, filtered, and concentrated. The crude product was purified by flash chromatography (silica, 10–20% methanol/DCM gradient), affording 1.64 g of the top spot corresponding to the cis-isomer (based on previous examples) and 1.27 g of the bottom spot corresponding to the trans-isomer (total yield: 73%). Top spot (cis-isomer): ESI-MS calc. for C18H21FN2O2: 316; Found: 317 (M+H). Bottom spot (trans-isomer): ESI-MS calc. for C18H21FN2O2: 316; Found: 317 (M+H).

Step E

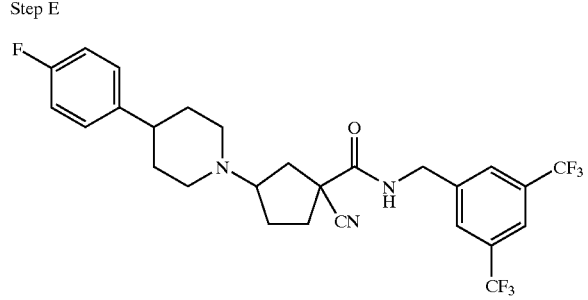

The cis-aminoacid prepared as described in the last step (1.40 g, 4.41 mmol) was combined with EDC (1.69 g, 8.82 mmol), 3,5-bis(trifluoromethyl)benzylamine hydrochloride (1.85 g, 6.62 mmol), triethylamine (0.923 mL, 6.62 mmol), and DMAP (~100 mg) in DCM (50 mL). After stirring at room temperature for 2.5 h, the reaction mixture was diluted with DCM and washed with water twice, then brine. The organic layer was dried over anhydrous MgSO₄, filtered, and concentrated. The crude product was purified by MPLC (silica, 5% methanol/ethyl acetate) to afford 1.72 g of product (72%) with the amine and amide groups cis-to each other. ESI-MS calc. for C27H26F7N3O: 541; Found: 542 (M+H).

INTERMEDIATE 45

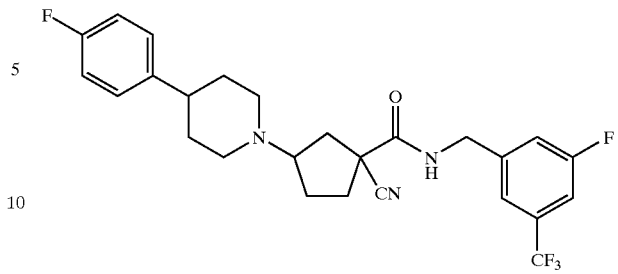

Intermediate 45 was prepared in the same fashion as intermediate 44, above, starting from the cis-aminoacid prepared as described in Step D (233 mg, 0.737 mmol) and 3-fluoro-5-trifluoromethylbenzylamine, giving after purification by preparative TLC (silica, 0.3/2.7/97 NH₄OH/ MeOH/DCM) 286 mg of product (79%). ESI-MS calc. for C26H26F5N3O: 491; Found: 492 (M+H).

EXAMPLE 189

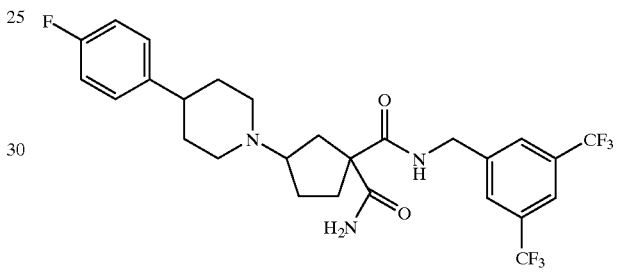

Intermediate 44 (50.4 mg, 0.0931 mmol) was dissolved in DMSO (1 mL) and treated with K₂CO₃ (3 mg), followed by 30% H₂O₂ solution (12 μL). The reaction mixture was stirred at room temperature for 0.5 h, then was quenched with 10% Na₂CO₃ solution. The aqueous mixture was extracted twice with ethyl acetate. The combined organic layers were washed four times with water and once with brine, then dried over anhydrous MgSO₄, filtered, and concentrated. The crude product (44.6 mg) was collected as a white solid and required no further purification. ESI-MS calc. for C27H31F7N3O2: 559; Found: 560 (M+H).

EXAMPLE 190

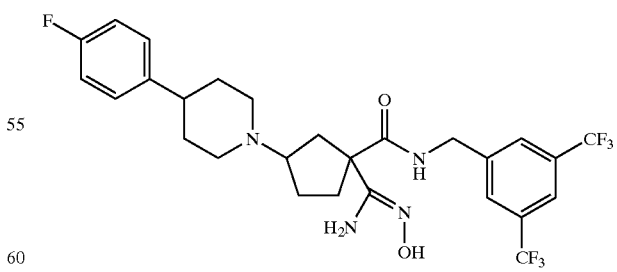

Triethylamine (248 μL, 1.78 mmol) was added to a suspension of hydroxylamine hydrochloride (124 mg, 1.78 mmol) in DMSO (1 mL). The resulting thick slurry was filtered and the filtercake was washed with THF (5 mL). The filtrate was concentrated to remove the THF and the remaining hydroxylamine in DMSO was added to Intermediate 44 (193 mg, 0.356 mmol). The reaction mixture was stirred at 75° C. for 2 h. After cooling to room temperature, the reaction mixture was diluted with ethyl acetate and washed three times with water and once with brine. The organic layer was dried over anhydrous MgSO$_4$, filtered, and concentrated, giving 197 mg of product. ESI-MS calc. for C27H29F7N4O2: 574; Found: 575 (M+H).

INTERMEDIATE 46

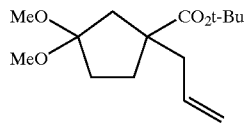

Step A

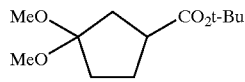

A solution of t-butyl 3-oxocylcobutanecarboxylate (see Intermediate 22, Step A) (11.54 g, 62.64 mmol) in DCM (20 mL) was treated with trimethylorthoformate (20.7 mL, 125.27 mmol) and a catalytic amount of toluenesulfonic acid (400 mg) and stirred at room temperature for 4 days. The reaction was quenched by pouring on a solution of saturated NaHCO$_3$ (450 mL) and extracted twice with DCM. The combined organic layers were dried over anhydrous MgSO$_4$, filtered, and concentrated to yield 15.86 g of crude product. It was further purified by distillation under reduced pressure to afford 12.32 g (85% yield) of pure prodcut. BP 104° C. at 4 torr. 1H NMR (CDCl$_3$, 500 MHz) δ 3.22 (s, 3H), 3.19 (s, 3H), 2.80 (m, 1H), 2.2–1.8 (br m, 6H), 1.46 (s, 9H).

Step B

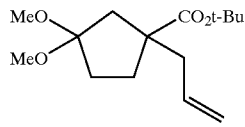

The ketal from Step A (1.31 g, 5.69 mmol) was dissolved in THF (25 mL) and cooled to −78° C. under a nitrogen atmosphere. A 1.5 M solution of LDA in cyclohexane (4.93 mL, 7.39 mmol) was added dropwise and the resulting mixture was stirred for 25 min. Neat allyl bromide (0.497 mL, 5.75 mmol) was added dropwise. After stirring at −78° C. for 10 min, the reaction mixture was warmed to 0° C., stirred an additional h, then warmed to room temperature. The reaction mixture was then quenched by pouring into brine. The aqueous mixture was extracted with ethyl acetate and the organic layer dried over anhydrous MgSO$_4$, filtered, and concentrated. Purification by MPLC (silica, 20% ethyl acetate/hexane) afforded 951 mg of product (62%).

INTERMEDIATE 47

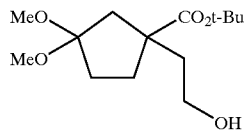

A solution of ester Intermediate 46 (519 mg, 1.92 mmol) in methanol (10 mL) was cooled to −78° C. and treated with ozone gas via a pipet until the reaction color became blue. Nitrogen was bubbled through the solution until the blue color disappeared. Then NaBH$_4$ (73 mg, 1.9 mmol) was added and the reaction mixture was permitted to warm to 0° C. and stirred for 1 h. The methanol was removed under reduced pressure and the residue was partitioned between ethyl acetate and saturated NaHCO$_3$ solution. The organic layer was dried over anhydrous MgSO$_4$, filtered, and concentrated. Purification by MPLC (silica, 90% ethyl acetate/hexane) afforded 515 mg of product (98%).

INTERMEDIATE 48

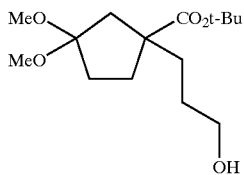

A solution of terminal olefin Intermediate 46 (399 mg, 1.48 mmol) in THF (10 mL) was cooled to 0° C. and treated with 1.0 M BH$_3$.THF in THF (0.74 mL, 0.74 mmol), dropwise. The reaction mixture was warmed to room temperature and stirred for 2 h. Then more 1.0 M BH$_3$.THF in THF (0.4 mL, 0.4 mmol) was added and the reaction mixture was stirred overnight. Since the reaction was still incomplete, two more portions of 1.0 M BH$_3$.THF in THF (0.8 mL, 0.8 mmol) were added until the reaction finally went to completion. Then water was added (10 mL), followed by NaBO$_3$.4H$_2$O (1.4 g, 9.1 mmol) and the reaction mixture was stirred for 24 h. The reaction mixture was then partitioned between ethyl acetate and saturated NaHCO$_3$ solution. The combined organic layers were washed with brine, dried over anhydrous MgSO$_4$, filtered, and concentrated. The crude product was purified by MPLC (silica, 100% ethyl acetate) to provide 215 mg of alcohol product.

EXAMPLE 191

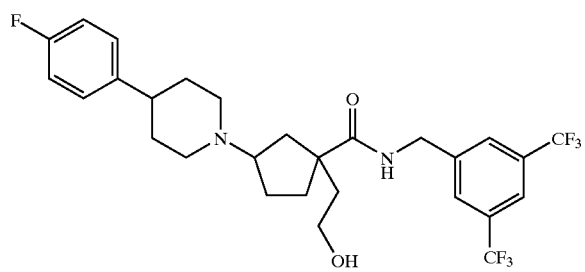

Step A

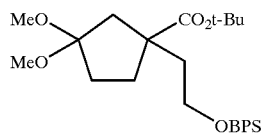

A solution of the alcohol Intermediate 47, prepared as described above (514 mg, 1.87 mmol) in DMF (10 mL) was treated with imidazole (382 mg, 5.61 mmol) followed by t-butyldiphenylchlorosilane (487 μL, 1.87 mmol). The reaction mixture was stirred at room temperature for one week, then poured into water and extracted twice with ether. The combined ethereal layers were washed with water three times, and brine once, then dried over anhydrous MgSO$_4$, filtered, and concentrated. Purification by MPLC (silica, 35% ethyl acetate/hexane) afforded 920 mg of product (96%).

Step B

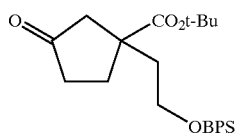

A solution of the BPS ether prepared as described in Step A above (880 mg, 1.72 mmol) in DCM (17 mL) at −78° C. was treated dropwise with bromodimethylborane (335 μL, 3.43 mmol). The reaction mixture was stirred at −78° C. for 1 h, then transferred via cannula to as rapidly stirring mixture of THF (20 mL) and saturated $NaHCO_3$ solution (10 mL). The mixture was stirred for 20 min, then the layers were separated. The aqueous phase was diluted with brine and extracted with DCM. The combined organic layers were dried over $MgSO_4$, filtered, and concentrated to give 740 mg of crude product, which was used in the following step without purification.

Step C

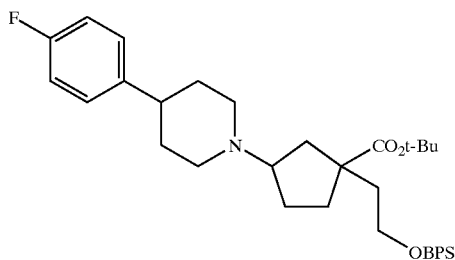

The ketone prepared as described in Step B above (702 mg, 1.50 mmol) was combined with 4-(4-fluorophenyl) piperidine hydrochloride (422 mg, 1.96 mmol), triethylamine (273 μL, 1.96 mmol), 4 Å powdered seives (~500 mg), and sodium triacetoxyborohydride (1.27 g, 6.00 mmol) in DCM (20 mL). The resulting mixture stirred at room temperature for 72 h. The reaction mixture was filtered through a pad of celite, washing with additional DCM. The filtrate was washed with saturated $NaHCO_3$ solution, then brine. The organic layer was dried over anhydrous $MgSO_4$, filtered, and concentrated. Purification by MPLC (silica, 5%, then 10% of methanol/ethyl acetate) furnished 621 mg of amine. ESI-MS calc. for $C_{39}H_{52}FNO_3Si$: 629; Found: 630 (M+H).

Step D

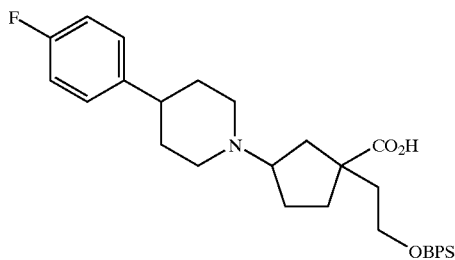

The aminoester prepared as described in Step C above (620 mg, 0.984 mmol) was dissolved in DCM (5 mL) and treated with TFA (5 mL). The resulting mixture was stirred at room temperature for 1.25 h, then was concentrated under reduced pressure at room temperature. The residue was partitioned between DCM and brine. The aqueous phase was treated with sufficient saturated $NaHCO_3$ solution so that the pH was ~7, then was extracted twice more with DCM. The combined organic layers were dried over anhydrous $MgSO_4$, filtered, and concentrated. The crude product was purified by preparative TLC (silica, 7% Methanol/DCM) giving 105 mg of the presumed cis-carboxylic acid product, along with 114 mg of the lactone resulting from deprotection of the BPS ether and cyclization. ESI-MS calc. for $C_{35}H_{44}FNO_3Si$: 573; Found: 574 (M+H).

Step E

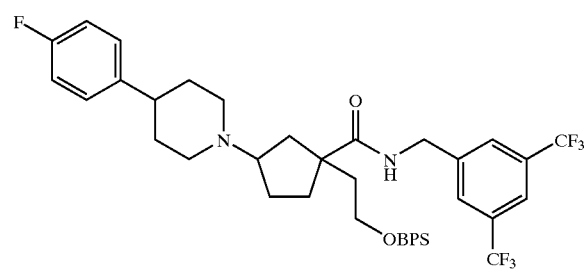

The amino acid prepared as described in the preceding steps (105 mg, 0.183 mmol) was combined with EDC (70 mg, 0.366 mmol), and 3,5-Bis(trifluoromethyl)benzylamine hydrochloride (102 mg, 0.366 mmol) in DCM (1 mL) and stirred overnight at room temperature. The crude reaction mixture was applied directly to a preparative TLC plate (silica, 0.3/2.7/97 NOH/methanol/DCM) and after elution afforded the desired amide. ESI-MS calc. for $C_{44}H_{49}F_7N_2O_2Si$: 798; Found: 799 (M+H).

Step F

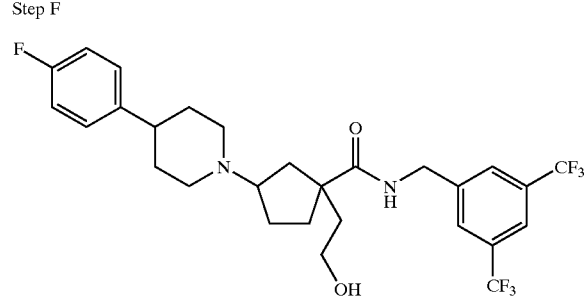

The product from Step E above (156 mg, 0.195 mmol) was dissolved in THF (3 mL) and treated with 1.0 M TBAF in THF (234 μL, 0.234 mmol). After stirring at room temperature for 2 h., the reaction mixture was poured into saturated $NaHCO_3$ solution and extracted with ether. The etheral layer was dried over anhydrous $MgSO_4$, filtered, and concentrated. The crude product was purified by preparative TLC (silica, 0.5/4.5/95 of $NH_4OH$/methanol/DCM) affording 64 mg of the product alcohol as a mixture of two cis isomers. ESI-MS calc. for $C_{28}H_{31}F_7N_2O_2$: 560; Found: 561 (M+H).

EXAMPLE 192

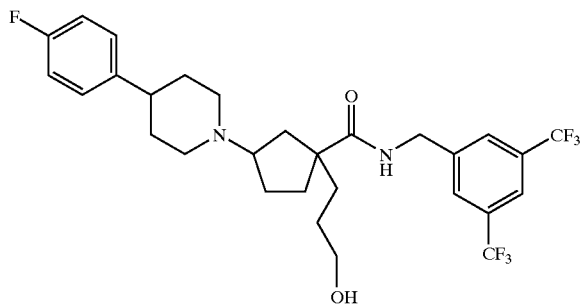

The hydroxy propyl analog (Example 192) was prepared starting from Intermediate 48 using the same procedure as detailed in Example 191.

ESI-MS calc. for C29H33F7N2O2: 574; Found: 575 (M+H).

INTERMEDIATE 49

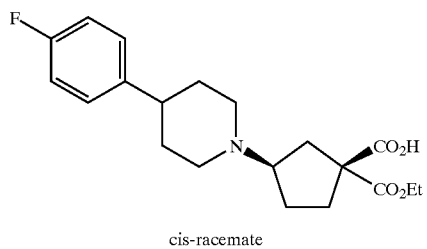
cis-racemate

Step A

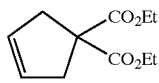

A solution of diethylmalonate (65 mL, 0.43 mol) in DMF (700 mL) was cooled to 0° C. and treated in several portions under a stream of nitrogen with lithium hydride (8.49 g, 1.07 mol). After gas evolution had subsided cis-1,4-dichloro-2-butene (52 mL, 0.49 mol) was added dropwise over 0.5 h under nitrogen via an addition funnel (gas evolution). After stirring for 1.5 h at 0° C., the reaction mixture was warmed to room temperature and stirred overnight. The reaction mixture was then poured onto ice water (500 mL) and extracted twice with ether (1 L). The combined ethereal layers were washed with water five times and with brine once. The organic layer was dried over anhydrous MgSO$_4$, filtered, and concentrated to afford 76 g of a yellow liquid which did not require further purification. 1H NMR (CDCl$_3$, 500 MHz) δ 5.59 (s, 2H), 4.18 (q, J=7 Hz, 4H), 2.99 (s, 4H), 1.23 (t, J=7 Hz, 6H).

Step B

A solution of olefin prepared as described in Step A (74.9 g, 0.353 mol) in THF (300 mL) was cooled to −78° C. and treated dropwise over 2 h via. addition funnel with a 1.0 M solution of BH$_3$.THF in THF (353 mL, 0.353 mol). The reaction mixture was warmed to room temperature, stirred for 3 h, then concentrated to remove the THF. The resulting oil was dissolved in DCM (1.5 L), and transferred to a 3 L 3-neck flask equipped with a mechanical stirring apparatus. The mixture was cooled to 0° C. and treated in portions with a premixed mixture of PCC (455 g) and MgSO$_4$ (450 g). During the addition, the reaction mixture turned brown and became thick and viscous. The mixture was warmed to room temperature and stirred for 1 h. The reaction mixture was filtered through a pad of silica with a pad of celite on top, washing with acetone. The filtrate was concentrated and filtered through silica a second time. This filtrate was concentrated and purified by flash chromatography (silica, 40% ethyl acetate/hexane) to give 11 g of the desired ketone. ESI-MS calc. for C11H16O5: 228; Found: 229 (M+H).

Step C

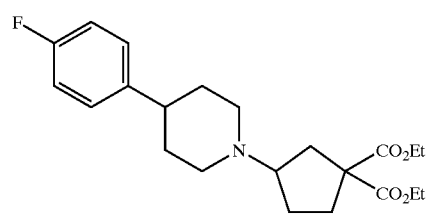

The ketone prepared as described in the preceding Step B (5.00 g, 21.9 mmol) was dissolved in DCM (150 mL) and treated with 4-(4-fluorophenyl)piperidine hydrochloride (5.66 g, 26.3 mmol), triethylamine (3.6 mL, 26 mmol), 4 Å powdered molecular seives (5 g), and triacetoxyborohydride (18.5 g, 87.3 mmol). The resulting mixture was stirred for 72 h, then filtered through celite, washing with additional DCM. The filtrate was washed with saturated NaHCO$_3$ solution twice and brine once. The organic layer was dried over anhydrous MgSO$_4$, filtered, and concentrated. The crude product was purified by flash chromatography (silica, 5% methanol/ethyl acetate) to give 6.43 g of product. ESI-MS calc. for C22H30FNO4: 391; Found: 392 (M+H).

Step D

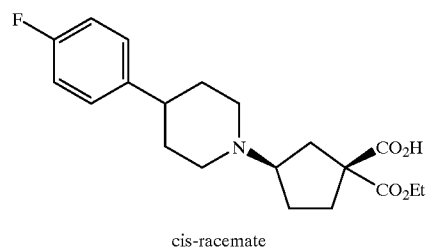
cis-racemate

To a solution of the aminodiester prepared according to Step C (6.4 g, 16 mmol) in ethanol (77 mL) cooled to 0° C. (ice/acetone) was added a solution of NaOH (688 mg, 17.2 mmol) in 7 mL of deionized water. After 1 h at −10° C., the reaction mixture was warmed to 0° C. (ice/water) and stirred for several h. Since the reaction was sluggish the reaction mixture was warmed to room temperature and stirred for 3 days. The reaction mixture was concentrated to remove as much ethanol as possible. Then the mixture was adjusted to pH~7 with 3 N HCl. The organic layer was extracted four times with CHCl$_3$. The combined organic layers were washed with brine, dried over MgSO$_4$, filtered, and concentrated. The residue, which contained some starting material, was partitioned between ethyl acetate and 1 N NaOH solution. The aqueous phase was neutralized with 3 N HCl and the resulting mixture was extracted twice with CHCl$_3$. The combined organic layers were washed with brine, dried over anhydrous MgSO$_4$, filtered, and concentrated to give 3.1 g of a 1:1 mixture of cis/trans aminoacid isomers. Flash chromatography (silica, 10% methanol/DCM) permitted separation of two spots corresponding to product. The top spot, presumed to be cis based on the repeated observation that the cis-aminoacids elute first, was collected as a white solid (2 g). ESI-MS calc. for C20H26FNO4: 363; Found: 364 (M+H).

EXAMPLE 193

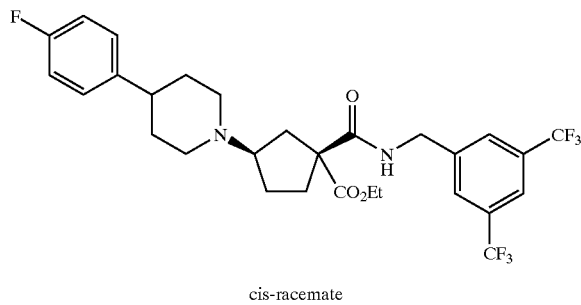

cis-racemate

The title compound cis-Aminoacid Intermediate 49 (1.1 g, 3.1 mmol) was combined with 3,5-bis(trifluoromethyl)benzylamine hydrochloride (1.3 g, 4.7 mmol), and EDC (880 mg, 6.2 mmol) in DCM (150 mL). The reaction mixture was stirred at room temperature overnight then was washed with saturated NaHCO$_3$ solution, followed by brine. The organic layer was dried over anhydrous MgSO$_4$, filtered, and concentrated to afford 1.82 g of product which required no further purification. ESI-MS calc. for C29H31F7N2O3: 588; Found: 589 (M+H).

EXAMPLE 194

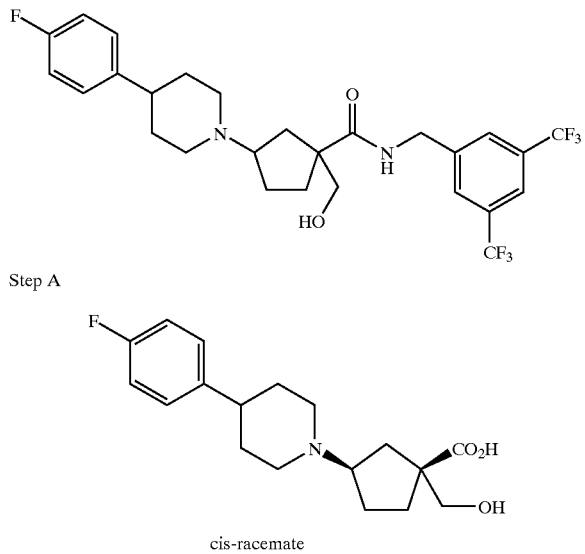

Step A cis-racemate

The title compound cis-Aminoacid Intermediate 49 (450 mg, 1.24 mmol) was dissolved in THF (20 mL) and cooled to 0° C. A 1.0 M solution of Super hydride in THF (4 mL, 4 mmol) was added dropwise. The reaction mixture was stirred for 1 h at 0° C., then was warmed to room tempera- ture. After 2 h, an additional portion of Super hydride (1.24 mL, 1.24 mmol) was added and the reaction mixture was stirred at room temperature for an additional 1 h. An aqueous 1 N HCl solution as added, adjusting the pH to ~7. The solvents were removed under reduced pressure. The crude residue was purified by flash chromatography (silica, 20% methanol/DCM) to give the desired product. ESI-MS calc. for C18H24FNO3: 321; Found: 322 (M+H).

Step B

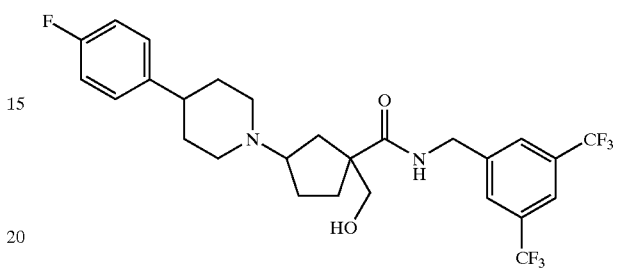

The hydroxyacid prepared according to Step A immediately above (530 mg, 1.65 mmol) was combined with 3,5-bis(trifluoromethyl)benzylamine hydrochloride (693 mg, 2.48 mmol), EDC (634 mg, 3.30 mmol), and HOAt (450 mg, 3.30 mmol) in DCM (50 mL). The reaction mixture was stirred for 5.5 h, then was stored in a freezer over the weekend. The mixture was then diluted with CHCl$_3$ and washed with saturated NaHCO$_3$ twice, and brine once. The organic layer was dried over anhydrous MgSO$_4$, filtered, and concentrated. Purification by flash chromatography (10% methanol/DCM) gave 700 mg of the target amide. ESI-MS calc. for C27H29F7N2O2: 546; Found: 547 (M+H).

EXAMPLE 195

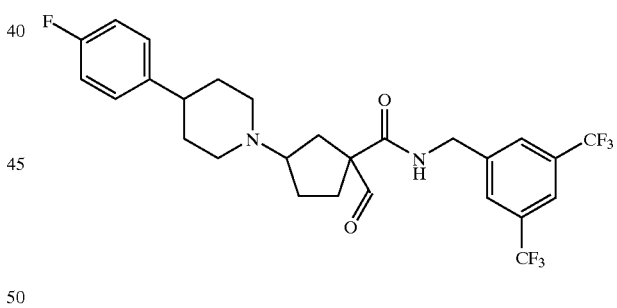

A solution of oxalyl chloride (152 µL, 1.75 mmol) in DCM (20 mL) was cooled to −78° C. and treated dropwise with a solution of DMSO (248 µL, 3.51 mmol). After stirring for an additional 5 min, a solution of the alcohol prepared as described in Example 194 (480 mg, 0.88 mmol) was added dropwise, and the reaction mixture was stirred for an additional 10 min. Then neat triethylamine (978 µL, 7.03 mmol) was added dropwise and the reaction mixture was permitted to warm to room temperature and stir for an additional 1 h. The reaction mixture was diluted with DCM and washed with saturated NaHCO$_3$ solution, then brine. The organic layer was dried over anhydrous MgSO$_4$, filtered, and concentrated. Purification by flash chromatography (silica, 1/9/90 of NH$_4$OH/methanol/DCM) gave 318 mg of aldehyde product as a racemic mixture of cis-aminoamides. ESI-MS calc. for C27H27F7N2O2: 544; Found: 545 (M+H).

EXAMPLE 196

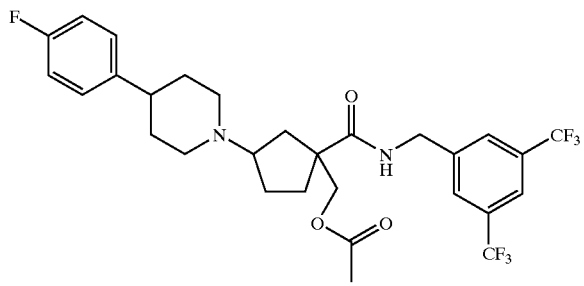

A solution of the alcohol prepared as described in Example 194 (8.0 mg, 0.015 mmol) in DCM (1 mL) was treated with acetic anhydride (15 mg, 0.15 mmol) and one crystal of DMAP. The reaction mixture was stirred at room temperature for 20 h. The reaction mixture was concentrated and the residue purified by preparative TLC (silica, 0.5/4.5/95 of $NH_4OH$/methanol/DCM). The pure product was converted to its hydrochloride salt with excess 4 N HCl in dioxane, concentrating to give 2.45 mg of a white solid. ESI-MS calc. for C29H31F7N2O3: 588; Found: 589 (M+H).

EXAMPLE 197

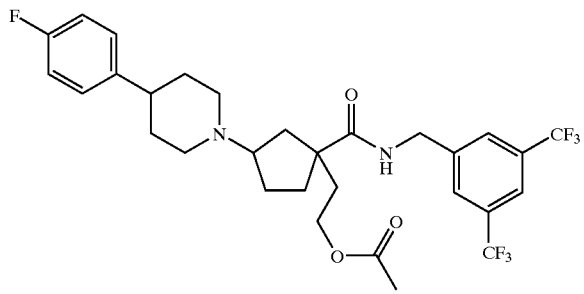

Example 197 was prepared starting from the product from Example 191 in an fashion essentially identical to that detailed for the synthesis of Example 196 immediately above. ESI-MS calc. for C30H33F7N2O3: 602; Found: 603 (M+H).

EXAMPLE 198

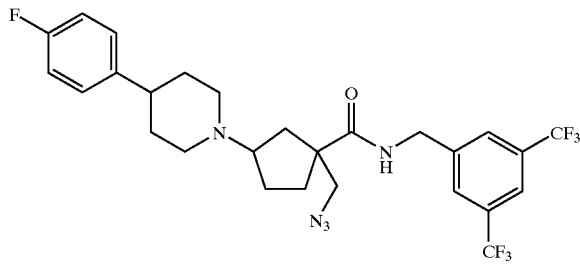

Step A

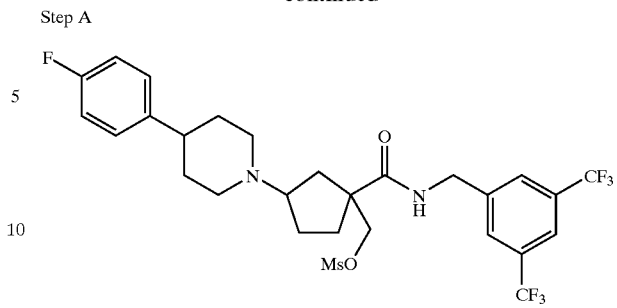

A solution of the alcohol prepared as described in Example 194 (240 mg, 0.43 mmol) in DCM (20 mL) at 0° C. was treated with triethylamine (66 µL, 0.48 mmol), followed by methanesulfonyl chloride (36 µL, 0.48 mmol) and a spatula tip (few crystals) of DMAP. The reaction mixture was stirred at room temperature for 1 h, then was diluted with DCM and washed with saturated $NaHCO_3$ solution, followed by brine. The organic layer was dried over anhydrous $MgSO_4$, filtered, and concentrated to give 240 mg of the mesylate which was used as is. ESI-MS calc. for C28H31F7N2O4S: 624; Found: 625 (M+H).

Step B

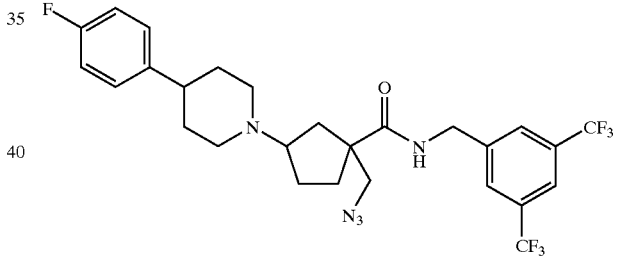

A solution of the mesylate prepared according to Step A immediately above (240 mg, 0.385 mmol) in DMSO (5 mL) was treated with sodium azide (125 mg, 1.92 mmol) and stirred at 50° C. for 2 days. Since the reaction was proceeding sluggishly, the reaction mixture was then warmed to 80° C. for one day. Then the temperature was raised to 100° C. for 1 day whereupon the reaction was complete. The reaction mixture was diluted with DCM and washed with water twice and brine once. The organic layer was dried over anhydrous $MgSO_4$, filtered, and concentrated.

Purification by preparative TLC (silica, DCM) provided 200 mg of product as a racemic mixture of cis-isomers. ESI-MS calc. for C27H28F7N5O: 571; Found: 572 (M+H).

EXAMPLE 199

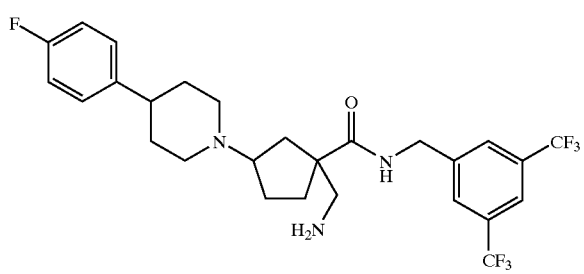

The azide analog prepared as described in Example 198 (200 mg, 0.350 mmol) was combined with Pd(OH)$_2$ on carbon (20 mg, 20% Pd) in methanol (10 mL) and stirred under a hydrogen atmosphere (balloon) for 24 h. The reaction mixture was filtered through celite, and concentrated. Purification by preparative TLC (silica, 0.5/4.5/95 of NH$_4$OH/methanol/DCM) afforded 35 mg of amine as a racemic mixture of cis isomers. ESI-MS calc. for C27H30F7N3O: 545; Found: 546 (M+H).

EXAMPLE 200

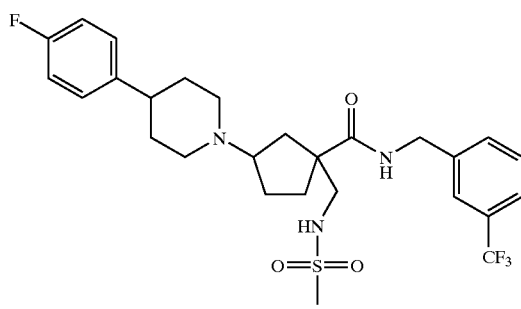

The amine compound prepared as described in Example 199 (3 mg, 6 mmol) was dissolved in DCM (2 mL), cooled to 0° C., and treated with triethylamine (1 μL), methanesulfonyl chloride (0.5 μL) and a crystal of DMAP. The reaction mixture was stirred at 0° C. for 3 h, then diluted with DCM and washed with saturated NaHCO$_3$ solution, followed by brine. The organic layer was dried over anhydrous MgSO$_4$, filtered, and concentrated. Dissolved the product in DCM/hexane and added 1 drop of 4 N HCl in dioxane, and concentrated the mixture to afford 1.23 mg of the product (cis-racemate) as its hydrochloride salt, requiring no further purification. ESI-MS calc. for C28H32F7N3O3S: 623; Found: 624 (M+H).

EXAMPLE 201

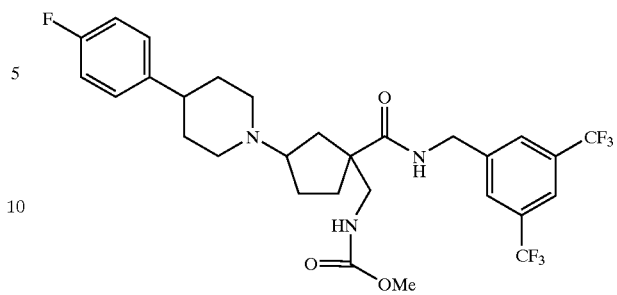

The amine compound prepared as described in Example 199 (6 mg, 12 mmol) was dissolved in DCM (2 mL), and treated with triethylamine (1 drop), methylchloroformate (1 drop) and one crystal of DMAP. The reaction mixture was stirred at room temperature for 2 days, then was concentrated and purified by preparative TLC (silica, 0.5/4.5/95 of NH$_4$OH/methanol/DCM) giving 2.95 mg of product as the cis-racemate. ESI-MS calc. for C29H32F7N4O3: 603; Found: 604 (M+H).

EXAMPLE 202

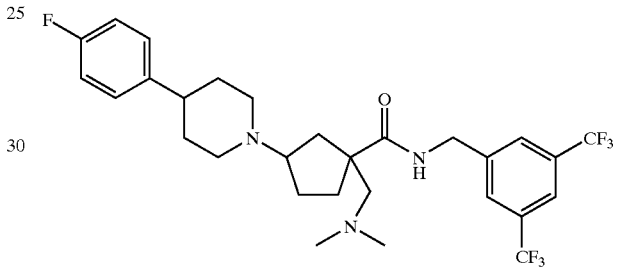

The amine compound prepared as described in Example 199 (6 mg, 12 mmol) was dissolved in DCM (2 mL), and treated with 37% aqueous formaldehyde (6 μL). After 15 minutes, 4 Å powdered molecular seives (10 mg) were added, followed by sodium triacetoxyborohydride (14 mg). The reaction mixture was stirred at room temperature for 2.5 h, then was filtered through celite, washing with methanol. The filtrate was concentrated, then redissolved in DCM and filtered again. The second filtrate was concentrated and the residue was purified by preparative TLC (silica, 0.7/6.3/93 of NH$_4$OH/methanol/DCM) to give 2.77 mg of diamine product (cis-racemate). ESI-MS calc. for C29H34F7N3O: 573; Found: 574 (M+H).

EXAMPLE 203

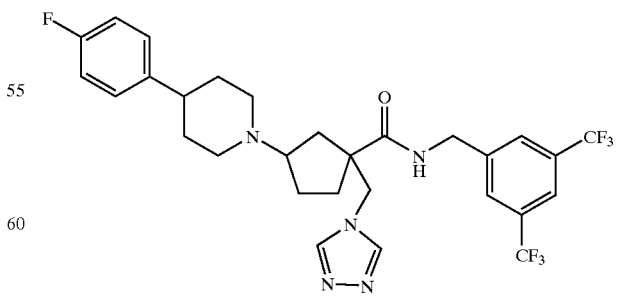

The amine compound prepared as described in Example 199 (15 mg, 0.028 mmol) was dissolved in toluene and treated with N,N-dimethylformamide azine (R. K. Bartlett et al., *J. Chem. Soc.* (C), (1967), 1664.; 10 mg, 0.083 mmol). The reaction mixture was stirred at reflux for 4 h, then concentrated. Purification by preparative TLC (silica, 0.5/4.5/95 of NH$_4$OH/methanol/DCM, eluted twice, then repeat with another prep plate) afforded 0.84 mg of triazole after conversion to the HCl salt with 4 N HCl in dioxane. ESI-MS calc. for C29H30F7N5O: 597; Found: 598 (M+H).

EXAMPLE 204

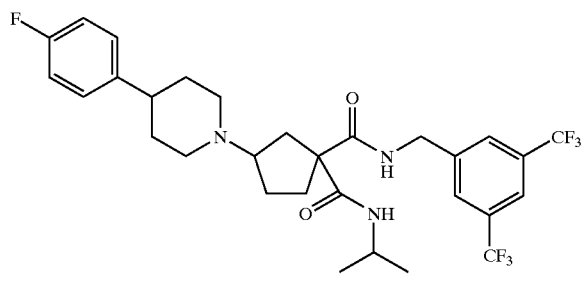

Step A

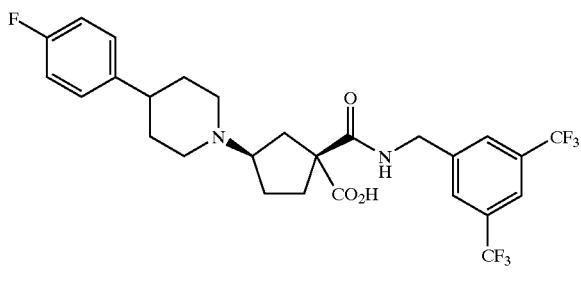

cis-racemate

The ester compound obtained in Example 193 (1.8 g, 3.1 mmol) was dissolved in THF (10 mL) and methanol (10 mL) and treated dropwise with a solution of LiOH.H$_2$O (390 mg, 9.3 mmol) in water (10 mL). The reaction mixture was stirred at room temperature for 3 h, then was neutralized with 3 N HCl (~pH 7). The organic solvents were removed under reduced pressure. Chloroform was added and the mixture was washed twice with brine. The combined aqueous phases were backwashed with CHCl$_3$, and the combined organic layers were dried over anhydrous MgSO$_4$, filtered, and concentrated. The crude product was purified by flash chromatography (silica, 20% methanol/DCM). After concentrating the pure fractions, the residue was dissolved in CHCl$_3$ and filtered to remove silica. The filtrate was concentrated to afford 620 mg of product. ESI-MS calc. for C27H27F7N2O3: 560; Found: 561 (M+H).

Step B

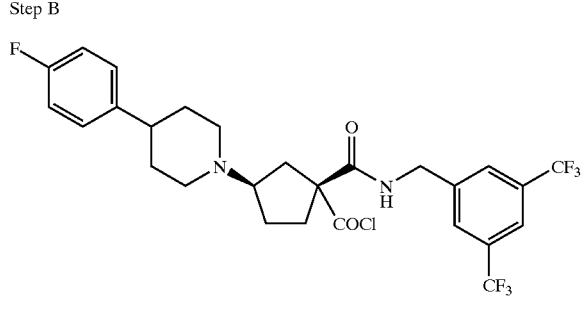

cis-racemate

The carboxylic acid prepared as described in Step A immediately above (235 mg, 0.42 mmol) was dissolved in DCM (5 mL) and THF (10 mL) and cooled to 0° C. One drop of DMF was added, followed by oxalyl chloride (73 μL, 0.84 mmol). After 4 h at 0° C. the mixture was warmed to room temperature. An additional amount of oxalyl chloride (50 μL) was added to drive the reaction to completion. After storing in the freezer for 3 days, the reaction mixture was concentrated to afford 308 mg of the acid chloride as its hydrochloride salt.

Step C

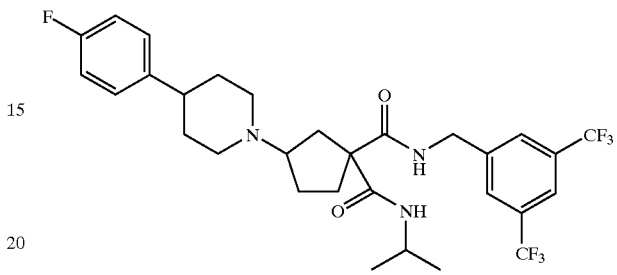

To a solution of the acid chloride prepared as described in Step B immediately above (10 mg, 0.017 mmol) in DCM (0.5 mL) was added i-propylamine (30 μL) and the mixture was stirred at room temperature for 30 min, then diluted with DCM and washed with saturated NaHCO$_3$ solution, then brine. The organic layer was dried over anhydrous MgSO$_4$, filtered, and concentrated to give 2.82 mg of product which did not require further purification. ESI-MS calc. for C30H34F7N3O2: 601; Found: 602 (M+H).

EXAMPLE 205

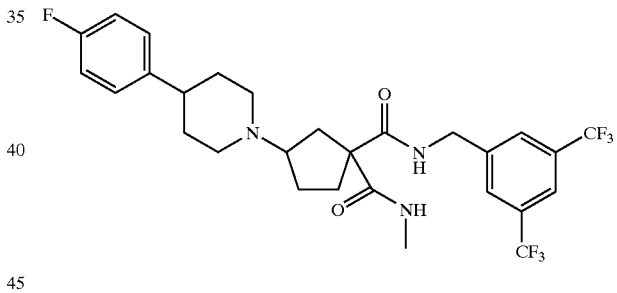

The preparation of methylamide Example 205 was identical to that detailed for the synthesis of isopropylamide Example 204, immediately above, except that methylamine was used. ESI-MS calc. for C28H30F7N3O2: 573; Found: 574 (M+H).

EXAMPLE 206

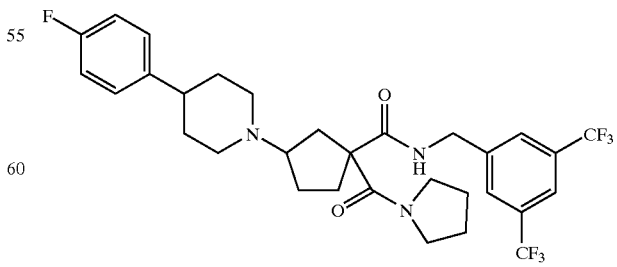

The preparation of pyrolidineamide Example 206 was identical to that detailed for the synthesis of isopropylamide Example 204 above, except that pyrrolidine was used. ESI-MS calc. for C31H34F7N3O2: 613; Found: 614 (M+H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula I:

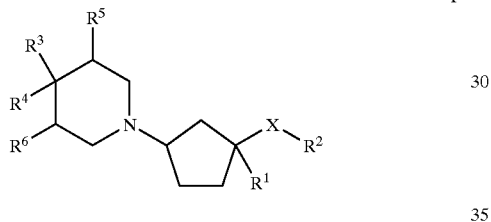

I wherein:
is selected from:
—$NR^{10}$—, —O—, —$CH_2O$—, —$CONR^{10}$—, —$NR^{10}CO$—, —$CO_2$—, —OCO—, —$CH_2(NR^{10})CO$—, —$N(COR^{10})$—, and —$CH_2N(COR^{10})$—,
and where $R^{10}$ is independently selected from: hydrogen, $C_{1-6}$ alkyl, benzyl, phenyl, and $C_{1-6}$ alkyl-$C_{3-6}$ cycloalkyl,
which is unsubstituted or substituted with 1–3 substituents where the substituents are independently selected from: halo, $C_{1-3}$alkyl, $C_{1-3}$alkoxy and trifluoromethyl;

$R^1$ is selected from:
hydrogen,
—$C_{0-6}$alkyl-Y—($C_{1-6}$alkyl)-, and
—($C_{0-6}$alkyl)—Y—($C_{0-6}$alkyl)—($C_{3-7}$cycloalkyl)—($C_{0-6}$alkyl),
where Y is selected from:
a single bond, —O—, —S—, —SO—, —$SO_2$—, and —$NR^{10}$—,
and where the alkyl and the cycloalkyl are unsubstituted or substituted with 1–7 substituents where the substituents are independently selected from:
(a) halo,
(b) hydroxy,
(c) —O—$C_{1-3}$alkyl, and
(d) trifluoromethyl,
(e) $C_{1-3}$alkyl,
(f) —O—$C_{1-3}$alkyl,
(g) —$CO_2R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$alkyl, $C_{1-3}$alkoxy and trifluoromethyl,
(h) —CN,
(i) heterocycle,
(j) —$NR^9R^{10}$,
(k) —$NR^9COR^{10}$,
(l) —$NR^9SO_2R^{10}$, and
(m) —$CONR^9R^{10}$;

$R^2$ is selected from:
($C_{0-6}$alkyl)-phenyl and ($C_{0-6}$alkyl)-heterocycle,
where the alkyl is unsubstituted or substituted with 1–7 substituents where the substituents are independently selected from:
(a) halo,
(b) hydroxy,
(c) —O—$C_{1-3}$alkyl,
(d) trifluoromethyl, and
(e) —$C_{1-3}$alkyl,
and where the phenyl and the heterocycle is unsubstituted or substituted with 1–5 substituents where the substituents are independently selected from:
(a) halo,
(b) trifluoromethyl,
(c) trifluoromethoxy,
(d) hydroxy,
(e) $C_{1-6}$alkyl,
(f) $C_{3-7}$cycloalkyl,
(g) —O—$C_{1-6}$alkyl,
(h) —O—$C_{3-7}$cycloalkyl,
(i) —$SCF_3$,
(j) —S—$C_{1-6}$alkyl,
(k) —$SO_2$—$C_{1-6}$alkyl,
(l) phenyl,
(m) heterocycle,
(n) —$CO_2R^9$,
(o) —CN,
(p) —$NR^9R^{10}$,
(q) —$NR^9$—$SO_2$—$R^{10}$,
(r) —$SO_2$—$NR^9R^{10}$, and
(s) —$CONR^9R^{10}$;

$R^3$ is selected from:
($C_{0-6}$alkyl)-phenyl,
where the alkyl is unsubstituted or substituted with 1–5 substituents where the substituents are independently selected from:
(a) halo,
(b) hydroxy,
(c) —O—$C_{1-3}$alkyl, and
(d) trifluoromethyl,
and where the phenyl is unsubstituted or substituted with 1–5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$;

$R^4$ is selected from:
a) hydrogen,
b) hydroxy, c) $C_{1-6}$alkyl,
d) $C_{1-6}$alkyl-hydroxy,
e) —O—$C_{1-3}$alkyl,
f) —$CO_2R^9$,
g) —$CONR^9R^{10}$, and
h) —CN;

or where $R^3$ and $R^4$ may be joined together to form a ring which is selected from:
(a) 1H-indene,
(b) 2,3-dihydro-1H-indene,
(c) 2,3-dihydro-benzofuran,
(d) 1,3-dihydro-isobenzofuran,
(e) 2,3-dihydro-benzothiofuran, and
(f) 1,3-dihydro-isobenzothiofuran, or where $R^3$ and $R^5$ or $R^4$ and $R^6$ may be joined together to form a ring which is phenyl,
wherein the ring is unsubstituted or substituted with 1–7 substituents where the substituents are independently selected from:
a) halo,
b) trifluoromethyl,
c) hydroxy,
d) $C_{1-3}$alkyl,
e) —O—$C_{1-3}$alkyl,
f) —$CO_2R^9$,
g) —CN,
h) —$NR^9R^{10}$, and
i) —$CONR^9R^{10}$;

$R^5$ and $R^6$ are independently selected from:
(a) hydrogen,
(b) hydroxy,
(c) $C_{1-6}$alkyl,
(d) $C_{1-6}$alkyl-hydroxy,
(e) —O—$C_{1-3}$alkyl,
(f) oxo, and
(g) halo;

and pharmaceutically acceptable salts thereof and individual diastereomers thereof.

2. The compound of claim 1 of the formula Ia:

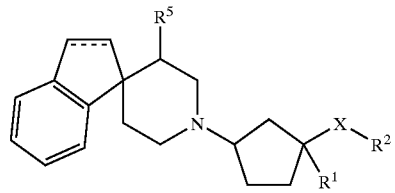

Ia wherein the dashed line represents a single or a double bond and wherein $R^1$, $R^2$, $R^5$ and X are as defined in claim 1; and pharmaceutically acceptable salts and individual diastereomers thereof.

3. The compound of claim 1 of the formula Ib;

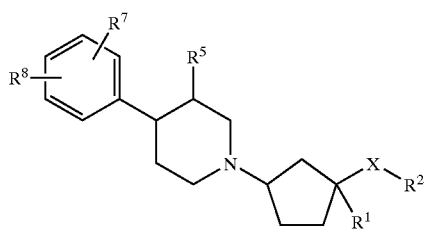

Ib wherein $R^1$, $R^2$, $R^5$ and X are as defined in claim 1, and wherein $R^7$ and $R^8$ are independently selected from:

(a) hydrogen,
(b) halo,
(c) trifluoromethyl,
(d) hydroxy,
(e) $C_{1-3}$alkyl,
(f) —O—$C_{1-3}$alkyl,
(g) —$CO_2H$,
(h) —$CO_2C_{1-3}$alkyl, and
(i) —CN;

and pharmaceutically acceptable salts and individual diastereomers thereof.

4. The compound of claim 1 of the formula Ic:

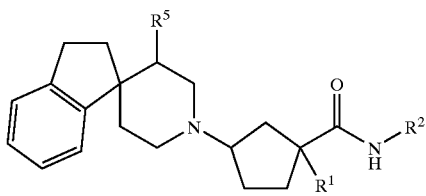

Ic wherein $R^1$, $R^2$ and $R^5$ are as defined in claim 1; and pharmaceutically acceptable salts and individual diastereomers thereof.

5. The compound of claim 1 of the formula Id:

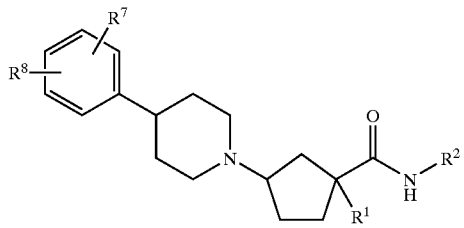

Id wherein $R^1$ and $R^2$ are as defined in claim 1, and wherein $R^7$ and $R^8$ are independently selected from:

(a) hydrogen,
(b) halo,
(c) trifluoromethyl,
(d) hydroxy,
(e) $C_{1-3}$alkyl,
(f) —O—$C_{1-3}$alkyl,
(g) —$CO_2H$,
(h) —$CO_2C_{1-3}$alkyl, and
(i) —CN;

and pharmaceutically acceptable salts and individual diastereomers thereof.

6. The compound of claim 1 of the formula Ie:

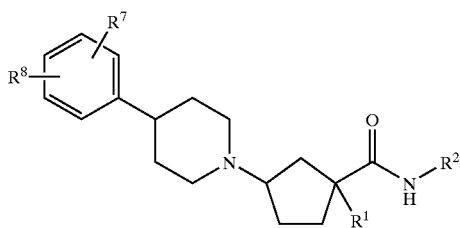

wherein $R^1$ and $R^2$ are as defined in claim 1, and wherein $R^7$ and $R^8$ are independently selected from:
(a) hydrogen,
(b) fluoro, and
(c) trifluoromethyl;
and pharmaceutically acceptable salts and individual diastereomers thereof.

7. The compound of claim 1 wherein X is —CONH—.

8. The compound of claim 1 wherein $R^1$ is selected from:
—$C_{1-6}$alkyl, —$C_{0-6}$alkyl-O—$C_{1-6}$alkyl-, —$C_{0-6}$alkyl-S—$C_{1-6}$alkyl-, and
—($C_{0-6}$alkyl)—($C_{3-7}$cycloalkyl)—($C_{0-6}$alkyl),
where the alkyl and the cycloalkyl are unsubstituted or substituted with 1–7 substituents where the substituents are independently selected from:
(a) halo,
(b) hydroxy,
(c) —O—$C_{1-3}$alkyl,
(d) trifluoromethyl,
(f) $C_{1-3}$alkyl,
(g) —O—$C_{1-3}$alkyl,
(h) —$CO_2R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$alkyl, $C_{1-3}$alkoxy and trifluoromethyl,
(i) —CN,
(j) —$NR^9R^{10}$, and
(k) —$CONR^9R^{10}$.

9. The compound of claim 1 wherein $R^1$ is selected from:
(1) —$C_{1-6}$alkyl, which is unsubstituted or substituted with 1–6 substituents where the substituents are independently selected from:
(a) halo,
(b) hydroxy,
(c) —O—$C_{1-3}$alkyl, and
(d) trifluoromethyl,
(2) —$C_{0-6}$alkyl-O—$C_{1-6}$alkyl-, which is unsubstituted or substituted with 1–6 substituents where the substituents are independently selected from:
(a) halo, and
(b) trifluoromethyl,
(3) —$C_{0-6}$alkyl-S—$C_{1-6}$alkyl-, which is unsubstituted or substituted with 1–6 substituents where the substituents are independently selected from:
(a) halo, and
(b) trifluoromethyl,
(4) —($C_{3-5}$cycloalkyl)—($C_{0-6}$alkyl), which is unsubstituted or substituted with 1–7 substituents where the substituents are independently selected from:
(a) halo,
(b) hydroxy,
(c) —O—$C_{1-3}$alkyl, and
(d) trifluoromethyl.

10. The compound of claim 1 wherein $R^1$ is selected from:
(1) —$CH_3$,
(2) —$CH_2CH_3$,
(3) —$CH(CH_3)_2$,
(4) —$CH_2CH_2CH_3$,
(5) —$CH_2CH(CH_3)_2$,
(6) -cyclopropyl,
(7) -cyclobutyl,
(8) -cyclopentyl,
(9) —$CH_2$-cyclopropyl,
(10) —$CH_2$-cyclobutyl,
(11) —$CH_2$-cyclopentyl,
(12) —$CH_2OH$,
(13) —$C(CH_3)_2(OH)$,
(14) —$C(CH_2OH)(CH_3)_2$,
(15) —(OH)cyclobutyl,
(16) —(OH)cyclopentyl,
(17) —$C(CH_3)_2(NHCOCH_3)$,
(18) —$C(CO_2H)(CH_3)_2$,
(19) —O—$CH_3$,
(20) —O-cyclopentyl,
(21) —O—$CH(CH_3)_2$,
(22) —S—$CH_3$,
(23) —S—$CF_3$,
(24) —$SO_2$—$CH_3$,
(25) —S—$CH(CH_3)_2$,
(26) —$SO_2$—$CH(CH_3)_2$, and
(27) —NH—$SO_2CH_3$.

11. The compound of claim 1 wherein $R^2$ is selected from:
—($C_{0-4}$alkyl)-phenyl and —($C_{0-4}$alkyl)-heterocycle,
where heterocycle is selected from:
furanyl, imidazolyl, oxadiazolyl, oxazolyl, pyrazolyl, pyrazinyl, pyridyl, pyridazinyl, pyrimidyl, pyrrolyl, thiadiazolyl, thiazolyl, thienyl, and triazolyl, and N-oxides thereof,
where the alkyl is unsubstituted or substituted with 1–7 substituents where the substituents are independently selected from:
(a) halo,
(b) hydroxy,
(c) —O—$C_{1-3}$alkyl, and
(d) trifluoromethyl,
and where the phenyl or heterocycle is unsubstituted or substituted with 1–5 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2R^9$,
(h) —S—$C_{1-3}$alkyl,
(i) —$SO_2$—$C_{1-3}$alkyl,
(j) —$SCF_3$,
(k) —$CO_2R^9$,
(l) —$NR^9R^{10}$,
(m) —$NR^9$—$SO_2$—$N^{10}$, (n) —SO$_2$—NR$^9$R$^{10}$, and
(o) —CONR$^9$R$^{10}$.

12. The compound of claim 1 wherein R$^2$ is selected from:
—(C$_{0-4}$alkyl)-phenyl and —(C$_{0-4}$alkyl)-heterocycle,
where heterocycle is selected from: pyridyl, pyridazinyl, and N-oxides thereof,
where the alkyl is unsubstituted or substituted with 1–7 substituents where the substituents are independently selected from:
(a) halo,
(b) hydroxy,
(c) —O—C$_{1-3}$alkyl, and
(d) trifluoromethyl,
and where the phenyl or heterocycle is unsubstituted or substituted with 1–3 substituents where the substituents are independently selected from:
(a) halo,
(b) trifluoromethyl,
(c) trifluoromethoxy,
(d) hydroxy,
(e) C$_{1-3}$alkyl,
(f) —O—C$_{1-3}$alkyl,
(g) —CO$_2$—C$_{1-3}$alkyl,
(h) —CO$_2$H,
(i) —S—C$_{1-3}$alkyl,
(j) —SO$_2$—C$_{1-3}$alkyl,
(k) —SCF$_3$,
(l) —NH$_2$,
(m) —NH—SO$_2$—C$_{1-3}$alkyl, and
(n) —SO$_2$—NH$_2$.

13. The compound of claim 1 wherein R$^2$ is selected from:
—CH$_2$-phenyl and —CH$_2$-heterocycle,
where heterocycle is selected from: pyridyl, pyridazinyl, and N-oxides thereof,
and where the phenyl or heterocycle is unsubstituted or substituted with 1–3 substituents where the substituents are independently selected from:
(a) halo,
(b) trifluoromethyl,
(c) trifluoromethoxy,
(d) hydroxy,
(e) C$_{1-3}$alkyl,
(f) —O—C$_{1-3}$alkyl,
(g) —CO$_2$—C$_{1-3}$alkyl,
(h) —CO$_2$H,
(i) —S—S$_{1-3}$alkyl,
(j) —SO$_2$—C$_{1-3}$alkyl,
(k) —SCF$_3$,
(l) —NH$_2$,
(m) —NH—SO$_2$—C$_{1-3}$alkyl, and
(n) —SO$_2$—NH$_2$.

14. The compound of claim 1 wherein R$^2$ is selected from:
(1) —CH$_2$-(phenyl),
(2) —CH$_2$-(4-bromophenyl),
(3) —CH$_2$-(3-chlorophenyl),
(4) —CH$_2$-(3,5-difluorophenyl),
(5) —CH$_2$-((2-trifluoromethyl)phenyl),
(6) —CH$_2$-((3-trifluoromethyl)phenyl),
(7) —CH$_2$-((4-trifluoromethyl)phenyl),
(8) —CH$_2$-((3-trifluoromethoxy)phenyl),
(9) —CH$_2$-((3-trifluoromethylthio)phenyl),
(10) —CH$_2$-((3-trifluoromethoxy-5-thiomethyl)phenyl),
(11) —CH$_2$-((3-trifluoromethoxy-5-methoxy)phenyl),
(12) —CH$_2$-((3-trifluoromethoxy-5-methanesulfonyl)phenyl),
(13) —CH$_2$-((3-trifluoromethoxy-5-amino)phenyl),
(14) —CH$_2$-((3-trifluoromethoxy-5-aminomethanesulfonyl)phenyl),
(15) —CH$_2$-((3-trifluoromethoxy-5-sulfonylamino)phenyl),
(16) —CH$_2$-((3,5-bis-trifluoromethyl)phenyl),
(17) —CH$_2$-((3-fluoro-5-trifluoromethyl)phenyl),
(18) —CH(CH$_3$)-((3,5-bis-trifluoromethyl)phenyl),
(19) —C(CH$_3$)$_2$-((3,5-bis-trifluoromethyl)phenyl),
(20) —CH$_2$-(4-(2-trifluoromethyl)pyridyl),
(21) —CH$_2$-(5-(3-trifluoromethyl)pyridyl),
(22) —CH$_2$-(5-(3-trifluoromethyl)pyridazinyl),
(23) —CH$_2$-(4-(2-trifluoromethyl)pyridyl-N-oxide), and
(24) —CH$_2$-(5-(3-trifluoromethyl)pyridyl-N-oxide).

15. The compound of claim 1 wherein R$^3$ is phenyl,
where the phenyl is unsubstituted or substituted with 1–5 substituents where the substituents are independently selected from:
(a) halo,
(b) trifluoromethyl,
(c) hydroxy,
(d) C$_{1-3}$alkyl,
(e) —O—C$_{1-3}$alkyl,
(f) —CO$_2$R$^6$,
(g) —CN,
(h) —NR$^9$R$^{10}$, and
(i) —CONR$^9$R$^{10}$.

16. The compound of claim 1 wherein R$^3$ is phenyl,
where the phenyl is unsubstituted or substituted with 1–3 substituents where the substituents are independently selected from:
(a) halo,
(c) hydroxy,
(d) C$_{1-3}$alkyl,
(e) —O—C$_{1-3}$alkyl, and
(f) —CO$_2$R$^6$.

17. The compound of claim 1 wherein R$^3$ is phenyl, or para-fluorophenyl.

18. The compound of claim 1 wherein R$^4$ is selected from:
(a) hydrogen,
(b) hydroxy,
(c) —CO$_2$H,
(d) —CO$_2$C$_{1-6}$alkyl,
(e) —CN.

19. The compound of claim 1 wherein R$^5$ and R$^6$ are independently selected from:
(a) hydrogen,
(b) hydroxy,
(c) —CH$_3$,
(d) —O—CH$_3$, and
(e) oxo.

20. The compound of claim 1 of the formula:

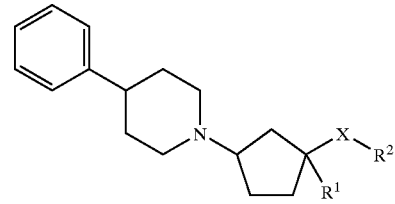

201
-continued
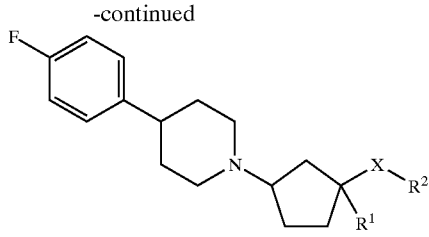
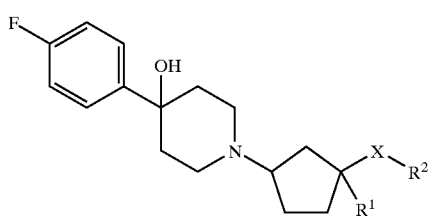
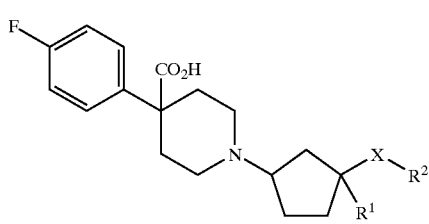
wherein R¹, R² and X are defined in claim 1;
and pharmaceutically acceptable salts and individual diastereomers thereof.
21. A compound which is selected from the group consisting of:
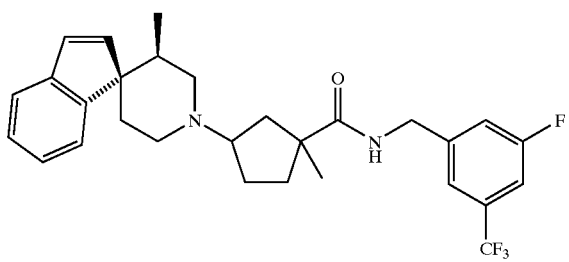
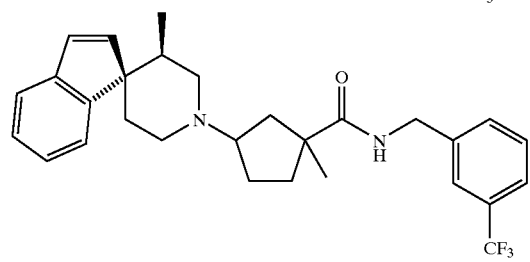
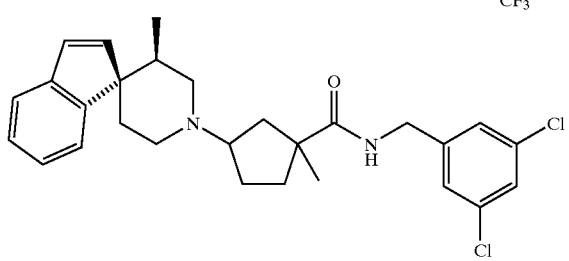
202
-continued
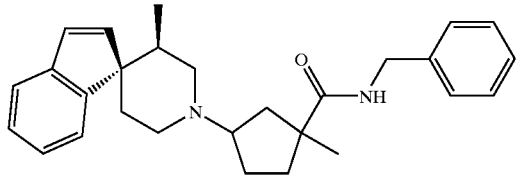
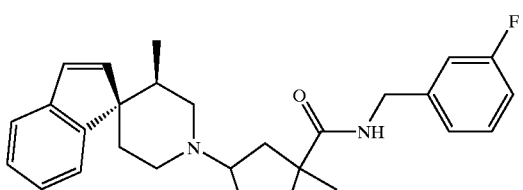
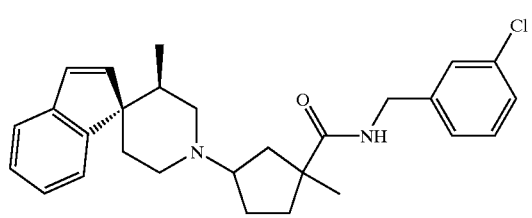
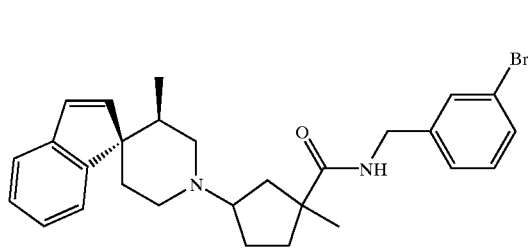
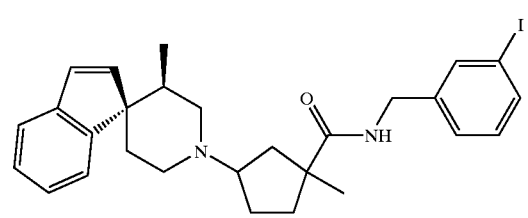
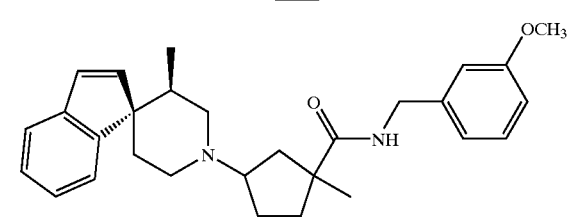
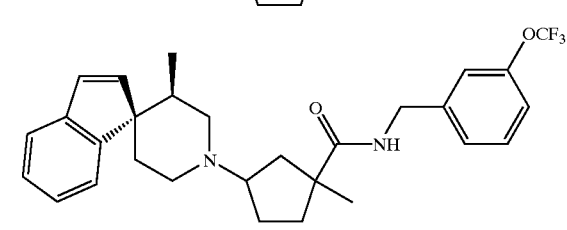

203
-continued
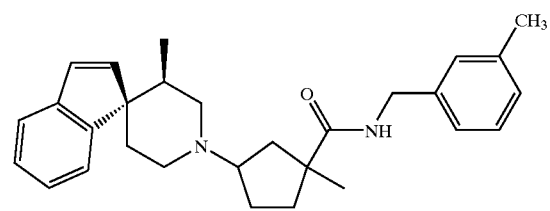
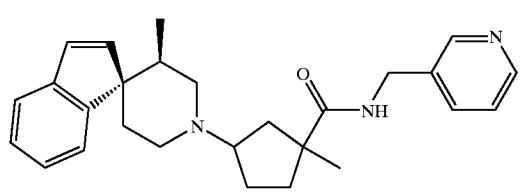
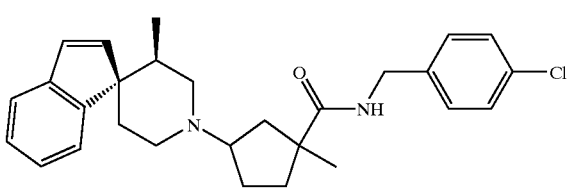
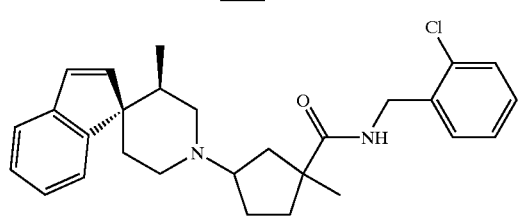
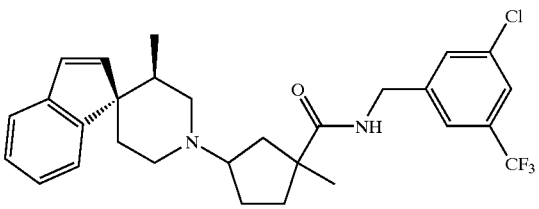
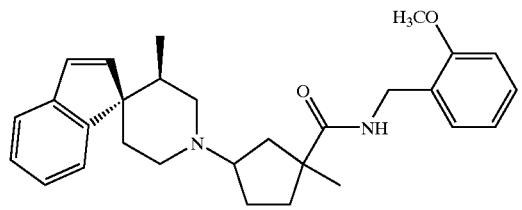
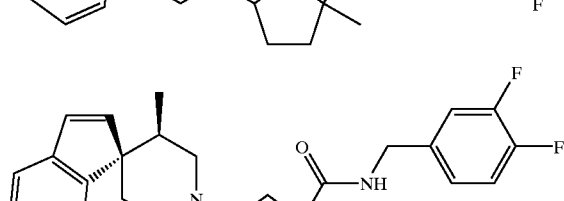
204
-continued
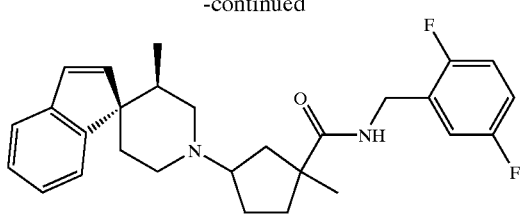
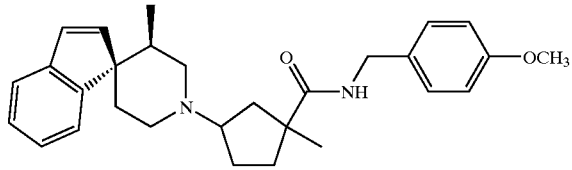
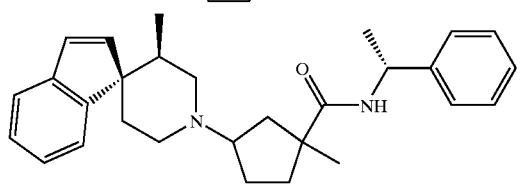
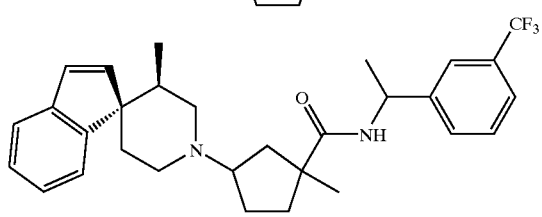
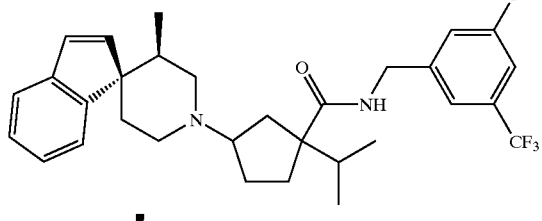
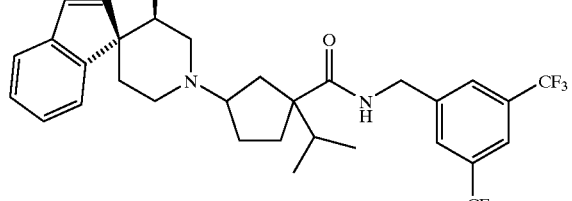
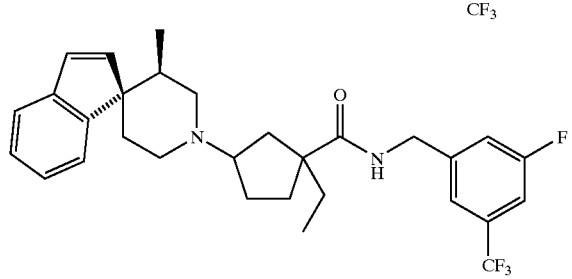

205
-continued
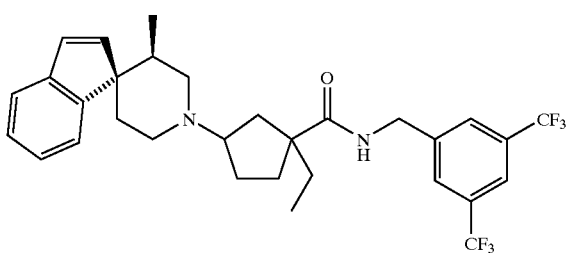
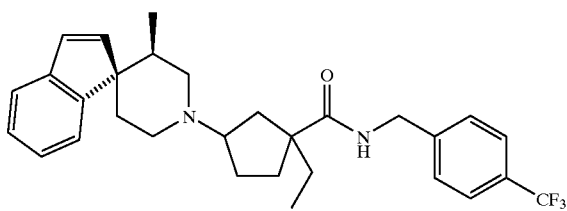
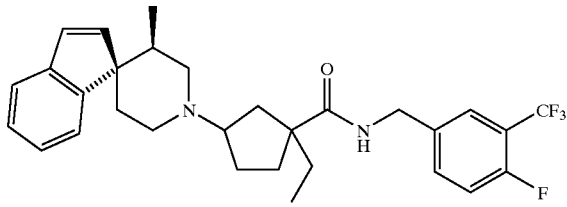
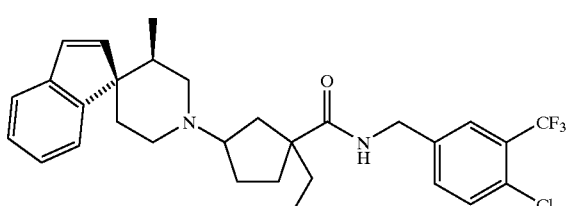
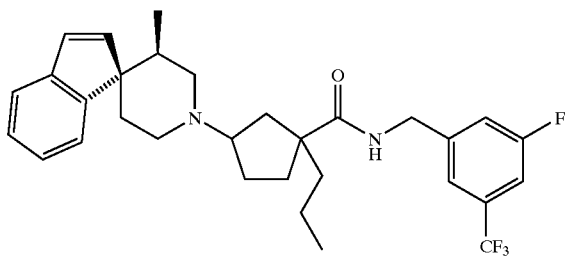
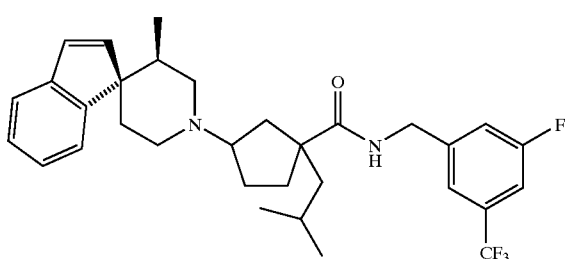
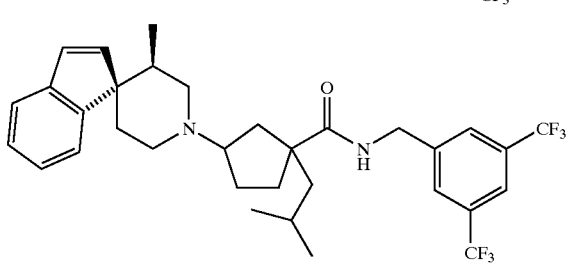
206
-continued
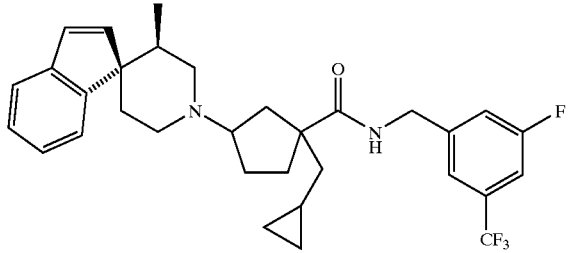
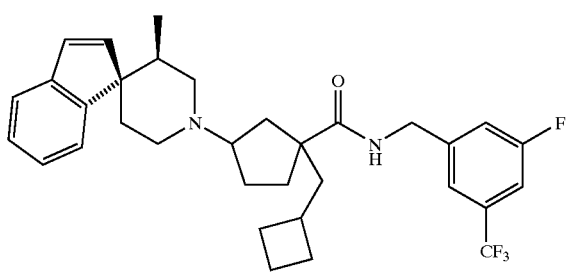
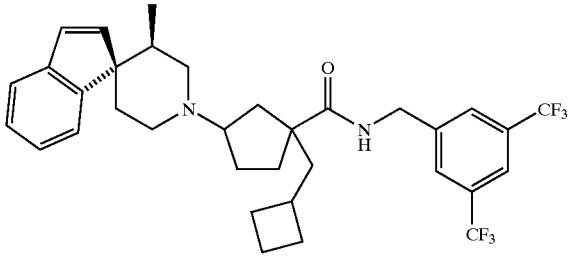
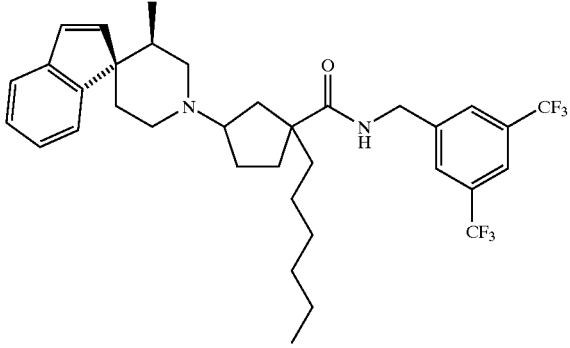
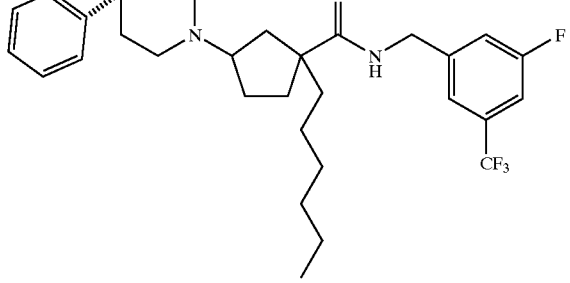

-continued
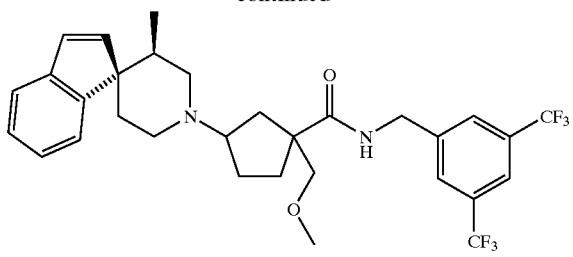
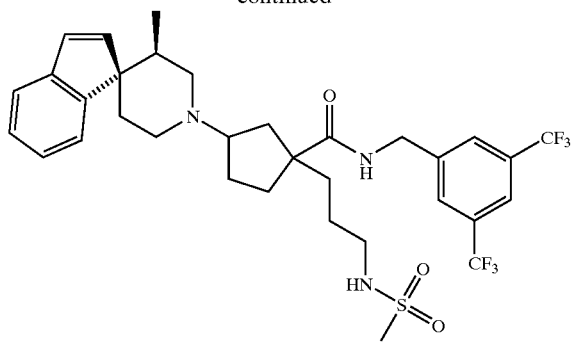
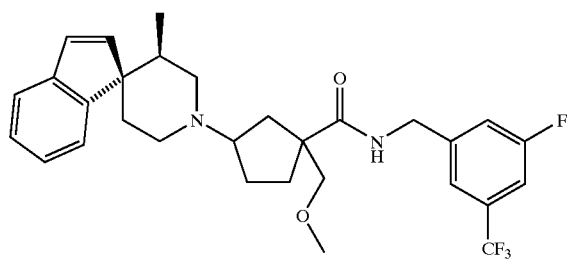
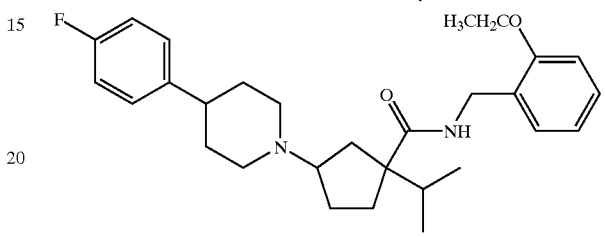
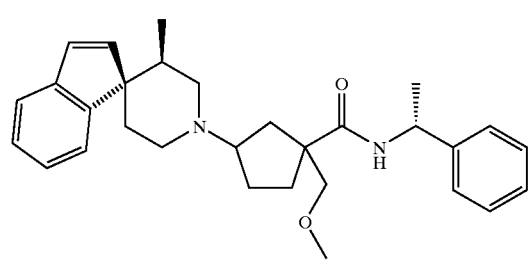
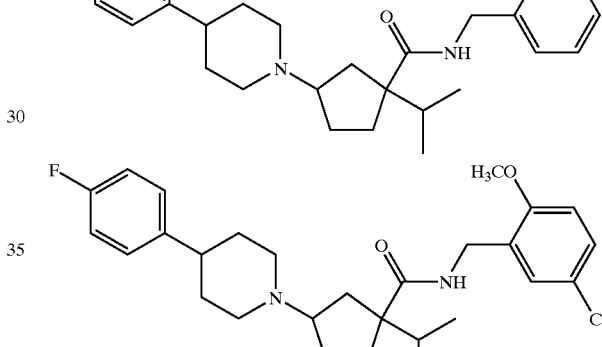
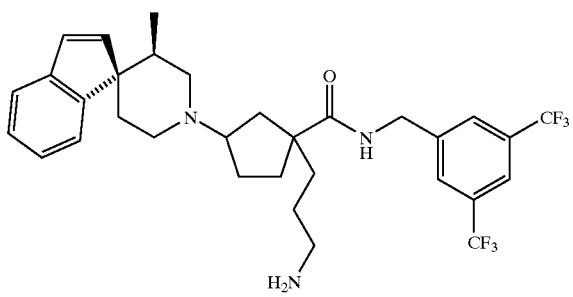
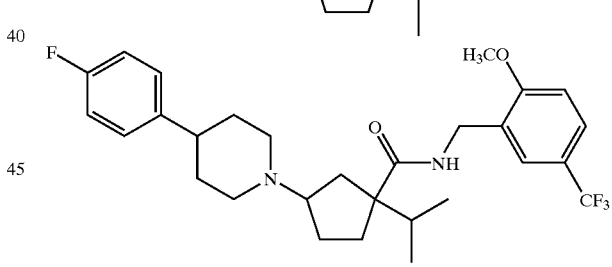
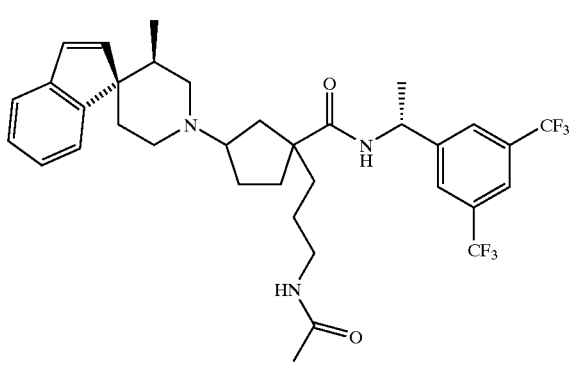
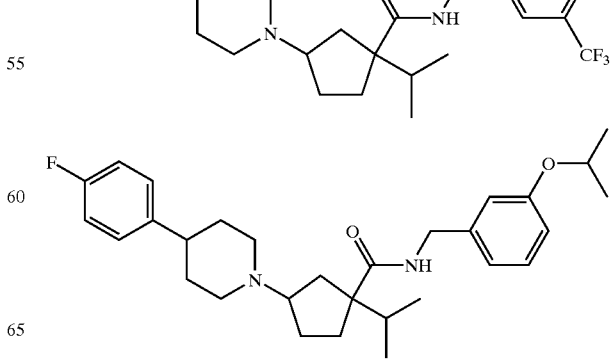

209
-continued
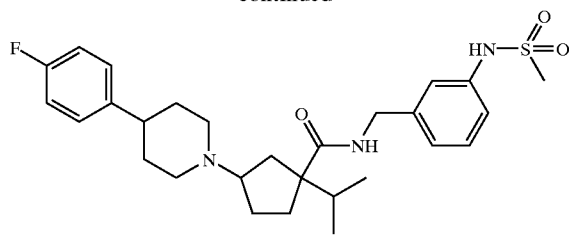
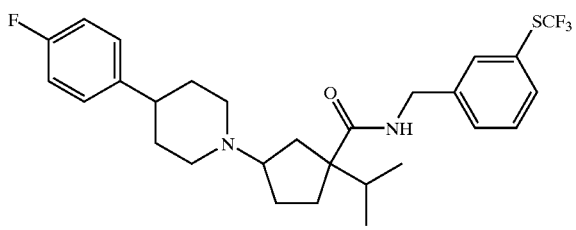
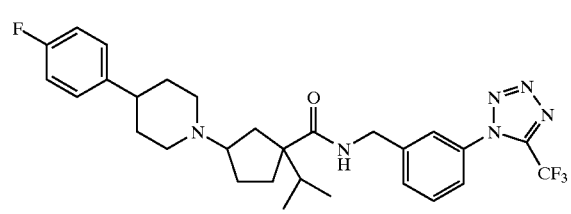
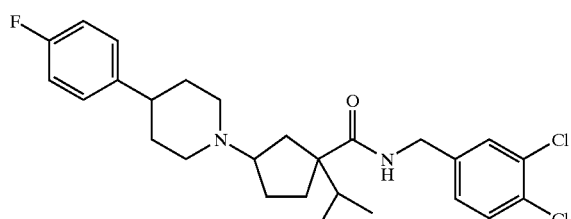
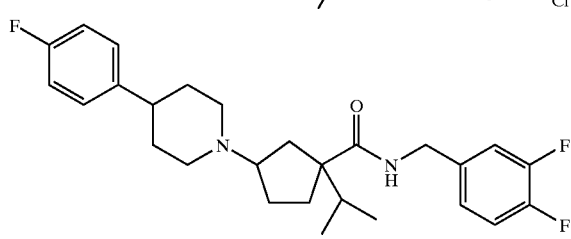
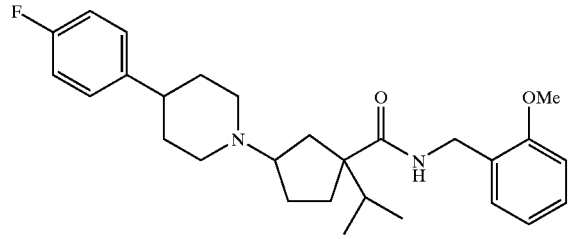
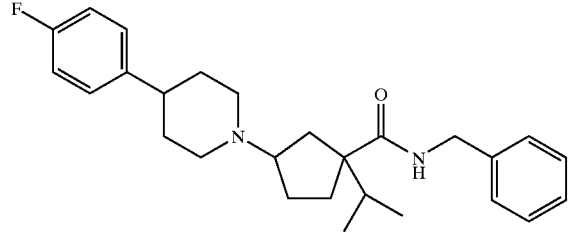
210
-continued
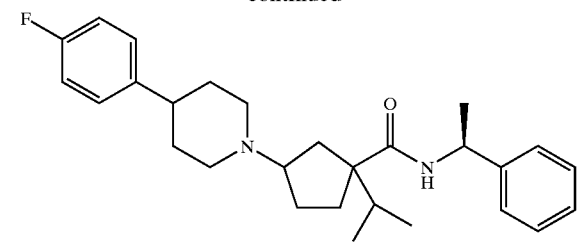
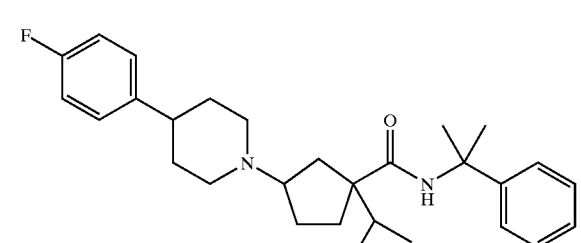
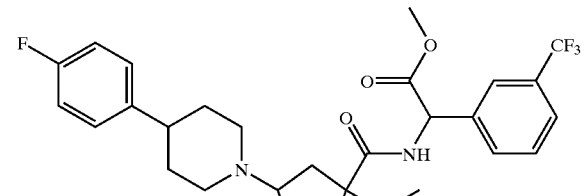
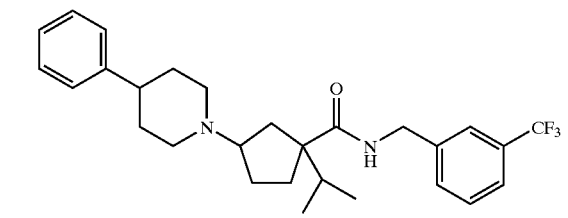
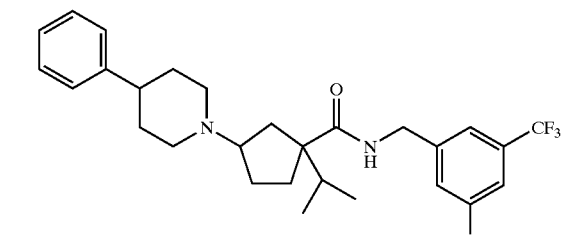
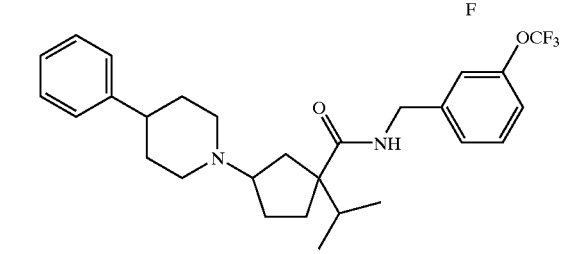
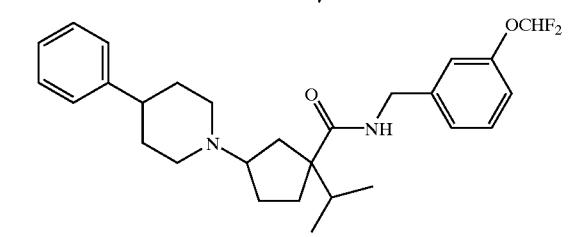

211
-continued
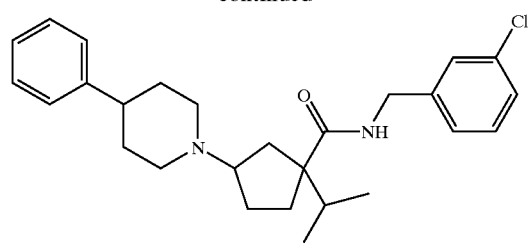
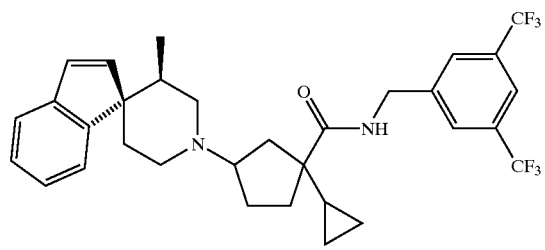
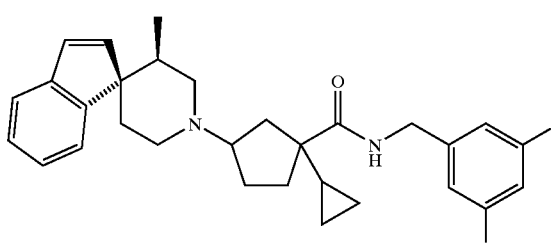
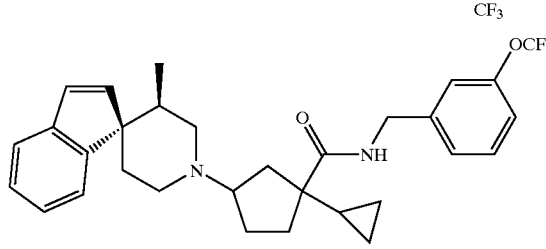
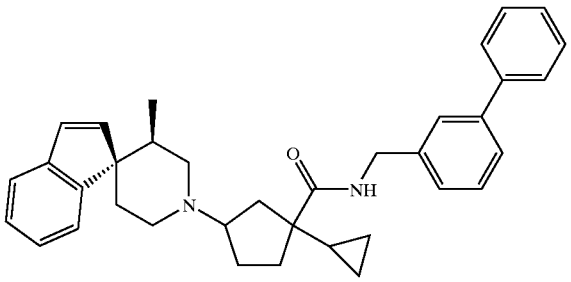
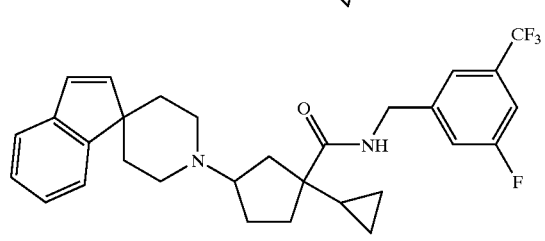
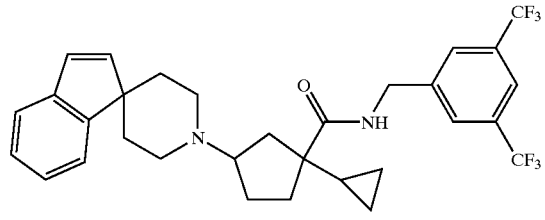
212
-continued
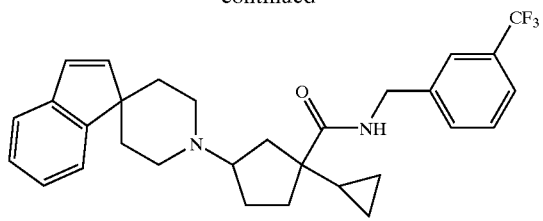
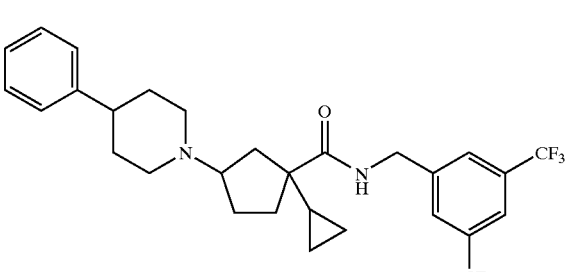
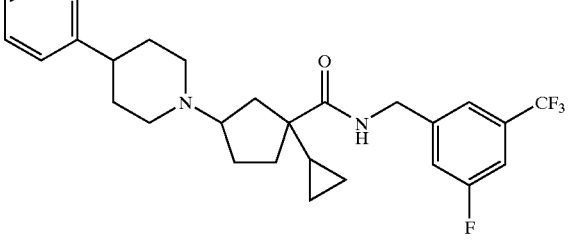
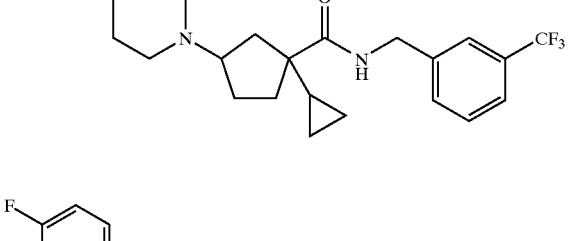
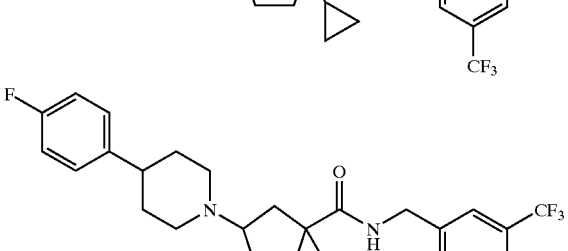

213
-continued
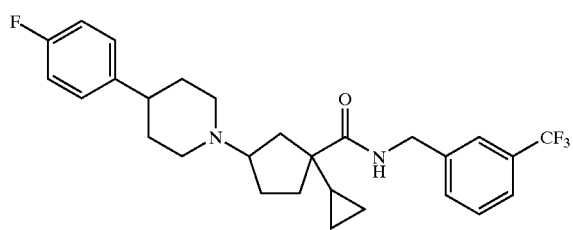
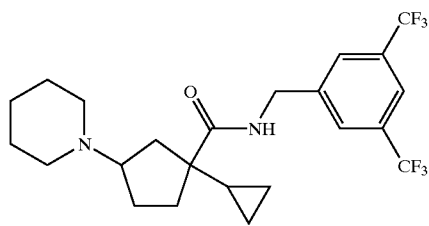
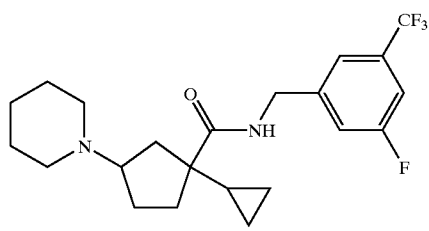
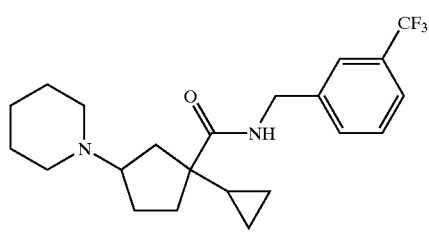
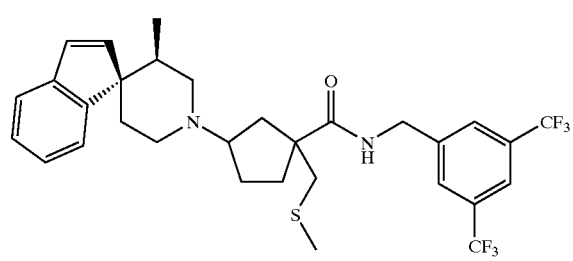
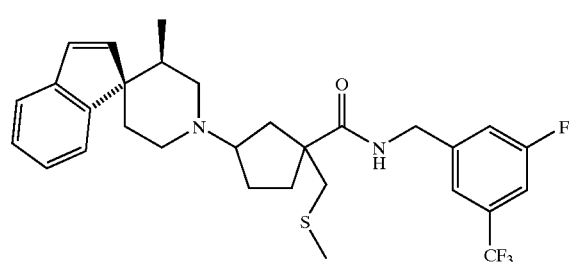
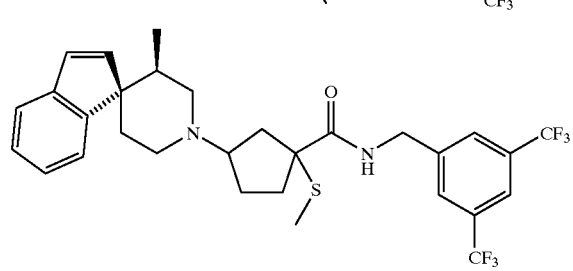
214
-continued
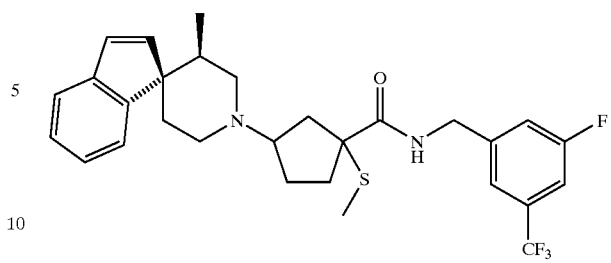
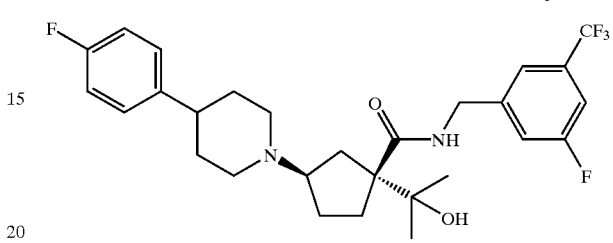
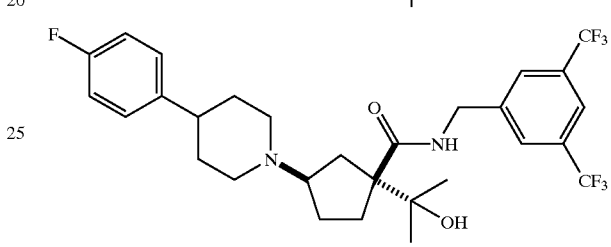
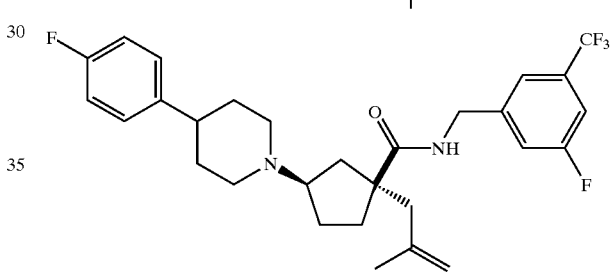
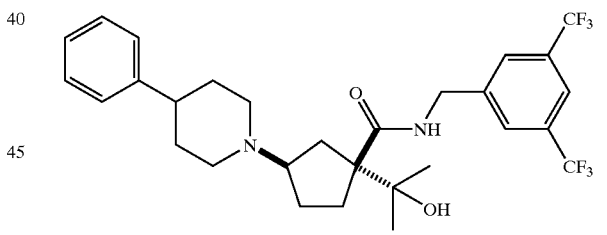
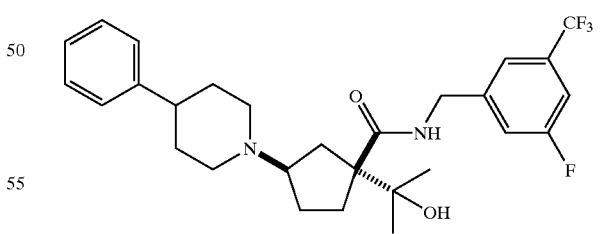
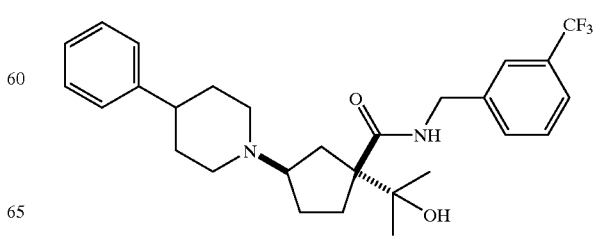

-continued
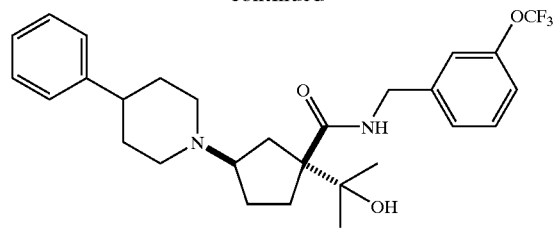
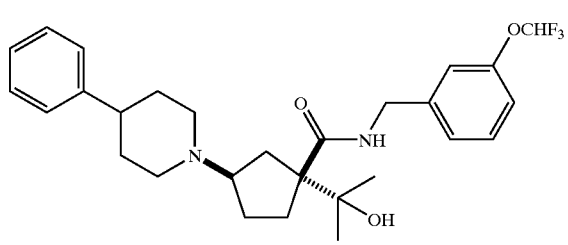
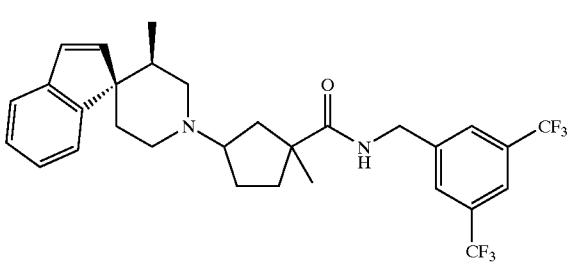
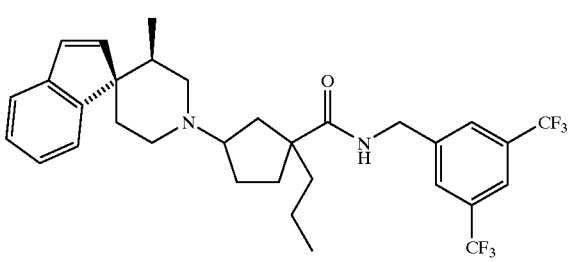
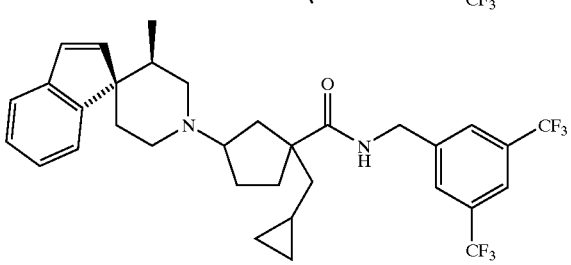
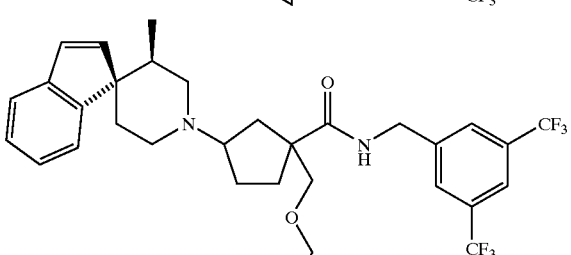
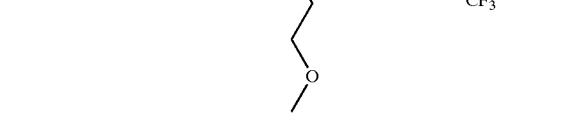
-continued
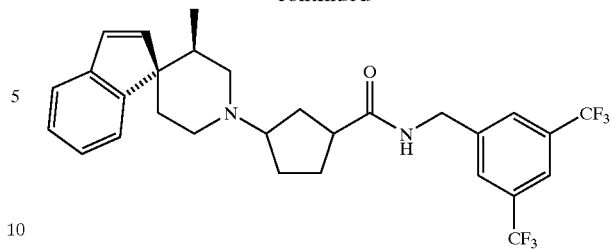
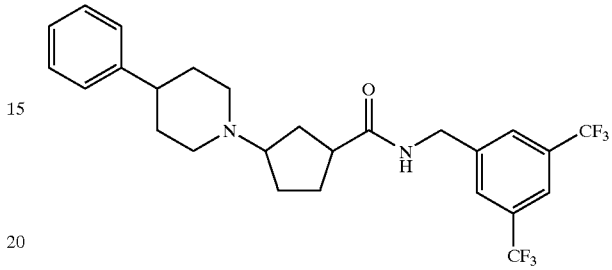
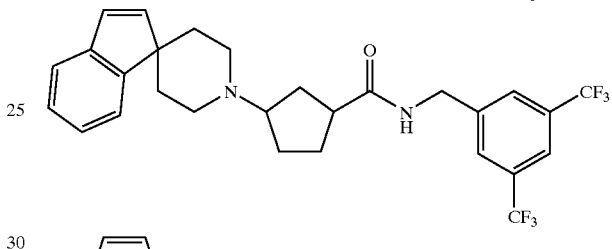
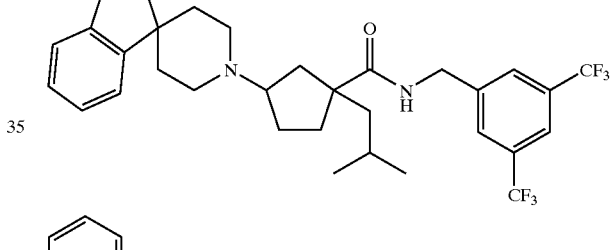
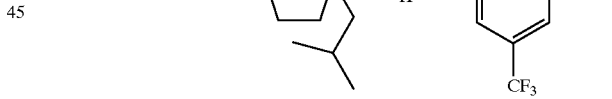
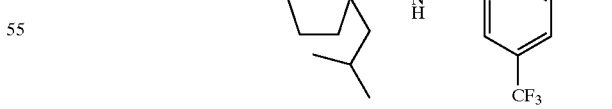
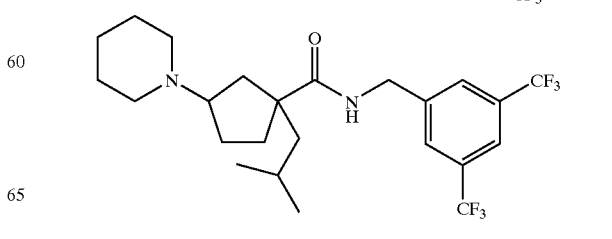

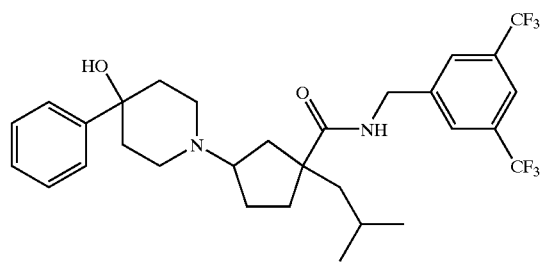
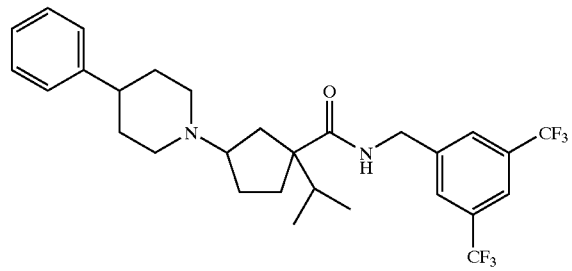
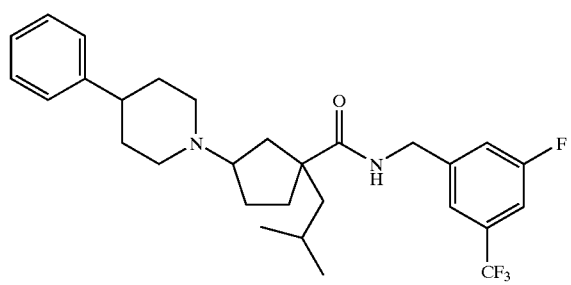
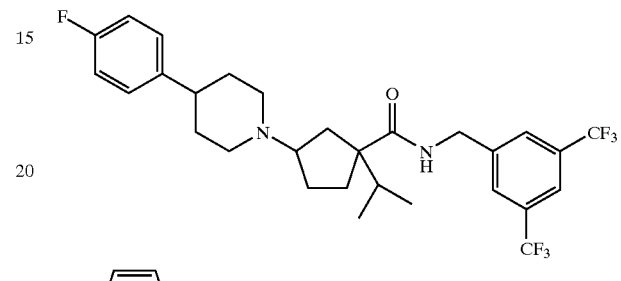
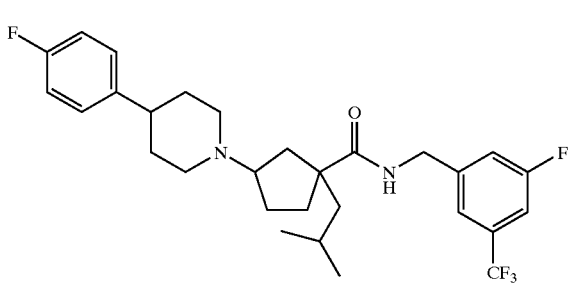
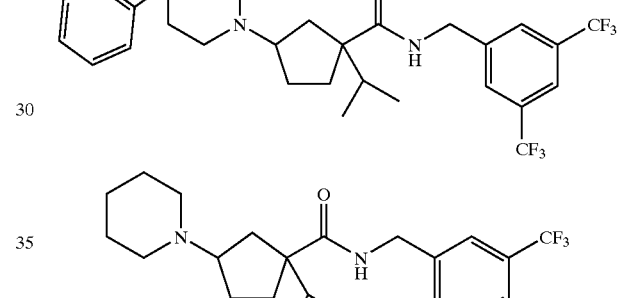
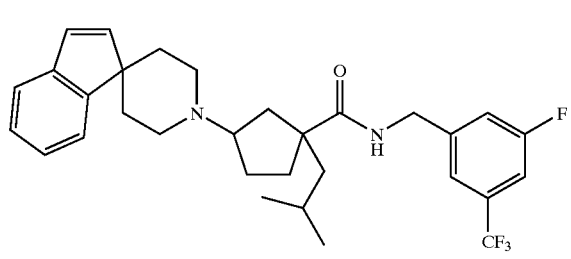
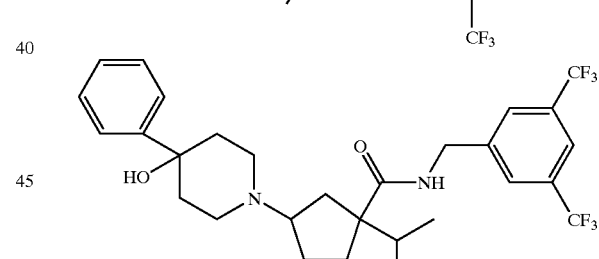
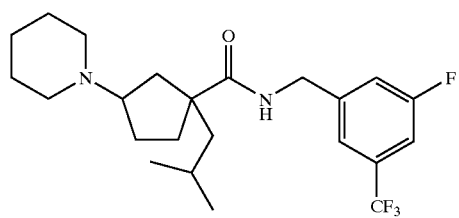
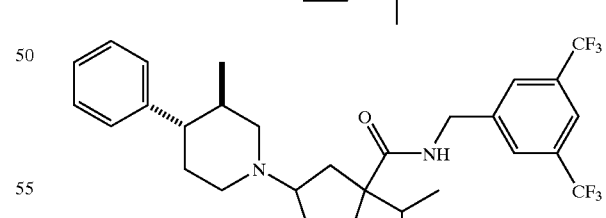
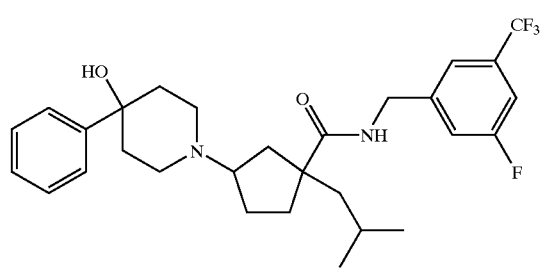
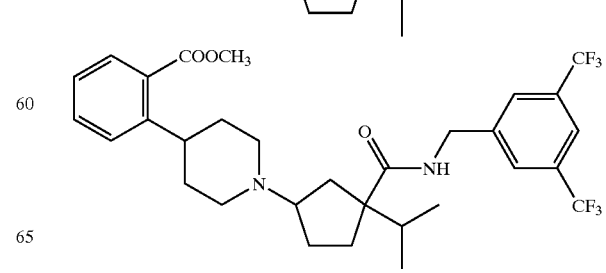

219
-continued
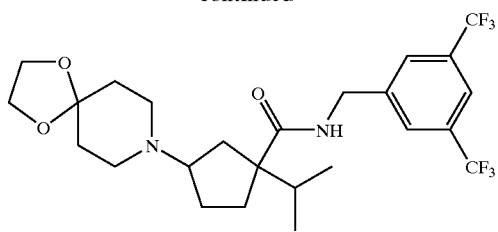
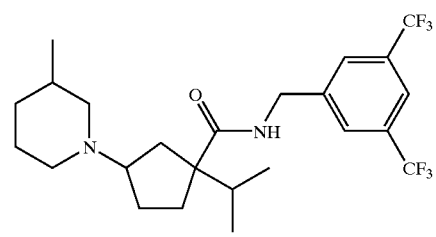
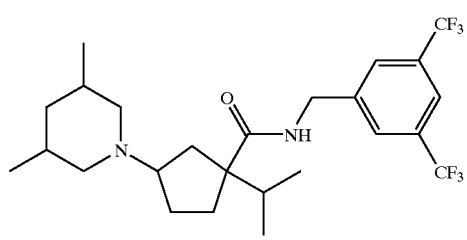
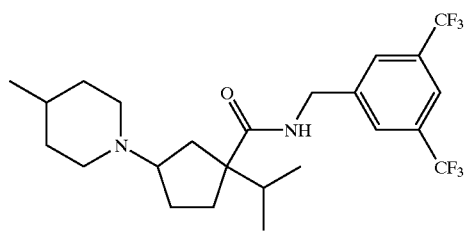
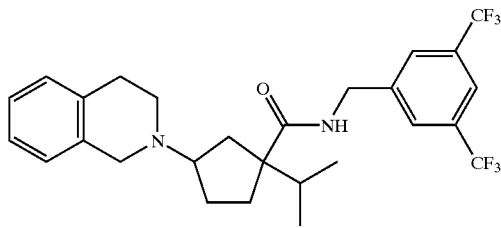
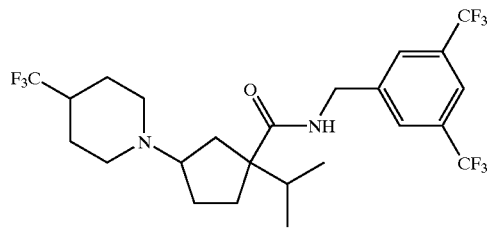
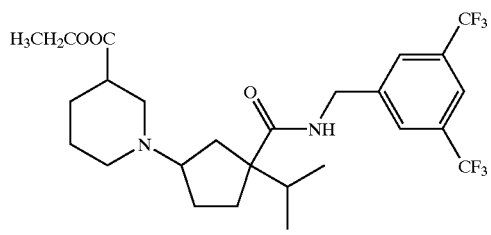
220
-continued
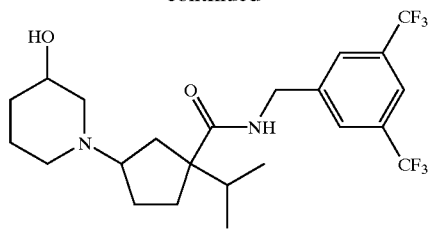
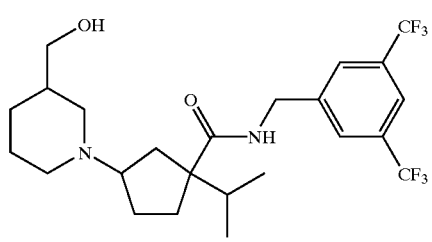
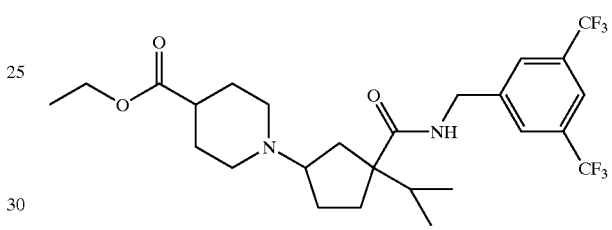
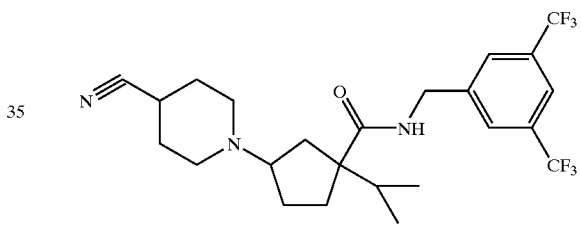
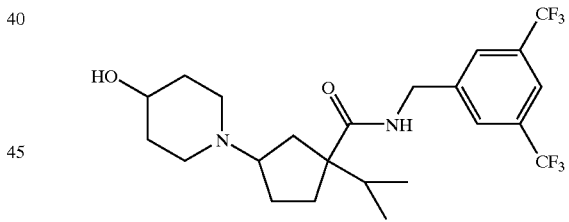
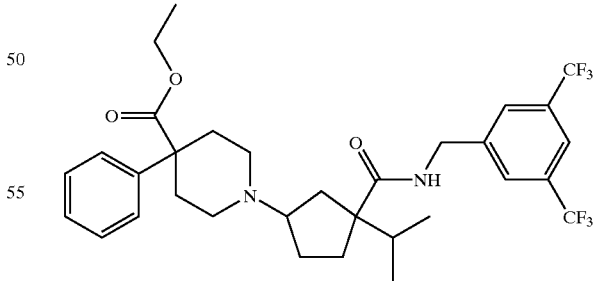
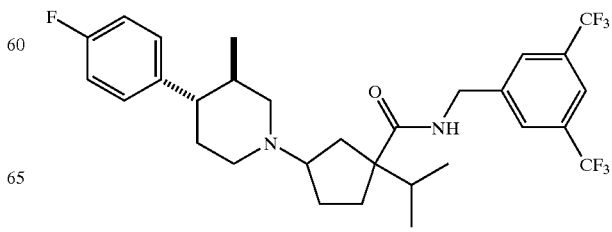

221
-continued
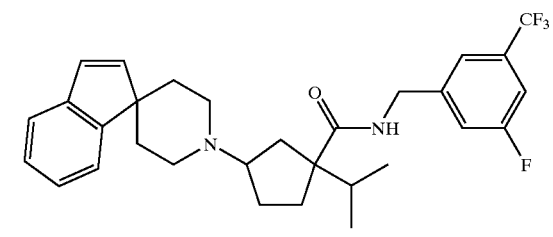
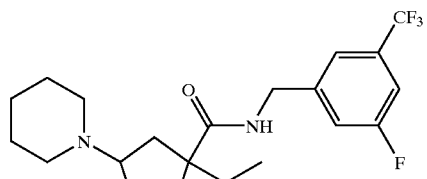
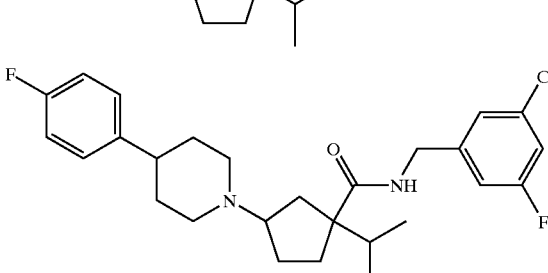
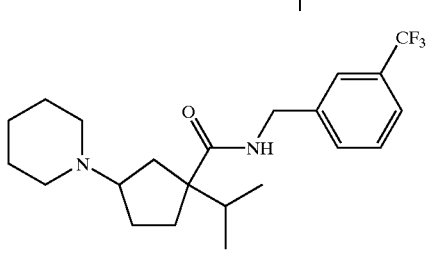
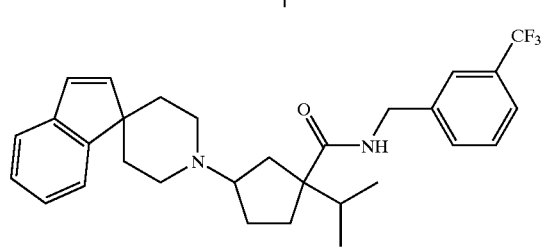
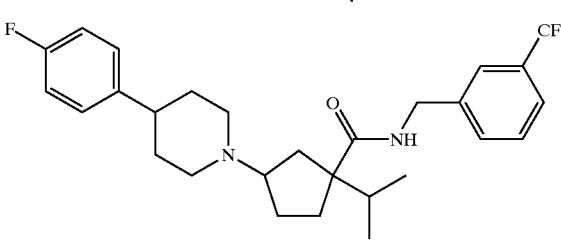
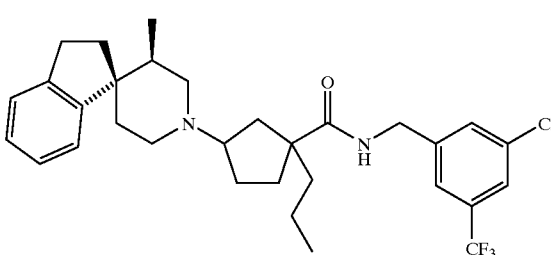
222
-continued
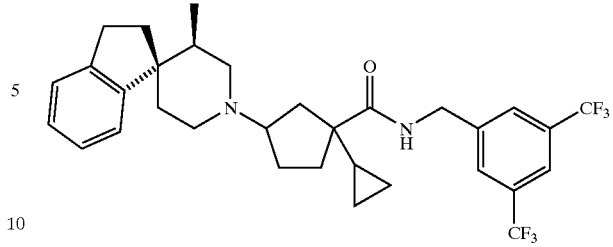
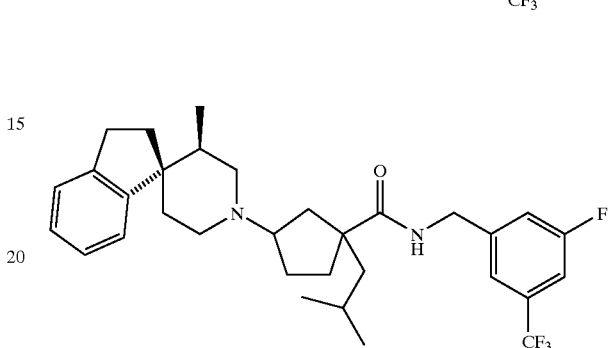
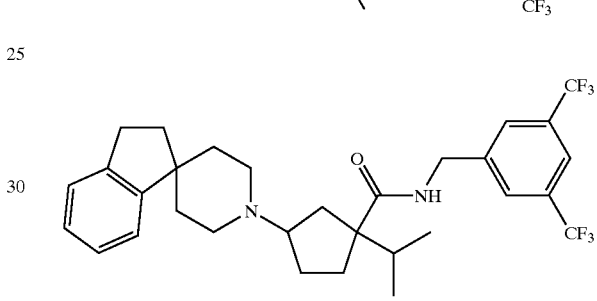
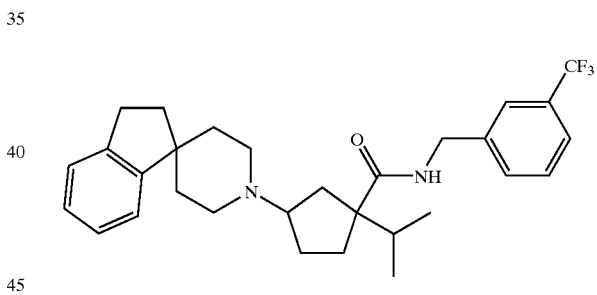
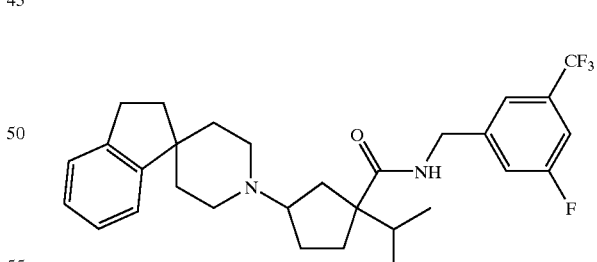
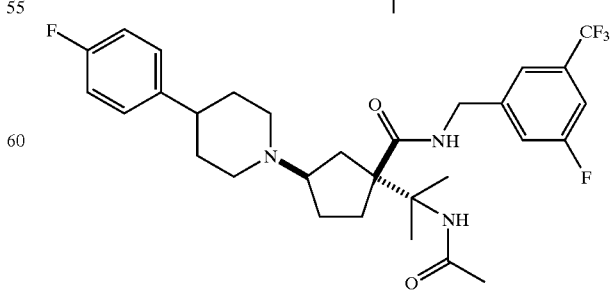

223
-continued
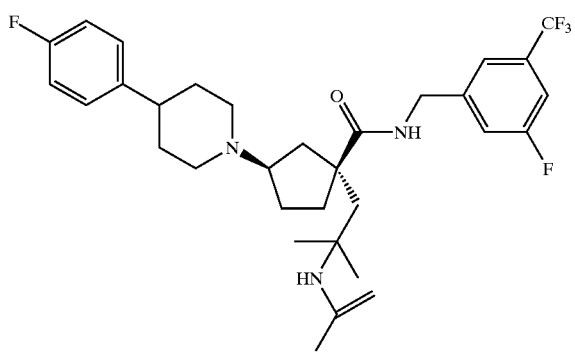
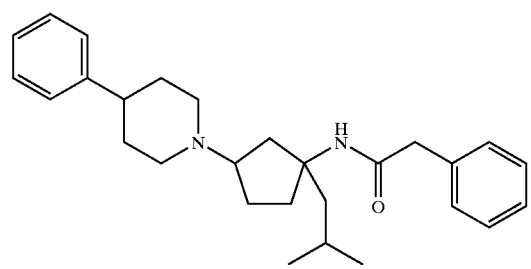
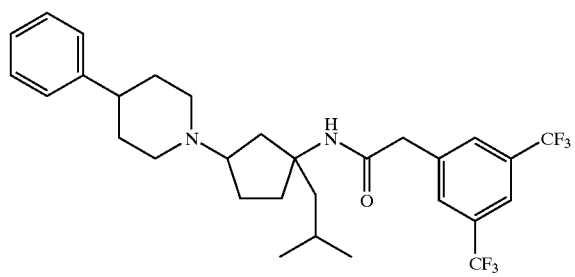
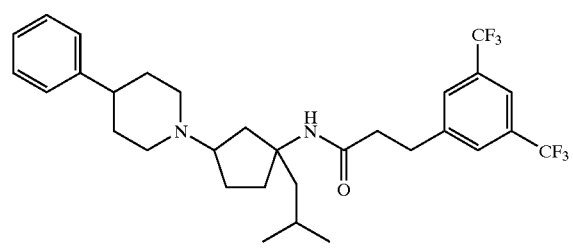
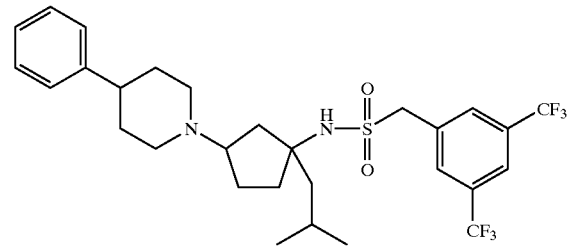
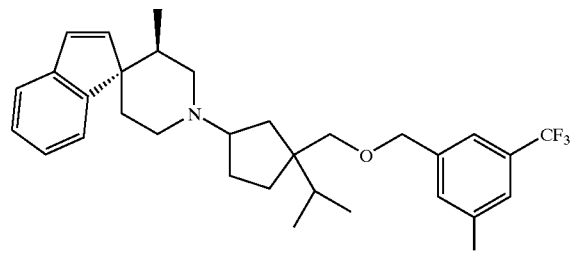
224
-continued
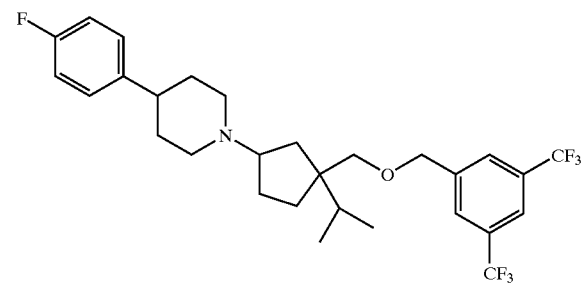
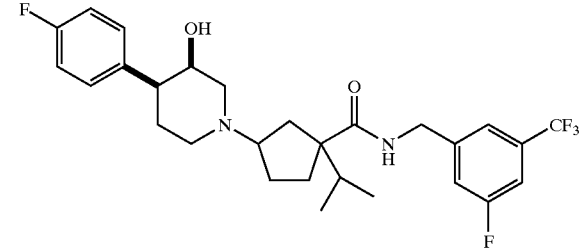
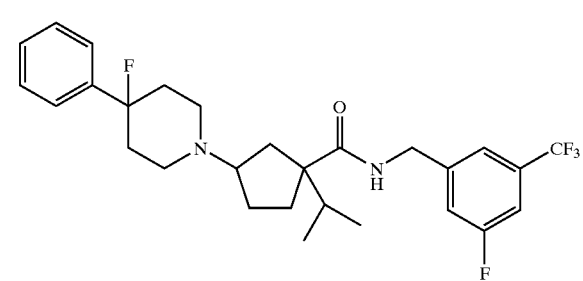
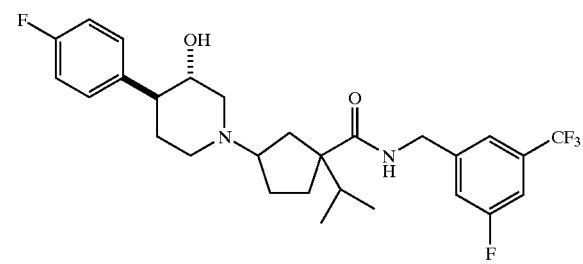
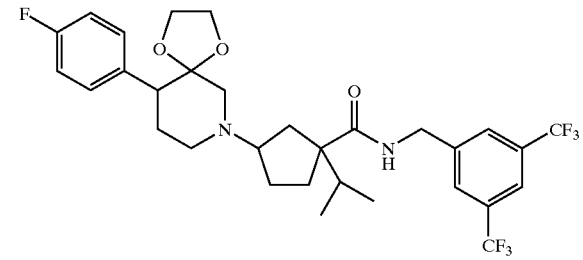
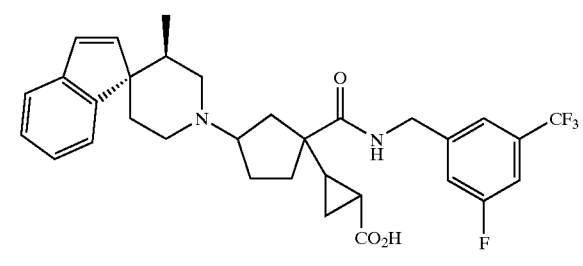

225
-continued
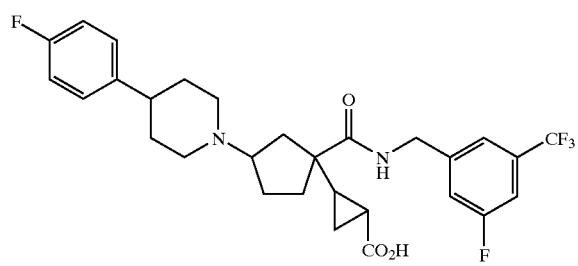
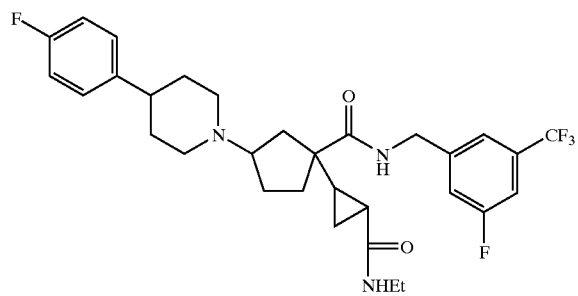
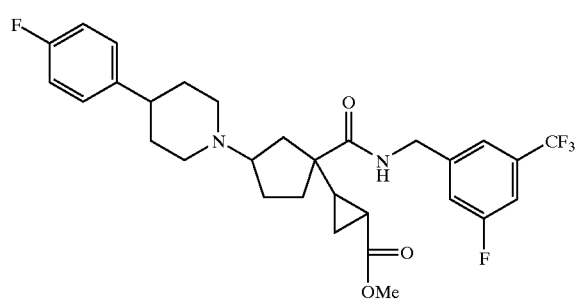
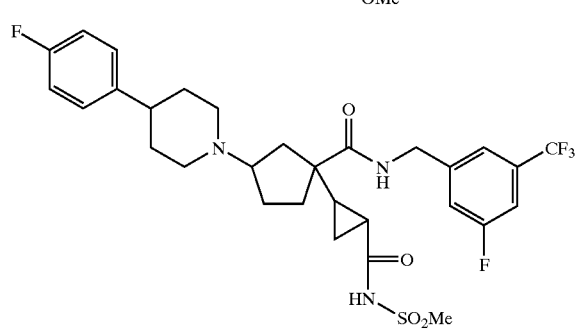
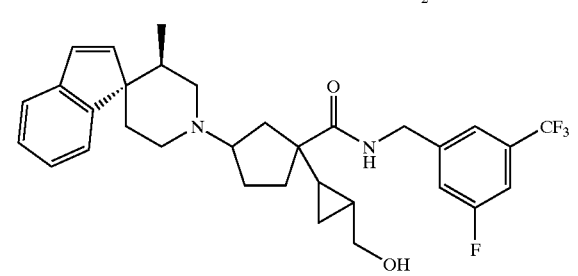
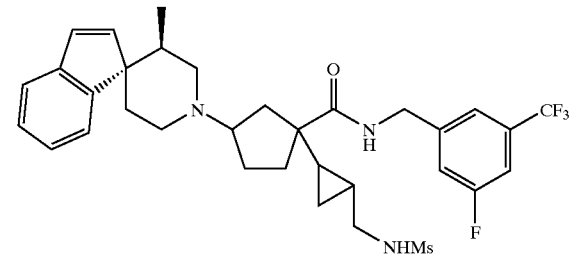
226
-continued
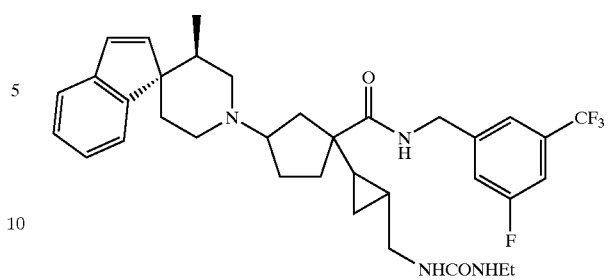
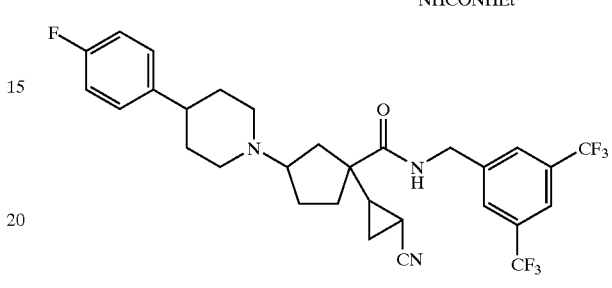
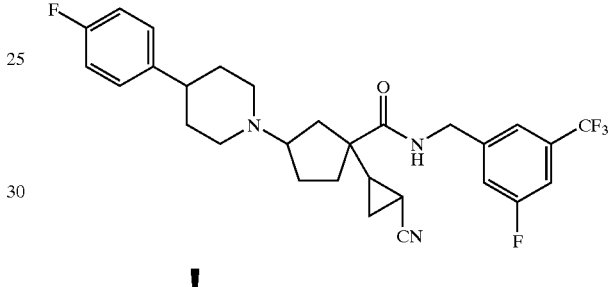
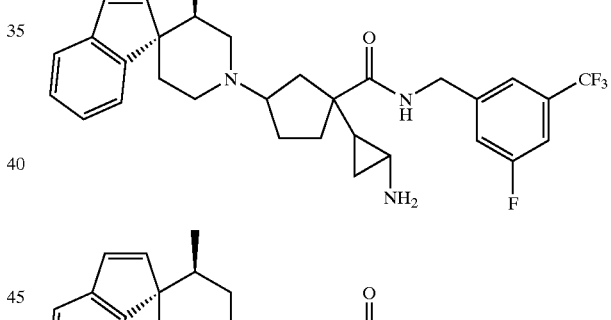
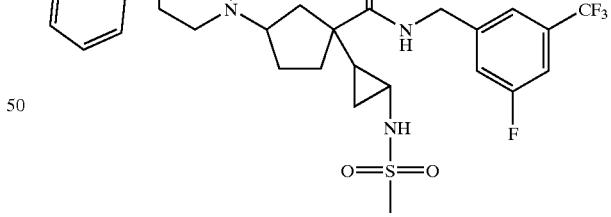
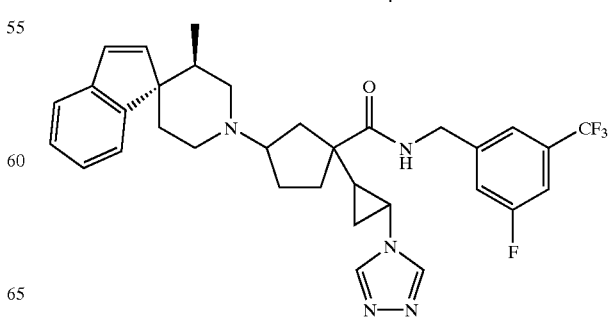

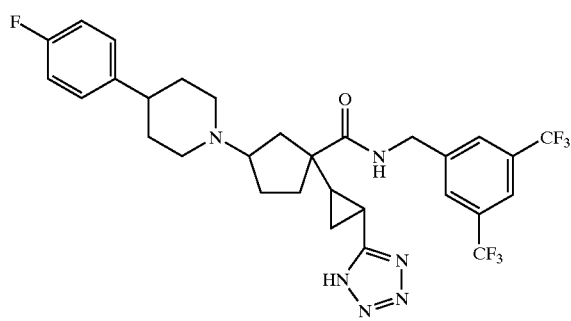
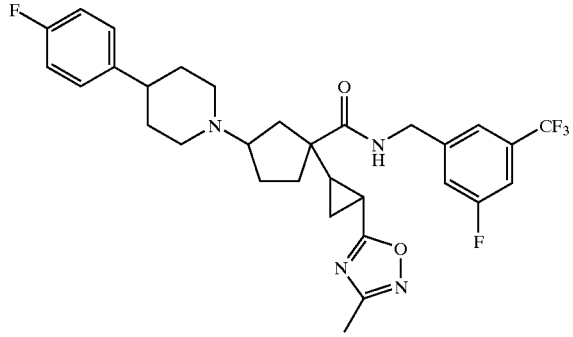
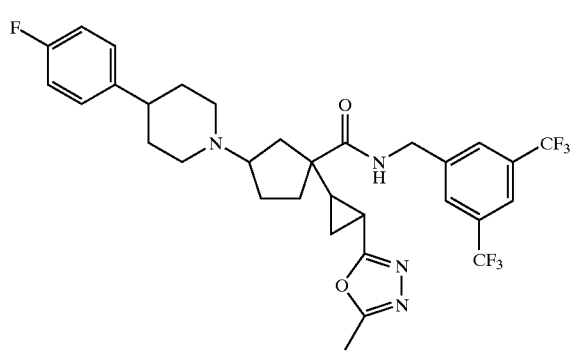
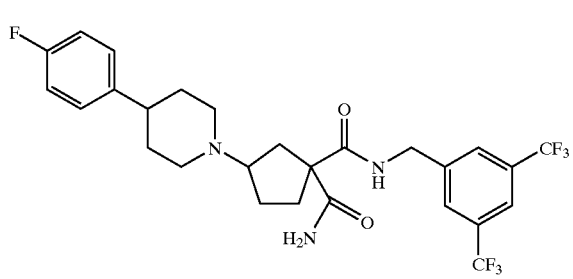
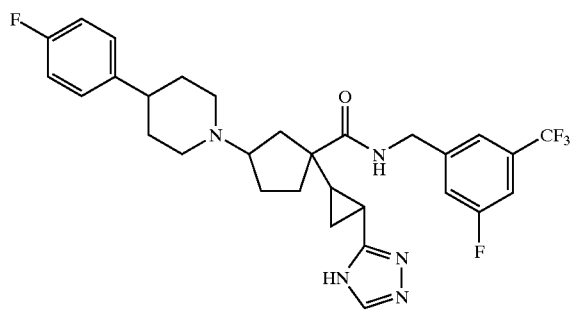
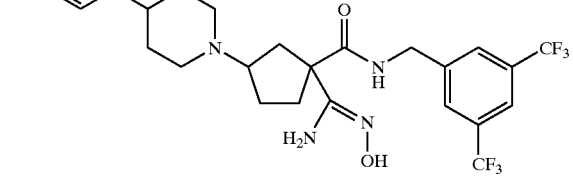
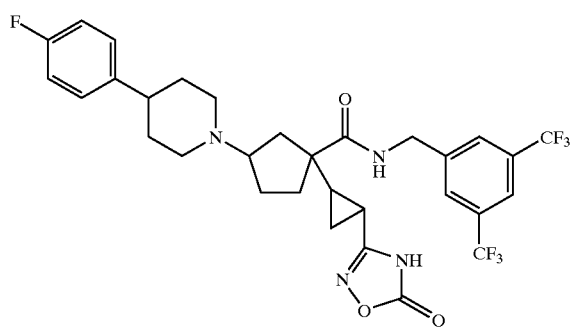
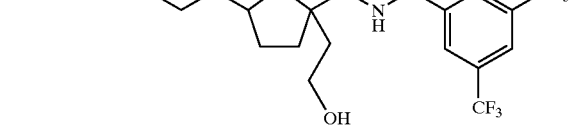
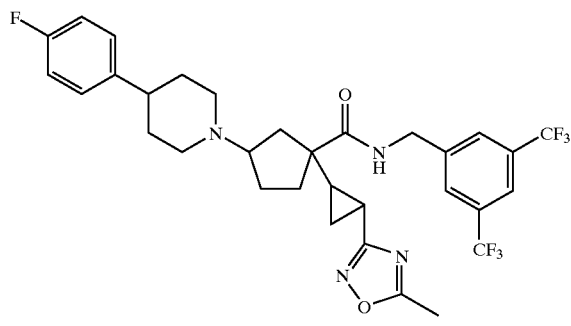
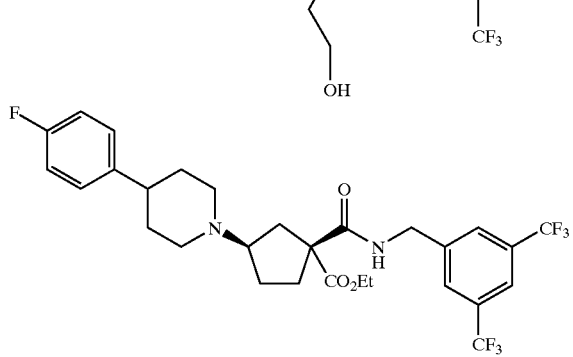

229
-continued
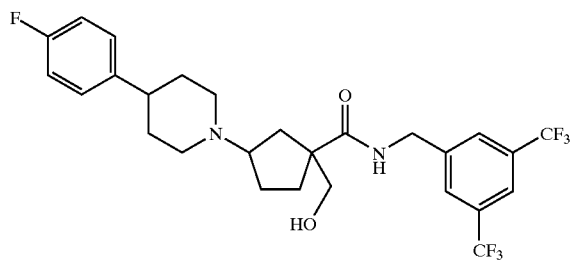
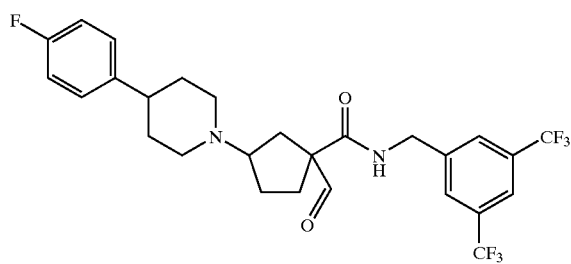
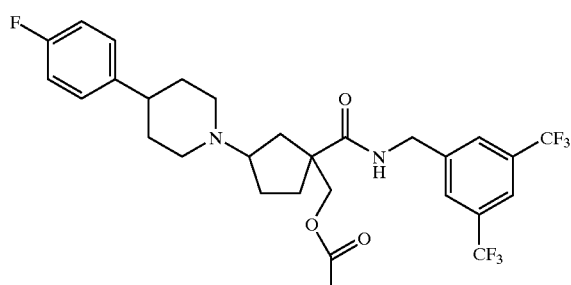
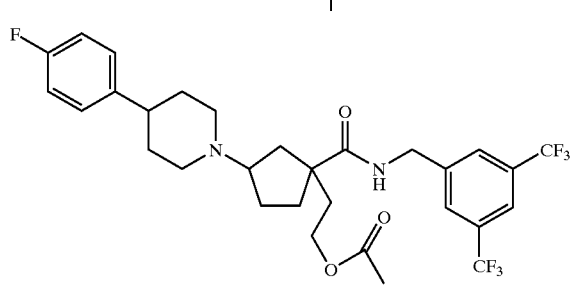
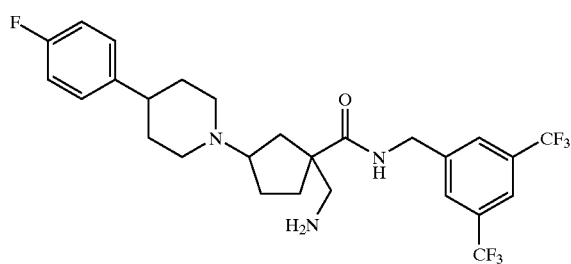
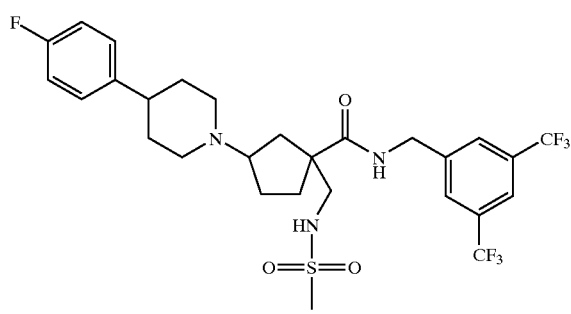
230
-continued
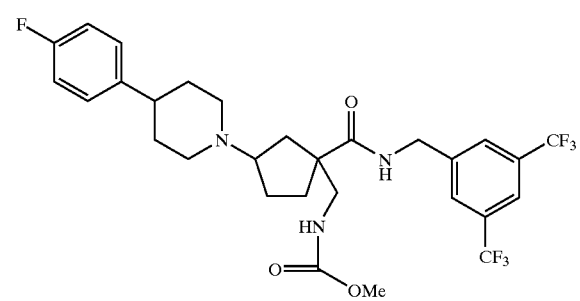
and pharmaceutically acceptable salts and individual diastereomers thereof.

22. A pharmaceutical composition which comprises an inert carrier and a therapeutically effective amount of a compound of claim 1.

23. A method for inhibition of chemokine receptor activity in a mammal which comprises the administration of an effective amount of the compound of claim 1.

24. A method for the treatment of an inflammatory and immunoregulatory disorder or disease which comprises the administration to a patient of an effective amount of the compound of claim 1.

25. A method for the treatment of rheumatoid arthritis which comprises the administration to a patient of an effective amount of the compound of claim 1.

* * * * *